US012691081B2

(12) United States Patent
Narain et al.

(10) Patent No.: US 12,691,081 B2
(45) Date of Patent: *Jul. 28, 2026

(54) METHODS FOR THE TREATMENT OF CANCER USING COENZYME Q10 COMBINATION THERAPIES

(71) Applicant: BPGbio, Inc., Framingham, MA (US)

(72) Inventors: Niven Rajin Narain, Cambridge, MA (US); Rangaprasad Sarangarajan, Boylston, MA (US)

(73) Assignee: BPGbio, Inc., Waltham, MA (US)

( * ) Notice: Subject to any disclaimer, the term of this patent is extended or adjusted under 35 U.S.C. 154(b) by 1194 days.

This patent is subject to a terminal disclaimer.

(21) Appl. No.: 17/141,499

(22) Filed: Jan. 5, 2021

(65) Prior Publication Data

US 2021/0369645 A1 Dec. 2, 2021

Related U.S. Application Data

(63) Continuation of application No. 14/248,313, filed on Apr. 8, 2014, now Pat. No. 10,933,032.

(60) Provisional application No. 61/809,840, filed on Apr. 8, 2013.

(51) Int. Cl.

| | |
|---|---|
| ***A61K 31/122*** | (2006.01) |
| ***A61K 31/4745*** | (2006.01) |
| ***A61K 31/513*** | (2006.01) |
| ***A61K 31/704*** | (2006.01) |
| ***A61K 31/7068*** | (2006.01) |
| ***A61K 33/243*** | (2019.01) |
| ***A61K 39/395*** | (2006.01) |
| ***A61K 45/06*** | (2006.01) |
| ***C07K 16/32*** | (2006.01) |

(52) U.S. Cl.

CPC ........ *A61K 31/122* (2013.01); *A61K 31/4745* (2013.01); *A61K 31/513* (2013.01); *A61K 31/704* (2013.01); *A61K 31/7068* (2013.01); *A61K 33/243* (2019.01); *A61K 39/39558* (2013.01); *A61K 45/06* (2013.01); *C07K 16/32* (2013.01)

(58) Field of Classification Search

CPC ........................ A61K 31/122; A61K 39/39558

See application file for complete search history.

(56) References Cited

U.S. PATENT DOCUMENTS

| | | | |
|---|---|---|---|
| 4,483,873 | A | 11/1984 | Ohashi et al. |
| 4,515,736 | A | 5/1985 | Deamer |
| 4,525,350 | A | 6/1985 | Casey et al. |
| 4,636,381 | A | 1/1987 | Takada et al. |
| 4,654,373 | A | 3/1987 | Bertelli |
| 4,824,669 | A | 4/1989 | Folkers et al. |
| 4,833,128 | A | 5/1989 | Solomon et al. |
| 4,895,727 | A | 1/1990 | Allen |
| 5,015,483 | A | 5/1991 | Haynes et al. |
| 5,045,559 | A | 9/1991 | Scott |
| 5,362,494 | A | 11/1994 | Zysman et al. |
| 5,378,461 | A | 1/1995 | Neigut |
| 5,527,789 | A | 6/1996 | Nyce |
| 5,602,184 | A | 2/1997 | Myers et al. |
| 5,603,958 | A | 2/1997 | Morein et al. |
| 5,605,930 | A | 2/1997 | Samid |
| 5,651,991 | A | 7/1997 | Sugiyama et al. |
| 5,700,482 | A | 12/1997 | Frederiksen et al. |
| 5,719,303 | A | 2/1998 | Yoshida et al. |
| 5,770,222 | A | 6/1998 | Unger et al. |
| 5,876,737 | A | 3/1999 | Schonrock et al. |
| 5,889,062 | A | 3/1999 | Hoppe et al. |
| 5,891,465 | A | 4/1999 | Keller et al. |
| 5,912,272 | A | 6/1999 | Hoppe et al. |
| 5,944,012 | A | 8/1999 | Pera |
| 5,962,243 | A | 10/1999 | Brown et al. |
| 6,005,086 | A | 12/1999 | Evans et al. |
| 6,048,886 | A | 4/2000 | Neigut |
| 6,063,820 | A | 5/2000 | Cavazza |
| 6,071,495 | A | 6/2000 | Unger et al. |
| 6,093,706 | A | 7/2000 | Zeligs |
| 6,093,743 | A | 7/2000 | Lai et al. |
| 6,184,353 | B1 | 2/2001 | Evans et al. |
| 6,228,891 | B1 | 5/2001 | Enzmann et al. |
| 6,261,575 | B1 | 7/2001 | Hoppe et al. |
| 6,348,506 | B2 | 2/2002 | Sneed |
| 6,372,234 | B1 | 4/2002 | Deckers et al. |

(Continued)

FOREIGN PATENT DOCUMENTS

| | | |
|---|---|---|
| CA | 2436374 A1 | 8/2002 |
| CA | 2553690 A1 | 8/2005 |

(Continued)

OTHER PUBLICATIONS

U.S. Appl. No. 10/597,378, filed Aug. 21, 2008, U.S. Pat. No. 8,147,825, Issued.
U.S. Appl. No. 13/410,085, filed Mar. 1, 2012, U.S. Pat. No. 8,293,227, Issued.
U.S. Appl. No. 13/791,313, filed Mar. 8, 2013, U.S. Pat. No. 8,586,030, Issued.
U.S. Appl. No. 13/366,224, filed Feb. 3, 2012, U.S. Pat. No. 8,562,976, Issued.
U.S. Appl. No. 14/031,706, filed Sep. 19, 2013, U.S. Pat. No. 8,771,680, Issued.
U.S. Appl. No. 14/282,336, filed May 20, 2014, 2014-0255372, Abandoned.

(Continued)

*Primary Examiner* — Thane Underdahl
(74) *Attorney, Agent, or Firm* — McCarter & English, LLP; Jill Mello

(57) ABSTRACT

Presented herein are methods for the treatment of oncological disorders by the co-administration of CoQ10 formulations and chemotherapeutic agents and/or surgery. The CoQ10 formulations may be at least one of intravenous, topical, or by inhalation. The chemotherapeutic agents may be at least one of antimetabolites or anthracyclines. Co-administration of the CoQ10 formulations may be prior to, concurrent or substantially concurrent with, intermittent with or subsequent to the administration of the chemotherapy.

22 Claims, 32 Drawing Sheets

(56) References Cited

U.S. PATENT DOCUMENTS 6,403,116 B1 6/2002 Anderson et al.
6,416,957 B1 7/2002 Evans et al.
6,417,233 B1 7/2002 Sears et al.
6,441,050 B1 8/2002 Chopra
6,461,593 B1 10/2002 Hanioka et al.
6,465,517 B1 10/2002 Van Der Zee
6,468,552 B1 10/2002 Stahl et al.
6,469,061 B1 10/2002 Flescher et al.
6,482,943 B1 11/2002 Blokhin et al.
6,503,506 B1 1/2003 Germano
6,503,523 B2 1/2003 Hoppe et al.
6,506,915 B1 1/2003 West
6,511,800 B1 1/2003 Singh
6,531,117 B2 3/2003 Heger et al.
6,569,463 B2 5/2003 Patel et al.
6,573,284 B1 6/2003 Riley et al.
6,576,660 B1 6/2003 Liao et al.
6,576,678 B1 6/2003 Bruening et al.
6,582,710 B2 6/2003 Deckers et al.
6,582,723 B2 6/2003 Gorsek
6,596,287 B2 7/2003 Deckers et al.
6,599,513 B2 7/2003 Deckers et al.
6,623,746 B1 9/2003 Wadle et al.
6,630,160 B1 10/2003 Evans et al.
6,632,443 B2 10/2003 Borowy-Borowski et al.
6,652,891 B2 11/2003 Selzer
6,682,763 B2 1/2004 Kuno et al.
6,686,485 B2 2/2004 West
6,696,484 B2 2/2004 Liao et al.
6,726,924 B2 4/2004 Keller
6,727,234 B2 4/2004 Wiemer et al.
6,733,790 B1 5/2004 Garces Garces
6,753,325 B2 6/2004 Rosenbloom
6,803,193 B1 10/2004 Hopper et al.
6,806,069 B2 10/2004 Chokshi
6,809,176 B2 10/2004 Blokhin et al.
6,866,864 B2 3/2005 Mousa
6,867,024 B2 3/2005 Chokshi
6,906,106 B2 6/2005 Chevalier
6,923,988 B2 8/2005 Patel et al.
7,005,274 B1 2/2006 Terkeltaub et al.
7,060,733 B2 6/2006 Pandol et al.
7,083,572 B2 8/2006 Unger et al.
7,083,780 B2 8/2006 Ansmann et al.
7,091,241 B2 8/2006 Gilloteaux et al.
7,101,536 B2 9/2006 Mongiat et al.
7,132,268 B2 11/2006 Miyake et al.
7,147,841 B2 12/2006 Herzog
7,169,385 B2 1/2007 Fantuzzi et al.
7,169,590 B2 1/2007 Ueda et al.
7,176,171 B2 2/2007 Nieendick et al.
7,179,880 B2 2/2007 Kawa et al.
7,182,938 B2 2/2007 Andre et al.
7,182,950 B2 2/2007 Garti et al.
7,198,801 B2 4/2007 Carrara et al.
7,208,298 B2 4/2007 Miyake et al.
7,247,714 B2 7/2007 Kunsch et al.
7,250,174 B2 7/2007 Lee et al.
7,268,107 B2 9/2007 Nieendick et al.
7,273,606 B2 9/2007 Fantuzzi et al.
7,279,456 B2 10/2007 Dufay et al.
7,311,897 B2 12/2007 Ehlis et al.
7,318,929 B2 1/2008 Schieferstein et al.
7,357,918 B2 4/2008 Comte et al.
7,456,161 B2 11/2008 Nyce
7,635,722 B1 12/2009 Bachynsky et al.
7,776,894 B2 8/2010 Ronai et al.
7,824,673 B2 11/2010 Wegman et al.
7,858,659 B2 12/2010 Hoffman et al.
7,879,823 B2 2/2011 Seiberg et al.
7,906,140 B2 3/2011 Bromley et al.
8,147,825 B2 4/2012 Hsia et al.
8,293,227 B2 10/2012 Hsia et al.
8,562,976 B2 10/2013 Hsia et al.
8,586,030 B2 11/2013 Hsia et al.
8,746,515 B2 6/2014 Fatherazi et al.
8,771,680 B2 7/2014 Hsia et al.
9,205,064 B2 12/2015 Narain et al.
9,220,776 B2 12/2015 Sharma et al.
9,896,731 B2 2/2018 Narain et al.
9,901,542 B2 2/2018 Narain et al.
9,926,580 B2 3/2018 Yajima et al.
10,351,915 B2 7/2019 Narain et al.
10,376,477 B2 8/2019 Jimenez et al.
10,519,504 B2 12/2019 Narain et al.
10,583,098 B2 3/2020 Hsia et al.
10,933,032 B2 3/2021 Narain et al.
11,028,446 B2 6/2021 Narain et al.
11,400,058 B2 8/2022 Narain et al.
2001/0022965 A1 9/2001 Heger et al.
2001/0043909 A1 11/2001 SaNogueira et al.
2001/0053356 A1 12/2001 Mousa
2002/0039595 A1 4/2002 Keller
2002/0044913 A1 4/2002 Hamilton
2002/0045230 A1 4/2002 Rosen et al.
2002/0048559 A1 4/2002 Shinoda et al.
2002/0048798 A1 4/2002 Avery et al.
2002/0049176 A1 4/2002 Anderson et al.
2002/0049253 A1 4/2002 Kaddurah-Daouk
2002/0049422 A1 4/2002 Brewitt
2002/0058712 A1 5/2002 Sneed
2002/0071852 A1 6/2002 Deckers et al.
2002/0091288 A1 7/2002 Wilbur et al.
2002/0098169 A1 7/2002 Smith
2002/0106337 A1 8/2002 Deckers et al.
2002/0114820 A1 8/2002 Deckers et al.
2002/0127252 A1 9/2002 Kramer et al.
2002/0136711 A1 9/2002 Cochran
2002/0146463 A1 10/2002 Clayton
2002/0155151 A1 10/2002 Enzmann et al.
2002/0156302 A1 10/2002 West
2002/0164317 A1 11/2002 Gorsek
2002/0182199 A1 12/2002 Hoppe et al.
2002/0198177 A1 12/2002 Horrobin
2003/0012762 A1 1/2003 Zulli et al.
2003/0012779 A1 1/2003 Grieb et al.
2003/0012825 A1 1/2003 Kapper
2003/0031688 A1 2/2003 Ghosh et al.
2003/0044441 A1 3/2003 Schmid et al.
2003/0077297 A1 4/2003 Chen et al.
2003/0077335 A1 4/2003 Richardson et al.
2003/0087331 A1 5/2003 Pettit et al.
2003/0091518 A1 5/2003 Pauly et al.
2003/0103954 A1 6/2003 Rosenbloom
2003/0104048 A1 6/2003 Patel et al.
2003/0104080 A1 6/2003 Singh et al.
2003/0105027 A1 6/2003 Rosenbloom
2003/0105030 A1 6/2003 Liao et al.
2003/0105031 A1 6/2003 Rosenbloom
2003/0108493 A1 6/2003 Henry et al.
2003/0113354 A1 6/2003 Schmid et al.
2003/0118525 A1 6/2003 Grigg
2003/0118536 A1 6/2003 Rosenbloom
2003/0118576 A1 6/2003 Brancato et al.
2003/0124158 A1 7/2003 Heidenfelder et al.
2003/0129150 A1 7/2003 Pauly et al.
2003/0138792 A1 7/2003 Schlegel et al.
2003/0143166 A1 7/2003 Heger et al.
2003/0144346 A1 7/2003 Liao et al.
2003/0152598 A1 8/2003 Heidenfelder et al.
2003/0161849 A1 8/2003 Heidenfelder et al.
2003/0167556 A1 9/2003 Kelley
2003/0170265 A1 9/2003 Henry et al.
2003/0180231 A1 9/2003 Danoux et al.
2003/0180278 A1 9/2003 Hoppe et al.
2003/0180352 A1 9/2003 Patel et al.
2003/0185865 A1 10/2003 Jentzsch et al.
2003/0207834 A1 11/2003 Dale et al.
2003/0212114 A1 11/2003 Sato
2003/0215406 A1 11/2003 Schreiner et al.
2003/0219472 A1 11/2003 Pauletti et al.
2003/0235812 A1 12/2003 Anderson et al.
2004/0028614 A1 2/2004 Corbella et al.
2004/0028668 A1 2/2004 Gaetani

(56) References Cited

U.S. PATENT DOCUMENTS

2004/0034107 A1 2/2004 Enzmann
2004/0043045 A1 3/2004 Seipel et al.
2004/0047896 A1 3/2004 Malnoe et al.
2004/0049022 A1 3/2004 Nyce et al.
2004/0063648 A1 4/2004 Pandol et al.
2004/0063661 A1 4/2004 Linnane
2004/0067260 A1 4/2004 Milley et al.
2004/0082522 A1 4/2004 Nyce
2004/0086538 A1 5/2004 Sauermann et al.
2004/0101874 A1 5/2004 Ghosh et al.
2004/0109880 A1 6/2004 Pauly et al.
2004/0110848 A1 6/2004 Peffley et al.
2004/0115181 A1 6/2004 Fujii et al.
2004/0122109 A1 6/2004 Fujii et al.
2004/0126367 A1 7/2004 Fujii et al.
2004/0133352 A1 7/2004 Bevilacqua et al.
2004/0142006 A1 7/2004 Bleckmann et al.
2004/0142007 A1 7/2004 Moussou et al.
2004/0142009 A1 7/2004 Ansmann et al.
2004/0151710 A1 8/2004 Bozzacco
2004/0151711 A1 8/2004 West
2004/0170560 A1 9/2004 Fossheim et al.
2004/0170581 A1 9/2004 Henry et al.
2004/0185071 A1 9/2004 Hatazaki
2004/0191190 A1 9/2004 Pauly et al.
2004/0191263 A1 9/2004 Hageman et al.
2004/0197279 A1 10/2004 Bleckmann et al.
2004/0197354 A1 10/2004 Doring et al.
2004/0202740 A1 10/2004 Tan
2004/0219114 A1 11/2004 Andersson et al.
2004/0228910 A1 11/2004 Enzmann et al.
2004/0234559 A1 11/2004 Bleckmann et al.
2004/0253323 A1 12/2004 Giles
2004/0258717 A1 12/2004 Sauermann et al.
2005/0000390 A1 1/2005 Nieendick et al.
2005/0008581 A1 1/2005 Parkhideh
2005/0019268 A1 1/2005 Enzmann
2005/0019278 A1 1/2005 Berg-Schultz
2005/0019353 A1 1/2005 Prinz et al.
2005/0025756 A1 2/2005 Erwin
2005/0026848 A1 2/2005 Robinson et al.
2005/0026850 A1 2/2005 Robinson et al.
2005/0036976 A1 2/2005 Rubin et al.
2005/0037036 A1 2/2005 Nielsen et al.
2005/0037102 A1 2/2005 Tan et al.
2005/0042678 A1 2/2005 Epstein et al.
2005/0043336 A1 2/2005 Hennequin et al.
2005/0058610 A1 3/2005 Baschong et al.
2005/0069582 A1 3/2005 Fantuzzi
2005/0070610 A1 3/2005 Fujii et al.
2005/0070611 A1 3/2005 Fantuzzi
2005/0079164 A1 4/2005 Fantuzzi et al.
2005/0100537 A1 5/2005 Evans et al.
2005/0106190 A1 5/2005 Kawa et al.
2005/0106199 A1 5/2005 Schreiber et al.
2005/0112156 A1 5/2005 Busch et al.
2005/0118151 A1 6/2005 Larsen et al.
2005/0118209 A1 6/2005 Jentszch et al.
2005/0136081 A1 6/2005 Kawa et al.
2005/0142123 A1 6/2005 Chen et al.
2005/0142153 A1 6/2005 Schreiber et al.
2005/0147598 A1 7/2005 Ueda et al.
2005/0148603 A1 7/2005 Jimenez et al.
2005/0152856 A2 7/2005 Andersson et al.
2005/0184275 A1 8/2005 Mora-Gutierrez et al.
2005/0202521 A1 9/2005 Crum
2005/0214333 A1 9/2005 Lanzendoerfer et al.
2005/0220726 A1 10/2005 Pauly et al.
2005/0220826 A1 10/2005 Kawa et al.
2005/0226824 A1 10/2005 Kawa et al.
2005/0226858 A1 10/2005 Kitamura et al.
2005/0226947 A1 10/2005 Kern
2005/0238679 A1 10/2005 Biergiesser et al.
2005/0239721 A1 10/2005 Rosenbloom
2005/0255057 A1 11/2005 Andre et al.
2005/0276764 A1 12/2005 Kolbe et al.
2005/0281772 A1 12/2005 Bromley et al.
2005/0287206 A1 12/2005 Fantuzzi et al.
2005/0288333 A1 12/2005 Kem
2005/0288378 A1 12/2005 Yan et al.
2006/0002911 A1 1/2006 Casteilla et al.
2006/0002964 A9 1/2006 Schreiber et al.
2006/0008482 A1 1/2006 Prinz et al.
2006/0010519 A1 1/2006 Kadowaki et al.
2006/0013888 A1 1/2006 Fantuzzi
2006/0035981 A1 2/2006 Mazzio et al.
2006/0039956 A1 2/2006 Hensen et al.
2006/0041017 A1 2/2006 Chopra
2006/0051462 A1 3/2006 Wang
2006/0052438 A1 3/2006 Ho et al.
2006/0057081 A1 3/2006 Boxrud
2006/0062755 A1 3/2006 Woodward
2006/0069068 A1 3/2006 Kajander et al.
2006/0073106 A1 4/2006 Berg-Schultz et al.
2006/0093633 A1 5/2006 Stab et al.
2006/0099158 A1 5/2006 Zander et al.
2006/0099244 A1 5/2006 Guilford
2006/0110415 A1 5/2006 Gupta
2006/0120997 A1 6/2006 Lipton
2006/0121016 A1 6/2006 Lee
2006/0127384 A1 6/2006 Capaccioli et al.
2006/0127928 A1 6/2006 Bacus et al.
2006/0128643 A1 6/2006 Kaddurah-Daouk et al.
2006/0153783 A1 7/2006 Ehlis et al.
2006/0188459 A1 8/2006 Heinrichs et al.
2006/0188492 A1 8/2006 Richardson et al.
2006/0193905 A1 8/2006 Ehringer et al.
2006/0205771 A1 9/2006 Noble et al.
2006/0251690 A1 11/2006 Lipshutz et al.
2006/0251708 A1 11/2006 Chen et al.
2006/0252042 A1 11/2006 Molero
2006/0286046 A1 12/2006 Haber
2006/0292220 A1 12/2006 Giordano et al.
2007/0021360 A1 1/2007 Nyce et al.
2007/0026072 A1 2/2007 Olsen et al.
2007/0053985 A1 3/2007 Ueda et al.
2007/0054282 A1 3/2007 Liew
2007/0071779 A1 3/2007 McKie
2007/0085059 A1 4/2007 Mora-Gutierrez et al.
2007/0092469 A1 4/2007 Jacobs
2007/0104701 A1 5/2007 Ueda et al.
2007/0104810 A1 5/2007 Kern
2007/0110731 A1 5/2007 Riley
2007/0129428 A1 6/2007 Richelle et al.
2007/0149618 A1 6/2007 Cuevas Sanchez et al.
2007/0160685 A1 7/2007 Knox et al.
2007/0172436 A1 7/2007 Zhang
2007/0184041 A1 8/2007 Burja
2007/0184076 A1 8/2007 Unger et al.
2007/0189994 A1 8/2007 Berg et al.
2007/0196349 A1 8/2007 Kitamura et al.
2007/0196914 A1 8/2007 Murray et al.
2007/0202090 A1 8/2007 Prosek et al.
2007/0202496 A1 8/2007 Beretta
2007/0203091 A1 8/2007 Rapaport
2007/0218042 A1 9/2007 Khaled
2007/0225255 A1 9/2007 Frohlich et al.
2007/0243180 A1 10/2007 Tanaka et al.
2007/0248590 A1 10/2007 Milne et al.
2007/0248693 A1 10/2007 Mazzio et al.
2007/0253941 A1 11/2007 Naidu et al.
2007/0258966 A1 11/2007 Ueda et al.
2007/0258967 A1 11/2007 Ueda et al.
2007/0259009 A1 11/2007 Linder
2007/0275021 A1 11/2007 Lee et al.
2008/0014187 A1 1/2008 Villeponteau
2008/0020018 A1 1/2008 Moodley et al.
2008/0020022 A1 1/2008 Udell
2008/0025929 A1 1/2008 Burton et al.
2008/0031862 A1 2/2008 Ghosal
2008/0038736 A1 2/2008 Llovet et al.
2008/0057116 A1 3/2008 Pleva
2008/0063674 A1 3/2008 Vollhardt et al.
2008/0069779 A1 3/2008 Tamarkin et al.

(56) References Cited

U.S. PATENT DOCUMENTS

| | | | |
|---|---|---|---|
| 2008/0069898 | A1 | 3/2008 | Smith et al. |
| 2008/0075684 | A1 | 3/2008 | Barg et al. |
| 2008/0081034 | A1 | 4/2008 | Zimmerman et al. |
| 2008/0081082 | A1 | 4/2008 | Zimmerman et al. |
| 2008/0089852 | A1 | 4/2008 | Hotz et al. |
| 2008/0089913 | A1 | 4/2008 | Kallmayer et al. |
| 2008/0095719 | A1 | 4/2008 | Herrmann et al. |
| 2008/0102313 | A1 | 5/2008 | Nilsen et al. |
| 2008/0103104 | A1 | 5/2008 | Moore et al. |
| 2008/0138326 | A1 | 6/2008 | Fujii et al. |
| 2008/0233183 | A1 | 9/2008 | McCook et al. |
| 2008/0260878 | A1 | 10/2008 | Harano et al. |
| 2008/0287541 | A1 | 11/2008 | Hoffman et al. |
| 2008/0299100 | A1 | 12/2008 | Hsia et al. |
| 2009/0005398 | A1 | 1/2009 | Dar |
| 2009/0010917 | A1 | 1/2009 | Rosenblum et al. |
| 2009/0036516 | A1 | 2/2009 | Scherrer et al. |
| 2009/0060891 | A1 | 3/2009 | Harris et al. |
| 2009/0068281 | A1 | 3/2009 | Toyomura et al. |
| 2009/0137556 | A1 | 5/2009 | Bonnichsen |
| 2009/0280987 | A1 | 11/2009 | Strobel |
| 2010/0062048 | A1 | 3/2010 | Hsia et al. |
| 2010/0150894 | A1 | 6/2010 | Wakabayashi et al. |
| 2010/0209388 | A1 | 8/2010 | Mazzio et al. |
| 2010/0209497 | A1 | 8/2010 | Thornthwaite |
| 2010/0239652 | A1 | 9/2010 | Rochlitz et al. |
| 2011/0020312 | A1 | 1/2011 | Narain et al. |
| 2011/0027247 | A1 | 2/2011 | Narain et al. |
| 2011/0064747 | A1 | 3/2011 | Sarangarajan et al. |
| 2011/0123550 | A1 | 5/2011 | Shibayama et al. |
| 2011/0123986 | A1 | 5/2011 | Narain et al. |
| 2011/0129503 | A1 | 6/2011 | Strober et al. |
| 2011/0136231 | A1 | 6/2011 | Narain et al. |
| 2011/0229554 | A1 | 9/2011 | Narain et al. |
| 2012/0164215 | A1 | 6/2012 | Hsia et al. |
| 2012/0183621 | A1 | 7/2012 | Sinko et al. |
| 2012/0201801 | A1 | 8/2012 | Hsia et al. |
| 2012/0269867 | A1 | 10/2012 | Jimenez et al. |
| 2012/0309086 | A1 | 12/2012 | Narain et al. |
| 2013/0203853 | A1 | 8/2013 | Jacobson |
| 2014/0017317 | A1 | 1/2014 | Narain et al. |
| 2014/0255372 | A1 | 9/2014 | Hsia et al. |
| 2015/0023940 | A1 | 1/2015 | Narain et al. |
| 2016/0145693 | A1 | 5/2016 | Narain et al. |
| 2017/0137879 | A1 | 5/2017 | Narain et al. |
| 2017/0189350 | A1 | 7/2017 | Narain et al. |
| 2017/0216223 | A1 | 8/2017 | Narain et al. |
| 2018/0021270 | A1 | 1/2018 | Nastke et al. |
| 2018/0334721 | A1 | 11/2018 | Narain et al. |
| 2018/0353425 | A1 | 12/2018 | Narain et al. |
| 2019/0010554 | A1 | 1/2019 | Narain et al. |
| 2020/0009377 | A1 | 1/2020 | Chang et al. |
| 2020/0078320 | A1 | 3/2020 | Jimenez et al. |
| 2020/0138744 | A1 | 5/2020 | Sarangarajan et al. |
| 2021/0002725 | A1 | 1/2021 | Narain et al. |
| 2021/0128453 | A1 | 5/2021 | Hsia et al. |
| 2021/0322339 | A1 | 10/2021 | Narain et al. |
| 2021/0332439 | A1 | 10/2021 | Narain et al. |
| 2022/0081720 | A1 | 3/2022 | Narain et al. |
| 2022/0096399 | A1 | 3/2022 | Narain et al. |
| 2022/0096400 | A1 | 3/2022 | Nastke et al. |
| 2022/0202741 | A1 | 6/2022 | Narain et al. |
| 2023/0149292 | A1 | 5/2023 | Hsia et al. |
| 2023/0285272 | A1 | 9/2023 | Narain et al. |
| 2026/0034073 | A1 | 2/2026 | Narain et al. |

FOREIGN PATENT DOCUMENTS

| | | | |
|---|---|---|---|
| CA | 2680825 | A1 | 9/2008 |
| CA | 2772068 | A1 | 3/2011 |
| CA | 2791693 | A1 | 9/2011 |
| CN | 1535605 | A | 10/2004 |
| CN | 1853507 | A | 11/2006 |
| CN | 1928556 | A | 3/2007 |
| CN | 1953743 | A | 4/2007 |
| CN | 101099084 | A | 1/2008 |
| CN | 101102768 | A | 1/2008 |
| CN | 101365806 | A | 2/2009 |
| CN | 102481269 | A | 5/2012 |
| DE | 4327063 | A1 | 2/1995 |
| EA | 201001624 | A1 | 6/2011 |
| EP | 1473043 | A1 | 11/2004 |
| EP | 1493437 | A1 | 1/2005 |
| EP | 1908459 | A1 | 4/2008 |
| EP | 2028492 | A1 | 2/2009 |
| EP | 2371362 | A1 | 10/2011 |
| EP | 2371363 | A1 | 10/2011 |
| EP | 2429512 | A2 | 3/2012 |
| EP | 2854528 | A1 | 4/2015 |
| JP | S57-075916 | A | 5/1982 |
| JP | S62-123113 | A | 6/1987 |
| JP | H01-143826 | A | 6/1989 |
| JP | H02-273619 | A | 11/1990 |
| JP | 2004-345988 | A | 12/2004 |
| JP | 2005-323573 | A | 11/2005 |
| JP | 2007-001922 | A | 1/2007 |
| JP | 2007-176804 | A | 7/2007 |
| JP | 2007-518805 | A | 7/2007 |
| JP | 2009-050168 | A | 3/2009 |
| JP | 2009-096757 | A | 5/2009 |
| JP | 2015-515272 | A | 5/2015 |
| JP | 2015-151900 | A | 8/2015 |
| JP | 2018-109093 | A | 7/2018 |
| JP | 2018-168164 | A | 11/2018 |
| KR | 10-2005-0112942 | A | 12/2005 |
| RU | 2307666 | C2 | 10/2007 |
| RU | 2345367 | | 1/2009 |
| WO | WO-1988/04173 | A1 | 6/1988 |
| WO | WO-1993/016704 | A1 | 9/1993 |
| WO | WO-1994/11547 | A1 | 5/1994 |
| WO | WO-1995/05164 | A1 | 2/1995 |
| WO | WO-1995/10271 | A2 | 4/1995 |
| WO | WO-1996/017626 | A2 | 6/1996 |
| WO | WO-1998/35660 | A1 | 8/1998 |
| WO | WO-1999/11242 | A1 | 3/1999 |
| WO | WO-1999/65469 | A2 | 12/1999 |
| WO | WO-2000/007607 | A1 | 2/2000 |
| WO | WO-2002/40012 | A1 | 5/2002 |
| WO | WO-2002/060484 | A1 | 8/2002 |
| WO | WO-2002/062329 | A1 | 8/2002 |
| WO | WO-2002/062338 | A1 | 8/2002 |
| WO | WO-2002/078727 | A1 | 10/2002 |
| WO | WO-2002/085297 | A2 | 10/2002 |
| WO | WO-2003/008405 | A1 | 1/2003 |
| WO | WO-2003/077895 | A1 | 9/2003 |
| WO | WO-2003/078456 | A2 | 9/2003 |
| WO | WO-2004/003564 | A2 | 1/2004 |
| WO | WO-2004/059293 | A2 | 7/2004 |
| WO | WO-2004/060316 | A2 | 7/2004 |
| WO | WO-2005/055738 | A1 | 6/2005 |
| WO | WO-2005/069916 | A2 | 8/2005 |
| WO | WO-2006/017494 | A2 | 2/2006 |
| WO | WO-2006/063402 | A1 | 6/2006 |
| WO | WO-2007/039184 | A2 | 4/2007 |
| WO | WO-2007/095186 | A2 | 8/2007 |
| WO | WO-2007/131047 | A2 | 11/2007 |
| WO | WO-2008/049330 | A1 | 5/2008 |
| WO | WO-2008/116135 | A2 | 9/2008 |
| WO | WO-2008/156654 | A2 | 12/2008 |
| WO | WO-2009/005215 | A1 | 1/2009 |
| WO | WO-2009/006366 | A2 | 1/2009 |
| WO | WO-2009/012718 | A1 | 1/2009 |
| WO | WO-2009/014639 | A2 | 1/2009 |
| WO | WO-2009/073843 | A1 | 6/2009 |
| WO | WO-2009/126764 | A1 | 10/2009 |
| WO | WO-2010/065601 | A1 | 6/2010 |
| WO | WO-2010/132440 | A2 | 11/2010 |
| WO | WO-2010/132507 | A2 | 11/2010 |
| WO | WO-2011/031503 | A2 | 3/2011 |
| WO | WO-2011/112900 | A2 | 9/2011 |
| WO | WO-2012/012347 | A2 | 1/2012 |
| WO | WO-2012/138765 | A1 | 10/2012 |
| WO | WO-2013/181639 | A1 | 12/2013 |
| WO | WO-2014/168993 | A1 | 10/2014 |

(56) References Cited

FOREIGN PATENT DOCUMENTS

| | | | |
|---|---|---|---|
| WO | WO-2015/035094 A1 | 3/2015 | |
| WO | WO-2016/054574 A1 | 4/2016 | |
| WO | WO-2016/062722 A1 | 4/2016 | |
| WO | WO-2016/094639 A1 | 6/2016 | |
| WO | 2017/087576 A1 | 5/2017 | |

OTHER PUBLICATIONS

U.S. Appl. No. 16/900,162, filed Jun. 12, 2020, 2021-0128453, Published.
U.S. Appl. No. 13/439,615, filed Apr. 4, 2012, 2012-0269867, Abandoned.
U.S. Appl. No. 15/376,243, filed Dec. 12, 2016, U.S. Pat. No. 10,373,477, Issued.
U.S. Appl. No. 16/444,296, filed Jun. 18, 2019, 2020-0078320, Published.
U.S. Appl. No. 14/248,313, filed Apr. 8, 2014, 2014-0302014, Published.
U.S. Appl. No. 13/9077,726, filed May 31, 2013, 2014-0017317, Abandoned.
U.S. Appl. No. 15/289,770, filed Oct. 10, 2016, 2017-0216223, Abandoned.
U.S. Appl. No. 17/321,699, filed May 17, 2021, Pending.
U.S. Appl. No. 14/477,828, filed Sep. 4, 2014, U.S. Pat. No. 9,901,542, Issued.
U.S. Appl. No. 15/869,630, filed Jan. 12, 2018, 2018-0353425, Published.
U.S. Appl. No. 15/656,986, filed Jul. 21, 2017, 2018-0021270, Published.
U.S. Appl. No. 17/376,357, filed Jul. 15, 2021, Pending.
U.S. Appl. No. 15/353,724, filed Nov. 16, 2016, 2017-0189350, Published.
U.S. Appl. No. 16/653,787, filed Oct. 15, 2019, 2020-0138744, Published.
U.S. Appl. No. 12/778,094, filed May 11, 2010, 2011-0027247, Abandoned.
U.S. Appl. No. 14/171,419, filed Feb. 3, 2014, U.S. Pat. No. 9,896,731, Issued.
U.S. Appl. No. 15/862,856, filed Jan. 5, 2018, U.S. Pat. No. 10,351,915, Issued.
U.S. Appl. No. 16/421,788, filed May 24, 2019, U.S. Pat. No. 11,028,446, Issued.
U.S. Appl. No. 17/232,795, filed Apr. 16, 2021, Pending.
U.S. Appl. No. 12/777,902, filed May 11, 2010, U.S. Pat. No. 10,519,504, Issued.
U.S. Appl. No. 12/778,029, filed May 11, 2010, U.S. Pat. No. 9,205,064, Issued.
U.S. Appl. No. 14/940,614, filed Nov. 13, 2015, 2016-0145693, Abandoned.
U.S. Appl. No. 15/841,972, filed Dec. 14, 2017, 2018-0334721, Abandoned.
U.S. Appl. No. 16/819,811, filed Mar. 19, 2020, Pending.
U.S. Appl. No. 12/778,054, filed May 11, 2010, 2011-0020312, Abandoned.
U.S. Appl. No. 12/778,010, filed May 11, 2010, 2011-0123986, Abandoned.
U.S. Appl. No. 15/011,196, filed Jan. 29, 2016, 2017-0137879, Abandoned.
U.S. Appl. No. 15/837,505, filed Dec. 11, 2017, 2019-0010554, Abandoned.
U.S. Appl. No. 16/456,257, filed Jun. 28, 2019, Abandoned.
U.S. Appl. No. 16/805,557, filed Feb. 28, 2020, 2021-0002725, Published.
U.S. Appl. No. 10/597,378 8,147,825 filed Aug. 21, 2008, U.S. Pat. No. 8,147,825, Issued.
U.S. Appl. No. 16/900,162, filed Jun. 12, 2020, 2021-0128453, Abandoned.
U.S. Appl. No. 17/712,326, filed Apr. 4, 2022, 2023-0149292, Published.
U.S. Appl. No. 14/248,313, filed Apr. 8, 2014, U.S. Pat. No. 10,933,032, Issued.
U.S. Appl. No. 17/321,699, filed May 17, 2021, 2022-0096399, Published.
U.S. Appl. No. 15/869,630, filed Jan. 12, 2018, U.S. Pat. No. 11,298,313, Issued.
U.S. Appl. No. 17/686,569, filed Mar. 4, 2022, Abandoned.
U.S. Appl. No. 17/962,608, filed Oct. 10, 2022, 2023-0285272, Published.
U.S. Appl. No. 15/656,986, filed Jul. 21, 2017, 2018-0021270, Abandoned.
U.S. Appl. No. 17/376,357, filed Jul. 15, 2021, 2022-0096400, Published.
U.S. Appl. No. 15/353,724, filed Nov. 16, 2016, 2017-0189350, Abandoned.
U.S. Appl. No. 17/572,092, filed Jan. 10, 2022, 2022-0202741, Published.
U.S. Appl. No. 17/100,674, filed Nov. 20, 2020, 2021-0322339, Published.
U.S. Appl. No. 16/819,811, filed Mar. 19, 2020, 2021-0332439, Abandoned.
U.S. Appl. No. 16/805,557, filed Feb. 28, 2020, 2021-0002725, Abandoned.
Abe et al., Effect of coenzyme Q10 in patients with mitochondrial myopathy, encephalopathy, lactic acidosis, and stroke-like episodes (MELAS): evaluation by noninvasive tissue oximetry. J Neurol Sci. Jan. 1, 1999;162(1):65-8.
Abe et al., Marked reduction in CSF lactate and pyruvate levels after CoQ therapy in a patient with mitochondrial myopathy, encephalopathy, lactic acidosis and stroke-like episodes (MELAS). Acta Neurol Scand. Jun. 1991;83(6):356-9.
Aizawa, Morphology of polysorbate 80 (Tween 80) micelles in aqueous dimethyl sulfoxide solutions. J Appl Crystallogr. Jun. 1, 2010;43(Pt 3):630-631.
American Cancer Society, Brain and Spinal Cord Tumors in Adults. Retrieved online at: http://www.cancer.org/cancer/braincnstumorsinadults/detailedguide/brain-and-spinal-cord-tumors-in-adults-what-are-brain-spinal-tumors. Nov. 12, 2009. 4 pages.
American Cancer Society, Colorectal Cancer. Retrieved online at: http:www.cancer.org/acs/groups/cid/documents/webcontent/003096-pdf.pdf. 122 pages, (2016).
Anderson et al., The transcriptional response to a peroxisome proliferator-activated receptor alpha agonist includes increased expression of proteome maintenance genes. J Biol Chem. Dec. 10, 2004;279(50):52390-8.
Ansell et al., Brain tumor signs and symptoms: analysis of primary health care records from the UKCCS. Pediatrics. Jan. 2010;125(1):112-9.
Antoneeva et al., Markers of Apoptosis and Proliferation of Tumor Cells in the Dynamic of Ovarian Cancer Progression. Oncologiya. 2008;10(2):234-237.
Aris et al., Noise filtering and nonparametric analysis of microarray data underscores discriminating markers of oral, prostate, lung, ovarian and breast cancer. BMC Bioinformatics. Nov. 29, 2004;5(185):1-9.
Barbiroli et al., Coenzyme Q10 improves mitochondrial respiration in patients with mitochondrial cytopathies. An in vivo study on brain and skeletal muscle by phosphorous magnetic resonance spectroscopy. Cell Mol Biol (Noisy-le-grand). Jul. 1997;43(5):741-9.
Bjarnason, Chronobiology. Implications for cancer chemotherapy. Acta Oncol. 1995;34(5):615-24.
Bliznakov et al., Coenzymes Q: stimulants of the phagocytic activity in rats and immune response in mice. Experientia. Sep. 26, 1970;26(9):953-4.
Bliznakov, Effect of stimulation of the host defense system by coenzyme Q 0 on dibenzpyrene-induced tumors and infection with Friend leukemia virus in mice. Proc Natl Acad Sci U S A. Feb. 1973;70(2):390-4.
Blom et al., The risk of a venous thrombotic event in lung cancer patients: higher risk for adenocarcinoma than squamous cell carcinoma. J Thromb Haemost. Oct. 2004;2(10):1760-5.

(56) References Cited

OTHER PUBLICATIONS

Bresolin et al., Clinical and biochemical correlations in mitochondrial myopathies treated with coenzyme Q10. Neurology. Jun. 1988;38(6):892-9.
Cancer.net, Brain Tumor: Symptoms and Signs. Retrieved online at: https://www.cancer.net/cancer-types/brain-tumor/symptoms-and-signs. 4 pages, (2005).
Cancer.net, Stages of Cancer. Doctor-Approved Patient Information from ASCO. Retrieved online at: https://www.cancer.net/navigating-cancer-care/diagnosing-cancer/stages-cancer. 4 pages, Mar. 2018.
Carmona et al., Coadministration of coenzyme Q prevents rosiglitazone-induced adipogenesis in ob/ob mice. Int J Obes (Lond). Feb. 2009;33(2):204-11.
Chan et al., Metabolic changes in patients with mitochondrial myopathies and effects of coenzyme Q10 therapy. J Neurol. Oct. 1998;245(10):681-5.
Chang et al., Patterns of resistance and incomplete response to docetaxel by gene expression profiling in breast cancer patients. J Clin Oncol. Feb. 20, 2005;23(6):1169-77.
Chen et al., Coenzyme Q10 treatment in mitochondrial encephalomyopathies. Short-term double-blind, crossover study. Eur Neurol. 1997;37(4):212-8.
Cheung et al., Novel markers of subclinical disease for Ewing family tumors from gene expression profiling. Clin Cancer Res. Dec. 1, 2007;13(23):6978-83.
Chew et al., Coenzyme Q10 and diabetic endotheliopathy: oxidative stress and the ‘recoupling hypothesis’. QJM. Aug. 2004;97(8):537-48.
Chop, Pediatric Leukemias. Children’s Hospital of Philadelphia, retrieved online at: https://www.chop.edu/conditions-diseases/pediatric-leukemias. 9 pages, (2021).
ClinicalTrials.gov, NCT01928394, A Study of Nivolumab by Itself or Nivolumab Combined With Ipilimumab in Patients With Advanced or Metastatic Solid Tumors. 9 pages, Oct. 4, 2019.
Colman et al., Hemostasis and Thrombosis. Basic Principles and Clinical Practice, 5th Edition, Lippincott Williams & Wilkins, p. 1161 (2006).
Colon cancer: Tests and diagnosis—MayoClinic.com. Retrieved online at: http://www.mayoclinic.com/health/colon-cancer/ds00035/dsection=tests-and-diagnosis. 3 pages, Aug. 13, 2011.
Conklin, Cancer chemotherapy and antioxidants. J Nutr. Nov. 2004;134(11):3201S-3204S.
Conklin, Coenzyme q10 for prevention of anthracycline-induced cardiotoxicity. Integr Cancer Ther. Jun. 2005;4(2):110-30.
Crane, New Functions for Coenzyme Q. Protoplasma. 2000;213:127-133.
Crawford et al., Multiplex standardized RT-PCR for expression analysis of many genes in small samples. Biochem Biophys Res Commun. Apr. 26, 2002;293(1):509-16.
De Oliveria, A Nutritious Cocktail for the Treatment of Melanoma: A Case Report. The Journal of Orthomolecular Medicine. 1998;13(3)13, 2 pages.
Deeb et al., Vitamin D signalling pathways in cancer: potential for anticancer therapeutics. Nat Rev Cancer. Sep. 2007;7(9):684-700.
Doi et al., The JAK/STAT pathway is involved in the upregulation of PD-L1 expression in pancreatic cancer cell lines. Oncol Rep. 2017;37(3):1545-1554.
Domae et al., Cardiomyopathy and other chronic toxic effects induced in rabbits by doxorubicin and possible prevention by coenzyme Q10. Cancer Treat Rep. Jan.-Feb. 1981;65(1-2):79-91.
Eisenhauer et al., New response evaluation criteria in solid tumours: Revised RECIST guideline (version 1.1). European Journal of Cancer. 2009;45:228-247.
Family Caregiver Alliance, Fact Sheet: Brain Tumor. Los Angeles Caregiver Resource Center. Retrieved online at: http://lacrc.usc.edu/forms/brain tumor.pdf. 12 pages (2004).
Fang et al., Expression of ectonucleotide pyrophosphatase/phosphodiesterase 1 in human ovary and its relationship with polycystic ovary syndrome. ACTA Anatomica Sinica. 2008;39(4):552-556.
Fernández-Ayala et al., Coenzyme Q protects cells against serum withdrawal-induced apoptosis by inhibition of ceramide release and caspase-3 activation. Antioxid Redox Signal. 2000 Summer;2(2):263-75.
Ferrara et al., Protective role of chronic ubiquinone administration on acute cardiac oxidative stress. J Pharmacol Exp Ther. Aug. 1995;274(2):858-65.
Folkers et al., Survival of cancer patients on therapy with coenzyme Q10. Biochem Biophys Res Commun. Apr. 15, 1993;192(1):241-5.
Folkers, Relevance of the biosynthesis of coenzyme Q10 and of the four bases of DNA as a rationale for the molecular causes of cancer and a therapy. Biochem Biophys Res Commun. Jul. 16, 1996;224(2):358-61.
Foulkes et al., Triple-negative breast cancer. N Engl J Med. Nov. 11, 2010;363(20):1938-48.
Friedman et al., Temozolomide and Treatment of Malignant Glioma. Clinical Cancer Research. Jul. 2000;6:2585-2597, plus supplemental material.
Gaby, The Role of Coenzyme Q10 in Clinical Medicine: Part I. Alt Med Rev. 1996;1:11-17.
Galili et al., Clinical response of myelodysplastic syndromes patients to treatment with coenzyme Q10. Leuk Res. Jan. 2007;31(1):19-26.
Gao et al., Effects of coenzyme Q10 on vascular endothelial function in humans: a meta-analysis of randomized controlled trials. Atherosclerosis. Apr. 2012;221(2):311-6.
Garrel et al., The diagnostic accuracy of reverse transcription-PCR quantification of cytokeratin mRNA in the detection of sentinel lymph node invasion in oral and oropharyngeal squamous cell carcinoma: a comparison with immunohistochemistry. Clin Cancer Res. Apr. 15, 2006;12(8):2498-505.
Gersten, Brain Cancer Overview. The New York Times. Retrieved online at: http://health.nytimes.com/health/guides/disease/brain-tumor-adults. 3 pages.
Gillet et al., Mechanisms of Multidrug Resistance in Cancer. Multi-Drug Resistance in Cancer, Methods in Molecular Biology, vol. 596, J. Zhou (Ed.). Humana Press. Chapter 4, pp. 47-76, (2010).
Gogvadze et al., Mitochondria as targets for chemotherapy. Apoptosis. Apr. 2009;14(4):624-40.
Golay et al., Link between obesity and type 2 diabetes. Best Pract Res Clin Endocrinol Metab. Dec. 2005;19(4):649-63.
Gorelick et al., Coenzyme Q10 and lipid-related gene induction in Hela cells. Am J Obstet Gynecol. May 2004;190(5):1432-4.
Groneberg et al., Coenzyme Q10 affects expression of genes involved in cell signaling, metabolism and transport in human CaCo-2 cells. The International Journal of Biochemistry and Cell Biology. 2005;37:1208-1218.
Haider et al., Effects of etanercept are distinct from infliximab in modulating proinflammatory genes in activated human leukocytes. J Investig Dermatol Symp Proc. May 2007;12(1):9-15.
Happold et al., Distinct molecular mechanisms of acquired resistance to temozolomide in glioblastoma cells. J Neurochem. Jul. 2012;122(2):444-55.
Higdon et al., Obesity and oxidative stress: a direct link to CVD? Arterioscler Thromb Vasc Biol. Mar. 1, 2003;23(3):365-7.
Hill et al., Pharmacokinetics of drug infusions. Continuing Education in Anaesthesia. 2004. 4(3):76-80.
Hodges et al., CoQ10: could it have a role in cancer management? Biofactors. 1999;9(2-4):365-70.
Hodgson et al., Coenzyme Q10 improves blood pressure and glycaemic control: a controlled trial in subjects with type 2 diabetes. Eur J Clin Nutr. Nov. 2002;56(11):1137-42.
Huang et al., Treatment of refractory recurrent malignant glioma with adoptive cellular immunotherapy: a case report. Critical Reviews in Oncology/Hematology. 2001;57:17-23.
Hudson et al., Characterization of potentially chemopreventive phenols in extracts of brown rice that inhibit the growth of human breast and colon cancer cells. Cancer Epidemiol Biomarkers Prev. Nov. 2000;9(11):1163-70.
Iarussi et al., Protective effect of coenzyme Q10 on anthracyclines cardiotoxicity: control study in children with acute lymphoblastic leukemia and non-Hodgkin lymphoma. Mol Aspects Med. 1994;15 Suppl:s207-12.

(56) References Cited

OTHER PUBLICATIONS

Izyumov, Programmed Death of Cells and Oxidative Stress Caused by Inhibitors of Mitochondrial Functions. (synopsis of Ph.D. thesis), Moscow, 2005, pp. 17-20: URL: <http://www.lib.ua.net/diss/cont/151000.html>>.
Johnson et al., Gene expression profiles differentiate between sterile SIRS and early sepsis. Ann Surg. Apr. 2007;245(4):611-21.
Judy et al., Coenzyme Q10 Facts or Fiction. Natural Products Insider. 3 pages. Oct. 22, 2007.
Kawase et al., Enhancing effect of coenzyme, Q10 on immunorestoration with *Mycobacterium bovis* BCG in tumor-bearing mice. Gan. Aug. 1978;69(4):493-7.
Khan et al., Prolongation of Survival of Mice Bearing Leukemia 1210; Treated with Adriamycin and Coenzyme Q10. Proceedings of the American Association for Cancer Research. 1990;31:388, Poster 2303.
Kokawa et al., Coenzyme Q10 in cancer chemotherapy—experimental studies on augmentation of the effects of masked compounds, especially in the combined chemotherapy with immunopotentiators. Gan To Kagaku Ryoho. Mar. 1983;10(3):768-74. (Abstract only).
Kunitomo et al., Beneficial effect of coenzyme Q10 on increased oxidative and nitrative stress and inflammation and individual metabolic components developing in a rat model of metabolic syndrome. J Pharmacol Sci. Jun. 2008;107(2):128-37.
Lamson et al., Antioxidants in cancer therapy; their actions and interactions with oncologic therapies. Altern Med Rev. Oct. 1999;4(5):304-29.
Langer et al., Protein expression profiling in esophageal adenocarcinoma patients indicates association of heat-shock protein 27 expression and chemotherapy response. Clin Cancer Res. Dec. 15, 2008;14(24):8279-87.
Langham et al., Increased renal gene transcription of protein kinase C-beta in human diabetic nephropathy: relationship to long-term glycaemic control. Diabetologia. Apr. 2008;51(4):668-74.
Langsjoen, Alleviating Congestive Heart Failure with Coenzyme Q10. LifeExtension. http://www.lef.org/. Feb. 2008. 7 pages.
Laohapensang et al., An Unusual Complication of EVAR, Spontaneous Rectus Sheath Hematoma: A Case Report. Ann Vasc Dis. 2009;2(2):122-5.
Larsson, Effects of isoprenoids on growth of normal human mammary epithelial cells and breast cancer cells in vitro. Anticancer Res. Jan.-Feb. 1994;14(1A):123-8.
Lassman, Molecular Biology of Gliomas. Current Neurology and Neuroscience Reports. 2004;4:228-233.
Li et al., Candidate genes responsible for human hepatocellular carcinoma identified from differentially expressed genes in hepatocarcinogenesis of the tree shrew (Tupaia belangeri chinesis). Hepatol Res. Jan. 2008;38(1):85-95.
Li et al., Protective Effect of Coenzyme Q10 against the Adverse Reaction of Mytomycin G in Mouse Liver. Acta Histochemica et Cytochemica. 1987;20(4):455-467.
Littman et al., Effect of Cholesterol-Free, Fat-Free Diet and Hypocholesteremic Agents on Growth of Transplantable Animal Tumors. Cancer Chemotherapy Reports. Jan.-Feb. 1966;50(1 and 2):25-45.
Lockwood et al., Apparent partial remission of breast cancer in 'high risk' patients supplemented with nutritional antioxidants, essential fatty acids and coenzyme Q10. Mol Aspects Med. 1994;15 Suppl:s231-40.
Lockwood et al., Partial and complete regression of breast cancer in patients in relation to dosage of coenzyme Q10. Biochem Biophys Res Commun. Mar. 30, 1994;199(3):1504-8.
Lockwood et al., Progress on therapy of breast cancer with vitamin Q10 and the regression of metastases. Biochem Biophys Res Commun. Jul. 6, 1995;212(1):172-7.
Mazoff, Bleeding Disorders & Hepatitis C. HCV Advocate, HCSP Fact Sheet. www.hcvadvocate.org. HCSP, Version 3, 5 pages. Dec. 2014.
Mazzio et al., Effects of enhancing mitochondrial oxidative phosphorylation with reducing equivalents and ubiquinone on 1-methyl-4-phenylpyridinium toxicity and complex I-IV damage in neuroblastoma cells. Biochem Pharmacol. Mar. 15, 2004;67(6):1167-84.
Merck Manual Japanese Edition, 17th ed., pp. 59-63 (2002).
Merlo et al., FOXP3 expression and overall survival in breast cancer. J Clin Oncol. Apr. 10, 2009;27(11):1746-52.
Miles et al., Coenzyme Q10 changes are associated with metabolic syndrome. Clin Chim Acta. Jun. 2004;344(1-2):173-9.
Modi et al., Effect of coenzyme Q10 on catalase activity and other antioxidant parameters in streptozotocin-induced diabetic rats. Biol Trace Elem Res. Jan. 2006;109(1):25-34.
Mohammed et al., Prognostic significance of vascular endothelial cell growth factors-A, -C and -D in breast cancer and their relationship with angio- and lymphangiogenesis. Br J Cancer. Apr. 10, 2007;96(7):1092-100.
Mousa, Antithrombotic Effects of Naturally Derived Products on Coagulation and Platelet Function. Anticoagulants, Antiplatelets, and Thrombolytics, 2nd Edition. Humana Press, 2010, Chapter 9, pp. 229-240.
Mura et al., Evaluation of transcutol as a clonazepam transdermal permeation enhancer from hydrophilic gel formulations. Eur J Pharm Sci. Feb. 2000;9(4):365-72.
Narain et al., API 31510 as a potential agent in management of CNS leukemia. Cancer Research. 2011;71 (Suppl 8), Abstract 1565. Proceedings: AACR 102nd Annual Meeting 2011.
Neidle, Cancer Drug Design and Discovery. Elsevier/Academic Press. p. 431, (2008).
Nih, National Cancer Institute, Continuous Infustion. Retrieved online at: https://www.cancer.gov/publications/dictionaries/cancer-terms/def/continuous-infusion. 1 page, (2020).
Nih, National Cancer Institute, Drugs Approved for Different Types of Cancer. 7 pages, Jan. 16, 2015.
Nissim, A Gentle Cancer Killer. University of Miami Medicine-Online. Retrieved online at: http://www6.miami.edu/ummedicine-magazine/fall2005/fstory4.html. 3 pages. 2005.
O'Driscoll et al., Feasibility and relevance of global expression profiling of gene transcripts in serum from breast cancer patients using whole genome microarrays and quantitative RT-PCR. Cancer Genomics Proteomics. Mar.-Apr. 2008;5(2):94-104.
Ohira et al., Expression profiling and characterization of 4200 genes cloned from primary neuroblastomas: identification of 305 genes differentially expressed between favorable and unfavorable subsets. Oncogene. Aug. 21, 2003;22(35):5525-36.
Okumura et al., Identification of biomarkers in ductal carcinoma in situ of the breast with microinvasion. BMC Cancer. Oct. 6, 2008;8:287.
Olopade et al., Overexpression of BCL-x protein in primary breast cancer is associated with high tumor grade and nodal metastases. Cancer J Sci Am. Jul.-Aug. 1997;3(4):230-7.
Olson, Karl August Folkers (1906-1997). American Society for Nutritional Sciences, J. Nutr. 2001;131:2227-2230.
Palan et al., Plasma concentrations of coenzyme Q10 and tocopherols in cervical intraepithelial neoplasia and cervical cancer. Eur J Cancer Prev. Aug. 2003;12(4):321-6.
Panwar et al., Preparation, characterization, and in vitro release study of albendazole-encapsulated nanosize liposomes. Int J Nanomedicine. Mar. 9, 2010;5:101-8.
Peddinghaus et al., Evaluation of the Usage Pattern and Safety Profile of a Frozen Plasma Transfusion Protocol. Transfusion. 2009;49:159A, Abstract SP285.
Persaud et al., Apoptotic affect of Ubiquinone precursors in melanoma. Cancer Research. Cellular and Molecular Biology. AACR Annual Meeting. 2 pages. Abstract 3281. May 1, 2009.
Perumal et al., Combined efficacy of tamoxifen and coenzyme Q10 on the status of lipid peroxidation and antioxidants in DMBA induced breast cancer. Mol Cell Biochem. May 2005;273(1-2):151-60.
Perumal et al., Therapeutic effect of tamoxifen and energy-modulating vitamins on carbohydrate-metabolizing enzymes in breast cancer. Cancer Chemother Pharmacol. 2005 ul;56(1):105-14.
Pfaffl et al., Real-time RT-PCR quantification of insulin-like growth factor (IGF)-1, IGF-1 receptor, IGF-2, IGF-2 receptor, insulin

(56) References Cited

OTHER PUBLICATIONS receptor, growth hormone receptor, IGF-binding proteins 1, 2 and 3 in the bovine species. Domest Anim Endocrinol. Apr. 2002;22(2):91-102.
Pravst et al., Coenzyme Q10 contents in foods and fortification strategies. Crit Rev Food Sci Nutr. Apr. 2010;50(4):269-80.
Prostate-Specific Antigen (PSA) Test. Retrieved online at: http://www.cancer.gov/cancertopics/factsheet/detection/PSA. Mar. 18, 2009.
Rastogi, Analytical control of preservative labelling on skin creams. Contact Dermatitis. Dec. 2000;43(6):339-43. (Abstract only).
Riethdorf et al., Differential expression of CD66a (BGP), a cell adhesion molecule of the carcinoembryonic antigen family, in benign, premalignant, and malignant lesions of the human mammary gland. J Histochem Cytochem. Jul. 1997;45(7):957-63.
Roffe et al., Efficacy of coenzyme Q10 for improved tolerability of cancer treatments: a systematic review. J Clin Oncol. Nov. 1, 2004;22(21):4418-24.
Rydberg et al., Toll-like receptor agonists induce inflammation and cell death in a model of head and neck squamous cell carcinomas. Immunology. Sep. 2009;128(1 Suppl):e600-11.
Sander et al., Vesicle associated membrane protein (VAMP)-7 and VAMP-8, but not VAMP-2 or VAMP-3, are required for activation-induced degranulation of mature human mast cells. Eur J Immunol. Mar. 2008;38(3):855-63.
Scambia et al., Cathepsin D and epidermal growth factor in human breast cyst fluid. Br J Cancer. Nov. 1991;64(5):965-7.
Scotton et al., Analysis of CC chemokine and chemokine receptor expression in solid ovarian tumours. Br J Cancer. Sep. 14, 2001;85(6):891-7.
Seifried et al., The antioxidant conundrum in cancer. Cancer Res. Aug. 1, 2003;63(15):4295-8.
Shaoqiong et al., Related gene expressions in anti-keratinocyte aging induced by Ganoderma lucidum polysaccharides. J of Medical Colleges of PLA. 2008;23:167-175.
Shekelle et al., Effect of the supplemental use of antioxidants vitamin C, vitamin E, and coenzyme Q10 for the prevention and treatment of cancer. Evid Rep Technol Assess (Summ). Oct. 2003;(75):1-3.
Shen et al., Bioactive Components from the Mycelium of Antrodia salmonea. Journal of the Chinese Chemical Society. 2008;55:854-857.
Sheng et al., The efficacy of combining antiangiogenic agents with chemotherapy for patients with advanced non-small cell lung cancer who failed first-line chemotherapy: a systematic review and meta-analysis. PLoS One. Jun. 2, 2015;10(6):e0127306.
Shimada et al., Effect of high dose of pyridoxine on mammary tumorigenesis. Nutr Cancer. 2005;53(2):202-7.
Shimizu, Paclitaxel Pirarubicin Weekly. Japan J. Cancer and Chemotherapy, Jan. 2003;30:105-109.
Sieben et al., Differential Gene Expressionin Ovarian Tumors Reveals Dusp 4 and Serpina 5 As Key Regulators for Benign Behavior of Serous Borderline Tumors. J Clinical Oncology. Oct. 1, 2005;23(29):7275-7264.
Small Cell Lung Cancer Treatment (PDQ®)—National Cancer Institute. Retrieved online at: http://www.cancer.gov/cancertopics/pdq/treatment/small-cell-lung/healthprofessional. Jan. 20, 2012.
Soule et al., A human cell line from a pleural effusion derived from a breast carcinoma. J Natl Cancer Inst. Nov. 1973;51(5):1409-16.
Stafford et al., Meningioma radiosurgery: tumor control, outcomes, and complications among 190 consecutive patients. Neurosurgery. Nov. 2001;49(5):1029-37.
The National Cancer Institute, Coenzyme Q10 (PDQ.RTM.) Patient Version. Retrieved online at: http://www.cancer.gov/cancertopics/pdq/cam/coenzymeQ10/patient/allpages. 13 pages, Jul. 10, 2009.
Thibault et al., Phase I Study of Lovastatin, an Inhibitor of the Mevalonate Pathway, in Patients with Cancer. Clinical Cancer Research. Mar. 1996;2:483-491.
Tockman et al., Considerations in bringing a cancer biomarker to clinical application. Cancer Res. May 1, 1992;52(9 Suppl):2711s-2718s.
Todaro et al., Apoptosis resistance in epithelial tumors is mediated by tumor-cell-derived interleukin-4. Cell Death Differ. Apr. 2008;15(4):762-72.
Tsubaki et al., [Investigation of the preventive effect of CoQ10 against the side-effects of anthracycline antineoplastic agents]. Gan To Kagaku Ryoho. Jul. 1984;11(7):1420-7.
Tsuneki et al., Coenzyme Q10 prevents high glucose-induced oxidative stress in human umbilical vein endothelial cells. Eur J Pharmacol. Jul. 2, 2007;566(1-3):1-10.
UT Health Cancer Center, Clinical trial to study the safety and efficacy of MBG453 given alone and in combination with PDR001 in adults with advanced cancer. Retrieved online at: http://www.uthscsa.edu/pateint-care/ctrc/clinical-trial/HSC20150730HU. 3 pages, Jul. 30, 2015.
Verhoeff et al., Bevacizumab and dose-intense temozolomide in recurrent high-grade glioma. Ann Oncol. Aug. 2010;21(8):1723-7.
Vermeer, Vitamin K: the effect on health beyond coagulation—an overview. Food & Nutrition Research. 2012;56(5329):1-6.
Women's Health Update: Coenzyme Q10 and Breast Cancer. Retrieved online at: http://www.encognitive.com/node/13574 on Dec. 26, 2012. 4 pages.
Yagasaki et al., Clinical significance of E-cadherin and vimentin co-expression in breast cancer. Int J Oncol. Oct. 1996;9(4):755-61.
Yang et al., Efficiency Observations of 116 cases on Coenzyme Q10 as an Auxiliary Therapy for Treating Diabetes Combined with Coronary Heart Disease. Journal of Chinese Physician. Oct. 2002;4(10):1148-1149.
Yunis et al., Human pancreatic carcinoma (MIA PaCa-2) in continuous culture: sensitivity to asparaginase. Int J Cancer. Jan. 1977;19(1):128-35.
Zhang et al., Preparation and Physico-chemical Property of Coenzyme Q10 Submicroemulsion. China Pharmacy. 2007;18(19):1476-1478.
Zhao et al., The Clinical Application of Coenzyme Q10. Shandong Medical Journal. Jan. 31, 1996;36(1):52.
Zucher et al., Liposome drugs' loading efficiency: a working model based on loading conditions and drug's physicochemical properties. J Control Release. Oct. 1, 2009;139(1):73-80.
Adeberg et al., Radiotherapy plus concomitant temozolomide in primary gliosarcoma. J Neurooncol. Jun. 2016;128(2):341-8.
Buric et al., Modulation of Antioxidant Potential with Coenzyme Q10 Suppressed Invasion of Temozolomide-Resistant Rat Glioma In Vitro and In Vivo. Oxid Med Cell Longev. Mar. 12, 2019;2019:3061607, 14 pages.
Cabrera et al., Radiation therapy for glioblastoma: Executive summary of an American Society for Radiation Oncology Evidence-Based Clinical Practice Guideline. Pract Radiat Oncol. Jul.-Aug. 2016;6(4):217-225.
ClinicalTrials.gov, BPM31510 Administered Intravenously With Gemcitabine in Advanced Pancreatic Cancer Patients. NCT02650804, 9 pages, Sep. 16, 2020.
Frontinan-Rubio et al., Regulation of the oxidative balance with coenzyme Q10 sensitizes human glioblastoma cells to radiation and temozolomide. Radiother Oncol. Aug. 2018;128(2):236-244.
Gesta et al., BPM31510, a clinical stage metabolic modulator demonstrates therapeutic efficacy in an in vivo C6 rat glioma model and synergizes with temozolomide. Cancer Research. Jul. 2017;77(Suppl. 13):Abstract 4067.
Hertz et al., Improved survival in patients with end-stage cancer treated with coenzyme Q(10) and other antioxidants: a pilot study. J Int Med Res. Nov.-Dec. 2009;37(6):1961-71.
Liao et al., The compounding effects of coenzyme q10 and radiation treatment on glial fibrillary acidic protein network of glioma in vitro. AACR Annual Meeting. Oncodevelopment Biology and Medicine. Abstract 2931, Jul. 2019.
Liu et al., The compounding effects of coenzyme q10 and radiation treatment on glial fibrillary acidic protein network of glioma in vitro. Cancer Res. 2019;79(13 Suppl):2931. 4 pages.
Marin et al., Overview of the molecular bases of resistance to chemotherapy in liver and gastrointestinal tumours. Curr Mol Med. Dec. 2009;9(9):1108-29.
Narain et al., Effect of pretreatment, dose and route of administration of BPM31510 (Coenxyme Q10 containing proprietry formu-

(56) References Cited

OTHER PUBLICATIONS lation) alone or in combination with gemcitabine improves survival in pancreatic cancer. Cancer Res. 2014;74(19 Suppl.):Abstract 4321.
NatMed Pro, Vitamin K1 vs K2: what you should know. Retrieved online at: https://naturalmedicines.therapeuticresearch.com/news/news-items/2019/may/vitamin-k1-vs-k2-what-you-should-know.aspx. 1 page, May 2019.
Ohanian et al., Is acute myeloid leukemia a liquid tumor? Int J Cancer. Aug. 1, 2013;133(3):534-43.
Recht et al., A Phase 1 Study of BPM31510 Plus Vitamin K in Subjects wtih High-grade Glioma that has Recurred on a Bevacizumab-containing Regimen. Neuro-Oncology. Nov. 2019;21(Suppl. 6):vi27, Abstract ACTR-59.
Sun et al., BPM31510 exploits differential redox vulnerabilities between normal and glioblastoma cells to mediate its anti-cancer effect. Molecular and Cellular Biology/Genetics. Abstract 3608, Jul. 1, 2019.
Sun et al., BPM31510, a Coenzyme Q10 (CoQ10) containing lipid nanodispersion, enhances radiation effects to prolong survival in a rodent glioblastoma model. Cancer Res. 80(16 Suppl):2968, 2 pages.
Zhipeng et al., Toxicity of coenzyme Q(10): a report of 90-day repeated dose toxicity study in rats. J Toxicol Sci. Dec. 2007;32(5):505-14.
Voulgaris et al., Intratumoral doxorubicin in patients with malignant brain gliomas. Am J Clin Oncol. Feb. 2002;25(1):60-4.
D'Alessandro et al., Vitamin K and its role in blood coagulation. The American Journal of Surgery. Jul. 1942;57(1):104-111.

EFFECT OF COENZYME Q10 ON PANCREATIC TUMOR SIZE

| Group 1 | Group 2 | Group 3 | Group 4 |
| --- | --- | --- | --- |
| Control | Coenzyme Q10 | Gemcitabine | Gem + CoQ10 |
| 20 Days | 50-60 Days | 40-50 Days | 50-60 Days |

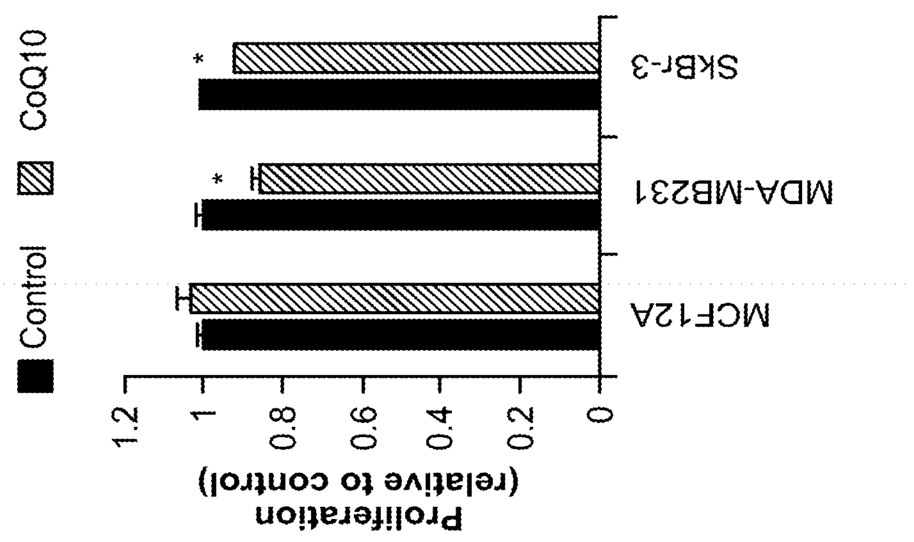
Figure 24
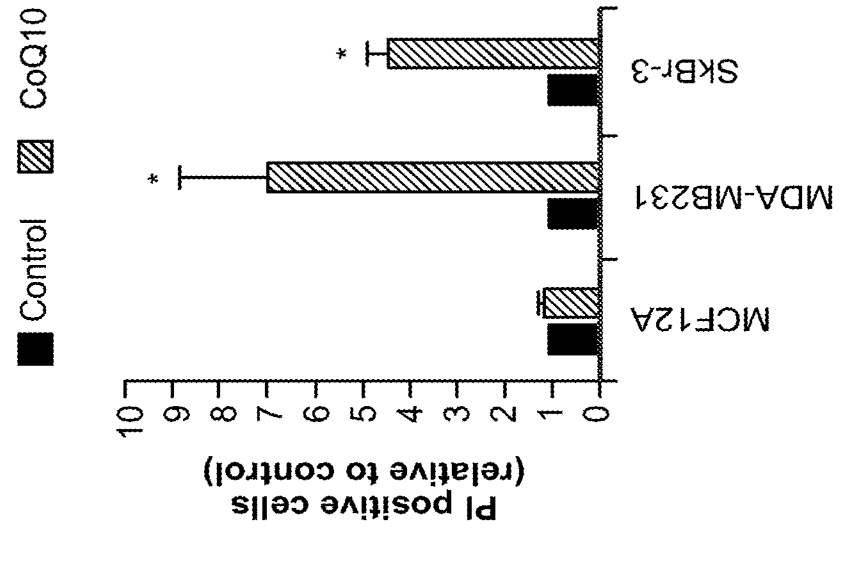

METHODS FOR THE TREATMENT OF CANCER USING COENZYME Q10 COMBINATION THERAPIES

RELATED APPLICATIONS

This application is a continuation of U.S. patent application Ser. No. 14/248,313 filed on Apr. 8, 2014 which, in turn, claims priority to U.S. Provisional Patent Application No. 61/809,840 filed on Apr. 8, 2013, the contents of which are incorporated herein in their entirety.

FIELD OF THE INVENTION

The invention generally relates to methods for the treatment of oncological disorders comprising administration of coenzyme Q10 (CoQ10) and a chemotherapeutic agent.

BACKGROUND

Cancer is presently one of the leading causes of death in developed nations. A diagnosis of cancer traditionally involves serious health complications. Cancer can cause disfigurement, chronic or acute pain, lesions, organ failure, or even death. Commonly diagnosed cancers include pancreatic cancer, breast cancer, lung cancer, melanoma, lymphoma, carcinoma, sarcoma non-Hodgkin's lymphoma, leukemia, endometrial cancer, colon and rectal cancer, prostate cancer, and bladder cancer. Traditionally, many cancers (e.g., breast cancer, leukemia, lung cancer, or the like) are treated with surgery, chemotherapy, radiation, or combinations thereof. Chemotherapeutic agents used in the treatment of cancer are known to produce several serious and unpleasant side effects in patients. For example, some chemotherapeutic agents cause neuropathy, nephrotoxicity (e.g., hyperlipidemia, proteinuria, hypoproteinemia, combinations thereof, or the like), stomatitis, mucositisemesis, alopecia, anorexia, esophagitis amenorrhoea, decreased immunity, anaemia, high tone hearing loss, cardiotoxicity, fatigue, neuropathy, or combinations thereof. Improved methods for the treatment of oncological diseases, including cancer, and composition capable of delivering bioactive agents to aid in the treatment of diseases and other conditions remain desirable.

Coenzyme Q10, also referred to herein as CoQ10, ubiquinone, or ubidecarenone, is a popular nutritional supplement and can be found in capsule form in nutritional stores, health food stores, pharmacies, and the like, as a vitamin-like supplement to help protect the immune system through the antioxidant properties of ubiquinol, the reduced form of CoQ10. CoQ10 is found throughout most tissues of the human body and the tissues of other mammals and is concentrated in the mitochondria. CoQ10 is very lipophilic and, for the most part, insoluble in water. The insolubility is related to the 50-carbon atom isoprenoid side chain, of hydrocarbon nature as shown in the following structure of CoQ10.

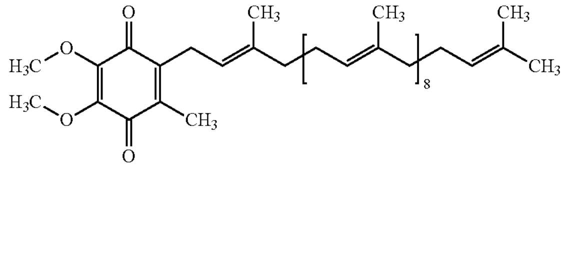

SUMMARY OF THE INVENTION

The present invention provides methods for treating oncological disorders in a subject by administering CoQ10 and at least one chemotherapeutic agent to the subject, such that the oncological disorder is treated.

In some embodiments, the method comprises (a) administering coenzyme Q10 (CoQ10) to the subject; (b) discontinuing administration of CoQ10; and (c)

administering at least one chemotherapeutic agent to the subject after administration with CoQ10 has been discontinued, such that the oncological disorder is treated. In other embodiments, the method comprises (a) administering coenzyme Q10 (CoQ10) to the subject; (b) administering at least one chemotherapeutic agent to the subject after administration of the CoQ10 is initiated; and (c) continuing treatment with CoQ10 after administration of the at least one chemotherapeutic agent is initiated, such that the oncological disorder is treated.

In certain embodiments, the CoQ10 is administered prior to administration of a first dose of the at least one chemotherapeutic agent. In a preferred embodiment, the CoQ10 is administered for at least 24 hours prior to administration of a dose of the at least one chemotherapeutic agent. In another preferred embodiment, the CoQ10 is administered for at least 48 hours prior to administration of a dose of the at least one chemotherapeutic agent. In a further preferred embodiment, the CoQ10 is administered for at least 1 week prior to administration of a dose of the at least one chemotherapeutic agent. In another preferred embodiment, the CoQ10 is administered for at least 2 weeks prior to administration of a dose of the at least one chemotherapeutic agent. In another preferred embodiment, the CoQ10 is administered for at least 3 weeks prior to administration of a dose of the at least one chemotherapeutic agent. In another preferred embodiment, the CoQ10 is administered for at least 4 weeks prior to administration of a dose of the at least one chemotherapeutic agent. In another preferred embodiment, the CoQ10 is administered for at least 5 weeks prior to administration of a dose of the at least one chemotherapeutic agent. In another preferred embodiment, the CoQ10 is administered for at least 6 weeks prior to administration of a dose of the at least one chemotherapeutic agent. In another preferred embodiment, the CoQ10 is administered for at least 7 weeks prior to administration of a dose of the at least one chemotherapeutic agent. In another preferred embodiment, the CoQ10 is administered for at least 8 weeks prior to administration of a dose of the at least one chemotherapeutic agent.

In other preferred embodiments, the CoQ10 is administered for about 24 hours prior to administration of a dose of the at least one chemotherapeutic agent. In another preferred embodiment, the CoQ10 is administered for about 48 hours prior to administration of a dose of the at least one chemotherapeutic agent. In a further preferred embodiment, the CoQ10 is administered for about 1 week prior to administration of a dose of the at least one chemotherapeutic agent. In another preferred embodiment, the CoQ10 is administered for about 2 weeks prior to administration of a dose of the at least one chemotherapeutic agent. In another preferred embodiment, the CoQ10 is administered for about 3 weeks prior to administration of a dose of the at least one chemotherapeutic agent. In another preferred embodiment, the CoQ10 is administered for about 4 weeks prior to administration of a dose of the at least one chemotherapeutic agent. In another preferred embodiment, the CoQ10 is administered for about 5 weeks prior to administration of a dose of the at least one chemotherapeutic agent. In another preferred embodiment, the CoQ10 is administered for about 6 weeks prior to administration of a dose of the at least one chemotherapeutic agent. In another preferred embodiment, the CoQ10 is administered for about 7 weeks prior to administration of a dose of the at least one chemotherapeutic agent. In another preferred embodiment, the CoQ10 is administered for about 8 weeks prior to administration of a dose of the at least one chemotherapeutic agent.

In certain embodiments, administration of the at least one chemotherapeutic agent is initiated at least 24 hours after administration of CoQ10 is initiated, one or more weeks after administration of CoQ10 is initiated, two or more weeks after administration of CoQ10 is initiated, three or more weeks after administration of CoQ10 is initiated, four or more weeks after administration of CoQ10 is initiated, five or more weeks after administration of CoQ10 is initiated, six or more weeks after administration of CoQ10 is initiated, seven or more weeks after administration of CoQ10 is initiated, or eight or more weeks after administration of CoQ10 is initiated.

In a preferred embodiment of the aforementioned methods, a response of the oncological disorder to treatment is improved relative to a treatment with the at least one chemotherapeutic agent alone, i.e., in the absence of administration of CoQ10 to the subject. In a further preferred embodiment, the response is improved by at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 55%, at least 60%, at least 65%, at least 70%, at least 75%, at least 80%, at least 85%, at least 90%, at least 95% or at least 100% relative to treatment with the at least one chemotherapeutic agent alone.

In certain embodiments, the response comprises any one or more of reduction in tumor burden, reduction in tumor size, inhibition of tumor growth, slowing of tumor growth, an improvement in RECIST criteria, achieving stable oncological disorder in a subject with a progressive oncological disorder prior to treatment, increased time to progression of the oncological disorder, and increased time of survival.

In a preferred embodiment of the aforementioned methods, the CoQ10 is administered topically. In another preferred embodiment, the CoQ10 is administered by inhalation. In another preferred embodiment, the CoQ10 is administered by injection or infusion. In another preferred embodiment, the CoQ10 is administered by intravenous administration. In a further preferred embodiment, the CoQ10 is administered by continuous intravenous infusion. In a still further preferred embodiment, the dose of CoQ10 is administered by continuous infusion over 24 hours.

In certain embodiments, the CoQ10 is administered at a dose of about 5 mg/kg, about 10 mg/kg, about 12.5 mg/kg, about 20 mg/kg, about 25 mg/kg, t about 30 mg/kg, about 35 mg/kg, about 40 mg/kg, about 45 mg/kg, about 50 mg/kg, about 55 mg/kg, about 58 mg/kg, about 58.6 mg/kg, about 60 mg/kg, about 75 mg/kg, about 78 mg/kg, about 100 mg/kg, about 104 mg/kg, about 125 mg/kg, about 150 mg/kg, about 175 mg/kg, about 200 mg/kg, about 300 mg/kg, or about 400 mg/kg.

The invention also provides a method of improving a chemotherapeutic treatment regimen for an oncological disorder in a subject, comprising pre-treating a subject having an oncological disorder with Coenzyme Q10 (CoQ10) for a sufficient time prior to initiation of a chemotherapeutic treatment regimen, wherein the chemotherapeutic treatment regimen comprises administration of one or more chemotherapeutic agents, such that a response of the oncological disorder is improved relative to treatment with the chemotherapeutic treatment regimen alone. In certain embodiments of the aforementioned method, the chemotherapeutic treatment regimen does not include administration of CoQ10. In some embodiments of the aforementioned methods, pre-treatment with CoQ10 is ceased prior to initiation of the chemotherapeutic treatment regimen.

In a preferred embodiment of the aforementioned methods, the subject is pre-treated with CoQ10 for at least 24 hours, at least 48 hours, at least 1 week, at least 2 weeks, at least 3 weeks, at least 4 weeks, at least 5 weeks, at least 6 weeks, at least 7 weeks, or at least 8 weeks prior to initiation of the chemotherapeutic treatment regimen. In another preferred embodiment, the subject is pre-treated with CoQ10 for about 24 hours, about 48 hours, about 1 week, about 2 weeks, about 3 weeks, about 4 weeks, about 5 weeks, about 6 weeks, about 7 weeks, or about 8 weeks prior to initiation of the chemotherapeutic treatment regimen.

In another preferred embodiment of the aforementioned methods, the chemotherapeutic treatment regimen is initiated at least 24 hours after pre-treatment with CoQ10 is initiated, one or more weeks after pre-treatment with CoQ10 is initiated, two or more weeks after pre-treatment with CoQ10 is initiated, three or more weeks after pre-treatment with CoQ10 is initiated, four or more weeks after pre-treatment with CoQ10 is initiated, five or more weeks after pre-treatment with CoQ10 is initiated, six or more weeks after pre-treatment with CoQ10 is initiated, seven or more weeks after pre-treatment with CoQ10 is initiated, or eight or more weeks after pre-treatment with CoQ10 is initiated.

In certain embodiments of the aforementioned methods, the response is improved by at least 2%, at least 3%, at least 4%, at least 5%, at least 6%, at least 7%, at least 8%, at least 9%, at least 10%, at least 11%, at least 12%, at least 13%, at least 14%, at least 15%, at least 16%, at least 17%, at least 18%, at least 19%, at least 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 55%, at least 60%, at least 65%, at least 70%, at least 75%, at least 80%, at least 85%, at least 90%, at least 95% or at least 100% relative to treatment with the chemotherapeutic treatment regimen alone.

In certain embodiments of the aforementioned methods the response comprises any one or more of reduction in tumor burden, reduction in tumor size, inhibition of tumor growth, slowing of tumor growth, an improvement in RECIST criteria, achieving stable oncological disorder in a subject with a progressive oncological disorder prior to treatment, increased time to progression of the oncological disorder, and increased time of survival.

In some embodiments, CoQ10 is administered topically. In other embodiments, CoQ10 is administered by inhalation.

In other embodiments, the CoQ10 is administered by injection or infusion. In another embodiment, the CoQ10 is administered by intravenous administration.

In a further embodiment, the CoQ10 is administered by continuous intravenous infusion. In a still further embodiment, the dose of CoQ10 is administered by continuous intravenous infusion over 24 hours.

In certain embodiments, the CoQ10 is administered at a dose of about 5 mg/kg, about 10 mg/kg, about 12.5 mg/kg, about 20 mg/kg, about 25 mg/kg, t about 30 mg/kg, about 35 mg/kg, about 40 mg/kg, about 45 mg/kg, about 50 mg/kg, about 55 mg/kg, about 58 mg/kg, about 58.6 mg/kg, about 60 mg/kg, about 75 mg/kg, about 78 mg/kg, about 100 mg/kg, about 104 mg/kg, about 125 mg/kg, about 150 mg/kg, about 175 mg/kg, about 200 mg/kg, about 300 mg/kg, or about 400 mg/kg.

The invention also provides a method of treating an oncological disorder in a subject comprising: (a) administering CoQ10 to the subject; and (b) administering at least one chemotherapeutic agent to the subject at a dosage that is lower than standard dosages of the chemotherapeutic agent used to treat the oncological disorder, such that the oncological disorder is treated. In certain embodiments administration of CoQ10 is discontinued before administering the at least one chemotherapeutic agent to the subject. In other embodiments, administration of CoQ10 is continued after administration of the at least one chemotherapeutic agent to the subject.

In certain embodiments of the aforementioned methods, the CoQ10 is administered for at least 24 hours, at least 48 hours, at least 1 week, at least 2 weeks, at least 3 weeks, at least 4 weeks, at least 5 weeks, at least 6 weeks, at least 7 weeks, or at least 8 weeks prior to administration of the at least one chemotherapeutic agent. In other embodiments of the aforementioned methods, the CoQ10 is administered for about 24 hours, about 48 hours, about 1 week, about 2 weeks, about 3 weeks, about 4 weeks, about 5 weeks, about 6 weeks, about 7 weeks, or about 8 weeks prior to administration of the at least one chemotherapeutic agent.

In other embodiments of the aforementioned methods, the at least one chemotherapeutic agent is administered at least 24 hours after administration of CoQ10 is initiated, one or more weeks after administration of with CoQ10 is initiated, two or more weeks after administration of CoQ10 is initiated, three or more weeks after administration of CoQ10 is initiated, four or more weeks after administration of CoQ10 is initiated, five or more weeks after administration of CoQ10 is initiated, six or more weeks after administration of CoQ10 is initiated, seven or more weeks after administration of CoQ10 is initiated, or eight or more weeks after administration of CoQ10 is initiated.

In certain embodiments of the aforementioned methods, the CoQ10 is administered topically. In other embodiments, the CoQ10 is administered by inhalation. In other embodiments, the CoQ10 is administered by injection or infusion. In other embodiments, the CoQ10 is administered by intravenous administration. In other embodiments, the CoQ10 is administered by continuous intravenous infusion. In other embodiments the CoQ10 is administered by continuous infusion over 24 hours.

In certain embodiments of the aforementioned methods, the CoQ10 is administered at a dose of about 5 mg/kg, about 10 mg/kg, about 12.5 mg/kg, about 20 mg/kg, about 25 mg/kg, t about 30 mg/kg, about 35 mg/kg, about 40 mg/kg, about 45 mg/kg, about 50 mg/kg, about 55 mg/kg, about 58 mg/kg, about 58.6 mg/kg, about 60 mg/kg, about 75 mg/kg, about 78 mg/kg, about 100 mg/kg, about 104 mg/kg, about 125 mg/kg, about 150 mg/kg, about 175 mg/kg, about 200 mg/kg, about 300 mg/kg, or about 400 mg/kg.

In certain embodiments of the aforementioned methods the at least one chemotherapeutic agent comprises a chemotherapeutic agent selected from the group consisting of a topoisomerase I inhibitor, a topoisomerase II inhibitor, a mitotic inhibitor, an alkylating agent, a platinum compound, and an antimetabolite. In some embodiments, the at least one chemotherapeutic agent comprises a Topoisomerase II inhibitor. In a preferred embodiment, the Topoisomerase II inhibitor comprises at least one of doxorubicin, epirubicin, idarubicin, mitoxantrone, losoxantrone, etoposide and teniposide. In other embodiments, the at least one chemotherapeutic agent comprises a Topoisomerase I inhibitor.

In a preferred embodiment, the Topoisomerase I inhibitor comprises at least one of irinotecan, topotecan, 9-nitrocamptothecin, camptothecin, and camptothecin derivatives. In other embodiments, the at least one chemotherapeutic agent comprises an antimetabolite. In a preferred embodiment the antimetabolite comprises at least one of 5-fluorouracil, capecitabine, gemcitabine, methotrexate and edatrexate. In other embodiments, the at least one chemotherapeutic agent comprises an alkylating agent.

In a preferred embodiment the alkylating agent comprises at least one of a nitrogen mustard, an ethyleneimine compound, an alkylsulphonate, a nitrosourea, dacarbazine, cyclophosphamide, ifosfamide and melphalan. In other embodiments, the at least one chemotherapeutic agent comprises a platinum compound. In a preferred embodiment, the platinum compound comprises at least one of cisplatin, oxaliplatin and carboplatin. In other embodiments, the at least one chemotherapeutic agent comprises a mitotic inhibitor. In a preferred embodiment, the mitotic inhibitor comprises at least one of paclitaxel, docetaxel, vinblastine, vincristine, vinorelbine and a podophyllotoxin derivative.

In certain embodiments of the aforementioned methods, the at least one chemotherapeutic agent comprises a chemotherapeutic agent selected from the group consisting of amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11,10-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof.

In preferred embodiments of the aforementioned methods, the at least one chemotherapeutic agent comprises at least one of gemcitabine, 5-fluorouracil, cisplatin, capecitabine, methotrexate, edatrexate, docetaxel, cyclophosphamide, doxorubicin, and irinotecan.

In certain embodiments of the aforementioned methods, the oncological disorder is selected from the group consisting of a carcinoma, sarcoma, lymphoma, melanoma, and leukemia. In a preferred embodiment, the oncological disorder is selected from the group consisting of pancreatic cancer, breast cancer, liver cancer, skin cancer, lung cancer, colon cancer, prostate cancer, thyroid cancer, bladder cancer, rectal cancer, endometrial cancer, kidney cancer, bone cancer, brain cancer, cervical cancer, stomach cancer, mouth and oral cancers, neuroblastoma, testicular cancer, uterine cancer, and vulvar cancer. In a further preferred embodiment, the skin cancer is selected from the group consisting of melanoma, squamous cell carcinoma, basal cell carcinoma, and cutaneous T-cell lymphoma (CTCL). In another preferred embodiment, the oncological disorder is triple negative breast cancer.

In certain embodiments of the aforementioned methods, the oncological disorder is a refractory disorder. In certain embodiments of the aforementioned methods, the oncological disorder has failed to respond to at least one, two, three, four, five, six, seven, eight or more previous treatments. In certain embodiments of the aforementioned methods, the oncological disorder is end stage cancer. In certain embodiments of the aforementioned methods, the methods further comprise selecting a subject having a refractory oncological disorder for treatment. In certain embodiments of the aforementioned methods, the methods further comprise selecting a subject having an oncological disorder that has failed to respond to at least one, two, three, four, five, six, seven, eight or more previous treatments for treatment. In certain embodiments of the aforementioned methods, the methods further comprise selecting a subject having end stage cancer for treatment.

In preferred embodiments of the aforementioned methods, the subject is human.

In certain embodiments of the aforementioned methods, the chemotherapeutic agent comprises at least one of gemcitabine, cisplatin, docetaxel, cyclophosphamide, doxorubicin, irinotecan, and 5-fluorouracil.

In a preferred embodiment of the aforementioned methods, the method comprises administering between about 100 mg/kg of gemcitabine and about 10 mg/kg of gemcitabine once per week for 3 weeks with one week rest.

In another preferred embodiment of the aforementioned methods, the method comprises administering 5 mg/kg docetaxel, 1 mg/kg doxorubicin, and 35 mg/kg cyclophosphamide to the subject every three weeks for six cycles.

In certain embodiments of the aforementioned methods, the chemotherapeutic agent is SN38 and the oncological disorder is prostate cancer, the chemotherapeutic agent is SN38 and the oncological disorder is liver cancer, the chemotherapeutic agent is doxorubicin and the oncological disorder is breast cancer, the chemotherapeutic agent is doxorubicin and the oncological disorder is pancreatic cancer, the chemotherapeutic agent is doxorubicin and the oncological disorder is liver cancer, the chemotherapeutic agent is 5-fluorouracil and the oncological disorder is breast cancer, the chemotherapeutic agent is 5-fluorouracil and the oncological disorder is triple-negative breast cancer, the chemotherapeutic agent is 5-fluorouracil and the oncological disorder is liver cancer, the chemotherapeutic agent is cisplatin and the oncological disorder is lung cancer, the chemotherapeutic agent is 4-HCP and the oncological disorder is breast cancer, the chemotherapeutic agent is 4-HCP and the oncological disorder is triple-negative breast cancer, the chemotherapeutic agent is 4-HCP and the oncological disorder is breast cancer, the chemotherapeutic agent is 4-HCP and the oncological disorder is ovarian cancer, the chemotherapeutic agent is tamoxifen and the oncological disorder is breast cancer, the chemotherapeutic agent is gemcitabine and the oncological disorder is lung cancer, the chemotherapeutic agent is flutamide and the oncological disorder is prostate cancer, or the chemotherapeutic agent is goserelin and the oncological disorder is prostate cancer.

In some embodiments, wherein the CoQ10 is provided in an intravenous CoQ10 formulation, the intravenous CoQ10 formulation comprises (1) an aqueous solution, (2) CoQ10 dispersed into a nano-dispersion of particles; and (3) at least one of a dispersion stabilizing agent and an opsonization reducer, wherein the nano-dispersion of the CoQ10 is dispersed into nano-particles having a mean particle size of less than 200-nm.

In some embodiments, the dispersion stabilizing agent is selected from the group consisting of pegylated castor oil, Cremophor EL, Cremophor RH 40, Pegylated vitamin E, Vitamin E TPGS, and Dimyristoylphosphatidyl choline (DMPC). In some embodiments, the dispersion stabilizing agent is preferably DMPC.

In some embodiments, the opsonization reducer is selected from the group consisting of poloxamers and poloxamines. In some preferred embodiments, the opsonization reducer is poloxamer 188. In some preferred embodiments, the opsonization reducer is poloxamer 188 and the dispersion stabilizing agent is DMPC.

In some embodiments, the CoQ10 formulation has a weight-per-volume of the CoQ10, DMPC and poloxamer 188 of 4%, 3% and 1.5%, respectively.

In some embodiments, the CoQ10 is provided in a topical CoQ10 formulation wherein the topical CoQ10 formulation is a 3% CoQ10 cream comprising: (1) a phase A having C12-15 alkyl benzoate at about 4.0% w/w of the composition, cetyl alcohol at about 2.00% w/w of the composition, stearyl alcohol at about 1.5% w/w, glyceryl stearate and PEG-100 at about 4.5% w/w; (2) a phase B having glycerin at about 2.00% w/w, propylene glycol at about 1.5% w/w, ethoxydiglycol at about 5.0% w/w, phenoxyethanol at about 0.475% w/w, a carbomer dispersion at about 40% w/w, purified water at about 16.7% w/w; (3) a phase C having triethanolamine at about 1.3% w/w, lactic acid at about 0.5% w/w, sodium lactate solution at about 2.0% w/w, water at about 2.5% w/w; (4) a phase D having titanium dioxide at about 1.0% w/w; and (5) a phase E having CoQ10 21% concentrate at about 15.0% w/w.

In certain embodiments, the CoQ10 is provided in a formulation for inhalation wherein the formulation comprises a pharmaceutical composition comprising a dispersion of liposomal particles suitable for continuous aerosolization, the composition comprising: a dispersion of liposomal particles having an average diameter between about 30 and 500 nm, each liposomal particle comprising a hydrophobic bioactive agent, a phospholipid, and an aqueous dispersion vehicle, wherein the ratio of hydrophobic bioactive agent:phospholipid is between about 5:1 and about 1:5, the hydrophobic bioactive agent is between about 0.1 and 30% w/w of the composition, the phospholipid is between about 0.1 and 30% w/w of the composition, and the liposomal particles are dispersed within the aqueous dispersion vehicle, and wherein, upon administration to a subject, the composition is characterized by continuous aerosolization sufficient to provide a therapeutic dose of the hydrophobic bioactive agent to the subject. In certain embodiments, the aqueous dispersion vehicle comprises water or an aqueous salt solution. In certain embodiments, the dispersion of liposomal particles is in the form of a continuous respirable aerosol comprising a plurality of aqueous droplets containing a dispersion of liposomal particles and having a mass median aerodynamic diameter (MMAD) between about 1 and 5 μm. In certain embodiments, the composition is characterized by an average percent transmission (APT) between about 50 and 100% over at least 15 minutes of continuous aerosolization. In certain embodiments, the plurality of droplets has a MMAD between about 1 and 5 μm over at least 15 minutes of continuous aerosolization.

Chemotherapeutic agents include, but are not limited to, cyclophosphamide, taxanes (e.g., paclitaxel or docetaxel), busulfan, cisplatin, methotrexate, daunorubicin, doxorubicin, melphalan, cladribine, vincristine, vinblastine, chlorambucil, tamoxifen, taxol, etoposide (VP-16), adriamycin, 5-fluorouracil (5FU), camptothecin, actinomycin-D, mitomycin C, cisplatin (CDDP), combretastatin(s), and irinotecan; and derivatives and prodrugs thereof. Chemotherapeutic agents include anti-angiogenic agents. Anti-angiogenic agents include, but are not limited to, angiostatin, endostatin, 16 kDa prolactin fragment, Laminin peptides, Fibronectin peptides, tissue metalloproteinase inhibitors (TIMP 1, 2, 3, 4), Plasminogen activator inhibitors (PAI-1, -2), Tumor necrosis factor alpha, TGF-β1, Interferons (IFN-α, β, γ), ELR-CXC Chemokines: IL-12; SDF-1; MIG; Platelet factor 4 (PF-4); IP-10, Thrombospondin (TSP), SPARC, 2-Methoxyoestradiol Proliferin-related protein, Suramin, Thalidomide, Cortisone, Fumagillin (AGM-1470; TNP-470), tamoxifen, Korean mistletoe extract (Viscum album coloratum), retinoids, CM101, dexamethasone, and leukemia inhibitory factor (LIF). Additional chemotherapeutic agents are provided herein.

In some embodiments, the antimetabolite includes at least one of a purine or pyrimidine analogues. In some embodiments, the antimetabolite includes at least one of gemcitabine, 5-fluorouracil, capecitabine, methotrexate and edatrexate. In some preferred embodiments, the antimetabolite is gemcitabine.

In some embodiments, the anthracycline antibiotic is a Topoisomerase II inhibitor. In some embodiments, the Topoisomerase II inhibitor includes at least one of doxorubicin, epirubicin, idarubicin, mitoxantrone, losoxantrone, etoposide and teniposide. In some preferred embodiments, the topoisomerase II inhibitor is doxorubicin.

In some embodiments, the chemotherapeutic agent is a Topoisomerase I inhibitor. In some embodiments, the Topoisomerase I inhibitor includes at least one of irinotecan, topotecan, 9-nitrocamptothecin, camptothecin, and camptothecin derivatives.

Routes and methods of administration of chemotherapeutic agents are known in the art.

In some embodiments, the method comprises a regimen wherein the subject is intravenously administered at least about 50 mg/kg/dose of intravenous CoQ10 formulation once daily for 3 weeks with one week rest, co-administered with a chemotherapeutic agent for one cycle.

In some embodiments, the method comprises a regimen wherein the subject is intravenously administered at least about 50 mg/kg/dose of intravenous CoQ10 formulation twice daily for 3 weeks with one week rest, and co-administered with a chemotherapeutic agent for one cycle.

In some embodiments, the method comprises a regimen wherein the subject is intravenously administered at least about 50 mg/kg/dose of intravenous CoQ10 formulation three times daily for 3 weeks with one week rest, and co-administered with a chemotherapeutic agent for one cycle.

In some embodiments, the method comprises a regimen wherein the subject is intravenously administered at least about 75 mg/kg/dose of intravenous CoQ10 formulation once daily for 3 weeks with one week rest, co-administered with a chemotherapeutic agent for one cycle.

In some embodiments, the method comprises a regimen wherein the subject is intravenously administered at least about 75 mg/kg/dose of intravenous CoQ10 formulation twice daily for 3 weeks with one week rest, and co-administered with a chemotherapeutic agent for one cycle.

In some embodiments, the method comprises a regimen wherein the subject is intravenously administered at least about 75 mg/kg/dose of intravenous CoQ10 formulation three times daily for 3 weeks with one week rest, and co-administered with a chemotherapeutic agent for one cycle.

In some embodiments, the method comprises a regimen wherein the subject is intravenously administered at least about 50 mg/kg/dose of intravenous CoQ10 formulation once daily for 3 weeks with one week rest, and subsequently administered with a chemotherapeutic agent for one cycle.

In some embodiments, the method comprises a regimen wherein the subject is intravenously administered at least about 50 mg/kg/dose of intravenous CoQ10 formulation twice daily for 3 weeks with one week rest, and subsequently administered with a chemotherapeutic agent for one cycle.

In some embodiments, the method comprises a regimen wherein the subject is intravenously administered at least about 50 mg/kg/dose of intravenous CoQ10 formulation three times daily for 3 weeks with one week rest, and subsequently administered with a chemotherapeutic agent for one cycle.

In some embodiments, the method comprises a regimen wherein the subject is intravenously administered at least about 75 mg/kg/dose of intravenous CoQ10 formulation once daily for 3 weeks with one week rest, and subsequently administered with a chemotherapeutic agent for one cycle.

In some embodiments, the method comprises a regimen wherein the subject is intravenously administered at least about 75 mg/kg/dose of intravenous CoQ10 formulation twice daily for 3 weeks with one week rest, and subsequently administered with a chemotherapeutic agent for one cycle.

In some embodiments, the method comprises a regimen wherein the subject is intravenously administered at least about 75 mg/kg/dose of intravenous CoQ10 formulation three times daily for 3 weeks with one week rest, and subsequently administered with a chemotherapeutic agent for one cycle.

In certain embodiments, the CoQ10 is administered every day without a week of rest at three week intervals. In certain embodiments, the CoQ10 is administered every day until limiting toxicities are observed.

In some embodiments, the method comprises a regimen wherein the subject is intravenously administered CoQ10 by continuous infusion prior to administration of a chemotherapeutic agent. In some embodiments, the continuous infusion is for 24 hours prior to administration of the chemotherapeutic agent.

In certain embodiments, administration of the chemotherapeutic agent is initiated within 24 hours of completion of administration of a dose of CoQ10. In certain embodiments, administration of the chemotherapeutic agent is initiated within 18 hours of completion of administration of a dose of CoQ10. In certain embodiments, administration of the chemotherapeutic agent is initiated within 12 hours of completion of administration of a dose of CoQ10. In certain embodiments, administration of the chemotherapeutic agent is initiated within 6 hours of completion of administration of a dose of CoQ10. In certain embodiments, administration of the chemotherapeutic agent is initiated within 4 hours of completion of administration of a dose of CoQ10. In certain embodiments, administration of the chemotherapeutic agent is initiated within 3 hours of completion of administration of a dose of CoQ10. In certain embodiments, administration of the chemotherapeutic agent is initiated within 2 hours of completion of administration of a dose of CoQ10. In certain embodiments, administration of the chemotherapeutic agent is initiated within 1 hour of completion of administration of a dose of CoQ10.

In certain embodiments, after pre-treatment with CoQ10, treatment with CoQ10 is continued during treatment with the chemotherapeutic agent.

In some embodiments wherein the CoQ10 is administered prior to the chemotherapeutic agent, two or more cycles of CoQ10 (e.g., 2, 3, 4, 5, 6, 7, 8, etc.) are administered prior to administration of two or more (e.g., 2, 3, 4, 5, 6, 7, 8, etc.) cycles of a chemotherapeutic agent.

In certain embodiments, CoQ10 is administered for a sufficient time and amount prior to administration of the chemotherapeutic agent to achieve a steady state of CoQ10.

In certain embodiments, a loading dose of CoQ10 is administered prior to initiation of treatment with a chemotherapeutic agent.

In some embodiments wherein the CoQ10 is administered prior to the chemotherapeutic agent, one cycle of CoQ10 is administered prior to administration of one cycle of a chemotherapeutic agent. In certain embodiments, CoQ10 is administered prior to each dose of chemotherapeutic agent in each treatment cycle. In certain embodiments, multiple cycles of CoQ10 are administered alternating with cycles of a chemotherapeutic agent. In certain embodiments, CoQ10 is administered prior to each dose of chemotherapeutic agent in each treatment cycle. In certain embodiments, CoQ10 is administered prior to and concurrently with each dose of chemotherapeutic agent. In certain embodiments, CoQ10 is administered prior to and concurrently with each cycle of administration of chemotherapeutic agent.

In some embodiments wherein the CoQ10 is administered prior to the chemotherapeutic agent, one cycle of CoQ10 is administered prior to administration of two or more (e.g., 2, 3, 4, 5, 6, 7, 8, etc.) cycles of a chemotherapeutic agent.

It is understood that chemotherapeutic agents are frequently administered in cocktails. As used herein, a chemotherapeutic agent should be understood as one or more (e.g., 1, 2, 3, 4, 5, 6, 7, 8, etc.) chemotherapeutic agents. Moreover, it is understood that when multiple cycles of chemotherapeutic agents are administered, that the specific dosing regimens and/or chemotherapeutic agents used in each of the cycles need not be the same. However, in certain embodiments, the chemotherapeutic agents and their dosing regimens are the same for all cycles.

In certain embodiments, the CoQ10 is administered by the same route of administration as the chemotherapeutic agent. In certain embodiments, the CoQ10 is administered by a different route of administration as the chemotherapeutic agent.

In some embodiments, the subject is treated for oncological disorders including at least one of pancreatic cancer, breast cancer, skin cancer, liver cancer, carcinoma, sarcoma, lymphoma, melanoma or leukemia. In certain embodiments, the subject is treated for an oncological disorder comprising a solid tumor. In certain embodiments, the subject is treated for an oncological disorder comprising a non-solid tumor.

BRIEF DESCRIPTION OF THE DRAWINGS

FIG. 24 shows MDA-MB231 and SkBr-3 breast cancer cells and MCF12A non-tumorigenic control cells treated with 100 μM CoQ10 (BPM 31510) for 48 hours. Propidium iodide (PI) and CFSE Cell Tracer were used to measure cell death and proliferation, respectively, in cells treated with CoQ10.

DETAILED DESCRIPTION

I. Definitions

Figure 1:
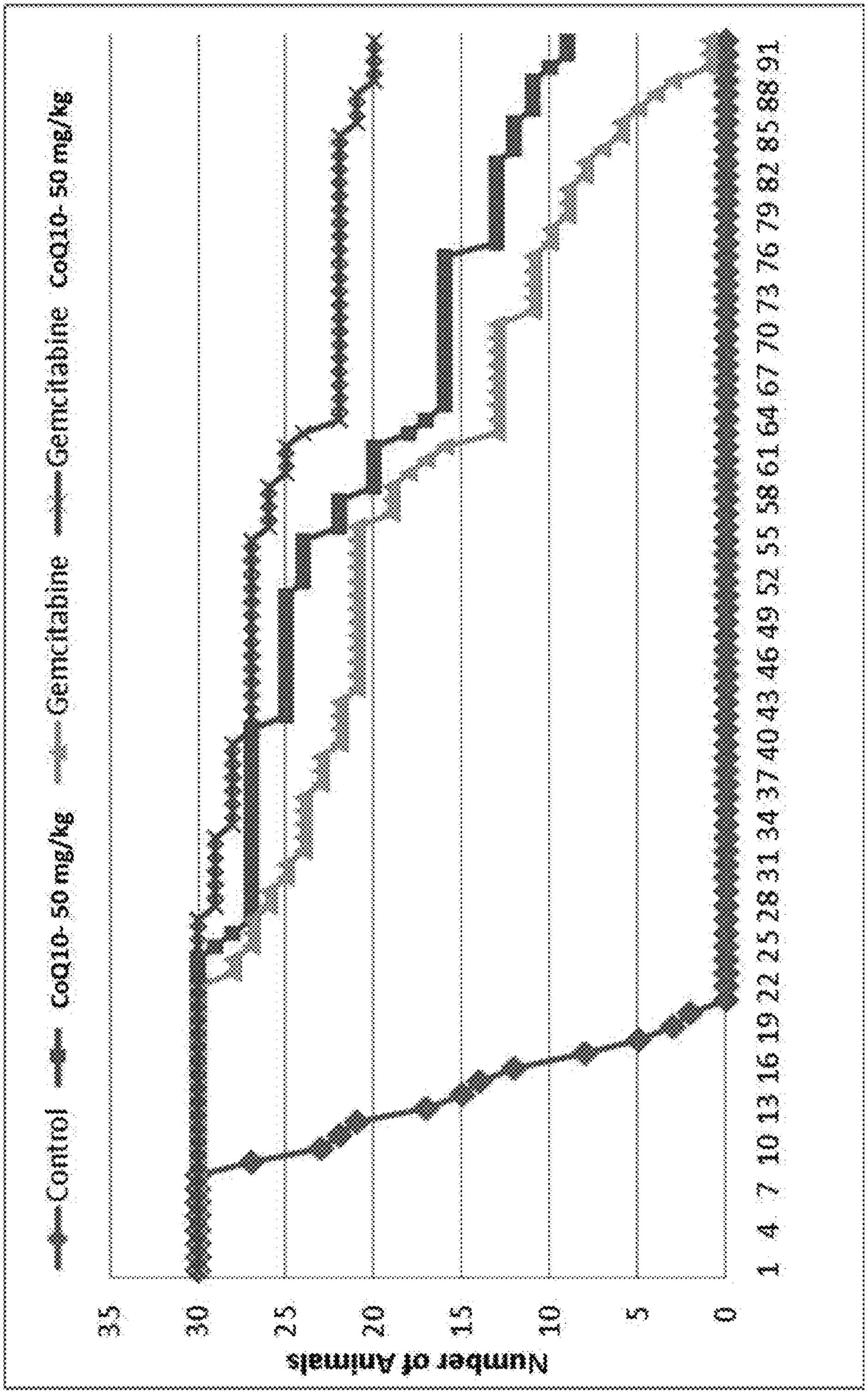
FIG. 1 is a graph showing the effect of once daily dosing with intravenous CoQ10, alone or in combination with gemcitabine (days), on survival time in a xenogeneic mouse model of pancreatic cancer using human pancreatic tumor MIAPaCa-2 cells. In the graph, Day 1 indicates the day that treatment was initiated.

In accordance with the present disclosure and as used herein, the following terms are defined with the following meanings, unless explicitly stated otherwise.

As used herein, a "pharmaceutically acceptable" component is one that is suitable for use with humans and/or animals without undue adverse side effects (such as toxicity, irritation, and allergic response) commensurate with a reasonable benefit/risk ratio.

"Treatment" is an intervention performed with the intention of preventing the development or altering the pathology, symptoms, or signs of a disorder. Accordingly, "treatment" refers to both therapeutic treatment and prophylactic or preventative measures. Those in need of treatment include those already with the disorder as well as those in which the disorder is to be prevented. As used herein, "treatment" refers to a symptom or sign which approaches a normalized value (for example a value obtained in a healthy patient or individual), e.g., is less than 50% different from a normalized value, in embodiments less than about 25% different from a normalized value, in other embodiments is less than 10% different from a normalized value, and in yet other embodiments the presence of a symptom is not significantly different from a normalized value as determined using routine statistical tests. As used herein, treatment can include reduction of tumor burden, inhibition of tumor growth, including inducing stable disease in a subject with progressive disease prior to treatment, increasing time to progression, or increasing survival time. Increases can be determined relative to an appropriate control or expected outcomes. As used herein, treatment can include increasing survival of a subject, with or without a decrease in tumor burden, as compared to appropriate controls. Treatment need not be curative.

As used herein, a "cycle" is understood as the regimen used for administration of CoQ10 or a chemotherapeutic agent. Typically, chemotherapeutic agents are not administered as single treatment, or treatment at continuing regular intervals (e.g., daily, weekly). A cycle includes the time of chemotherapy treatment and then a break before the next treatment, to permit recovery. For example a cycle lasts 4 weeks, may have treatment on the 1st, 2nd and 3rd days and then nothing from the 4th to the 28th day. Then the cycle starts again. Or, as another example, a 3 week cycle may have treatment on the 1st and 8th days, but nothing on days 2 to 7 and days 9 to 21. In certain embodiments, a cycle can include treatment with a combination of chemotherapeutic agents, on the same or different schedules, followed by a non-treatment window to permit recovery.

In certain embodiments, one cycle of CoQ10 is administered prior to administration of at least one cycle of at least one chemotherapeutic agent. In other embodiments, two or more cycles of CoQ10 are administered prior to administration of at least one cycle of at least one chemotherapeutic agent. In further embodiments, three or more cycles of CoQ10 are administered prior to administration of at least one cycle of a chemotherapeutic agent. In yet further embodiments, four or more cycles of CoQ10 are administered prior to administration of at least one cycle of a chemotherapeutic agent.

As used herein, "continuous infusion" is understood as administration of a therapeutic agent continuously for a period of at least 24 hours. Continuous infusion is typically accomplished by the use of a pump, optionally an implantable pump. A continuous infusion may be administered within the context of a treatment cycle. For example, a dose of a therapeutic agent can be administered by continuous infusion over a 24 hour period once per week each week. Treatment with continuous infusion does not require infusion of the therapeutic agent to the subject for the entire treatment period.

It is understood that continuous infusion can include short interruptions of administration, for example, to change the reservoir of coenzyme Q10 being administered. Continuous administration is typically facilitated by the use of a pump. Continuous infusion is carried out without including any significant interruptions of dosing by design. As used herein, interruptions to assess vital signs and/or perform laboratory assessments to ensure the safety of the patients and that no unacceptable adverse event have occurred are not considered to be significant interruptions. Interruptions resulting from equipment failure, e.g., pump failure, are not interruptions by design.

The terms "oncological disorder", "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features.

As used herein, "oncological disorder", "cancer" or "tumor" refers to all types of cancer or neoplasm or malignant tumors found in humans, including, but not limited to: leukemias, lymphomas, melanomas, carcinomas and sarcomas. As used herein, the terms or language "oncological disorder", "cancer," "neoplasm," and "tumor," are used interchangeably and in either the singular or plural form, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also cancer stem cells, as well as cancer progenitor cells or any cell derived from a cancer cell ancestor. This includes metastasized cancer cells, and in vitro cultures and cell lines derived from cancer cells.

A "solid tumor" is a tumor that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient. The tumor does not need to have measurable dimensions.

When referring to a type of cancer that normally manifests as a solid tumor, a "clinically detectable" tumor is one that is detectable on the basis of tumor mass; e.g., by procedures such as CAT scan, MR imaging, X-ray, ultrasound or palpation, and/or which is detectable because of the expression of one or more cancer-specific antigens in a sample obtainable from a patient.

As used herein, a "detectable tumor" is a tumor that can be confirmed to be present in a subject, for example, using imaging methods (e.g., x-ray, CT scan, magnetic resonance imaging either with or without contrast agents, ultrasound), palpation or other physical examination methods, and/or direct observation by surgical methods or biopsy, typically coupled with histological analysis, in the case of a solid tumors; or by analysis of blood samples, e.g., completely blood count or histological analysis in the case of non-solid tumors, e.g., leukemias. In certain embodiments, a tumor can be detected based on the presence or certain markers. It is understood that diagnosis and detection of a tumor may involve multiple tests and diagnostic methods.

The term "sarcoma" generally refers to a tumor which is made up of a substance like the embryonic connective tissue and is generally composed of closely packed cells embedded in a fibrillar or homogeneous substance. Examples of sarcomas which can be treated with a colloidal dispersion of CoQ10 in an IV formulation include, for example, a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, and telangiectaltic sarcoma.

The term "melanoma" is taken to mean a tumor arising from the melanocytic system of the skin and other organs. Melanomas which can be treated with the colloidal dispersions of CoQ10 in IV formulation include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, and superficial spreading melanoma.

The term "carcinoma" refers to a malignant new growth made up of epithelial cells tending to infiltrate the surrounding tissues and give rise to metastases. Carcinomas which can be treated with the colloidal dispersions of CoQ10 in IV formulation, as described herein, include, for example, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniform carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypemephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, merkel cell carcinoma, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroti, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, and carcinoma villosum.

Specific criteria for the staging of cancer are dependent on the specific cancer type based on tumor size, histological characteristics, tumor markers, and other criteria known by those of skill in the art. Generally, cancer stages can be described as follows:

Stage 0 Carcinoma in situ

Stage I, Stage II, and Stage III Higher numbers indicate more extensive disease: Larger tumor size and/or spread of the cancer beyond the organ in which it first developed to nearby lymph nodes and/or tissues or organs adjacent to the location of the primary tumor Stage IV The cancer has spread to distant tissues or organs As used herein, the terms "treat," "treating" or "treatment" refer, preferably, to an action to obtain a beneficial or desired clinical result including, but not limited to, alleviation or amelioration of one or more signs or symptoms of a disease or condition (e.g., regression, partial or complete), diminishing the extent of disease, stability (i.e., not worsening, achieving stable disease) state of disease, amelioration or palliation of the disease state, diminishing rate of or time to progression, and remission (whether partial or total). "Treatment" of a cancer can also mean prolonging survival as compared to expected survival in the absence of treatment. Treatment need not be curative. In certain embodiments, treatment includes one or more of a decrease in pain or an increase in the quality of life (QOL) as judged by a qualified individual, e.g., a treating physician, e.g., using accepted assessment tools of pain and QOL. In certain embodiments, treatment does not include one or more of a decrease in pain or an increase in the quality of life (QOL) as judged by a qualified individual, e.g., a treating physician, e.g., using accepted assessment tools of pain and QOL.

RECIST criteria are clinically accepted assessment criteria used to provide a standard approach to solid tumor measurement and provide definitions for objective assessment of change in tumor size for use in clinical trials. Such criteria can also be used to monitor response of an individual undergoing treatment for a solid tumor. The RECIST 1.1 criteria are discussed in detail in Eisenhauer et al., New response evaluation criteria in solid tumors: Revised RECIST guideline (version 1.1). *Eur. J. Cancer.* 45:228-247, 2009, which is incorporated herein by reference. Response criteria for target lesions include:

Complete Response (CR): Disappearance of all target lesions. Any pathological lymph nodes (whether target or non-target) must have a reduction in short axis to <10 mm.

Partial Response (PR): At least a 30% decrease in the sum of diameters of target lesion, taking as a reference the baseline sum diameters.

Progressive Diseases (PD): At least a 20% increase in the sum of diameters of target lesions, taking as a reference the smallest sum on the study (this includes the baseline sum if that is the smallest on the study). In addition to the relative increase of 20%, the sum must also demonstrate an absolute increase of at least 5 mm. (Note: the appearance of one or more new lesions is also considered progression.)

Stable Disease (SD): Neither sufficient shrinkage to qualify for PR nor sufficient increase to qualify for PD, taking as a reference the smallest sum diameters while on study.

RECIST 1.1 criteria also consider non-target lesions which are defined as lesions that may be measureable, but need not be measured, and should only be assessed qualitatively at the desired time points. Response criteria for non-target lesions include:

Complete Response (CR): Disappearance of all non-target lesions and normalization of tumor marker levels. All lymph nodes must be non-pathological in size (<10 mm short axis).

Non-CR/Non-PD: Persistence of one or more non-target lesion(s) and/or maintenance of tumor marker level above the normal limits.

Progressive Disease (PD): Unequivocal progression (emphasis in original) of existing non-target lesions. The appearance of one or more new lesions is also considered progression. To achieve "unequivocal progression" on the basis of non-target disease, there must be an overall level of substantial worsening of non-target disease such that, even in the presence of SD or PR in target disease, the overall tumor burden has increased sufficiently to merit discontinuation of therapy. A modest "increase" in the size of one or more non-target lesions is usually not sufficient to qualify for unequivocal progression status. The designation of overall progression solely on the basis of change in non-target disease in the face of SD or PR in target disease will therefore be extremely rare.

Clinically acceptable criteria for response to treatment in acute leukemias are as follows:

Complete remission (CR): The patient must be free of all symptoms related to leukemia and have an absolute neutrophil count of ≥$1.0\times10^9$/L, platelet count ≥$100\times10^9$/L, and normal bone marrow with ≤5% blasts and no Auer rods.

Complete remission with incomplete blood count recovery (Cri): As per CE, but with residual thrombocytopenia (platelet count <$100\times10^9$/L) or residual neutropenia (absolute neutrophil count <$1.0\times10^9$/L).

Partial remission (PR): A ≥50% decrease in bone marrow blasts to 5 to 25% abnormal cells in the marrow; or CR with ≤5% blasts if Auer rods are present.

Treatment failure: Treatment has failed to achieve CR, Cri, or PR. Recurrence.

Relapse after confirmed CR: Reappearance of leukemic blasts in peripheral blood or ≥5% blasts in the bone marrow not attributable to any other cause (e.g., bone marrow regeneration after consolidated therapy) or appearance of new dysplastic changes.

"Chemotherapeutic agent" refers to a drug used for the treatment of cancer. Chemotherapeutic agents include, but are not limited to, small molecules, hormones and hormone analogs, and biologics (e.g., antibodies, peptide drugs, nucleic acid drugs). In certain embodiments, chemotherapy does not include hormones and hormone analogs.

A "chemotherapeutic regimen" is a clinically accepted dosing protocol for the treatment of cancer that includes administration of one or more chemotherapeutic agents to a subject in specific amounts on a specific schedule. In certain embodiments, the chemotherapeutic agent can be an agent in clinical trials.

As used herein, "co-administration" or "combination therapy" is understood as administration of two or more active agents using separate formulations or a single pharmaceutical formulation, or consecutive administration in any order such that, there is a time period while both (or all) active agents simultaneously exert their biological activities. It is contemplated herein that one active agent (e.g., CoQ10) can improve the activity of a second agent, for example, can sensitize target cells, e.g., cancer cells, to the activities of the second agent. Co-administration does not require that the agents are administered at the same time, at the same frequency, or by the same route of administration. As used herein, "co-administration" or "combination therapy" includes administration of a CoQ10 compound with one or more additional anti-cancer agents, e.g., chemotherapeutic agents, or administration of two or more CoQ10 compounds. Examples of anticancer agents, including chemotherapeutic agents, are provided herein.

In a preferred embodiment, the additional anti-cancer agents, e.g., chemotherapeutic agents or chemotherapeutic regimen, administered in combination with CoQ10 in the methods of treatment provided herein do not include, i.e., exclude, CoQ10.

Chemotherapeutic regimens can include administration of a drug on a predetermined "cycle" including intervals of dosing and not dosing with one or more agents for the treatment of cancer. For example, an agent can be administered one or more times per week for three consecutive weeks followed by a week of no agent administered to provide a four week cycle. The cycle can be repeated so that the subject would be subjected to three treatment weeks, one no treatment week, three treatment weeks, one no treatment week, etc., for the desired number of cycles. In certain embodiments, treatment of efficacy and laboratory values (e.g., liver enzymes, blood count, kidney function) are assessed at the end of each cycle or every other cycle.

A "subject who has failed a chemotherapeutic regimen" is a subject with cancer that does not respond, or ceases to respond to treatment with a chemotherapeutic regimen per RECIST 1.1 criteria (see, Eisenhauer et al., 2009 and as discussed above), i.e., does not achieve at least stable disease (i.e., stable disease, partial response, or complete response) in the target lesion; or does not achieve at least non-CR/non-PD (i.e., non-CR/non-PD or complete response) of non-target lesions, either during or after completion of the chemotherapeutic regimen, either alone or in conjunction with surgery and/or radiation therapy which, when possible, are often clinically indicated in conjunction with chemotherapy. A failed chemotherapeutic regime results in, e.g., tumor growth, increased tumor burden, and/or tumor metastasis. In some embodiments, failed chemotherapeutic regimen as used herein includes a treatment regimen that was terminated due to a dose limiting toxicity, e.g., a grade III or a grade IV toxicity that cannot be resolved to allow continuation or resumption of treatment with the chemotherapeutic agent or regimen that caused the toxicity. In some embodiments, a "failed chemotherapeutic regimen includes a treatment regimen that does not result in at least stable disease for all target and non-target lesions for an extended period, e.g., at least 1 month, at least 2 months, at least 3 months, at least 4 months, at least 5 months, at least 6 months, at least 12 months, at least 18 months, or any time period less than a clinically defined cure. In some embodiments, a failed chemotherapeutic regimen includes a treatment regimen that results in progressive disease of at least one target lesion during treatment with the chemotherapeutic agent, or results in progressive disease less than 2 weeks, less than 1 month, less than two months, less than 3 months, less than 4 months, less than 5 months, less than 6 months, less than 12 months, or less than 18 months after the conclusion of the treatment regimen, or less than any time period less than a clinically defined cure.

A failed chemotherapeutic regimen does not include a treatment regimen wherein the subject treated for a cancer achieves a clinically defined cure, e.g., 5 years of complete response after the end of the treatment regimen, and wherein the subject is subsequently diagnosed with a distinct cancer, e.g., more than 5 years, more than 6 years, more than 7 years, more than 8 years, more than 9 years, more than 10 years, more than 11 years, more than 12 years, more than 13 years, more than 14 years, or more than 15 years after the end of the treatment regimen. For example, a subject who suffered from a pediatric cancer may develop cancer later in life after being cured of the pediatric cancer. In such a subject, the chemotherapeutic regimen to treat the pediatric cancer is considered to have been successful.

A "refractory cancer" is a malignancy for which surgery is ineffective, which is either initially unresponsive to chemo- or radiation therapy, or which becomes unresponsive to chemo- or radiation therapy over time.

A "therapeutically effective amount" is that amount sufficient to treat a disease in a subject. A therapeutically effective amount can be administered in one or more administrations.

The terms "administer", "administering" or "administration" include any method of delivery of a pharmaceutical composition or agent into a subject's system or to a particular region in or on a subject. In certain embodiments, the agent is delivered orally. In certain embodiments, the agent is administered parenterally. In certain embodiments, the agent is delivered by injection or infusion. In certain embodiments, the agent is delivered topically including transmucosally. In certain embodiments, the agent is delivered by inhalation. In certain embodiments of the invention, an agent is administered by parenteral delivery, including, intravenous, intramuscular, subcutaneous, intramedullary injections, as well as intrathecal, direct intraventricular, intraperitoneal, intranasal, or intraocular injections. In one embodiment, the compositions provided herein may be administered by injecting directly to a tumor. In some embodiments, the formulations of the invention may be administered by intravenous injection or intravenous infusion. In certain embodiments, the formulation of the invention can be administered by continuous infusion. In certain embodiments, administration is not oral. In certain embodiments, administration is systemic. In certain embodiments, administration is local. In some embodiments, one or more routes of administration may be combined, such as, for example, intravenous and intratumoral, or intravenous and peroral, or intravenous and oral, intravenous and topical, or intravenous and transdermal or transmucosal. Administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc.; or for delivery by a trained professional, e.g., intravenous delivery, intramuscular delivery, intratumoral delivery, etc.

"Adverse events" or "AEs" are characterized by grade depending on the severity. Some AE (e.g., nausea, low blood counts, pain, reduced blood clotting) can be treated so that the specific chemotherapeutic regimen can be continued or resumed. Some adverse events (e.g., loss of cardiac, liver, or kidney function; nausea) may not be treatable, requiring termination of treatment with the drug. Determination of AE grade and appropriate interventions can be determined by those of skill in the art. Common Terminology Criteria for Adverse Events v4.0 (CTCAE) (Publish Date: May 28, 2009) provide a grading scale for adverse events as follows:

Grade 1 Mild; asymptomatic or mild symptoms; clinical or diagnostic observations only; intervention not indicated.

Grade 2 Moderate; minimal, local or noninvasive intervention indicated; limiting age-appropriate instrumental activities of daily life (ADL).

Grade 3 Severe or medically significant but not immediately life-threatening; hospitalization or prolongation of hospitalization indicated; disabling, limiting self care ADL.

Grade 4 Life-threatening consequences; urgent intervention indicated.

Grade 5 Death related to adverse event.

As used herein, the term "survival" refers to the continuation of life of a subject which has been treated for a disease or condition, e.g., cancer. The time of survival can be defined from an arbitrary point such as time of entry into a clinical trial, time from completion or failure or an earlier treatment regimen, time from diagnosis, etc.

As used herein, "opsonization" refers to the process by which a lipophilic bioactive agent as described herein is marked for ingestion and destruction by a phagocyte. Opsonization involves the binding of an opsonin to bioactive agent. After opsonin binds to the membrane, phagocytes are attracted to the active agent. An opsonin is any molecule that acts as a binding enhancer for the process of phagocytosis.

As used herein, the term "opsonization reducer" refers to any agent that works in conjunction with the active agent to reduce the ability of opsonins to act as a binding enhancer for the process of phagocytosis.

As used herein, a "dispersion" refers to a system in which particles of colloidal size of any nature (e.g., solid, liquid or gas) are dispersed in a continuous phase of a different composition or state. In intravenous drug delivery the continuous phase is substantially water and the dispersed particles can be solid (a suspension) or an immiscible liquid (emulsion).

A "subject" to be treated by the method of the invention can mean either a human or non-human animal, preferably a mammal, more preferably a human. In certain embodiments, a subject has a detectable tumor prior to initiation of treatments using the methods of the invention. In certain embodiments, the subject has a detectable tumor at the time of initiation of the treatments using the methods of the invention.

As used herein, the term "safe and therapeutic effective amount" refers to the quantity of a component which is sufficient to yield a desired therapeutic response without undue adverse side effects (such as toxicity, irritation, or allergic response) commensurate with a reasonable benefit/risk ratio when used in the manner of this disclosure.

"Therapeutically effective amount" means the amount of a compound that, when administered to a patient for treating a disease, is sufficient to effect such treatment for the disease. When administered for preventing a disease, the amount is sufficient to avoid or delay onset of the disease. The "therapeutically effective amount" will vary depending on the compound, the disease and its severity and the age, weight, etc., of the patient to be treated. A therapeutically effective amount need not be curative. A therapeutically effective amount need not prevent a disease or condition from ever occurring. Instead a therapeutically effective amount is an amount that will at least delay or reduce the onset, severity, or progression of a disease or condition. Disease progression can be monitored, for example, by one or more of tumor burden, time to progression, survival time, or other clinical measurements used in the art.

The term "therapeutic effect" refers to a local or systemic effect in animals, particularly mammals, and more particularly humans caused by a pharmacologically active substance. The term thus means any substance intended for use in the diagnosis, cure, mitigation, treatment or prevention of disease or in the enhancement of desirable physical or mental development and conditions in an animal or human. The phrase "therapeutically-effective amount" means that amount of such a substance that produces some desired local or systemic effect at a reasonable benefit/risk ratio applicable to any treatment. In certain embodiments, a therapeutically-effective amount of a compound will depend on its therapeutic index, solubility, and the like.

"Preventing" or "prevention" refers to a reduction in risk of acquiring a disease or disorder (i.e., causing at least one of the clinical signs or symptoms of the disease not to develop in a patient that may be exposed to or predisposed to the disease but does not yet experience or display symptoms of the disease). Prevention does not require that the disease or condition never occur, or recur, in the subject.

The terms "disorders" and "diseases" are used inclusively and refer to any deviation from the normal structure or function of any part, organ or system of the body (or any combination thereof). A specific disease is manifested by characteristic symptoms and signs, including biological, chemical and physical changes, and is often associated with a variety of other factors including, but not limited to, demographic, environmental, employment, genetic and medically historical factors. Certain characteristic signs, symptoms, and related factors can be quantitated through a variety of methods to yield important diagnostic information.

In all occurrences in this application where there are a series of recited numerical values, it is to be understood that any of the recited numerical values may be the upper limit or lower limit of a numerical range. It is to be further understood that the invention encompasses all such numerical ranges, i.e., a range having a combination of an upper numerical limit and a lower numerical limit, wherein the numerical value for each of the upper limit and the lower limit can be any numerical value recited herein. Ranges provided herein are understood to include all values within the range. For example, 1-10 is understood to include all of the values 1, 2, 3, 4, 5, 6, 7, 8, 9, and 10, and fractional values as appropriate. Ranges expressed as "up to" a certain value, e.g., up to 5, is understood as all values, including the upper limit of the range, e.g., 0, 1, 2, 3, 4, and 5, and fractional values as appropriate. Up to or within a week is understood to include, 0.5, 1, 2, 3, 4, 5, 6, or 7 days. Similarly, ranges delimited by "at least" are understood to include the lower value provided and all higher numbers.

All percent formulations are w/w unless otherwise indicated.

As used herein, "about" is understood to include within three standard deviations of the mean or within standard ranges of tolerance in the specific art. In certain embodiments, about is understood a variation of no more than 0.5.

The articles "a" and "an" are used herein to refer to one or to more than one (i.e. to at least one) of the grammatical object of the article. By way of example, "an element" means one element or more than one element.

The term "including" is used herein to mean, and is used interchangeably with, the phrase "including but not limited to".

The term "or" is used inclusively herein to mean, and is used interchangeably with, the term "and/or," unless context clearly indicates otherwise.

The term "such as" is used herein to mean, and is used interchangeably, with the phrase "such as but not limited to".

The term "standard dosage" as used herein refers to a dosage of a therapeutic agent that is commonly used for treatment of a disorder. For example, the recommended dosage of a therapeutic agent described in a product insert by a manufacturer of the therapeutic agent would be considered a standard dosage. Examples of standard dosages of chemotherapeutic agents are provided in Table 3.

For example, as shown in Table 3, the standard dose of gemcitabine for intravenous use for treatment of ovarian cancer is 1000 mg/m2 over 30 minutes on Days 1 and 8 of each 21-day cycle; the standard dose of gemcitabine for intravenous use for treatment of breast cancer is 1250 mg/m2 over 30 minutes on Days 1 and 8 of each 21-day cycle; the standard dose of gemcitabine for intravenous use for treatment of Non-Small Cell Lung Cancer is 1000 mg/m2 over 30 minutes on Days 1, 8, and 15 of each 28-day cycle or 1250 mg/m2 over 30 minutes on Days 1 and 8 of each 21-day cycle; and the standard dose of gemcitabine for intravenous use for treatment of pancreatic Cancer: 1000 mg/m2 over 30 minutes once weekly for the first 7 weeks, then one week rest, then once weekly for 3 weeks of each 28-day cycle.

II. Coenzyme Q10 Compounds

It will be understood that all of the methods provided in the instant invention may involve administration of, in place of Coenzyme Q10, any other Coenzyme Q10 compound, or a combination thereof. Coenzyme Q10 compounds are intended to include a class of CoQ10 compounds. Coenzyme Q10 compounds effective for the methods described herein include CoQ10, a metabolite of CoQ10, a biosynthetic precursor of CoQ10, an analog of CoQ10, a derivative of CoQ10, and CoQ10 related compounds. An analog of CoQ10 includes analogs having no or at least one isoprenyl repeats. CoQ10 has the following structure:

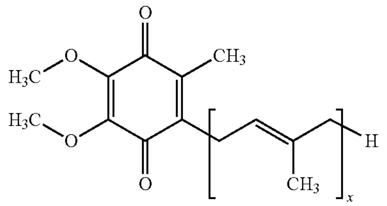

wherein x is 10. In the instant invention, CoQ10 compounds can include derivatives of CoQ10 in which x is any number of isoprenyl units from 4-10, or any number of isoprenyl units from 6-10, or any number of isoprenyl units from 8-10, or 9-10 isoprenyl units. CoQ10 includes the fully oxidized version, also known as ubiquinone, the partially oxidized version, also known as semiquinone or ubisemiquinone, or the fully reduced version, also known as ubiquinol; or any mixtures or combinations thereof. In certain embodiments, the CoQ10 compound for treatment of cancer is ubiquinone. In certain embodiments, the CoQ10 compound for treatment of cancer is ubiquinol.

In certain embodiments of the present invention, the therapeutic agent is Coenzyme Q10 (CoQ10). Coenzyme Q10, also referred to herein as CoQ10, is also known as ubiquinone, or ubidecarenone. CoQ10 is art-recognized and further described in International Publication No. WO 2005/069916 (Appln. No. PCT/US2005/001581), WO 2008/116135 (Appln. No. PCT/US08/57786), WO2010/132507 (Appln. No. PCT/US2010/034453), WO 2011/112900 (Appln. No. PCT/US2011/028042), and WO2012/174559 (Appln. No. PCT/US2012/043001) the entire contents of each of which are expressly incorporated by reference herein. CoQ10 is one of a series of polyprenyl 2,3-dimethoxy-5-methylbenzoquinone (ubiquinone) present in the mitochondrial electron transport systems of eukaryotic cells. Human cells produce CoQ10 exclusively and it is found in cell and mitochondrial membranes of all human cells, with the highest levels in organs with high energy requirements, such as the liver and the heart. The body pool of CoQ10 has been estimated to be about 2 grams, of which more than 50% is endogenous. Approximately 0.5 grams of CoQ10 is required from the diet or biosynthesis each day. CoQ10 is produced in ton quantities from the worldwide supplement market and can be obtained from Kaneka, with plants in Pasadena, Texas and Takasagoshi, Japan.

Coenzyme Q10 related compounds include, but are not limited to, benzoquinones, isoprenoids, farnesols, farnesyl acetate, farnesyl pyrophosphate, 1-phenylalanine, d-phenylalanine, dl-phenylalanine, 1-tyrosine, d-tyrosine, dl-tyrosine, 4-hydroxy-phenylpyruvate, 4-hydroxy-phenyllactate, 4-hydroxy-cinnamate, dipeptides and tripeptides of tyrosine or phenylalanine, 3,4-dihydroxymandelate, 3-methoxy-4-hydroxyphenylglycol, 3-methoxy-4-hydroxymandelate, vanillic acid, phenylacetate, pyridoxine, S-adenosyl methionine, panthenol, mevalonic acid, isopentyl pyrophosphate, phenylbutyrate, 4-hydroxy-benzoate, decaprenyl pyrophosphate, beta-hydroxybutyrate, 3-hydroxy-3-methyl-glutarate, acetylcarnitine, acetoacetylcarnitine, acetylglycine, acetoacetylglycine, carnitine, acetic acid, pyruvic acid, 3-hydroxy-3-methylglutarylcarnitine, all isomeric forms of serine, alanine, cysteine, glycine, threonine, hydroxyproline, lysine, isoleucine, and leucine, even carbon number C4 to C8 fatty acids (butyric, caproic, caprylic, capric, lauric, myristic, palmitic, and stearic acids) salts of carnitine and glycine, e.g., palmitoylcarnitine and palmitoylglycine, and 4-hydroxy-benzoate polyprenyltransferase, any salts of these compounds, as well as any combinations thereof, and the like. In certain embodiments, such agents can be used for the treatment of a cancer according to the methods provided herein.

Metabolites and biosynthetic precursors of CoQ10 include, but are not limited to, those compounds that are formed between the chemical/biological conversion of tyrosine and acetyl-CoA to ubiquinol. Intermediates of the coenzyme biosynthesis pathway include tyrosine, acetyl-CoA, 3-hexaprenyl-4-hydroxybenzoate, 3-hexaprenyl-4,5-dihydroxybenzoate, 3-hexaprenyl-4-hydroxy-5-methoxybenzoate, 2-hexaprenyl-6-methoxy-1,4-benzoquinone, 2-hexaprenyl-3-methyl-6-methoxy-1,4-benzoquinone, 2-hexaprenyl-3-methyl-5-hydroxy-6-methoxy-1,4-benzoquinone, 3-Octaprenyl-4-hydroxybenzoate, 2-octaprenylphenol, 2-octaprenyl-6-metholxyphenol, 2-octaprenyl-3-methyl-6-methoxy-1,4-benzoquinone, 2-octaprenyl-3-methyl-5-hydroxy-6-methoxy-1,4-benzoquinone, 2-decaprenyl-3-methyl-5-hydroxy-6-methoxy-1,4-benzoquinone, 2-decaprenyl-3-methyl-6-methoxy-1,4-benzoquinone, 2-decaprenyl-6-methoxy-1,4-benzoquinone, 2-decaprenyl-6-methoxyphenol, 3-decaprenyl-4-hydroxy-5-methoxybenzoate, 3-decaprenyl-4,5-dihydroxybenzoate, 3-decaprenyl-4-hydroxybenzoate, 4-hydroxy phenylpyruvate, 4-hydroxyphenyllactate, 4-hydroxy-benzoate, 4-hydroxycinnamate, and hexaprenydiphosphate. In certain embodiments, such agents can be used for the treatment of a cancer according to the methods provided herein.

III. Compositions

The present disclosure provides compositions containing a CoQ10 compound, e.g., Coenzyme Q10, for the treatment and prevention of cancer. The compositions of the present disclosure can be administered to a patient either by themselves, or in pharmaceutical compositions where it is mixed with suitable carriers or excipient(s). In treating a patient exhibiting an oncological disorder, a therapeutically effective amount of the CoQ10 compound is administered.

Suitable routes of administration of the present compositions of the invention may include parenteral delivery, including, intravenous, intramuscular, subcutaneous, intramedullary injections, as well as intrathecal, direct intraventricular, intraperitoneal, intranasal, or intraocular injections, just to name a few. In one embodiment, the compositions provided herein may be administered by injecting directly to a tumor. In some embodiments, the formulations of the invention may be administered by intravenous injection or intravenous infusion. In some embodiments, the formulation is administered by continuous infusion. In one embodiment, the compositions of the invention are administered by intravenous injection. In one embodiment, the compositions of the invention are administered by intravenous infusion. Where the route of administration is, for example intravenous infusion, embodiments are provided herein where the IV infusion comprises the active agent, e.g., CoQ10, at approximately a 40 mg/mL concentration. Where the composition is administered by IV infusion, it can be diluted in a pharmaceutically acceptable aqueous solution such as phosphate buffered saline or normal saline. In some embodiments, one or more routes of administration may be combined, such as, for example, intravenous and intratumoral, or intravenous and peroral, or intravenous and oral, or intravenous and topical, transdermal, or transmucosal.

The compositions described herein may be administered to a subject in any suitable formulation. These include, for example, liquid, semi-solid, and solid dosage forms, such as liquid solutions (e.g., injectable and infusible solutions), dispersions or suspensions, tablets, pills, powders, creams, lotions, liniments, ointments, or pastes, drops for administration to the eye, ear or nose, liposomes, and suppositories. The preferred form depends on the intended mode of administration and therapeutic application.

In certain embodiments, a CoQ10 compound, e.g., CoQ10, may be prepared with a carrier that will protect against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

For example, a CoQ10 compound e.g., CoQ10, can be formulated for parenteral delivery, e.g., for subcutaneous, intravenous, intramuscular, or intratumoral injection. The compositions may be administered in a single bolus, multiple injections, or by continuous infusion (for example, intravenously or by peritoneal dialysis). For parenteral administration, the compositions may be formulated in a sterilized pyrogen-free form.

Use of pharmaceutically acceptable carriers to formulate the compounds herein disclosed, for the practice of the present invention, into dosages suitable for systemic administration is within the scope of the present disclosure. With proper choice of carrier and suitable manufacturing practice, the compositions of the present disclosure, in particular, those formulated as solutions, may be administered parenterally, such as by intravenous injection.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices may be desirable. The data obtained from these cell culture assays and animal studies can be used in formulating a range of dosage for use in human. The dosage of such compounds may be within a range of circulating concentrations that include the ED50 with little or no toxicity. The dosage may vary within this range depending upon the dosage form employed and the route of administration utilized.

Pharmaceutical compositions suitable for use in the present invention include compositions wherein the active ingredients are contained in an effective amount to achieve its intended purpose. Determination of the effective amounts is well within the capability of those skilled in the art, especially in light of the detailed disclosure provided herein. In addition to the active ingredients, these pharmaceutical compositions may contain suitable pharmaceutically acceptable carriers including excipients and auxiliaries which facilitate processing of the active compounds into preparations which can be used pharmaceutically. The preparations formulated for intravenous administration may be in the form of solutions of colloidal dispersion.

Pharmaceutical compositions for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

IV. Formulations

The active agent, e.g., a CoQ10 compound, e.g., CoQ10, can be delivered in any pharmaceutically acceptable carrier for the desired route of administration. As used herein, formulations including CoQ10 compounds are formulated for any route of administration unless otherwise clearly indicated. In preferred embodiments, the formulations are for administration by injection, infusion, or topical administration. In certain embodiments, the CoQ10 compounds are not delivered orally.

Preferred therapeutic formulations for use in the methods of the invention comprise the active agent (e.g., a CoQ10 compound, e.g., CoQ10) in a microparticle formation, e.g., for intravenous administration. Such intravenous formulations are provided, for example, in WO2011/112900 (Appln. No. PCT/US2011/028042), the entire contents of which are expressly incorporated herein by reference, and an exemplary intravenous formulation as described in WO2011/112900 (Appln. No. PCT/US2011/028042) is used in the examples set forth below. Through high pressure homogenization, active agent (e.g., a CoQ10 compound, e.g., CoQ10) particles are reduced to produce particles that are small enough to pass through a 200-nm sterilizing filter. Particles that are small enough to pass through a 200-nm sterilizing filter can be injected intravenously. These particles are much smaller than blood cells and therefore will not embolize capillaries. Red blood cells for example are 6-micron×2-micron disks. The particles are dispersed to and are encased or surrounded by a stabilizing agent. While not wishing to be bound by any theory, it is believed that the stabilizing agents are attracted to the hydrophobic therapeutic agent such that the dispersed particles of the hydrophobic therapeutic agent are surrounded by the stabilizing agent forming a suspension or an emulsion. The dispersed particles in the suspension or emulsion comprises a stabilizing agent surface and a core consisting of the hydrophobic therapeutic agent, e.g., a CoQ10 compound, e.g., CoQ10, in a solid particulate form (suspension) or in an immiscible liquid form (emulsion). The dispersed particles can be entrenched in the lipophilic regions of a liposome.

Dispersed colloidal systems permit a high drug load in the formulation without the use of co-solvents. Additionally, high and relatively reproducible plasma levels are achieved without the dependence on endogenous low-density lipoprotein carriers. More importantly, the formulations allow sustained high drug levels in solid tumors due to the passive accumulation of the colloidal particles of the hydrophobic therapeutic agent.

A preferred intravenous formulation substantially comprises a continuous phase of water and dispersed solids (suspension) or dispersed immiscible liquid (emulsion). Dispersed colloidal systems, in which the particles are composed largely of the active agent (drug) itself, can often deliver more drug per unit volume than continuous solubilizing systems, if the system can be made adequately stable.

As the formulation medium, the aqueous solution may include Hank's solution, Ringer's solution, phosphate buffered saline (PBS), physiological saline buffer or other suitable salts or combinations to achieve the appropriate pH and osmolarity for parenterally delivered formulations. Aqueous solutions can be used to dilute the formulations for administration to the desired concentration. For example, aqueous solutions can be used to dilute a formulation for intravenous administration from a concentration of about 4% w/v to a lower concentration to facilitate administration of lower doses of CoQ10. The aqueous solution may contain substances which increase the viscosity of the solution, such as sodium carboxymethyl cellulose, sorbitol, or dextran.

The active agent (e.g., a CoQ10 compound, e.g., CoQ10) is dispersed in the aqueous solution such that a colloidal dispersion is formed wherein the nano-dispersion particles of the hydrophobic therapeutic agent are covered or encased or encircled by the dispersion stabilizing agents to form nano-dispersions of the active agent (e.g., a CoQ10 compound, e.g., CoQ10) particles. The nano-dispersed active agent (e.g., a CoQ10 compound, e.g., CoQ10) particles have a core formed of the hydrophobic therapeutic agent that is surrounded by the stabilizing agent. Similarly, in certain aspects, the stabilizing agent is a phospholipid having both a hydrophilic and lipophilic portion. The phospholipids form liposomes or other nanoparticles upon homogenization. In certain aspects these liposomes are bi-layered unilamellar liposomes while in other embodiments the liposomes are bi-layered multi-lamellar liposomes. The dispersed active agent (e.g., a CoQ10 compound, e.g., CoQ10) particles are dispersed in the lipophilic portion of the bi-layered structure of the liposome formed from the phospholipids. In certain other aspects the core of the liposome, like the core of the nano-dispersion of active agent (e.g., a CoQ10 compound, e.g., CoQ10) particles, is formed of the hydrophobic therapeutic agent and the outer layer is formed of the bi-layered structure of the phospholipid. In certain embodiments the colloidal dispersions are treated by a lyophilization process whereby the nanoparticle dispersion is converted to a dry powder.

In some embodiments, the formulation for injection or infusion used is a 4% sterile aqueous colloidal dispersion containing CoQ10 in a nanosuspension as prepared in WO2011/112900. In certain embodiments, the formulation includes an aqueous solution; a hydrophobic active agent, e.g., CoQ10, a CoQ10 precursor or metabolite or a CoQ10 related compound, dispersed to form a colloidal nano-dispersion of particles; and at least one of a dispersion stabilizing agent and an opsonization reducer; wherein the colloidal nano-dispersion of the active agent is dispersed into nano-dispersion particles having a mean size of less than 200-nm.

In certain embodiments, the dispersion stabilizing agent includes, but is not limited to, pegylated castor oil, Cremphor® EL, Cremophor® RH 40, Pegylated vitamin E, Vitamin E TPGS, and Dimyristoylphosphatidyl choline (DMPC).

In certain embodiments, the opsonization reducer is a poloxamer or a poloxamines.

In certain embodiments, the colloidal nano-dispersion is a suspension or an emulsion. Optionally, a colloidal nano-dispersion is in a crystalline form or a super-cooled melt form.

In certain embodiments, the formulation for injection or infusion includes a lyoprotectant such as a nutritive sugar including, but not limited to, lactose, mannose, maltose, galactose, fructose, sorbose, raffinose, neuraminic acid, glucosamine, galactosamine, N-methylglucosamine, mannitol, sorbitol, arginine, glycine and sucrose, or any combination thereof.

In certain embodiments, the formulation for injection or infusion includes an aqueous solution; a hydrophobic active agent dispersed to form a colloidal nano-dispersion of particles; and at least one of a dispersion stabilizing agent and an opsonization reducer. The colloidal nano-dispersion of the active agent is dispersed into nano-dispersion particles having sizes of less than 200-nm. In some embodiments the dispersion stabilizing agent is selected from natural or semisynthetic phospholipids. For example, suitable stabilizing agents include polyethoxylated (a/k/a pegylated) castor oil (Cremophor® EL), polyethoxylated hydrogenated castor oil (Cremophor® RH 40), Tocopherol polyethylene glycol succinate (Pegylated vitamin E, Vitamin E TPGS), Sorbitan fatty acid esters (Spans®), Bile acids and bile-acid salts or Dimyristoylphosphatidyl choline (DMPC). In some embodiments the stabilizing agent is DMPC.

In certain embodiments the formulation is suitable for parenteral administration, including intravenous, intraperitoneal, orthotopical, intracranial, intramuscular, subcutaneous, intramedullary injections, as well as intrathecal, direct intraventricular, intranasal, or intraocular injections. In certain embodiments, the formulation contains CoQ10, dimyristoyl-phophatidylcholine, and poloxamer 188 in a ratio of 4:3:1.5 respectively that is designed to stabilize the nanosuspension of the particles. In some embodiments, the formulation includes a phosphate buffer saline solution which contains sodium phosphate dibasic, potassium phosphate monobasic, potassium chloride, sodium chloride and water for injection. In certain embodiments, the 4% sterile aqueous colloidal dispersion containing CoQ10 in a nanosuspension is diluted in the phosphate buffered saline solution provided, e.g., 1:1, 1:2, 1:3, 1:4. 1:5, 1:6, 1:7, 1:8. 1:9, 1:10, 1:11, 1:12, 1:13, 1:14. 1:15, 1:16, 1:17, 1:18. 1:19, 1:20, or other appropriate ratio bracketed by any two of the values.

In some embodiments, the formulation is a topical formulation. Topical formulations of CoQ10 compounds are provided, for example in WO2010/132507 (PCT Appln. No. PCT/US2010/034453), WO2008116135 (PCT Appln. No. PCT/US2008/116135), and WO2005/069916 (PCT Appln. PC/US2005/001581), the entire contents of each of which are expressly incorporated herein by reference.

Formulations suitable for topical administration include liquid or semi-liquid preparations suitable for penetration through the skin, such as liniments, lotions, creams, ointments or pastes, and drops suitable for administration to the eye, ear, or nose. Drops according to the present disclosure may include sterile aqueous or oily solutions or suspensions and may be prepared by dissolving the active ingredient in a suitable aqueous solution of a bactericidal and/or fungicidal agent and/or any other suitable preservative, and in some embodiments including a surface active agent. The resulting solution may then be clarified and sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present disclosure include those suitable for application to the skin or eye. An eye lotion may include a sterile aqueous solution optionally containing a bactericide and may be prepared by methods similar to those for the preparation of drops. Lotions or liniments for application to the skin may also include an agent to hasten drying and to cool the skin, such as an alcohol, and/or a moisturizer such as glycerol or an oil such as castor oil or arachis oil.

Creams, ointments or pastes useful in the methods of the invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy basis. The basis may include hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogels. The formulation may incorporate any suitable surface active agent such as an anionic, cationic or non-ionic surface active such as sorbitan esters or polyoxyethylene derivatives thereof. Suspending agents such as natural gums, cellulose derivatives or inorganic materials such as silicaceous silicas, and other ingredients such as lanolin, may also be included.

In some embodiments, the remaining component of a topical delivery vehicle may be water or a water phase, in embodiments purified, e.g. deionized, water, glycerine, propylene glycol, ethoxydiglycol, phenoxyethanol, and cross linked acrylic acid polymers. Such delivery vehicle compositions may contain water or a water phase in an amount of from about 50 to about 95 percent, based on the total weight of the composition. The specific amount of water present is not critical, however, being adjustable to obtain the desired viscosity (usually about 50 cps to about 10,000 cps) and/or concentration of the other components. The topical delivery vehicle may have a viscosity of at least about 30 centipoises.

Topical formulations can also include an oil phase including, for example, oil phase which, in turn, may include emollients, fatty alcohols, emulsifiers, combinations thereof, and the like. For example, an oil phase could include emollients such as C12-15 alkyl benzoates (commercially available as FINSOLV™ TN from Finetex Inc. (Edison, N.J.)), capric-caprylic triglycerides (commercially available from Huls as MIGLYOL™ 812), and the like. Other suitable emollients which may be utilized include vegetable derived oils (corn oil, safflower oil, olive oil, macadamian nut oil, etc.); various synthetic esters, including caprates, linoleates, dilinoleates, isostearates, fumarates, sebacates, lactates, citrates, stearates, palmitates, and the like; synthetic medium chain triglycerides, silicone oils or polymers; fatty alcohols such as cetyl alcohol, stearyl alcohol, cetearyl alcohol, lauryl alcohol, combinations thereof, and the like; and emulsifiers including glyceryl stearate, PEG-100 stearate, Glyceryl Stearate, Glyceryl Stearate SE, neutralized or partially neutralized fatty acids, including stearic, palmitic, oleic, and the like; vegetable oil extracts containing fatty acids, Ceteareth®-20, Ceteth®-20, PEG-150 Stearate, PEG-8 Laurate, PEG-8 Oleate, PEG-8 Stearate, PEG-20 Stearate, PEG-40 Stearate, PEG-150 Distearate, PEG-8 Distearate, combinations thereof, and the like; or other non-polar cosmetic or pharmaceutically acceptable materials used for skin emolliency within the purview of those skilled in the art, combinations thereof, and the like.

Topical formulations can also include a liposomal concentrate including, for example, a phospholipid such as lecithin, lysolecithin, phosphatidylcholine, phosphatidylethanolamine, phosphatidylinositol, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, and combinations thereof, at least one lipophilic bioactive agent, and at least one solubilizer. The liposomal concentrate may be in combination with at least one pharmaceutically acceptable carrier possessing at least one permeation enhancer in an amount from about 0.5% by weight to about 20% by weight of the composition. The phospholipid may present in the composition in an amount from about 2% to about 20% by weight of the composition and the bioactive agent may be present in an amount from about 0.5% to about 20% by weight of the composition.

Transdermal skin penetration enhancers can also be used to facilitate delivery of CoQ10. Illustrative are sulfoxides such as ethoxydiglycol, 1,3-butylene glycol, isopentyl diol, 1,2-pentane diol, propylene glycol, 2-methyl propan-2-ol, propan-2-ol, ethyl-2-hydroxypropanoate, hexan-2,5-diol, di(2-hydroxypropyl)ether, pentan-2,4-diol, acetone, polyoxyethylene(2)methyl ether, 2-hydroxypropionic acid, 2-hydroxyoctanoic acid, propan-1-ol, 1,4 dioxane, tetrahydrofuran, butan-1,4-diol, propylene glycol dipelargonate, polyoxypropylene 15 stearyl ether, octyl alcohol, polyoxyethylene ester of oleyl alcohol, oleyl alcohol, lauryl alcohol, dioctyl adipate, dicapryl adipate, diisopropyl adipate, diisopropyl sebacate, dibutyl sebacate, diethyl sebacate, dimethyl sebacate, dioctyl sebacate, dibuyl suberate, dioctyl azelate, dibenzyl sebacate, dibutyl phthalate, dibutyl azelate, ethyl myristate, dimethyl azelate, butyl myristate, dibutyl succinate, didecyl phthalate, decyl oleate, ethyl caproate, ethyl salicylate, isopropyl palmitate, ethyl laurate, 2-ethyl-hexyl pelargonate, isopropyl isostearate, butyl laurate, benzyl benzoate, butyl benzoate, hexyl laurate, ethyl caprate, ethyl caprylate, butyl stearate, benzyl salicylate, 2-hyroxyoctanoic acid, dimethyl sulphoxide, methyl sufonyl methane, n,n-dimethyl acetamide, n,n-dimethyl formamide, 2-pyrrolidone, 1-methyl-2-pyrrolidone, 5-methyl-2-pyrrolidone, 1,5-dimethyl-2-pyrrolidone, 1-ethyl-2-pyrrolidone, phosphine oxides, sugar esters, tetrahydrofurfural alcohol, urea, diethyl-m-toluamide, 1-dodecylazacyloheptan-2-one, and combinations thereof.

Solubilizers, particularly for topical administration can include, but are not limited to, polyoxyalkylene dextrans, fatty acid esters of saccharose, fatty alcohol ethers of oligoglucosides, fatty acid esters of glycerol, fatty acid esters of polyoxyethylenes, polyethoxylated fatty acid esters of sorbitan, fatty acid esters of poly(ethylene oxide), fatty alcohol ethers of poly(ethylene oxide), alkylphenol ethers of poly(ethylene oxide), polyoxyethylene-polyoxypropylene block copolymers, ethoxylated oils, and combinations thereof.

Topical formulations can include emollients, including, but not limited to, C12-15 alkyl benzoates, capric-caprylic triglycerides, vegetable derived oils, caprates, linoleates, dilinoleates, isostearates, fumarates, sebacates, lactates, citrates, stearates, palmitates, synthetic medium chain triglycerides, silicone oils, polymers and combinations thereof; the fatty alcohol is selected from the group consisting of cetyl alcohol, stearyl alcohol, cetearyl alcohol, lauryl alcohol and combinations thereof; and the emulsifier is selected from the group consisting of glyceryl stearate, polyethylene glycol 100 stearate, neutralized fatty acids, partially neutralized fatty acids, polyethylene glycol 150 stearate, polyethylene glycol 8 laurate, polyethylene glycol oleate, polyethylene glycol 8 stearate, polyethylene glycol 20 stearate, polyethylene glycol 40 stearate, polyethylene glycol 150 distearate, polyethylene glycol 8 distearate, and combinations thereof.

Topical formulations can include a neutralization phase comprising one or more of water, amines, sodium lactate, and lactic acid.

The water phase can further optionally include one or more of water phase comprises the permeation enhancer optionally in combination with a viscosity modifier selected from the group consisting of cross linked acrylic acid polymers, pullulan, mannan, scleroglucans, polyvinylpyrrolidone, polyvinyl alcohol, guar gum, hydroxypropyl guar gum, xanthan gum, acacia gum, arabia gum, tragacanth, galactan, carob gum, karaya gum, locust bean gum, carrageenin, pectin, amylopectin, agar, quince seed, rice starch, corn starch, potato starch, wheat starch, algae extract, dextran, succinoglucan, carboxymethyl starch, methylhydroxypropyl starch, sodium alginate, alginic acid propylene glycol esters, sodium polyacrylate, polyethylacrylate, polyacrylamide, polyethyleneimine, bentonite, aluminum magnesium silicate, laponite, hectonite, and anhydrous silicic acid.

Topical formulations can also include a pigment such as titanium dioxide.

In an embodiment, a topical formulation for use in the methods of the invention includes an oil phase comprising C12-15 alkyl benzoates or capric/caprylic triglyceride, cetyl alcohol, stearyl alcohol, glyceryl stearate, and polyethylene glycol 100 stearate, in an amount of from about 5% to about 20% by weight of the composition; a water phase comprising glycerin, propylene glycol, ethoxydiglycol, phenoxyethanol, water, and a crosslinked acrylic acid polymer, in an amount of from about 60 to about 80% by weight of the composition; a neutralization phase comprising water, triethanolamine, sodium lactate, and lactic acid, in an amount of from about 0.1% to about 15% by weight of the composition; a pigment comprising titanium dioxide in an amount of from about 0.2% to about 2% by weight of the composition; and a liposomal concentrate comprising a polyethoxylated fatty acid ester of sorbitan, coenzyme Q10, a phosphatidylcholine lecithin, phenoxyethanol, propylene glycol, and water, in an amount of from about 0.1% to about 30% by weight of the composition, wherein the propylene glycol and ethoxydiglycol are present in a combined amount of from 3% by weight to about 15% by weight of the composition and the coenzyme Q10 is present in an amount of from about 0.75% by weight to about 10% by weight of the composition. Other formulations for use in the methods of the invention are provided, for example, in WO2008/116135 (PCT Application No. PCT/US08/57786), and in WO2010/132507 (PCT/US2010/034453), the entire contents of each of which are expressly incorporated herein by reference.

In one embodiment, a topical formulation for use in the methods of the invention is a 3% CoQ10 cream as described in US 2011/0027247, the entire contents of which are incorporated by reference herein. In one embodiment, the 3% CoQ10 comprises:

(1) a phase A having C12-15 alkyl benzoate or capric/caprylic triglyceride at about 4.0% w/w of the composition, cetyl alcohol at about 2.00% w/w of the composition, stearyl alcohol at about 1.5% w/w, glyceryl stearate and PEG-100 at about 4.5% w/w;

(2) a phase B having glycerin at about 2.00% w/w, propylene glycol at about 1.5% w/w, ethoxydiglycol at about 5.0% w/w, phenoxyethanol at about 0.475% w/w, a carbomer dispersion at about 40% w/w, purified water at about 16.7% w/w;

(3) a phase C having triethanolamine at about 1.3% w/w, lactic acid at about 0.5% w/w, sodium lactate solution at about 2.0% w/w, water at about 2.5% w/w;

(4) a phase D having titanium dioxide at about 1.0% w/w; and (5) a phase E having CoQ10 21% concentrate at about 15.0% w/w.

A CoQ10 21% concentrate composition (phase E in above 3% cream) can be prepared by combining phases A and B as described below. Phase A includes Ubidecarenone USP (CoQ10) at 21% w/w and polysorbate 80 NF at 25% w/w. Phase B includes propylene glycol USP at 10.00% w/w, phenoxyethanol NF at 0.50% w/w, lecithin NF (PHOSPHOLIPON 85G) at 8.00% w/w and purified water USP at 35.50% w/w. All weight percentages are relative to the weight of the entire CoQ10 21% concentrate composition. The percentages and further details are listed in the following table.

TABLE 1

| Phase | Trade Name | INCI Name | Percent |
|---|---|---|---|
| A | RITABATE 80 | POLYSORBATE 80 | 25.000 |
| A | UBIDECARENONE | UBIQUINONE | 21.000 |
| B | PURIFIED WATER | WATER | 35.500 |
| B | PROPYLENE GLYCOL | PROPYLENE GLYCOL | 10.000 |
| B | PHENOXYETHANOL | PHENOXYETHANOL | 0.500 |
| B | PHOSPHOLIPON 85G | LECITHIN | 8.000 |
| Totals | | | 100.000 |

The phenoxyethanol and propylene glycol are placed in a suitable container and mixed until clear. The required amount of water is added to a second container (Mix Tank 1). Mix Tank 1 is heated to between 45 and 55° C. while being mixed. The phenoxyethanol/propylene glycol solution is added to the water and mixed until it was clear and uniform. When the contents of the water phase in Mix Tank 1 are within the range of 45 to 55° C., Phospholipon G is added with low to moderate mixing. While avoiding any foaming, the contents of Mix Tank 1 is mixed until the Phospholipon 85G was uniformly dispersed. The polysorbate 89 is added to a suitable container (Mix Tank 2) and heated to between 50 and 60° C. The Ubidecarenone is then added to Mix Tank 2. While maintaining the temperature at between 50 and 60° C. Mix Tank 2 is mixed until all the Ubidecarenone is dissolved. After all the Ubidecarenone has been dissolved, the water phase is slowly transferred to Mix Tank 2. When all materials have been combined, the contents are homogenized until dispersion is smooth and uniform. While being careful not to overheat, the temperature is maintained at between 50 and 60° C. The homogenization is then stopped and the contents of Mix Tank 2 are transferred to a suitable container for storage.

In some embodiments, a formulation for any route of administration for use in the invention may include from about 0.001% to about 20% (w/w) of CoQ10, more preferably between about 0.01% and about 15% and even more preferably between about 0.1% to about 10% (w/w) of CoQ10. In certain embodiments, a formulation for any route of administration for use in the invention may include from about 1% to about 10% (w/w) of CoQ10. In certain embodiments, a formulation for any route of administration for use in the invention may include from about 2% to about 8% (w/w) of CoQ10. In certain embodiments, a formulation for any route of administration for use in the invention may include from about 2% to about 7% (w/w) of CoQ10. In certain embodiments, a formulation for any route of administration for use in the invention may include from about 3% to about 6% (w/w) of CoQ10. In certain embodiments, a formulation for any route of administration for use in the invention may include from about 3% to about 5% (w/w) of CoQ10. In certain embodiments, a formulation for any route of administration for use in the invention may include from about 3.5% to about 4.5% (w/w) of CoQ10. In certain embodiments, a formulation for any route of administration for use in the invention may include from about 3.5% to about 5% (w/w) of CoQ10. In one embodiment a formulation includes about 4% (w/w) of CoQ10. In one embodiment a formulation includes about 8% (w/w) of CoQ10. In various embodiments, the formulation includes about 0.1%, 0.2%, 0.3%, 0.4%, 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10, or any range bracketed by any two values recited. In certain embodiments, the formulations can be prepared as a percent weight to volume rather than a percent weight to weight. Depending on the formulation, the concentration of CoQ10 may be the same, or about the same in the w/w and the w/v percent formulations. CoQ10 can be obtained from Kaneka Q10 as Kaneka Q10 (USP UBIDECARENONE) in powdered form (Pasadena, Texas, USA). CoQ10 used in the methods exemplified herein have the following characteristics: residual solvents meet USP 467 requirement; water content is less than 0.0%, less than 0.05% or less than 0.2%; residue on ignition is 0.0%, less than 0.05%, or less than 0.2% less than; heavy metal content is less than 0.002%, or less than 0.001%; purity of between 98-100% or 99.9%, or 99.5%.

In certain embodiments, the concentration of CoQ10 in the formulation is 1 mg/mL to 150 mg/mL. In one embodiment, the concentration of CoQ10 in the formulation is 5 mg/mL to 125 mg/mL. In one embodiment, the concentration of CoQ10 in the formulation is 10 mg/mL to 100 mg/mL. In one embodiment, the concentration of CoQ10 in the formulation is 20 mg/mL to 90 mg/mL. In one embodiment, the concentration of CoQ10 is 30 mg/mL to 80 mg/mL. In one embodiment, the concentration of CoQ10 is 30 mg/mL to 70 mg/mL. In one embodiment, the concentration of CoQ10 is 30 mg/mL to 60 mg/mL. In one embodiment, the concentration of CoQ10 is 30 mg/mL to 50 mg/mL. In one embodiment, the concentration of CoQ10 is 35 mg/mL to 45 mg/mL. It should be understood that additional ranges having any one of the foregoing values as the upper or lower limits are also intended to be part of this invention, e.g., 10 mg/mL to 50 mg/mL, or 20 mg/mL to 60 mg/mL.

In certain embodiments, the concentration of CoQ10 in the formulation is about 10, 15, 20, 25, 30, 31, 32, 33, 34, 35, 36, 37, 38, 39, 40, 41, 42, 43, 44, 45, 46, 47, 48, 49, 50, 55, 60, 65, 70, 75, 80, 85, 90 or 95 mg/mL. In one embodiment, the concentration of CoQ10 in the formulation is about 50 mg/mL. In one embodiment, the concentration of CoQ10 in the formulation is about 60 mg/mL. In one embodiment, the concentration of CoQ10 in the formulation is about 30 mg/mL. In a preferred embodiment, the concentration of CoQ10 in the formulation is about 40 mg/mL. It should be understood that ranges having any one of these values as the upper or lower limits are also intended to be part of this invention, e.g. between 37 mg/mL and 47 mg/mL, or between 31 mg/mL and 49 mg/mL.

It is understood that formulations can similarly be prepared containing CoQ10 precursors, metabolites, and related compounds.

IV. Combination Therapies

Provided herein are methods of treating oncological disorders in a subject by co-administering CoQ10 and at least one chemotherapeutic agent to a subject in need thereof. As used herein, the term “co-administering” refers to administration of CoQ10 prior to, concurrently or substantially concurrently with, subsequently to, or intermittently with the administration of the chemotherapeutic agent. In certain embodiments, CoQ10 is administered prior to and concurrently with the chemotherapeutic agent. In certain embodiments, CoQ10 is administered prior to but not concurrently with the chemotherapeutic agent, i.e., CoQ10 administration is discontinued prior to initiation of treatment with or administration of a chemotherapeutic agent. In one embodiment, an intravenous (IV) CoQ10 formulation can be used in combination therapy with at least one other chemotherapeutic agent according to the methods of the invention. In one embodiment, a topical CoQ10 formulation can be used in combination therapy with at least one other chemotherapeutic agent according to the methods of the invention. In one embodiment, an inhalable CoQ10 formulation can be used in combination therapy with at least one other chemotherapeutic agent according to the methods of the invention. CoQ10 and/or pharmaceutical formulations thereof and the other chemotherapeutic agent can act additively or, more preferably, synergistically. In one embodiment, CoQ10 and/or a formulation thereof is administered concurrently with the administration of another chemotherapeutic agent. In another embodiment, CoQ10 and/or pharmaceutical formulation thereof is administered prior to or subsequent to administration of another chemotherapeutic agent. In one embodiment, the CoQ10 and additional chemotherapeutic agent act synergistically. In some embodiments the synergistic results are in the treatment of the oncological disorder. In other embodiments the synergistic results are in modulation of the toxicity associated with the chemotherapeutic agent. In one embodiment, the CoQ10 and the additional therapeutic agent act additively. In one embodiment, the CoQ10 sensitizes the oncological disorder, cancer or cancer cells to treatment with another chemotherapeutic agent. In one embodiment, pre-treatment with CoQ10 prior to treatment with the chemotherapeutic agent sensitizes the oncological disorder, cancer or cancer cells to treatment with another chemotherapeutic agent. In one embodiment, pretreatment with CoQ10 and discontinuation of said treatment prior to treatment with the chemotherapeutic agent sensitizes the oncological disorder, cancer or cancer cells to treatment with another chemotherapeutic agent.

In some embodiments, the CoQ10 is in the form of an intravenous CoQ10 formulation, an inhalation CoQ10 formulation, or a topical CoQ10 formulation. Intravenous CoQ10 formulations are disclosed in WO2011/112900, filed on Mar. 11, 2011. The disclosure of WO2011/112900 is incorporated herein in its entirety. Topical CoQ10 formulations are disclosed in US Patent Application Publication No. US2011/0027247, filed on May 11, 2010. The disclosure of US2011/0027247 is incorporated herein in its entirety. Inhalation CoQ10 formulations are disclosed in US Patent Publication Nos. 20120321698, filed on Jun. 18, 2012 and 20110142914 filed Dec. 5, 2008. The CoQ10 and the chemotherapeutic agent need not be delivered by the same route of administration. In certain embodiments, the CoQ10 is not administered orally.

In some embodiments, methods are provided for the treatment of oncological disorders by co-administering intravenous CoQ10 formulations with a chemotherapeutic agent. In certain embodiments, the chemotherapeutic agents are gemcitabine, doxorubicin, cisplatin, 5-fluorouracil, and irinotecan. In some embodiments, the chemotherapeutic agents are antimetabolites or an anthracycline. Chemotherapeutic agents generally belong to various classes including, for example: 1. Topoisomerase II inhibitors (cytotoxic antibiotics), such as the anthracyclines/anthracenediones, e.g., doxorubicin, epirubicin, idarubicin and nemorubicin, the anthraquinones, e.g., mitoxantrone and losoxantrone, and the podophillotoxines, e.g., etoposide and teniposide; 2. Agents that affect microtubule formation (mitotic inhibitors), such as plant alkaloids (e.g., a compound belonging to a family of alkaline, nitrogen-containing molecules derived from plants that are biologically active and cytotoxic), e.g., taxanes, e.g., paclitaxel and docetaxel, and the vinka alkaloids, e.g., vinblastine, vincristine, and vinorelbine, and derivatives of podophyllotoxin; 3. Alkylating agents, such as nitrogen mustards, ethyleneimine compounds, alkyl sulphonates and other compounds with an alkylating action such as nitrosoureas, dacarbazine, cyclophosphamide, ifosfamide and melphalan; 4. Antimetabolites (nucleoside inhibitors), for example, folates, e.g., folic acid, fluoropyrimidines, purine or pyrimidine analogues such as 5-fluorouracil, capecitabine, gemcitabine, methotrexate and edatrexate; 5. Topoisomerase I inhibitors, such as topotecan, irinotecan, and 9-nitrocamptothecin, and camptothecin derivatives; and 6. Platinum compounds/complexes, such as cisplatin, oxaliplatin, and carboplatin.

Exemplary chemotherapeutic agents for use in the methods of the invention include, but are not limited to, amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-I1,lO-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10,11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof which are readily apparent to one of skill in the art based on the appropriate standard of care for a particular tumor or cancer.

In certain embodiments, an additional chemotherapeutic agent for use in the combination therapies of the invention is a biologic agent. Biologic agents (also called biologics) are the products of a biological system, e.g., an organism, cell, or recombinant system. Examples of such biologic agents include nucleic acid molecules (e.g., antisense nucleic acid molecules), interferons, interleukins, colony-stimulating factors, antibodies, e.g., monoclonal antibodies, anti-angiogenesis agents, and cytokines. Exemplary biologic agents are discussed in more detail below and generally belong to various classes including, for example: 1. Hormones, hormonal analogues, and hormonal complexes, e.g., estrogens and estrogen analogs, progesterone, progesterone analogs and progestins, androgens, adrenocorticosteroids, antiestrogens, antiandrogens, antitestosterones, adrenal steroid inhibitors, and anti-leuteinizing hormones; and 2. Enzymes, proteins, peptides, polyclonal and/or monoclonal antibodies, such as interleukins, interferons, colony stimulating factor, etc.

In one embodiment, the biologic is an interfereon. Interferons (IFN) are a type biologic agent that naturally occurs in the body. Interferons are also produced in the laboratory and given to cancer patients in biological therapy. They have been shown to improve the way a cancer patient's immune system acts against cancer cells.

Interferons may work directly on cancer cells to slow their growth, or they may cause cancer cells to change into cells with more normal behavior. Some interferons may also stimulate natural killer cells (NK) cells, T cells, and macrophages which are types of white blood cells in the bloodstream that help to fight cancer cells.

In one embodiment, the biologic is an interleukin. Interleukins (IL) stimulate the growth and activity of many immune cells. They are proteins (cytokines and chemokines) that occur naturally in the body, but can also be made in the laboratory. Some interleukins stimulate the growth and activity of immune cells, such as lymphocytes, which work to destroy cancer cells.

In another embodiment, the biologic is a colony-stimulating factor. Colony-stimulating factors (CSFs) are proteins given to patients to encourage stem cells within the bone marrow to produce more blood cells. The body constantly needs new white blood cells, red blood cells, and platelets, especially when cancer is present. CSFs are given, along with chemotherapy, to help boost the immune system. When cancer patients receive chemotherapy, the bone marrow's ability to produce new blood cells is suppressed, making patients more prone to developing infections. Parts of the immune system cannot function without blood cells, thus colony-stimulating factors encourage the bone marrow stem cells to produce white blood cells, platelets, and red blood cells. With proper cell production, other cancer treatments can continue enabling patients to safely receive higher doses of chemotherapy.

In another embodiment, the biologic is an antibody. Antibodies, e.g., monoclonal antibodies, are agents, produced in the laboratory, that bind to cancer cells.

Monoclonal antibody agents do not destroy healthy cells. Monoclonal antibodies achieve their therapeutic effect through various mechanisms. They can have direct effects in producing apoptosis or programmed cell death. They can block growth factor receptors, effectively arresting proliferation of tumor cells. In cells that express monoclonal antibodies, they can bring about anti-idiotype antibody formation.

Examples of antibodies which may be used in the combination treatment of the invention include anti-CD20 antibodies, such as, but not limited to, cetuximab, Tositumomab, rituximab, and Ibritumomab. Anti-HER2 antibodies may also be used in combination with coenzyme Q10 for the treatment of cancer. In one embodiment, the anti-HER2 antibody is Trastuzumab (Herceptin). Other examples of antibodies which may be used in combination with coenzyme Q10 for the treatment of cancer include anti-CD52 antibodies (e.g., Alemtuzumab), anti-CD-22 antibodies (e.g., Epratuzumab), and anti-CD33 antibodies (e.g., Gemtuzumab ozogamicin). Anti-VEGF antibodies may also be used in combination with coenzyme Q10 for the treatment of cancer. In one embodiment, the anti-VEGF antibody is bevacizumab. In other embodiments, the biologic agent is an antibody which is an anti-EGFR antibody e.g., cetuximab. Another example is the anti-glycoprotein 17-1A antibody edrecolomab. Numerous other anti-tumor antibodies are known in the art and would be understood by the skilled artisan to be encompassed by the present invention.

In another embodiment, the biologic is a cytokine. Cytokine therapy uses proteins (cytokines) to help a subject's immune system recognize and destroy those cells that are cancerous. Cytokines are produced naturally in the body by the immune system, but can also be produced in the laboratory. This therapy is used with advanced melanoma and with adjuvant therapy (therapy given after or in addition to the primary cancer treatment). Cytokine therapy reaches all parts of the body to kill cancer cells and prevent tumors from growing.

In another embodiment, the biologic is a fusion protein. For example, recombinant human Apo2L/TRAIL (GENETECH) may be used in a combination therapy. Apo2/TRAIL is the first dual pro-apoptotic receptor agonist designed to activate both pro-apoptotic receptors DR4 and DR5, which are involved in the regulation of apoptosis (programmed cell death).

In one embodiment, the biologic is a therapeutic nucleic acid molecule. Nucleic acid therapeutics are well known in the art. Nucleic acid therapeutics include both single stranded and double stranded (i.e., nucleic acid therapeutics having a complementary region of at least 15 nucleotides in length) nucleic acids that are complementary to a target sequence in a cell. Therapeutic nucleic acids can be directed against essentially any target nucleic acid sequence in a cell. In certain embodiments, the nucleic acid therapeutic is targeted against a nucleic acid sequence encoding a stimulator of angiogenesis, e.g., VEGF, FGF, or of tumor growth, e.g., EGFR.

Antisense nucleic acid therapeutic agents are single stranded nucleic acid therapeutics, typically about 16 to 30 nucleotides in length, and are complementary to a target nucleic acid sequence in the target cell, either in culture or in an organism.

In another aspect, the agent is a single-stranded antisense RNA molecule. An antisense RNA molecule is complementary to a sequence within the target mRNA. Antisense RNA can inhibit translation in a stoichiometric manner by base pairing to the mRNA and physically obstructing the translation machinery, see Dias, N. et al., (2002) Mol Cancer Ther 1:347-355. The antisense RNA molecule may have about 15-30 nucleotides that are complementary to the target mRNA. Patents directed to antisense nucleic acids, chemical modifications, and therapeutic uses are provided, for example, in U.S. Pat. No. 5,898,031 related to chemically modified RNA-containing therapeutic compounds, and U.S. Pat. No. 6,107,094 related methods of using these compounds as therapeutic agent. U.S. Pat. No. 7,432,250 related to methods of treating patients by administering single-stranded chemically modified RNA-like compounds; and U.S. Pat. No. 7,432,249 related to pharmaceutical compositions containing single-stranded chemically modified RNA-like compounds. U.S. Pat. No. 7,629,321 is related to methods of cleaving target mRNA using a single-stranded oligonucleotide having a plurality RNA nucleosides and at least one chemical modification. The entire contents of each of the patents listed in this paragraph are incorporated herein by reference.

Nucleic acid therapeutic agents for use in the methods of the invention also include double stranded nucleic acid therapeutics. An "RNAi agent," "double stranded RNAi agent," double-stranded RNA (dsRNA) molecule, also referred to as "dsRNA agent," "dsRNA", "siRNA", "iRNA agent," as used interchangeably herein, refers to a complex of ribonucleic acid molecules, having a duplex structure comprising two anti-parallel and substantially complementary, as defined below, nucleic acid strands. As used herein, an RNAi agent can also include dsiRNA (see, e.g., US Patent publication 20070104688, incorporated herein by reference). In general, the majority of nucleotides of each strand are ribonucleotides, but as described herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. Such modifications may include all types of modifications disclosed herein or known in the art. Any such modifications, as used in a siRNA type molecule, are encompassed by "RNAi agent" for the purposes of this specification and claims. The RNAi agents that are used in the methods of the invention include agents with chemical modifications as disclosed, for example, in U.S. Provisional Application No. 61/561,710, filed on Nov. 18, 2011, International Application No. PCT/US2011/051597, filed on Sep. 15, 2010, and PCT Publication WO 2009/073809, the entire contents of each of which are incorporated herein by reference.

Additional exemplary biologic agents for use in the methods of the invention include, but are not limited to, gefitinib (Iressa), anastrazole, diethylstilbesterol, estradiol, premarin, raloxifene, progesterone, norethynodrel, esthisterone, dimesthisterone, megestrol acetate, medroxyprogesterone acetate, hydroxyprogesterone caproate, norethisterone, methyltestosterone, testosterone, dexamthasone, prednisone, Cortisol, solumedrol, tamoxifen, fulvestrant, toremifene, aminoglutethimide, testolactone, droloxifene, anastrozole, bicalutamide, flutamide, nilutamide, goserelin, flutamide, leuprolide, triptorelin, aminoglutethimide, mitotane, goserelin, cetuximab, erlotinib, imatinib, Tositumomab, Alemtuzumab, Trastuzumab, Gemtuzumab, Rituximab, Ibritumomab tiuxetan, Bevacizumab, Denileukin diftitox, Daclizumab, interferon alpha, interferon beta, anti-4-1BB, anti-4-1BBL, anti-CD40, anti-CD 154, anti-OX40, anti-OX40L, anti-CD28, anti-CD80, anti-CD86, anti-CD70, anti-CD27, anti-HVEM, anti-LIGHT, anti-GITR, anti-GITRL, anti-CTLA-4, soluble OX40L, soluble 4-IBBL, soluble CD154, soluble GITRL, soluble LIGHT, soluble CD70, soluble CD80, soluble CD86, soluble CTLA4-Ig, GVAX®, and combinations thereof which are readily apparent to one of skill in the art based on the appropriate standard of care for a particular tumor or cancer. The soluble forms of agents may be made as, for example fusion proteins, by operatively linking the agent with, for example, Ig-Fc region.

It should be noted that more than one additional anticancer chemotherapeutic agents, e.g., 2, 3, 4, 5, or more, may be administered in combination with the coenzyme Q10 and coenzyme Q10 formulations provided herein. For example, in one embodiment, two additional chemotherapeutic agents may be administered in combination with coenzyme Q10. In one embodiment, three additional chemotherapeutic agents may be administered in combination with coenzyme Q10. In one embodiment, four additional chemotherapeutic agents may be administered in combination with coenzyme Q10. In one embodiment, five additional chemotherapeutic agents may be administered in combination with coenzyme Q10. Appropriate doses and routes of administration of the chemotherapeutic agents provided herein are known in the art.

In certain embodiments, the methods of the invention comprise treatment of cancer by continuous infusion of coenzyme Q10 provided and combination therapies with additional anticancer agents or interventions (e.g., radiation, surgery, bone marrow transplant). In certain embodiments, "combination therapy" includes a treatment with coenzyme Q10 to decrease tumor burden and/or improve clinical response. Administration of coenzyme Q10 with palliative treatments or treatments to mitigate drug side effects (e.g., to decrease nausea, pain, anxiety, or inflammation, to normalize clotting) is not considered to be a combination treatment of the cancer.

In certain embodiments, treatment with coenzyme Q10 by continuous infusion is combined with the standard of care for treatment of the particular cancer to be treated, for example by administering a standard dosage of one or more chemotherapeutic agents. The standard of care for a particular cancer type can be determined by one of skill in the art based on, for example, the type and severity of the cancer, the age, weight, gender, and/or medical history of the subject, and the success or failure of prior treatments.

In certain embodiments, treatment of subjects with leukemia, particularly ALL or AML, administration (e.g., intravenous, e.g., continuous infusion) of coenzyme Q10 is combined with one, or preferably both, of the following treatments.

1. Fludarabine, preferably at a dose of 15 $mg/m^2$ administered intravenously over 15-30 minutes±15 minutes, every 12 hours for 5 days (or for 4 days in patients over 65 years of age or with ECOG Performance Status of 3).
2. Cytarabine, preferably administered at 0.5 $g/m^2$ in 250 ml of normal saline administered intravenously over 2 hours±20 minutes every 12 hours±2 hours for 5 days (or for 4 days in patients over 65 years of age or with ECOG Performance Status of 3).

In certain embodiments, 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

In certain embodiments, treatment of subjects with solid tumors by continuous infusion of coenzyme Q10 is combined with one or more of the following treatments.

1. Gemcitabine, preferably by intravenous administration at a weekly dose starting at 600 $mg/m^2$, with the dose being adjusted based on the tolerance of the subject to the drug.
2. 5-Fluorouracil (5-FU), preferably by intravenous administration at a weekly starting dose of 350 $mg/m^2$, with the dose being adjusted based on the tolerance of the subject to the drug, in combination with leucovorin at 100 $mg/m^2$.
3. Docetaxel, preferably by intravenous administration once weekly at a starting dose of 20 $mg/m^2$, with the dose being adjusted based on the tolerance of the subject to the drug.

In certain embodiments, 1, 2, 3, 4, or 5 cycles of the combination therapy are administered to the subject. The subject is assessed for response criteria at the end of each cycle. The subject is also monitored throughout each cycle for adverse events (e.g., clotting, anemia, liver and kidney function, etc.) to ensure that the treatment regimen is being sufficiently tolerated.

In other embodiments, the chemotherapeutic agent is administered at a dosage that is lower than the standard dosages of the chemotherapeutic agent used to treat the oncological disorder under the standard of care for treatment for a particular oncological disorder. Standard dosages of chemotherapeutic agents are known to a person skilled in the art and may be obtained, for example, from the product insert provided by the manufacturer of the chemotherapeutic agent. Examples of standard dosages of chemotherapeutic agents are provided in Table 3. In certain embodiments, the dosage administered of the chemotherapeutic agent is 5%, 10%, 20%, 30%, 40%, 50%, 60%, 70%, 80%, or 90% lower than the standard dosage of the chemotherapeutic agent for a particular oncological disorder. In certain embodiments, the dosage administered of the chemotherapeutic agent is 95%, 90%, 85%, 80%, 75%, 70%, 65%, 60%, 55%, 50%, 45%, 40%, 35%, 30%, 25%, 20%, 15%, 10% or 5% of the standard dosage of the chemotherapeutic agent for a particular oncological disorder. In one embodiment, where a combination of non-CoQ10 chemotherapeutic agents are administered, at least one of the chemotherapeutic agents is administered at a dose that is lower than the standard dosage of the chemotherapeutic agent for a particular oncological disorder. In one embodiment, where a combination of chemotherapeutic agents (e.g., non-CoQ10) are administered, at least two of the chemotherapeutic agents are administered at a dose that is lower than the standard dosage of the chemotherapeutic agents for a particular oncological disorder. In one embodiment, where a combination of chemotherapeutic agents (e.g., non-CoQ10) are administered, at least three of the chemotherapeutic agents are administered at a dose that is lower than the standard dosage of the chemotherapeutic agents for a particular oncological disorder. In one embodiment, where a combination of chemotherapeutic agents (e.g., non-CoQ10) are administered, all of the chemotherapeutic agents are administered at a dose that is lower than the standard dosage of the chemotherapeutic agents for a particular oncological disorder.

In certain embodiments, coenzyme Q10 is administered in an amount that would be therapeutically effective if delivered alone, i.e., coenzyme Q10 is administered and/or acts as a therapeutic anti-cancer agent, and not predominantly as an agent to ameliorate side effects of other chemotherapy or other cancer treatments.

V. Treatment of Oncological Disorders

The combination therapies of the present invention may be utilized for the treatment of oncological disorders. Accordingly, the present invention provides methods of treating or preventing an oncological disorder in a subject, comprising administering the formulations of the invention to the subject in an amount sufficient to treat or prevent the oncological disorder, thereby treating or preventing the oncological disorder. The formulations of the invention may also be utilized for inhibiting tumor cell growth. Accordingly, the invention further provides methods of inhibiting tumor cell growth in a subject, comprising intravenously administering the formulations of the invention to the subject, such that tumor cell growth is inhibited. In certain embodiments, treating cancer comprises extending survival or extending time to tumor progression as compared to control, e.g., a population control. In certain embodiments, the subject is a human subject. In preferred embodiments, the subject is identified as having a tumor prior to administration of the first dose of CoQ10. In certain embodiments, the subject has a tumor at the time of the first administration of CoQ10.

Such combination therapies include, for example, CoQ10 formulations that are co-administered with the chemotherapeutic agents described or incorporated herein. In certain embodiments, the method of treating an oncological disorder in a subject comprises: (a) administering coenzyme Q10 (CoQ10) to the subject; (b) discontinuing treatment with CoQ10; and (c) administering at least one chemotherapeutic agent to the subject after administration of CoQ10 has been discontinued, wherein the oncological disorder is treated.

In other embodiments, the method of treating an oncological disorder in a subject comprises: (a) administering coenzyme Q10 (CoQ10) to the subject; (b) administering at least one chemotherapeutic agent to the subject after administration of the CoQ10 is initiated; and (c) continuing treatment with CoQ10 after administration of the at least one chemotherapeutic agent is initiated, wherein the oncological disorder is treated.

In other embodiments, the method of treating an oncological disorder in a subject comprises: pre-treating a subject having an oncological disorder with Coenzyme Q10 (CoQ10) for a sufficient time prior to initiation of a chemotherapeutic treatment regimen, wherein the chemotherapeutic treatment regimen comprises administration of one or more chemotherapeutic agents, such that a response of the oncological disorder is improved relative to treatment with the chemotherapeutic treatment regimen alone.

In yet other embodiments, the method of treating an oncological disorder in a subject comprises: (a) administering coenzyme Q10 (CoQ10) to the subject; and (b) administering at least one chemotherapeutic agent to the subject at a dosage that is lower than standard dosages of the chemotherapeutic agent used to treat the oncological disorder, such that the oncological disorder is treated.

In the foregoing various embodiments, administration of the at least one chemotherapeutic agent may be initiated at least 24 hours after administration of CoQ10 is initiated, one or more weeks after administration of CoQ10 is initiated, two or more weeks after administration of CoQ10 is initiated, three or more weeks after administration of CoQ10 is initiated, four or more weeks after administration of CoQ10 is initiated, five or more weeks after administration of CoQ10 is initiated, six or more weeks after administration of CoQ10 is initiated, seven or more weeks after administration of CoQ10 is initiated, or eight or more weeks after administration of CoQ10 is initiated.

In a preferred embodiment, administration of the at least one chemotherapeutic agent is initiated at least 24 hours after administration of CoQ10 is initiated. In another preferred embodiment, administration of the at least one chemotherapeutic agent is initiated from 24 hours to 4 weeks after administration of CoQ10 is initiated. In a further preferred embodiment, administration of the at least one chemotherapeutic agent is initiated from 2 to 4 weeks after administration of CoQ10 is initiated. In yet a further preferred embodiment, administration of the at least one chemotherapeutic agent is initiated 2 weeks after administration of CoQ10 is initiated. In yet a further preferred embodiment, administration of the at least one chemotherapeutic agent is initiated 1 week after administration of CoQ10 is initiated. In yet a further preferred embodiment, administration of the at least one chemotherapeutic agent is initiated 3 weeks after administration of CoQ10 is initiated. In yet a further preferred embodiment, administration of the at least one chemotherapeutic agent is initiated 4 weeks after administration of CoQ10 is initiated. In yet a further preferred embodiment, administration of the at least one chemotherapeutic agent is initiated 5 weeks after administration of CoQ10 is initiated. In yet a further preferred embodiment, administration of the at least one chemotherapeutic agent is initiated 6 weeks after administration of CoQ10 is initiated. In yet a further preferred embodiment, administration of the at least one chemotherapeutic agent is initiated 7 weeks after administration of CoQ10 is initiated. In yet a further preferred embodiment, administration of the at least one chemotherapeutic agent is initiated 8 weeks after administration of CoQ10 is initiated.

The CoQ10 formulations may be inhalation formulations, intravenous formulations or topical formulations. In certain embodiments, the CoQ10 formulation is not an oral formulation. For example, the intravenous formulations may include CoQ10 or its metabolites, in a pharmaceutically acceptable carrier. In some embodiments, such a formulation may include from about 0.001% to about 20% (w/w) of CoQ10, more preferably between about 0.01% and about 15% and even more preferably between about 0.1% to about 10% (w/w) of CoQ10, more preferably about 3% to about 5% (w/w) of CoQ10. In one embodiment a formulation includes about 4% (w/w) of CoQ10. In one embodiment a formulation includes about 8% (w/w) of CoQ10. In various embodiments, the formulation includes about 0.5%, 1%, 2%, 3%, 4%, 5%, 6%, 7%, 8%, 9%, 10%, 11%, 12%, 13%, 14%, 15%, 16%, 17%, 18%, 19% or 20% (w/w) of CoQ10. As also noted herein, compositions of the present disclosure may be in a liquid form, capable of introduction into a subject by any means or route of administration within the purview of those skilled in the art. For example, compositions may be administered by routes of administration including, but not limited to, intravenous, intratumoral, intraperitoneal, combinations thereof, and the like.

In some embodiments, a chemotherapy regimen is co-administered with a CoQ10 formulation to treat the oncological disorder. The CoQ10 formulation may be administered prior to, concurrently or substantially concurrently with, prior to and concurrently with, intermittently with or subsequently to the administration of the chemotherapy regimen. In certain embodiments, a loading dose of CoQ10 is administered prior to administration of the chemotherapeutic agent. In certain embodiments, CoQ10 is administered to achieve a steady state level of CoQ10 prior to administration of the chemotherapeutic agent. Where the combination therapy includes intravenous CoQ10 formulations, the subject is intravenously administered the CoQ10 such that oncological disorders are treated or prevented. In one embodiment, the subject is intravenously administered the CoQ10 such that response to the chemotherapeutic agent is improved, e.g., relative to treatment with the chemotherapeutic agent alone.

The subject is administered a dose of CoQ10 in the range of about 0.5 mg/kg to about 10,000 mg/kg, about 5 mg/kg to about 5,000 mg/kg, about 10 mg/kg to about 3,000 mg/kg. In one embodiment, Coenzyme Q10 is administered in the range of about 10 mg/kg to about 1,400 mg/kg. In one embodiment, Coenzyme Q10 is administered in the range of about 10 mg/kg to about 650 mg/kg. In one embodiment, Coenzyme Q10 is administered in the range of about 10 mg/kg to about 200 mg/kg. In various embodiments, Coenzyme Q10 is administered at a dose of about 2 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 55 mg/kg, 58 mg/kg, 58.6 mg/kg, 60 mg/kg, 65 mg/kg, 70 mg/kg, 75 mg/kg, 78 mg/kg, 80 mg/kg, 85 mg/kg, 90 mg/kg, 95 mg/kg, 100 mg/kg, 104 mg/kg, 110 mg/kg, 120 mg/kg, 130 mg/kg, 140 mg/kg, 150 mg/kg, 160 mg/kg, 170 mg/kg, 180 mg/kg, 190 mg/kg or 200 mg/kg. It should be understood that ranges having any one of these values as the upper or lower limits are also intended to be part of this invention, e.g., about 50 mg/kg to about 200 mg/kg, or about 650 mg/kg to about 1400 mg/kg. In one embodiment the administered dose is at least about 1 mg/kg, at least about 5 mg/kg, at least about 10 mg/kg, at least about 12.5 mg/kg, at least about 20 mg/kg, at least about 25 mg/kg, at least about 30 mg/kg, at least about 35 mg/kg, at least about 40 mg/kg, at least about 45 mg/kg, at least about 50 mg/kg, at least about 55 mg/kg, at least about 58 mg/kg, at least about 58.6 mg/kg, at least about 60 mg/kg, at least about 75 mg/kg, at least about 78 mg/kg, at least about 100 mg/kg, at least about 104 mg/kg, at least about 125 mg/kg, at least about 150 mg/kg, at least about 175 mg/kg, at least about 200 mg/kg, at least about 300 mg/kg, or at least about 400 mg/kg.

In certain embodiments, the CoQ10 is administered in at least one dose per day. In certain embodiments, the CoQ10 is administered in at least two doses per day. In certain embodiments, the CoQ10 is administered in at least three dose per day. In certain embodiments, the CoQ10 is administered in one dose per day. In certain embodiments, the CoQ10 is administered in two doses per day. In certain embodiments, the CoQ10 is administered in three doses per day. In certain embodiments, the CoQ10 is administered by continuous infusion.

For example, in some embodiments, the aforementioned methods comprise a regimen of intravenously administering CoQ10, e.g., at least about 50 mg/kg of CoQ10, once daily for 3 weeks, optionally with one week rest, and subsequently administering a chemotherapeutic agent. In other embodiments, the method comprises a regimen of intravenously administering CoQ10, e.g., at least about 75 mg/kg of CoQ10, once daily for 3 weeks, optionally with one week rest, and subsequently administering a chemotherapeutic agent.

Dosing ranges for inhaled formulations of CoQ10 can be similar to those provided for administration by injection. It is understood that nebulizers or other devices for delivery by inhalation are known in the art and can be used in conjunction with the methods of the invention.

Dosages of topical CoQ10 typically depend on the size of the area to be treated. For example, topically administered CoQ10 can be used for the treatment of skin cancer. CoQ10 is applied topically, typically once or twice per day, to the site of the cancerous lesion in an amount sufficient to cover the lesion, e.g., as applying acne medicine to a pimple. If the subject has many lesions for treatment, the CoQ10 is applied to many sites, increasing the total dose administered to the subject. If the subject has a single lesion, the CoQ10 is applied to the single site.

In one embodiment, the chemotherapy agent of the combination therapy is gemcitabine. Where the combination therapy includes administration of the CoQ10 formulation and gemcitabine, the subject is administered the CoQ10 formulation and gemcitabine (e.g., both intravenously) such that oncological disorders are treated or prevented. The subject is administered a dose of gemcitabine in the range of about 10 mg/m$^2$ to about 10,000 mg/m$^2$, about 10 mg/m$^2$ to about 5,000 mg/m$^2$, about 10 mg/m$^2$ to about 3,000 mg/m$^2$. In one embodiment, gemcitabine is administered in the range of about 10 mg/m$^2$ to about 1,500 mg/m$^2$. In one embodiment, gemcitabine is administered in the range of about 10 mg/m$^2$ to about 1000 mg/m$^2$. In one embodiment, gemcitabine is administered in the range of about 10 mg/m$^2$ to about 750 mg/m$^2$. In one embodiment, gemcitabine is administered in the range of about 10 mg/m$^2$ to about 500 mg/m$^2$. In one embodiment, gemcitabine is administered in the range of about 10 mg/m$^2$ to about 400 mg/m$^2$. In one embodiment, gemcitabine is administered in the range of about 10 mg/m$^2$ to about 300 mg/m$^2$. In one embodiment, gemcitabine is administered in the range of about 10 mg/m$^2$ to about 200 mg/m$^2$. In one embodiment, gemcitabine is administered in the range of about 10 mg/m$^2$ to about 100 mg/m$^2$. In one embodiment, gemcitabine is administered in the range of about 10 mg/m$^2$ to about 70 mg/m$^2$. In various embodiments, gemcitabine is administered at a dose of about 10 mg/m$^2$, 20 mg/m$^2$, 30 mg/m$^2$, 40 mg/m$^2$, 50 mg/m$^2$, 60 mg/m$^2$, 65 mg/m$^2$, 70 mg/m$^2$, 80 mg/m$^2$, 90 mg/m$^2$, 100 mg/m$^2$, 100 mg/m$^2$, 200 mg/m$^2$, 300 mg/m$^2$, 400 mg/m$^2$, 500 mg/m$^2$, 600 mg/m$^2$, 700 mg/m$^2$, 800 mg/m$^2$, 900 mg/m$^2$, 1000 mg/m$^2$, 1500 mg/m$^2$, 2000 mg/m$^2$, 3000 mg/m$^2$. It should be understood that ranges having any one of these values as the upper or lower limits are also intended to be part of this invention. In one embodiment the administered dose of gemcitabine is at least about 10 mg/m$^2$, at least about 30 mg/m$^2$, at least about 50 mg/m$^2$, at least about 65 mg/m$^2$, at least about 100 mg/m$^2$, at least about 150 mg/m$^2$, at least about 200 mg/m$^2$, at least about 300 mg/m$^2$, at least about 400 mg/m$^2$, at least about 500 mg/m$^2$, at least about 600 mg/m$^2$, at least about 700 mg/m$^2$, at least about 750 mg/m$^2$, at least about 800 mg/m$^2$, at least about 900 mg/m$^2$, at least about 1000 mg/m$^2$, or at least about 1500 mg/m$^2$. In some embodiments, a regimen comprises co-administering intravenous CoQ10 formulation and a chemotherapeutic agent such as gemcitabine.

In a first exemplary regimen (Once Daily Regimen), a dose of at least about 50 mg/kg/dose or at least about 75 mg/kg/dose of the intravenous CoQ10 formulation is administered once daily for 3 consecutive weeks followed with one week of rest, while the 150 mg/kg/dose of the gemcitabine is administered once per week for 3 consecutive weeks followed with one week rest. FIG. 1, shows the results of a combination therapy regimen co-administering intravenous CoQ10 formulation and intravenous gemcitabine according to the first regimen.

Figure 4:
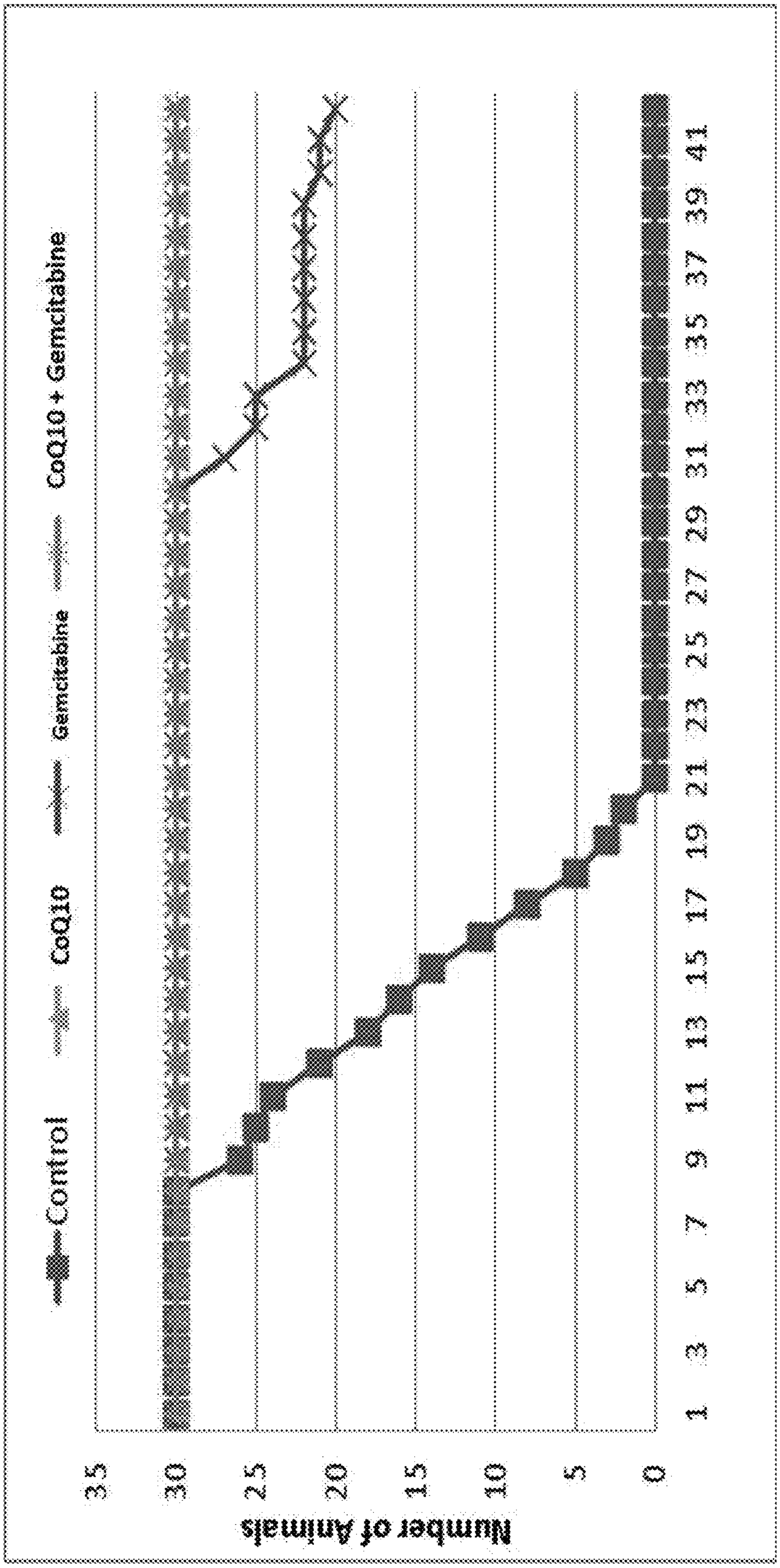
FIG. 4 is a graph showing the effect of twice daily dosing with intravenous CoQ10, alone or in combination with gemcitabine, on survival time (days) in a xenogeneic mouse model of pancreatic cancer using human pancreatic tumor MIAPaCa-2 cells. In the graph, Day 1 indicates the day that treatment was initiated.

In a second exemplary regimen (Twice Daily Regimen), a dose of at least about 50 mg/kg/dose or at least about 75 mg/kg of the intravenous CoQ10 formulation is administered twice daily for 3 consecutive weeks followed with one week rest, while 150 mg/kg/dose of the gemcitabine is administered once per week for 3 weeks with one week rest. FIG. 4, shows the results of a combination therapy regimen co-administering intravenous CoQ10 formulation and intravenous gemcitabine according to the second regimen.

Figure 8:
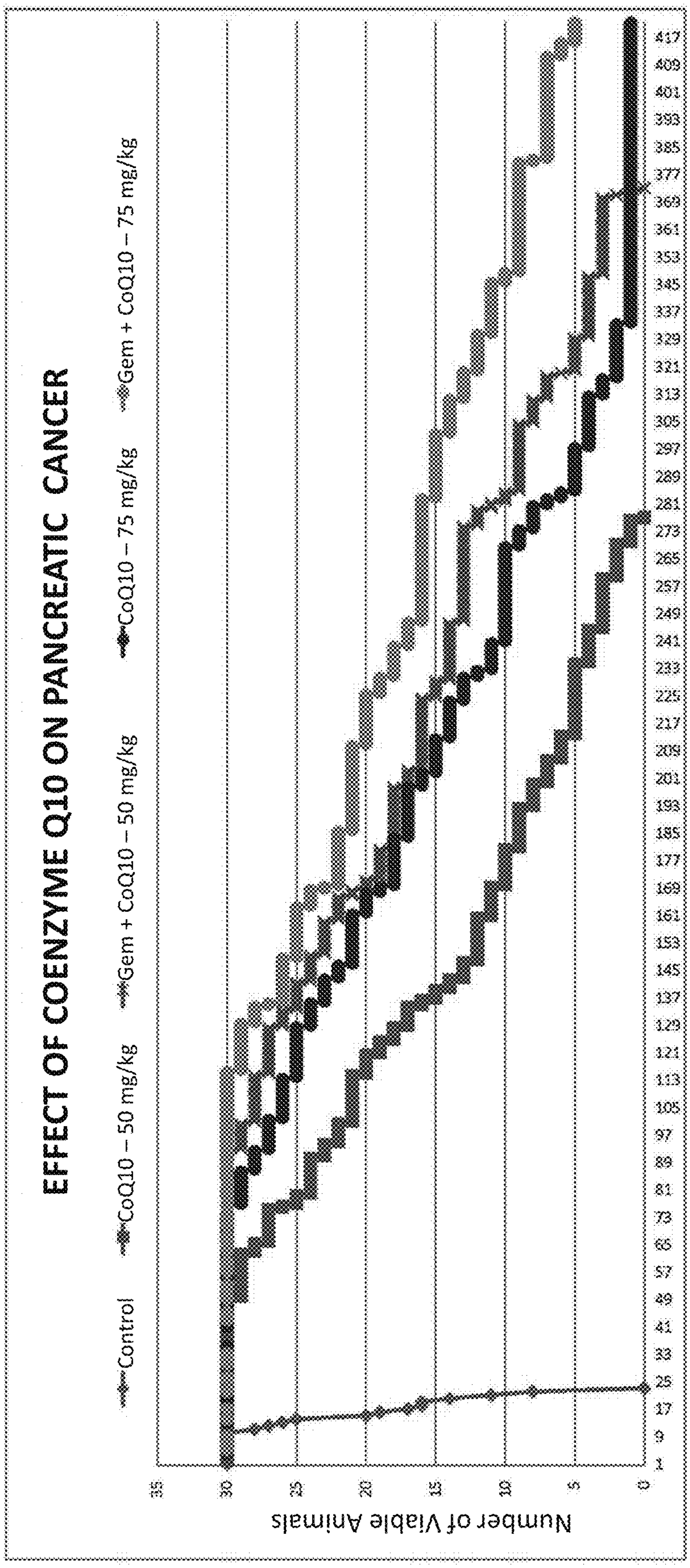
FIG. 8 is a graph showing the effect of three times daily intraperitoneal dosing at the indicated doses with intravenous formulation of CoQ10, alone or in combination with gemcitabine, on survival time in a xenogeneic mouse model of pancreatic cancer using human pancreatic tumor MIAPaCa-2 cells. In the graph, Day 1 indicates the day that treatment was initiated.
Figure 9B:
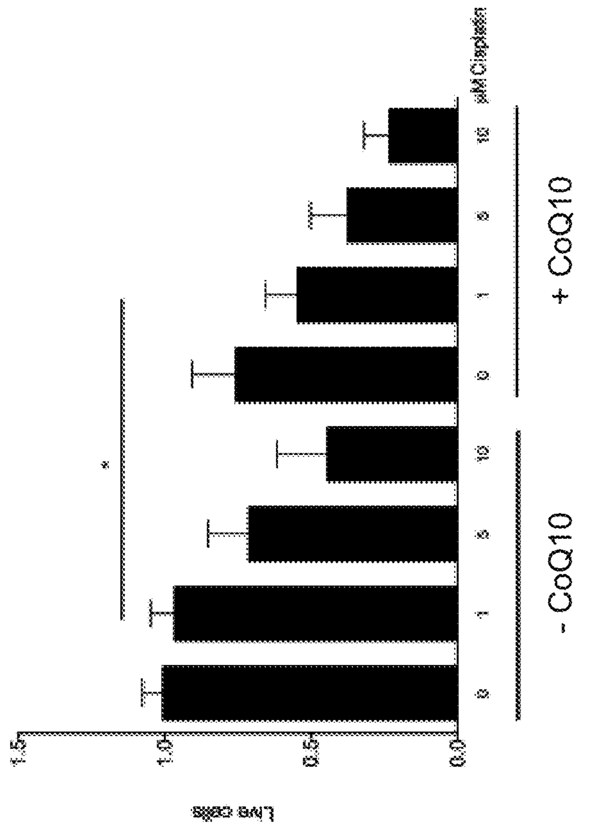
FIG. 9B is a graph showing the effect on viability in Hep3B liver cancer cells in vitro of treatment with the chemotherapeutic agent cisplatin alone or in combination with CoQ10 (100 Viability was assessed by live cell counting. Values are normalized to the number of cells treated with neither CoQ10 nor the chemotherapeutic agent.
Figure 9A:
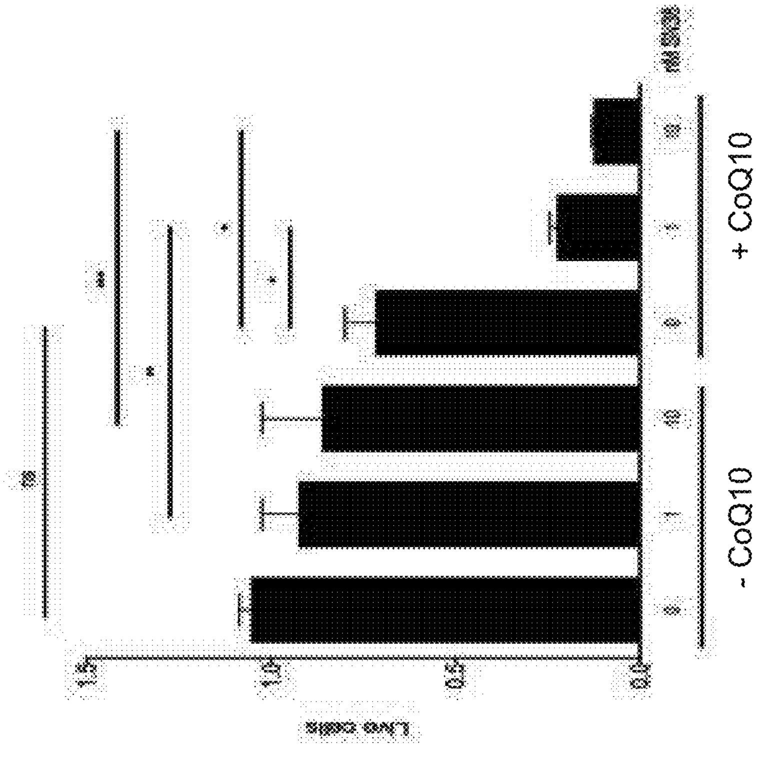
FIG. 9A is a graph showing the effect on viability of Hep3B liver cancer cells in vitro of treatment with the chemotherapeutic agent irinotecan (SN38) alone or in combination with CoQ10 (100 Viability was assessed by live cell counting. Values are normalized to the number of cells treated with neither CoQ10 nor the chemotherapeutic agent.
Figure 9C:
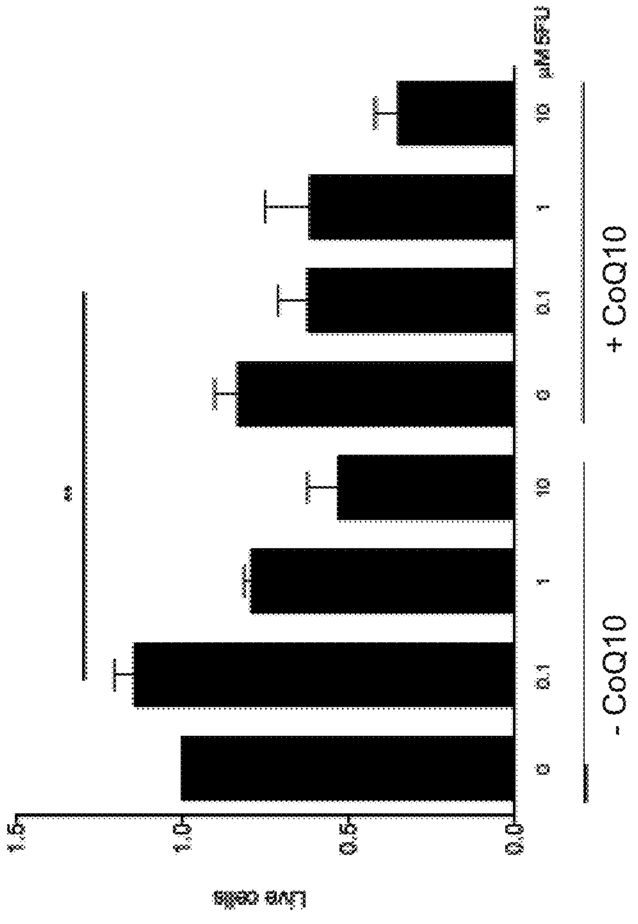
FIG. 9C is a graph showing the effect on viability in Hep3B liver cancer cells in vitro of treatment with the chemotherapeutic agent 5-fluorouracil alone or in combination with CoQ10 (100 Viability was assessed by live cell counting. Values are normalized to the number of cells treated with neither CoQ10 nor the chemotherapeutic agent.
Figure 10:
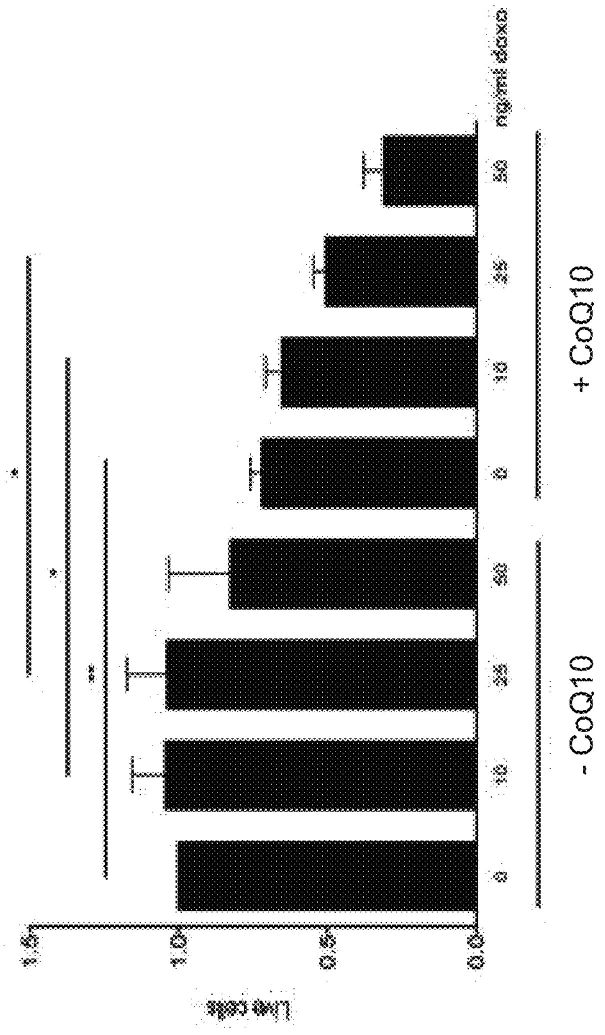
FIG. 10 is a graph showing the effect on viability in Hep3B liver cancer cells in vitro of treatment with the chemotherapeutic agent doxorubicin alone or in combination with CoQ10 (100 Viability is assessed by live cell counting. Values are normalized to the number of cells treated with neither CoQ10 nor the chemotherapeutic agent.
Figure 11A:
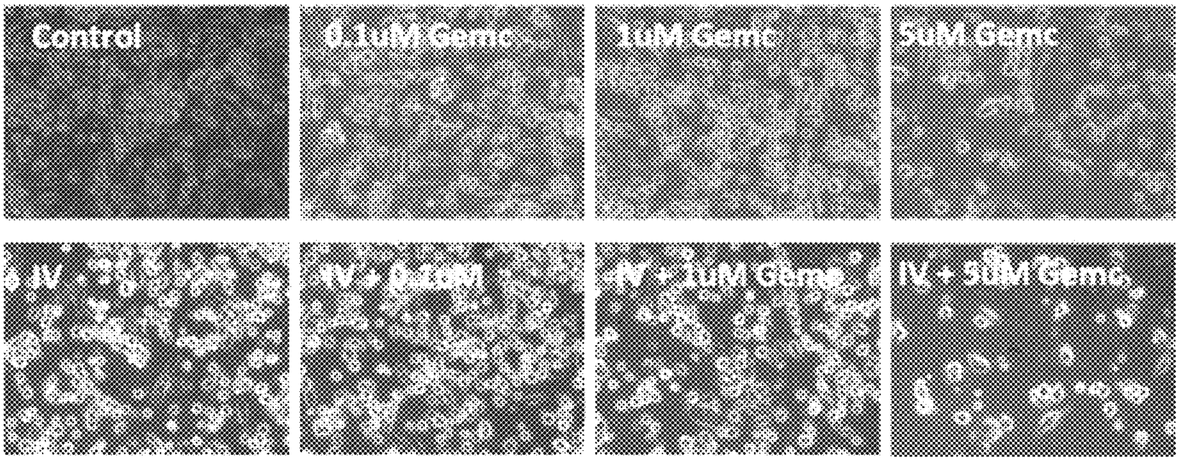
FIGS. 11A-11B show images of Mia-PaCa2 pancreatic cancer cells treated with gemcitabine alone or in combination with CoQ10 (100 (FIG. 11A) Coenzyme Q10 was added 6 hours prior to addition of chemotherapy or (FIG. 11B) at the same time as chemotherapy.
Figure 11B:
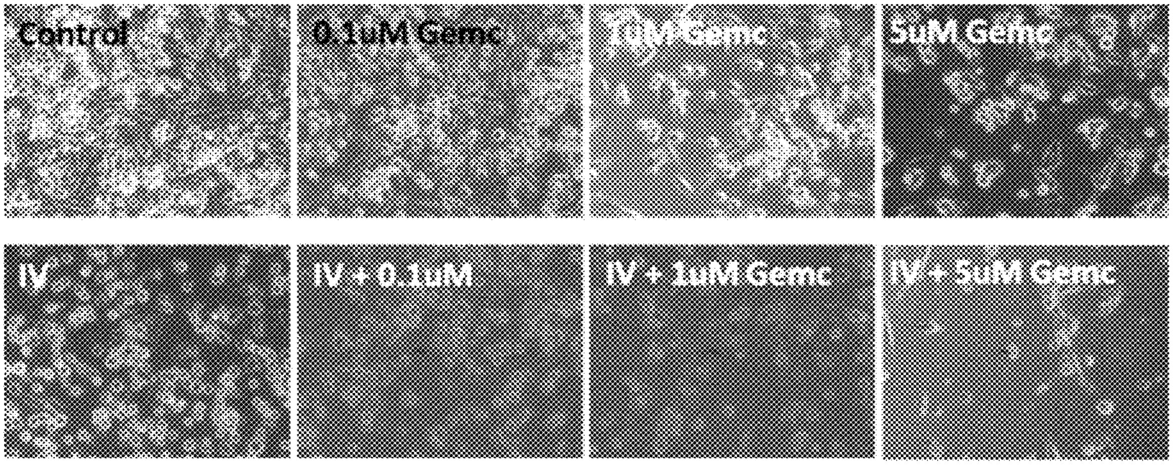
Figure 12A:
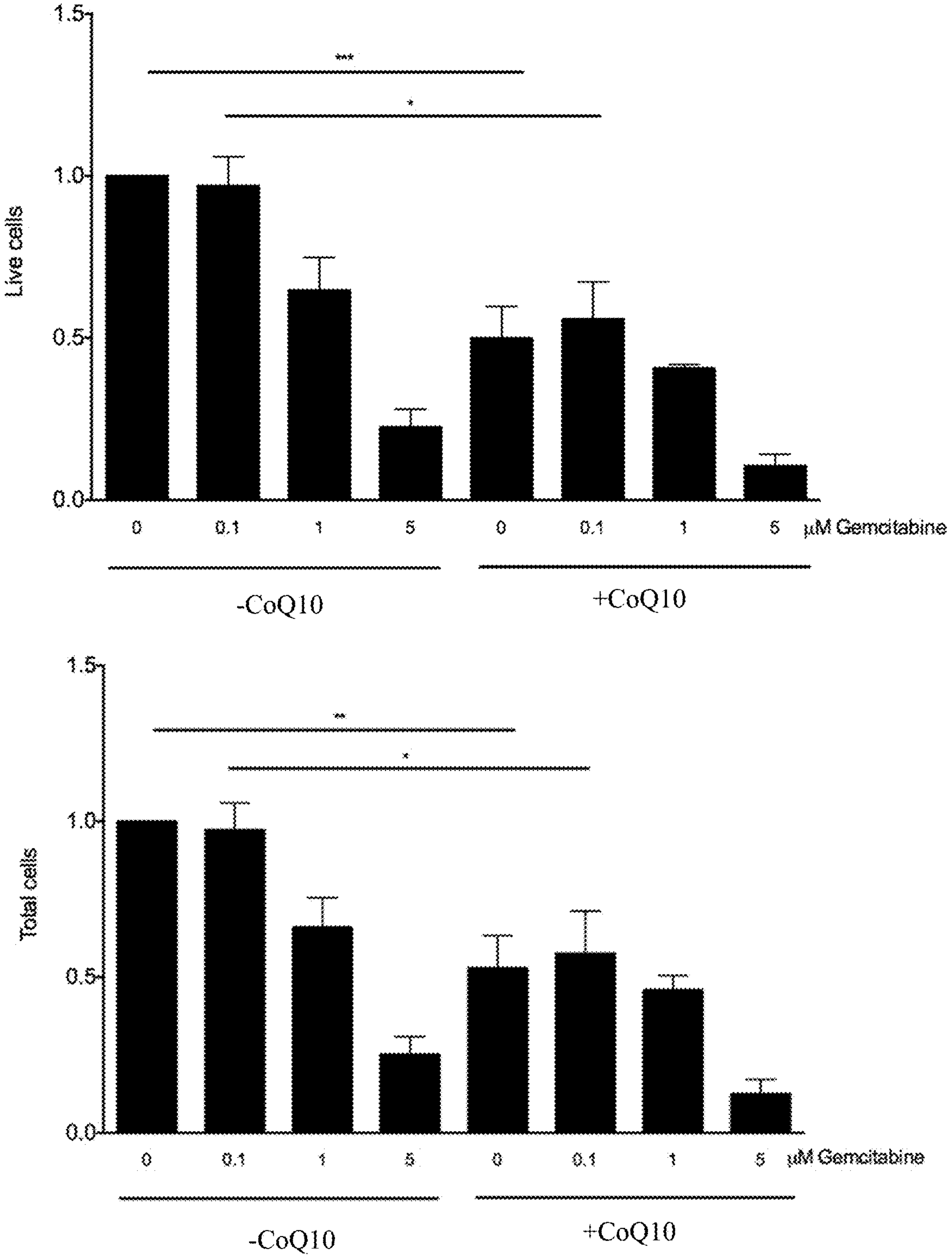
FIGS. 12A-12B are graphs of the results from a growth inhibition/promotion of cell death assay in which MIAPaCa2 pancreatic cancer cells were treated with gemcitabine, alone or in combination with CoQ10 (100 (A) Coenzyme Q10 was added 6 hours prior to addition of chemotherapy, or (B) at the same time as chemotherapy. Growth inhibition/promotion of cell death was assessed by live cell counting. Values are normalized to the number of cells treated with neither CoQ10 nor the chemotherapeutic agent.
Figure 12B:
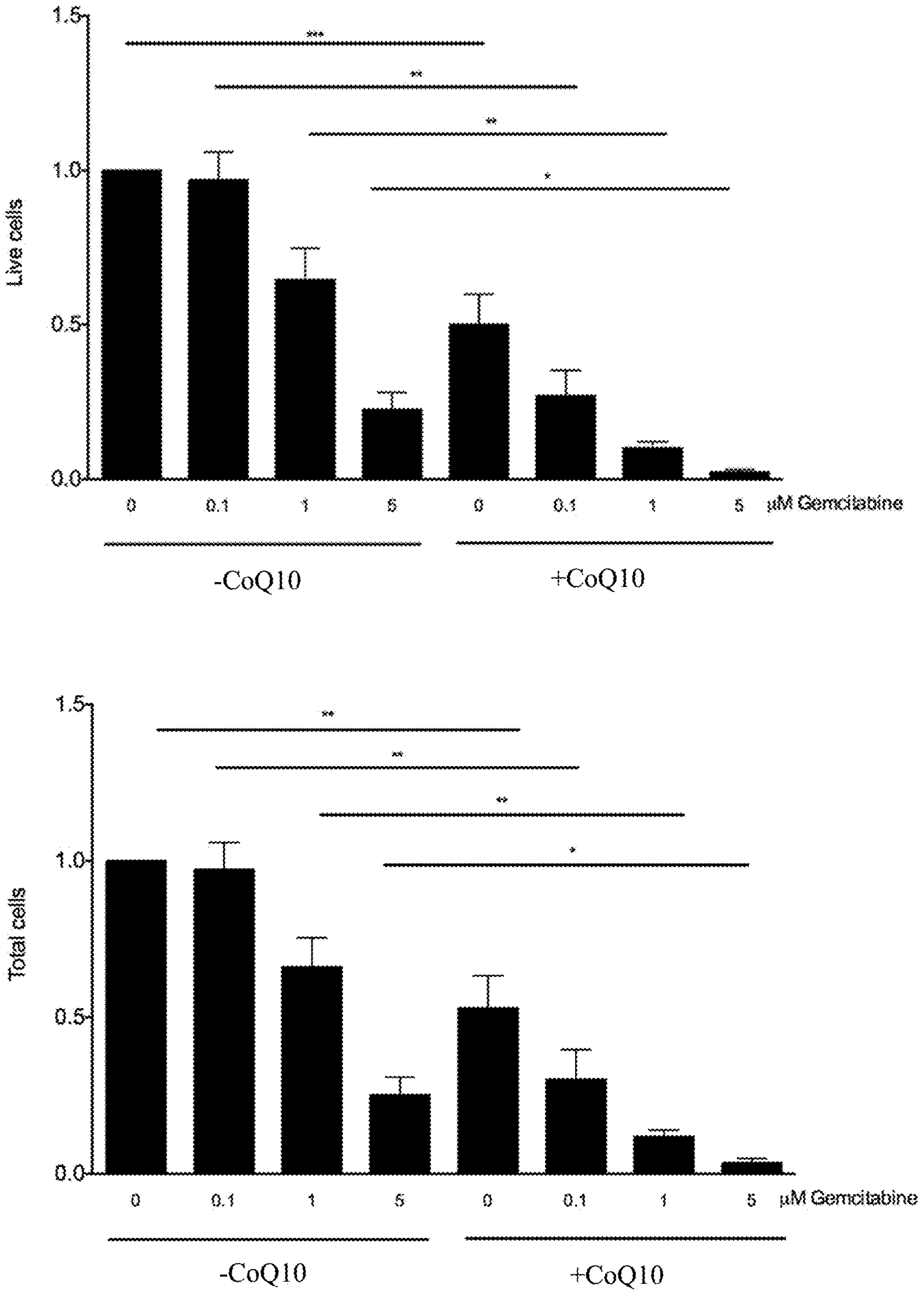
Figure 13:
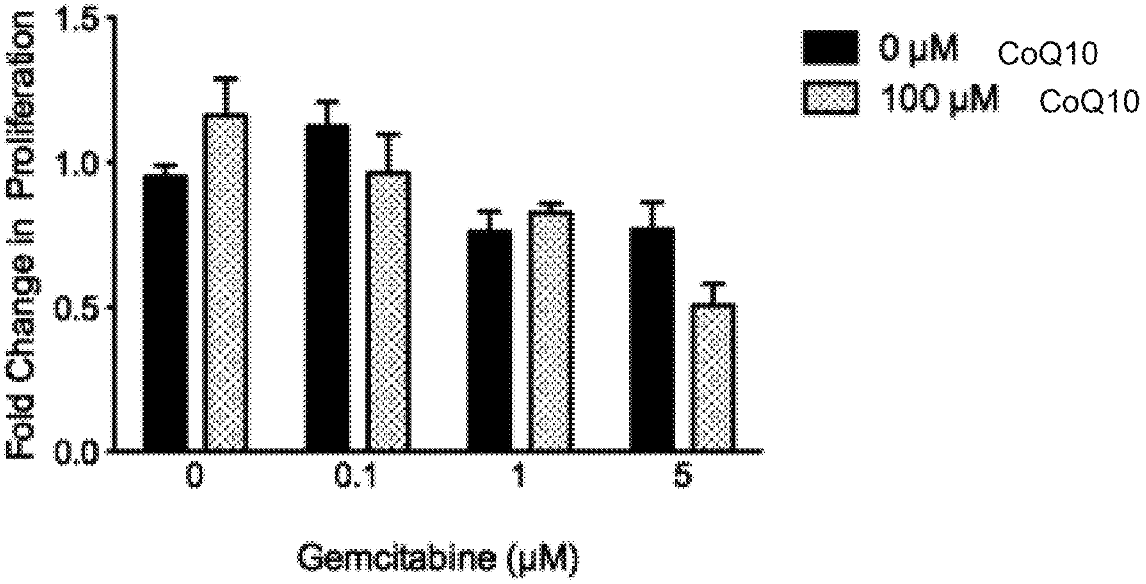
FIG. 13 is a graph showing results from proliferation assay in which MIAPaCa2 pancreatic cancer cells were treated with gemcitabine alone or in combination with CoQ10 prior to assessment of proliferation via flow cytometric analysis using the cell tracer dye CFSE which stains live cells. Values are normalized to the number of cells treated with neither CoQ10 nor the chemotherapeutic agent.
Figure 14:
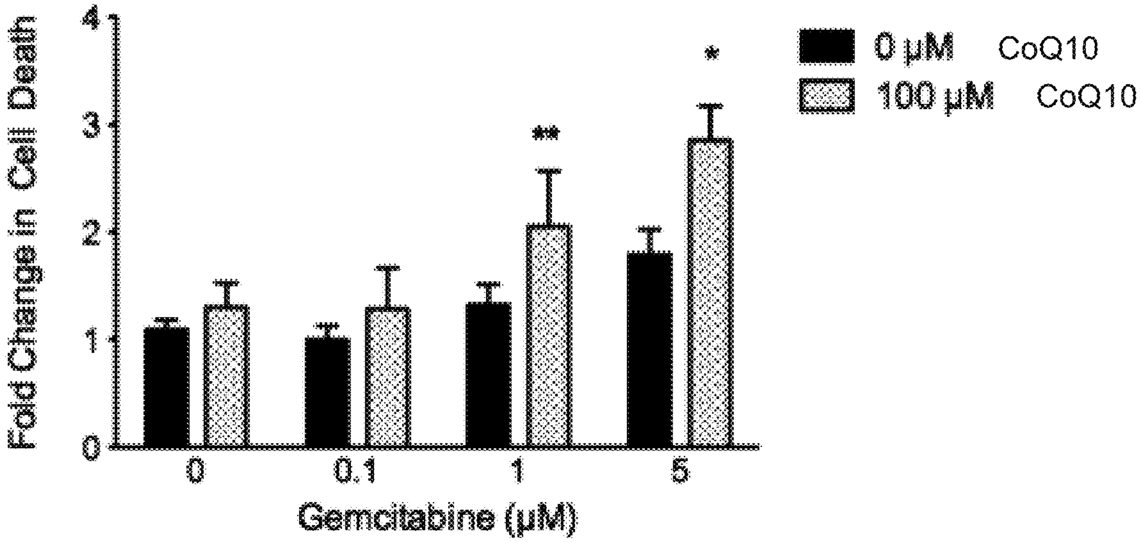
FIG. 14 is a graph showing results from assays in which MIAPaCa2 pancreatic cancer cells were treated with gemcitabine, alone or in combination with CoQ10, prior to assessment of apoptosis of remaining adherent cells via flow cytometric analysis using propidium iodide which stains dead cells. Values are normalized to the number of cells treated with neither CoQ10 nor the chemotherapeutic agent.

In a third exemplary regimen (Three Times Daily Regimen), a dose of at least about 50 mg/kg/dose or at least about 75 mg/kg/dose of the intravenous CoQ10 formulation is administered three times daily for 3 consecutive weeks followed with one week of rest, while the 150 mg/kg/dose of the gemcitabine is administered once per week for 3 weeks with one week rest. FIG. 8, shows the results a the combination therapy regimen co-administering intravenous CoQ10 formulation and intravenous gemcitabine according to the third regimen.

In a fourth exemplary regimen (pretreatment regimen), a dose of at least about 75 mg/kg/dose of the intravenous CoQ10 formulation is administered three times daily for at least 24 hours, 1 day, 2, days, 3 days, 4, days, 5 days, 6, days, 1 week, 2 weeks, 3 weeks, or more. In certain embodiments, the pretreatment regimen is used prior to administration of the first dose of chemotherapy. In certain embodiments, the pretreatment regimen is used prior to administration of each dose of chemotherapy. In certain embodiments, the pretreatment regimen is used prior to administration of each cycle of chemotherapy.

In modified regimens 1 to 4, the CoQ10 is administered at the daily indicated dose by continuous infusion rather than in 1, 2, or 3 separate doses daily.

For example, in certain embodiments, the aforementioned methods comprise a regimen of intravenously administering at least about 50 mg/kg of intravenous CoQ10 formulation once daily for 3 weeks with one week rest, and administering between about 100 mg/kg of gemcitabine and about 10 mg/kg of gemcitabine once per week for 3 weeks with one week rest.

In other embodiments, the methods comprise a regimen of intravenously administering at least about 50 mg/kg of intravenous CoQ10 formulation twice daily for 3 weeks with one week rest, and administering between about 100 mg/kg of gemcitabine and about 10 mg/kg of gemcitabine once per week for 3 weeks with one week rest. In other embodiments, the method comprises a regimen of intravenously administering at least about 50 mg/kg of intravenous CoQ10 formulation three times daily for 3 weeks with one week rest, and administering between about 100 mg/kg of gemcitabine and about 10 mg/kg of gemcitabine once per week for 3 weeks with one week rest. In further embodiments, the methods comprise a regimen of intravenously administering at least about 75 mg/kg of intravenous CoQ10 formulation once daily for 3 weeks with one week rest, and administering between about 100 mg/kg of gemcitabine and about 10 mg/kg of gemcitabine once per week for 3 weeks with one week rest. In further embodiments, the methods comprise a regimen of intravenously administering at least about 75 mg/kg of intravenous CoQ10 formulation twice daily for 3 weeks with one week rest, and administering between about 100 mg/kg of gemcitabine and about 10 mg/kg of gemcitabine once per week for 3 weeks with one week rest. In yet other embodiments, the methods comprise a regimen of intravenously administering at least about 75 mg/kg of intravenous CoQ10 formulation three times daily for 3 weeks with one week rest, and administering between about 100 mg/kg of gemcitabine and about 10 mg/kg of gemcitabine once per week for 3 weeks with one week rest.

In certain embodiments the aforementioned methods comprise administering 5 mg/kg docetaxel, 1 mg/kg doxorubicin, and 35 mg/kg cyclophosphamide to the subject every three weeks for six cycles.

In some embodiments, a combination therapy regimen comprises co-administering intravenous CoQ10 formulation and a chemotherapeutic agent, such as gemcitabine, to a patient in need thereof. In one embodiment, the gemcitabine of the combination therapy is administered by intravenous infusion at a dose of about 1000 $mg/m^2$ once weekly for up to 7 weeks (or until toxicity necessitates reducing or holding a dose), followed by a week of rest from treatment as a first cycle of treatment. In certain embodiments, in the absence of dose limiting toxicities, the CoQ10 is administered daily at the desired dose and frequency. In one embodiment the first cycle of administration is followed by subsequent cycles consisting of infusions once weekly for 3 consecutive weeks out of every 4 weeks. In one embodiment, dosage of gemcitabine is adjusted based upon the degree of hematologic toxicity experienced by the patient. In one embodiment, when the absolute granulocyte count of the patient is greater than or equal to $1000\times10^6$/L, and the platelet count of the patient is greater than or equal to $100{,}000\times10^6$/L, a full dose of 1000 $mg/m^2$ once weekly may be administered to the patient. In one embodiment, when the absolute granulocyte count of the patient is between about $500\text{-}999\times10^6$/L, or the platelet count of the patient is between about $50{,}000\text{-}99{,}000\times10^6$/L, a 75% of full dose, e.g. 750 $mg/m^2$ once weekly may be administered to the patient. In one embodiment, when the absolute granulocyte count of the patient is less than $500\times10^6$/L, or the platelet count of the patient is less than $50{,}000\times10^6$/L, gemcitabine administration should be hold until the absolute granulocyte count of the patient is greater than or equal to $500\times10^6$/L, or the platelet count of the patient is greater than or equal to $50{,}000\times10^6$/L.

Guidance for appropriate dosing regimens for chemotherapeutic agents approved for use in various cancer types are known in the art. The CoQ10 treatment regimens provided herein can be combined with other known treatment regimens based on the exemplary teachings provided herein.

In some embodiments, a regimen comprises co-administering intravenous CoQ10 formulation and a chemotherapeutic agent such as gemcitabine. In the first regimen (Once Daily Regimen), a dose of at least about 58 mg/kg, at least about 58.6 mg/kg, at least about 78 mg/kg, or at least about 104 mg/kg of the intravenous CoQ10 formulation is administered once daily for up to 7 weeks (or until toxicity necessitates reducing or holding a dose), optionally followed by subsequent cycles consisting of infusion once daily for 3 consecutive weeks out of every 4 weeks; while the at least about 1000 $mg/m^2$, or at least about 750 $mg/m^2$ of the gemcitabine is administered once weekly for up to 7 weeks (or until toxicity necessitates reducing or holding a dose), optionally followed by subsequent cycles consisting of infusion once daily for 3 consecutive weeks out of every 4 weeks. In the second regimen (Twice Daily Regimen), a dose of at least about 58 mg/kg, at least about 58.6 mg/kg, at least about 78 mg/kg, or at least about 104 mg/kg of the intravenous CoQ10 formulation is administered twice daily for up to 7 weeks (or until toxicity necessitates reducing or holding a dose), optionally followed by subsequent cycles consisting infusion once daily for 3 consecutive weeks out of every 4 weeks; while the at least about 1000 $mg/m^2$, or at least about 750 $mg/m^2$ of the gemcitabine is administered once weekly for up to 7 weeks (or until toxicity necessitates reducing or holding a dose), optionally followed by subsequent cycles consisting of infusion once daily for 3 consecutive weeks out of every 4 weeks. In the third regimen (Three Times Daily Regimen), a dose of at least about 58 mg/kg, at least about 58.6 mg/kg, at least about 78 mg/kg, or at least about 104 mg/kg of the intravenous CoQ10 formulation is administered three times daily for up to 7 weeks (or until toxicity necessitates reducing or holding a dose), optionally followed by subsequent cycles consisting infusion once daily for 3 consecutive weeks out of every 4 weeks; while the at least about 1000 $mg/m^2$, or at least about 750 $mg/m^2$ of the gemcitabine is administered once weekly for up to 7 weeks (or until toxicity necessitates reducing or holding a dose), optionally followed by subsequent cycles consisting of infusion once daily for 3 consecutive weeks out of every 4 weeks. In certain embodiments, the CoQ10 is administered by continuous infusion with total daily doses based on those provided in regimens 1-3 above. In certain embodiments, in the absence of dose limiting toxicities, the CoQ10 is administered daily at the desired dose and frequency.

In one embodiment, the dosage of gemcitabine is adjusted based upon the degree of hematologic toxicity experienced by the patient. In one embodiment, when the absolute granulocyte count of the patient is greater than or equal to $1000\times10^6$/L, and the platelet count of the patient is greater than or equal to $100{,}000\times10^6$/L, a full dose of 1000 $mg/m^2$ once weekly may be administered to the patient. In one embodiment, when the absolute granulocyte count of the patient is between about $500\text{-}999\times10^6$/L, or the platelet count of the patient is between about $50{,}000\text{-}99{,}000\times10^6$/L, a 75% of full dose, e.g. 750 $mg/m^2$ once weekly may be administered to the patient. In one embodiment, when the absolute granulocyte count of the patient is less than $500\times10^6$/L, or the platelet count of the patient is less than $50{,}000\times10^6$/L, gemcitabine administration should be hold until the absolute granulocyte count of the patient is greater than or equal to $500\times10^6$/L, or the platelet count of the patient is greater than or equal to $50{,}000\times10^6$/L.

In one embodiment of the combination treatment methods provided herein, the CoQ10 formulation is administered one time per week. In one embodiment, the CoQ10 formulation is administered 2 times per week. In one embodiment, the CoQ10 formulation is administered 3 times per week. In another embodiment, the CoQ10 formulation is administered 5 times per week. In one embodiment, the CoQ10 formulation is administered once per day. In one embodiment, the CoQ10 formulation is administered twice per day. In one embodiment, the CoQ10 formulation is administered three times per day. In some embodiments, where the IV formulation is administered by infusion, the dosage is administered by infusion over about 1 hour, 2 hours, 3 hours, 4 hours or longer. In one embodiment, the IV CoQ10 formulation is administered by infusion over about 4 hours. In certain embodiments, the IV CoQ10 formulation is administered by infusion over about 6, 8, 10, 12, 14, 16, 18, 20, 22 or 24 hours.

In another embodiment, the CoQ10 is administered in the form of a intravenous CoQ10 formulation at a dosage of between about 10 mg/kg and about 10,000 mg/kg of CoQ10, about 20 mg/kg to about 5000 mg/kg, about 50 mg/kg to about 3000 mg/kg, about 100 mg/kg to about 2000 mg/kg, about 200 mg/kg to about 1000 mg/kg, or about 300 mg/kg to about 500 mg/kg, wherein the CoQ10 formulation comprises between about 1% and 10% of Coenzyme Q10. In one embodiment, the CoQ10 formulation comprises about 3% to about 5% of Coenzyme Q10. In one embodiment, the CoQ10 formulation comprises about 4% of Coenzyme Q10. In one embodiment, the CoQ10 IV formulation comprises about 8% of Coenzyme Q10. In other embodiments, the CoQ10 IV formulation comprises about 1%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% of Coenzyme Q10. It should be understood that ranges having any one of these values as the upper or lower limits are also intended to be part of this invention.

In certain embodiments, administration of CoQ10 is initiated at least 8 hours, at least 12 hours, at least 18 hours, at least 24 hours, at least 36 hours, at least 48 hours, at least 3 days, at least 4 days, at least 5 days, at least 6 days, at least 1 week, at least 2 weeks, at least 3 weeks, at least 4 weeks, at least 5 weeks, at least 6 weeks, at least 7 weeks, or at least 8 weeks prior to administration of the first dose of a chemotherapeutic agent or chemotherapeutic regimen. In one embodiment, the administration of CoQ10 is discontinued before initiation of treatment with the chemotherapeutic agent or chemotherapeutic regimen, i.e., and treatment with the chemotherapeutic agent excludes treatment with CoQ10. In one embodiment, the administration of CoQ10 is continued or resumed after initiation of treatment with the chemotherapeutic agent or chemotherapeutic regimen such that the CoQ10 and chemotherapeutic agent are concurrently administered, e.g., for at least one cycle.

Where utilized in the combination therapy to treat cancer, the intravenous CoQ10 formulations may be in a pharmaceutically acceptable carrier that may be administered in a therapeutically effective amount to an area of oncogenesis as either a mono-therapy, in combination with at least one other chemotherapeutic agent for a given indication, in combination with radiotherapy, following surgical intervention to radically remove a tumor, in combination with other alternative and/or complementary acceptable treatments for cancer, and the like. In certain embodiments, the present disclosure also provides a method for reactivating a mutated/inactivated p53 protein by administering to an area of oncogenesis in a patient a composition of the present disclosure.

In general, the combination therapy including any of the CoQ10 formulations and the chemotherapeutic agents described herein may be used to prophylactically or therapeutically treat any neoplasm. In a particular embodiment, the combination therapy is used to treat solid tumors. In various embodiments of the invention, the combination therapy is used for treatment or prevention of cancer of the brain, central nervous system, head and neck, prostate, breast, testicular, pancreas, liver, colon, bladder, urethra, gall bladder, kidney, lung, non-small cell lung, melanoma, mesothelioma, uterus, cervix, ovary, sarcoma, bone, stomach, skin, and medulloblastoma. In a preferred embodiment, the combination therapy is used to treat triple-negative breast cancer (TNBC). In one embodiment, the combination therapy including CoQ10 described herein may be used to treat a chloroleukemia, e.g., a primary chloroleukemia or a secondary or metastatic chloroleukemia, e.g., that presents, migrates or metastasizes to a particular organ such as, e.g., the lung, the liver or the central nervous system.

However, treatment using combination therapies of the invention is not limited to the foregoing types of cancers. Examples of cancers amenable to treatment with the combination therapies include, but are not limited to, for example, Hodgkin's Disease, Non-Hodgkin's Lymphoma, multiple myeloma, neuroblastoma, breast cancer, ovarian cancer, lung cancer, rhabdomyosarcoma, primary thrombocytosis, primary macroglobulinemia, small-cell lung tumors, primary brain tumors, stomach cancer, colon cancer, malignant pancreatic insulanoma, malignant carcinoid, urinary bladder cancer, premalignant skin lesions, skin cancer, testicular cancer, lymphomas, thyroid cancer, neuroblastoma, esophageal cancer, genitourinary tract cancer, malignant hypercalcemia, cervical cancer, endometrial cancer, adrenal cortical cancer, and prostate cancer. In one embodiment, a CoQ10 IV formulation described herein may be used in combination with a chemotherapeutic agent to treat or prevent various types of skin cancer (e.g., Squamous cell Carcinoma or Basal Cell Carcinoma), pancreatic cancer, breast cancer, prostate cancer, liver cancer, or bone cancer. In one embodiment, the combination therapy including CoQ10 is used for treatment of a skin oncological disorder including, but not limited to, squamous cell carcinomas (including SCCIS (in situ) and more aggressive squamous cell carcinomas), basal cell carcinomas (including superficial, nodular and infiltrating basal cell carcinomas), melanomas, and actinic keratosis. In one embodiment, the oncological disorder or cancer which can be treated with the combination therapy including CoQ10 is not melanoma. In one embodiment, the oncological disorder is merkel cell carcinoma (MCC). In one embodiment, the oncological disorder or cancer which can be treated with the combination therapy including CoQ10 is not skin cancer.

In certain embodiments, the effect that combination therapy including CoQ10 may have on cancer cells may depend, in part, on the various states of metabolic and oxidative flux exhibited by the cancer cells. CoQ10 may be utilized to interrupt and/or interfere with the conversion of an oncogenic cell's dependency of glycolysis and increased lactate utility. As it relates to a cancer state, this interference with the glycolytic and oxidative flux of the tumor microenvironment may influence apoptosis and angiogenesis in a manner which reduces the development of a cancer cell. In some embodiments, the interaction of CoQ10 with glycolytic and oxidative flux factors may enhance the ability of CoQ10 to exert its restorative apoptotic effect in cancer while establishing viable drug targets for drug discovery and development.

In one embodiment, administration of CoQ10 and the chemotherapeutic agent as described or incorporated herein, reduces tumor size, weight or volume, increases time to progression, inhibits tumor growth and/or prolongs the survival time of a subject having an oncological disorder. In a preferred embodiment, CoQ10 is administered by injection, e.g., by intravenous administration, of an intravenous CoQ10 formulation as described or incorporated herein. In certain embodiments, administration of CoQ10 and the chemotherapeutic agent reduces tumor size, weight or volume, increases time to progression, inhibits tumor growth and/or prolongs the survival time of the subject by at least 1%, 2%, 3%, 4%, 5%, 10%, 20%, 30%, 40%, 50%, 60%, 70%, 80%, 90%, 100%, 200%, 300%, 400% or 500% relative to a corresponding control subject that is administered CoQ10 alone or the chemotherapeutic agent alone. In other embodiments, administration of CoQ10 and the chemotherapeutic agent stabilizes the oncological disorder in a subject with a progressive oncological disorder prior to treatment.

This invention also relates to a method of treating tumors in a human or other animal by intravenously administering to such human or animal an effective, non-toxic amount of CoQ10. One skilled in the art would be able, by routine experimentation, to determine what an effective, non-toxic amount of CoQ10 would be for the purpose of treating malignancies. For example, a therapeutically active amount of CoQ10 may vary according to factors such as the disease stage (e.g., stage I versus stage IV), age, sex, medical complications (e.g., immunosuppressed conditions or diseases) and weight of the subject, and the ability of the CoQ10 to elicit a desired response in the subject. The dosage regimen may be adjusted to provide the optimum therapeutic response. For example, several divided doses may be administered daily or administered by continuous infusion or the dose may be proportionally reduced as indicated by the exigencies of the therapeutic situation.

The invention also provides, in another aspect, methods for treating or preventing aggressive oncological disorders in humans. These methods include intravenously administering CoQ10 to the human at a therapeutically effective dose while co-administering a chemotherapeutic agent, so that treatment or prevention of the aggressive oncological disorder occurs. In one embodiment, these methods include intravenously administering CoQ10 to the subject at a selected lower dosage than a dosage regimen used or selected for less aggressive or non-aggressive oncological disorder, so that treatment or prevention of the aggressive oncological disorder occurs. In certain embodiments the aggressive oncological disorder includes pancreatic carcinoma, hepatocellular carcinoma, Ewing's sarcoma, metastatic breast cancer, metastatic melanoma, brain cancer (astrocytoma, glioblastoma), neuroendocrine cancer, colon cancer, liver cancer, lung cancer, osteosarcoma, androgen-independent prostate cancer, ovarian cancer, skin cancer, and non-Hodgkin's Lymphoma.

In another aspect, the invention provides methods for topical administration of CoQ10, especially in the treatment of skin cancer, in combination with administration of chemotherapeutic agents by any route of administration. Such methods include pre-treatment with CoQ10 prior to first administration of the chemotherapeutic agent.

In a related aspect, the invention provides a method for treating or preventing a non-aggressive oncological disorder in a human. These methods include intravenously co-administering CoQ10 and a chemotherapeutic agent to the subject at a therapeutically effective dose, so that treatment or prevention of the non-aggressive oncological disorder occurs. In one embodiment, these methods include administering CoQ10 to the subject at a selected higher dosage over a dosage regimen used or selected for aggressive oncological disorders so that treatment or prevention of the non-aggressive oncological disorder occurs. In certain embodiments, the non-aggressive oncological disorder includes non-metastatic breast cancer, androgen-dependent prostate cancer, small cell lung cancer and acute lymphocytic leukemia.

In some embodiments of the invention, the treatment or prevention of the oncological disorder occurs via an interaction of CoQ10 with a protein or other cellular component selected from the group consisting of HNF4-alpha, Bcl-xl, Bcl-xS, BNIP-2, Bcl-2, Birch, Bcl-2-L11 (Bim), XIAP, BRAF, Bax, c-Jun, Bmf, PUMA, cMyc, transaldolase 1, CoQ1, CoQ3, CoQ6, prenyltransferase, 4-hydrobenzoate, neutrophil cytosolic factor 2, nitric oxide synthase 2A, superoxide dismutase 2, VDAC, Bax channel, ANT, Cytochrome c, complex 1, complex II, complex III, complex IV, Foxo 3a, DJ-1, IDH-1, Cpt1C and Cam Kinase II. In some embodiments the oncological disorder is selected from the group consisting of leukemia, a lymphoma, a melanoma, a carcinoma, and a sarcoma.

In some embodiments the chemotherapeutic agent, for example gemcitabine, works by damaging RNA or DNA that tells cancerous cells how to copy itself in mitosis. If the cells are unable to divide, then they will die. In some instances, the chemotherapeutic agent induces apoptosis. Gemcitabine incorporates itself into the cancerous cells and prevents them from dividing. As with fluorouracil and other pyrimidines, the triphosphate analogue of gemcitabine replaces one of the building blocks of nucleic acids (i.e., cytidine) during DNA replication. This halts tumor growth, as only one additional nucleoside can be attached to the faulty nucleoside, which results in apoptosis. Gemcitabine also targets the enzyme ribonucleotide reductse (RNR). The diphosphate analogue binds to RNR active site and inactivates the enzyme irreversibly. Once RNA is inhibited, the cell cannot produce deoxyribonucleotides required for DNA replication and repair and the cell apoptosis occurs. In some embodiments, the gemcitabine is administered by the GemCarbo regimen, wherein gemcitabine is administered in combination with carboplatin over a 21 day cycle.

International Patent Application Publication No. WO/2009/126764, filed Apr. 9, 2009, discloses the treatment of cancer with CoQ10 and International Patent Application Publication No. WO2011/11290, filed Mar. 11, 2011, discloses intravenous formulations of CoQ10. US Patent Application Publication No.: US2011/0027247 filed May 11, 2010, discloses methods of treating oncological disorders using topically administered CoQ10. International Patent Application Nos. WO2009073843, filed Jun. 11, 2009, and WO2012174559, filed Jun. 18, 2012 disclose formulations of CoQ10 for administration by inhalation. These applications are each hereby incorporated by reference in their entirety. In certain embodiments of the invention, the methods further include a treatment regimen which includes any one of or a combination of surgery, radiation, hormone therapy, antibody therapy, therapy with growth factors, cytokines, and chemotherapy.

Reference will now be made in detail to preferred embodiments of the invention. While the invention will be described in conjunction with the preferred embodiments, it will be understood that it is not intended to limit the invention to those preferred embodiments. To the contrary, it is intended to cover alternatives, modifications, and equivalents as may be included within the spirit and scope of the invention as defined by the appended claims.

EXAMPLES

The following examples provide non-limiting exemplary methods and results from the treatment of oncological disorders with the combination therapy of CoQ10 and a chemotherapeutic agent.

Methods

Example 1—Regimen 1—Once Daily IV CoQ10 and Once Weekly Gemcitabine Combination Pancreatic Carcinoma is one of the deadliest types of cancers and certainly one that is most clinically difficult to manage given that most diagnoses occur in late-stage disease. Gemcitabine is among the few FDA approved drugs used alone and in combination with other antineoplastic agents for pancreatic cancer. An intravenous 4% formulation of CoQ10 was used alone or in combination with gemcitabine in in vitro cell based assays and in a xenogeneic mouse human pancreatic cancer model to demonstrate the increased efficacy of the combination of CoQ10 with gemcitabine in the treatment of pancreatic cancer. The specific formulation used is provided in International Patent Publication WO2011/112900 filed on Mar. 11, 2011 which is incorporated herein by reference in its entirety.

Xenogeneic Mouse Human Pancreatic Cancer Model

Equal numbers of MIAPaCa-2 human pancreatic tumor cells were suspended in MATRIGEL® and injected into NOD scid gamma (NSG) mice. The NSG mouse model is devoid of innate and adaptive immune systems and provides a biological environment suitable for the growth of human tumors in vivo. The MIAPaCa-2 is a well established human derived pancreatic carcinoma cell line that can be used to establish pancreatic tumors in immunosuppressed animals. MIAPaca-2 tumors were allowed to develop for, on average, at least 3 weeks in mice prior to initiation of treatment. Animals with palpable tumors were randomized into treatment groups. Results shown in graphs indicate the number of days of survival from the first day of treatment in the study.

MIAPaca-2 cells ($1\times10^7$ cells per animal) were injected into NSG mice using the method provided above. Mice having palpable tumors were randomized into 4 groups of 30 mice each as follows:

i. Group 1—No treatment.
ii. Group 2—Intravenous dose of 4% Coenzyme Q10, 50 mg/kg/day.
iii. Group 3—Intravenous single weekly dose of gemcitabine at 150 mg/kg/week for 3 weeks with one week rest. This cycle was repeated at four week intervals.
iv. Group 4—Combination of intravenous dose of 4% Coenzyme Q10, 50 mg/kg/day and intravenous single weekly dose of gemcitabine at 150 mg/kg for 3 weeks with one week rest. This cycle was repeated at four week intervals.

Mice were observed for viability and secondary symptoms, and tumor growth was monitored by palpation. At mortality, tumors were harvested from the mice, and were measured, weighed, and analyzed for the presence of tumor vasculature.

Survival curves are shown in FIG. 1. As shown, the untreated group exhibited steep death rates, whereas in CoQ10, gemcitabine alone and the combination of CoQ10 resulted in prolongation of life as compared to untreated control. CoQ10 alone had significantly greater impact on survival than gemcitabine alone. Animals treated with a combination of gemcitabine and CoQ10 exhibited prolonged survival and long-term remission that was statistically significant compared to other groups.

Figure 2:
FIG. 2 is a photograph showing the effect of once daily dosing with intravenous CoQ10, alone or in combination with gemcitabine, on tumor size at the time of death in a xenogeneic mouse model of pancreatic cancer using human pancreatic tumor MIAPaCa-2 cells. Tumors in Group 1 were harvested at 20 days after initiation of treatment. Tumors in Group 2 were harvested at 50-60 days after initiation of treatment. Tumors in Group 3 were harvested at 40-50 days after initiation of treatment. Tumors in Group 4 were harvested at 50-60 days after initiation of treatment.

Tumors harvested from animals at mortality are shown in FIG. 2. Tumors were harvested from animals in Group 1 (control) at day 20 after the initiation of treatment. Tumors were harvested from animals in Group 2 (Coenzyme Q10 alone) at days 50-60 after the initiation of treatment. Tumors were harvested from animals in Group 3 (gemcitabine alone) at days 40-50 after the initiation of treatment. Tumors were harvested from animals in Group 4 (gemcitabine+Coenzyme Q10) at days 50-60 after the initiation of treatment. The tumor sizes shown in FIG. 2 are representative of the tumor size overall observed in each group at the indicated time period.

Although tumors were harvested from animals in the control group (Group 1) 20-40 days prior to the date that the tumors were harvested from the treatment groups (Groups 2-4), it is evident from FIG. 2 that the tumors in the control group, on average, were significantly larger than those in any of the treatment groups at the time of death. These results show that both Coenzyme Q10 and gemcitabine inhibited the growth of pancreatic tumors in the xenogeneic mouse human tumor model.

Figure 3:
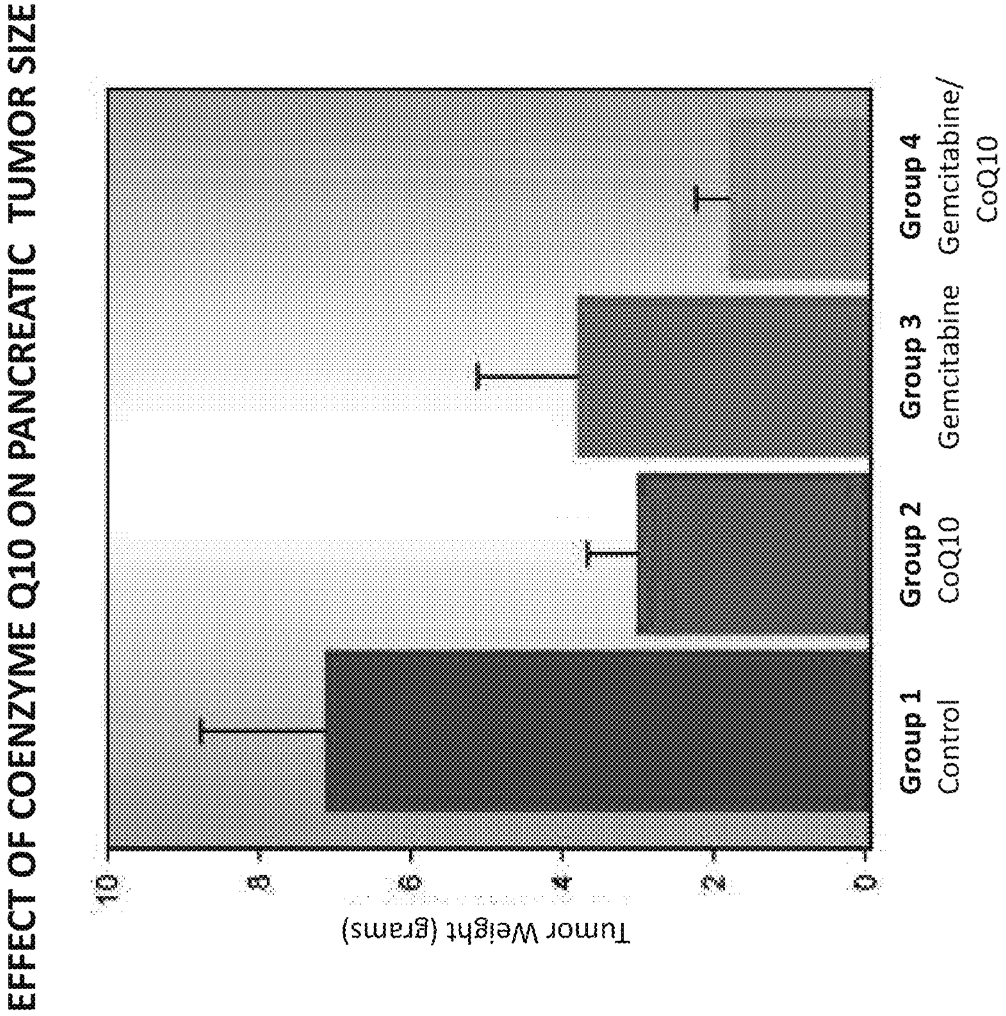
FIG. 3 is a graph showing the effect of once daily dosing with intravenous CoQ10, alone or in combination with gemcitabine, on tumor size at the time of death in a xenogeneic mouse model of pancreatic cancer using human pancreatic tumor MIAPaCa-2 cells. Tumors in Group 1 were harvested at 20 days after initiation of treatment. Tumors in Group 2 were harvested at 50-60 days after initiation of treatment. Tumors in Group 3 were harvested at 40-50 days after initiation of treatment. Tumors in Group 4 were harvested at 50-60 days after initiation of treatment.

Additionally, tumors were weighed to quantitatively determine size. These results are shown in FIG. 3. On average, tumors from the mice treated with Coenzyme Q10 alone (Group 2) were significantly smaller than tumors from mice in the control group (Group 2 vs. Group 1, $p<0.001$) or tumors from mice in the gemcitabine treated group (Group 2 vs. Group 3, $p<0.001$). Tumors from mice treated with a combination of Coenzyme Q10 and gemcitabine (Group 4) were found, on average, to be significantly smaller than tumors from mice treated with Coenzyme Q10 alone (Group 2 vs. Group 4, $p=0.01$) or gemcitabine alone (Group 3 vs Group 4, $p<0.0001$).

Similarly, palpable tumors were noted to be decreased in the treatment groups as compared to the tumors in the control group. Further, histological analysis of the tumors revealed decreased tumor vasculature in the tumors from the mice treated with Coenzyme Q10 as compared, at least, to tumors from untreated control mice (data not shown). No quantitative analysis of tumor vasculature was performed.

These data demonstrate that intravenously administering Coenzyme Q10 to mice bearing pancreatic tumors inhibits pancreatic tumor growth, as compared to control untreated mice and as compared to mice treated with gemcitabine alone, an agent approved for the treatment of pancreatic tumors in humans. Moreover, the combination of intravenously administered Coenzyme Q10 and gemcitabine was more effective at inhibiting the growth of pancreatic tumors in mice than treatment with either agent alone.

Intravenously administered Coenzyme Q10 was also observed to result in a decrease in the amount of vasculature in pancreatic tumors as compared to, at least, tumors from untreated control mice, further demonstrating the effectiveness of Coenzyme Q10 in the treatment of cancer.

These data further demonstrate that intravenously administering Coenzyme Q10 to mice bearing pancreatic tumors increases survival time of the mice, as compared to control untreated animals and as compared to animals treated with gemcitabine alone, an agent approved for the treatment of pancreatic tumors in humans. Moreover, the combination of Coenzyme Q10 and gemcitabine was more effective at increasing survival time in mice bearing pancreatic tumors than treatment with either agent alone.

Example 2—Regimen 2—Twice Daily IV CoQ10 and Once Weekly Gemcitabine Combination for Treating Pancreatic Cancer MIAPaca-2 cells ($1\times10^7$ cells per animal) were injected into NSG mice using the method provided above. Mice having palpable tumors were randomized into 4 groups of 30 mice each as follows:

In the second regimen, a dose of i. Control, no treatment.

ii. 50 mg/kg of intravenous 4% CoQ10 intravenous formulation administered intraperitoneally twice daily for 3 weeks with one week of rest.

iii. 150 mg/kg of gemcitabine once per week for 3 weeks with one week of rest.

iv. 50 mg/kg of intravenous 4% CoQ10 intravenous formulation administered intraperitoneally twice daily for 3 weeks with one week of rest and a dose of 150 mg/kg of gemcitabine once per week for 3 weeks with one week of rest.

In this example, the intravenous formulation of CoQ10 was administered intraperitoneally to prevent vascular damage that would result from the frequency of administration.

Mice were monitored for survival. The results, as shown in FIG. 4, demonstrate an increase in survival of mice treated with CoQ10, either alone or in combination with gemcitabine as compared to untreated mice or mice treated with gemcitabine alone. These data demonstrate that CoQ10, either alone or in combination with gemcitabine, is more effective in treating pancreatic cancer than gemcitabine alone.

Example 3—In Vitro Combination Therapy (CoQ10+Gemcitabine) of Pancreatic and Breast Cancer In Vitro Cell Viability Assay Cell lines (e.g., MIAPaCa-2, Hep3B, and/or SK-Br3) cell lines were maintained in culture using standard culture conditions for each cell line. Cells were treated with CoQ10 or the indicated chemotherapeutic agents at the indicated concentrations for the indicated times. After the predetermined incubation time, the cells were stained to distinguish between viable and non-viable cells using routine methods. Cells were counted by microscopy or flow cytometry. The number of cells after treatment were normalized to the number of cells in the untreated sample.

Figure 5A:
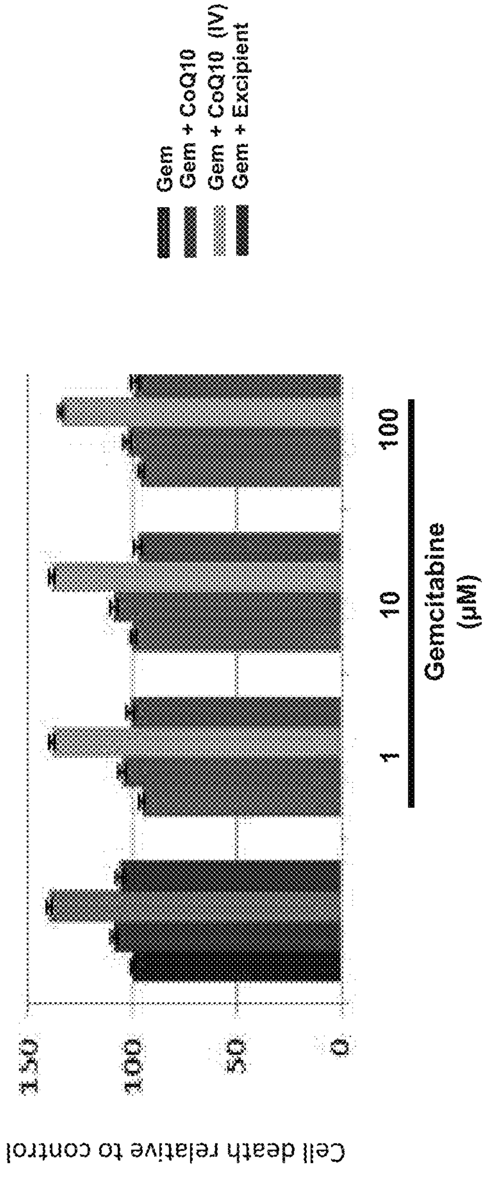
FIG. 5A is a graph showing the effect on viability of MIAPaCa-2 pancreatic cancer cells in vitro of 6 hour treatment with gemcitabine, CoQ10, an intravenous formulation of CoQ10, or the intravenous formulation of CoQ10 in combination with gemcitabine.
Figure 5B:
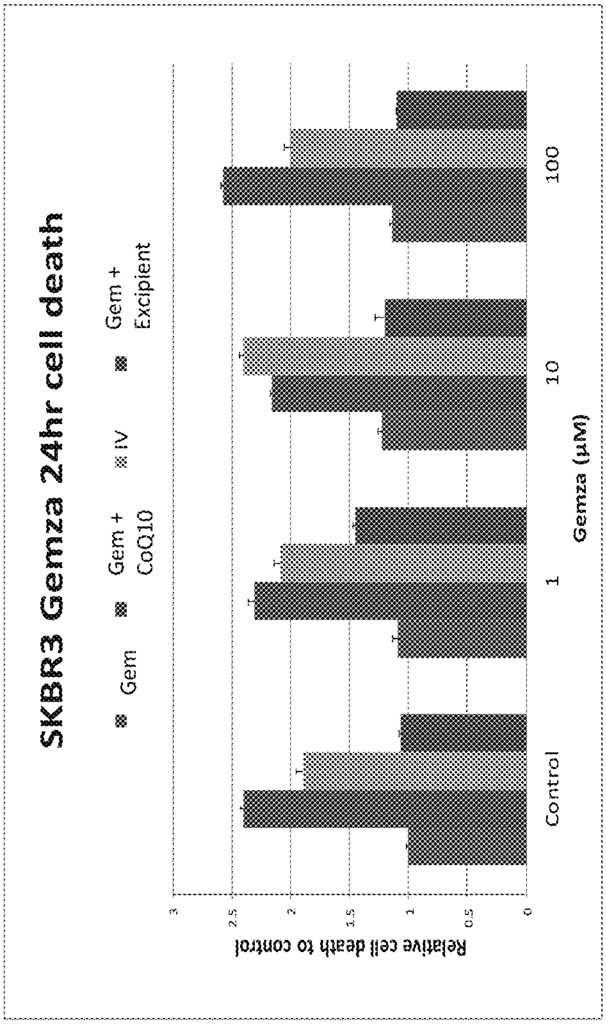
FIG. 5B is a graph showing the effect on viability of SK-Br3 breast cancer cells in vitro of 6 hour treatment with gemcitabine, CoQ10, an intravenous formulation of CoQ10, or the intravenous formulation of CoQ10 in combination with gemcitabine.

Specifically, to assess the efficacy of CoQ10 in combination with gemcitabine in vitro, MIAPaCa-2 pancreatic carcinoma cells were maintained in culture and exposed to increasing concentrations of gemcitabine in combination with CoQ10, the 4% CoQ10 intravenous formulation, or the excipient of the CoQ10 intravenous formulation. FIG. 5A shows the effect of 6 hour treatment with CoQ10 or the 4% CoQ10 intravenous formulation, either alone or in combination with gemcitabine on MIAPaCa-2 pancreatic cancer cells. FIG. 5B shows the effect of 6 hour treatment with CoQ10 or the 4% CoQ10 intravenous formulation alone, or in combination with gemcitabine, on SK-Br3 breast cancer cells. The results demonstrate increased cell death in both pancreatic and breast cancer cells following exposure to the 4% CoQ10 intravenous formulation in combination with gemcitabine, at 6 hours. The combination treatment with gemcitabine and the 4% CoQ10 intravenous formulation results in an increase in cell death as compared to gemcitabine treatment alone.

Figure 6A:
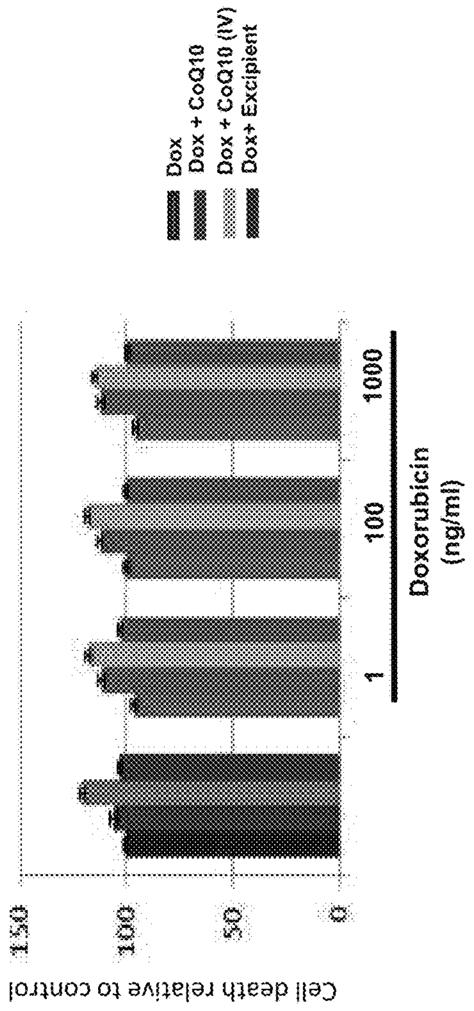
FIG. 6A is a graph showing the effect on viability of MIAPaCa-2 pancreatic cancer cells in vitro of 6 hour treatment with doxorubicin, CoQ10, an intravenous formulation of CoQ10, or the intravenous formulation of CoQ10 in combination with doxorubicin.
Figure 6B:
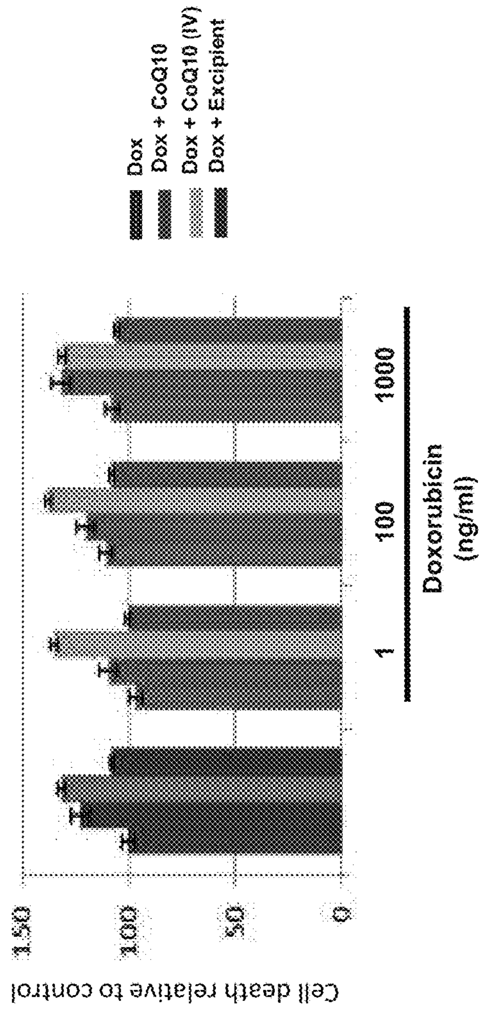
FIG. 6B is a graph showing the effect on viability of SK-Br3 breast cancer cells in vitro of 6 hour treatment with doxorubicin, CoQ10, an intravenous formulation of CoQ10, or the intravenous formulation of CoQ10 in combination with doxorubicin.

Example 4—In Vitro Combination Therapy (CoQ10+Doxorubicin) of Pancreatic and Breast Cancer To assess the efficacy of CoQ10 in combination with doxorubicin in vitro, MIAPaCa-2 pancreatic carcinoma cells were maintained in culture and exposed to increasing concentrations of gemcitabine in combination with CoQ10, the 4% CoQ10 intravenous formulation, or the excipient of the CoQ10 intravenous formulation. FIG. 6A shows the effect of 6 hour treatment with CoQ10 or the intravenous formulation of CoQ10, either alone or in combination with doxorubicin on MIAPaCa-2 pancreatic cancer cells. FIG. 6B shows the effect of 6 hour treatment with CoQ10 or the 4% CoQ10 intravenous formulation alone, or in combination with doxorubicin, on SK-Br3 breast cancer cells. The results demonstrate that both pancreatic and breast cancer cells induce increased cell death following exposure to 4% CoQ10 intravenous formulation of CoQ10 in combination with doxorubicin, at 6 hours. The combination treatment with doxorubicin and the 4% CoQ10 intravenous formulation results in an increase in cell death as compared to doxorubicin treatment alone.

Figure 7:
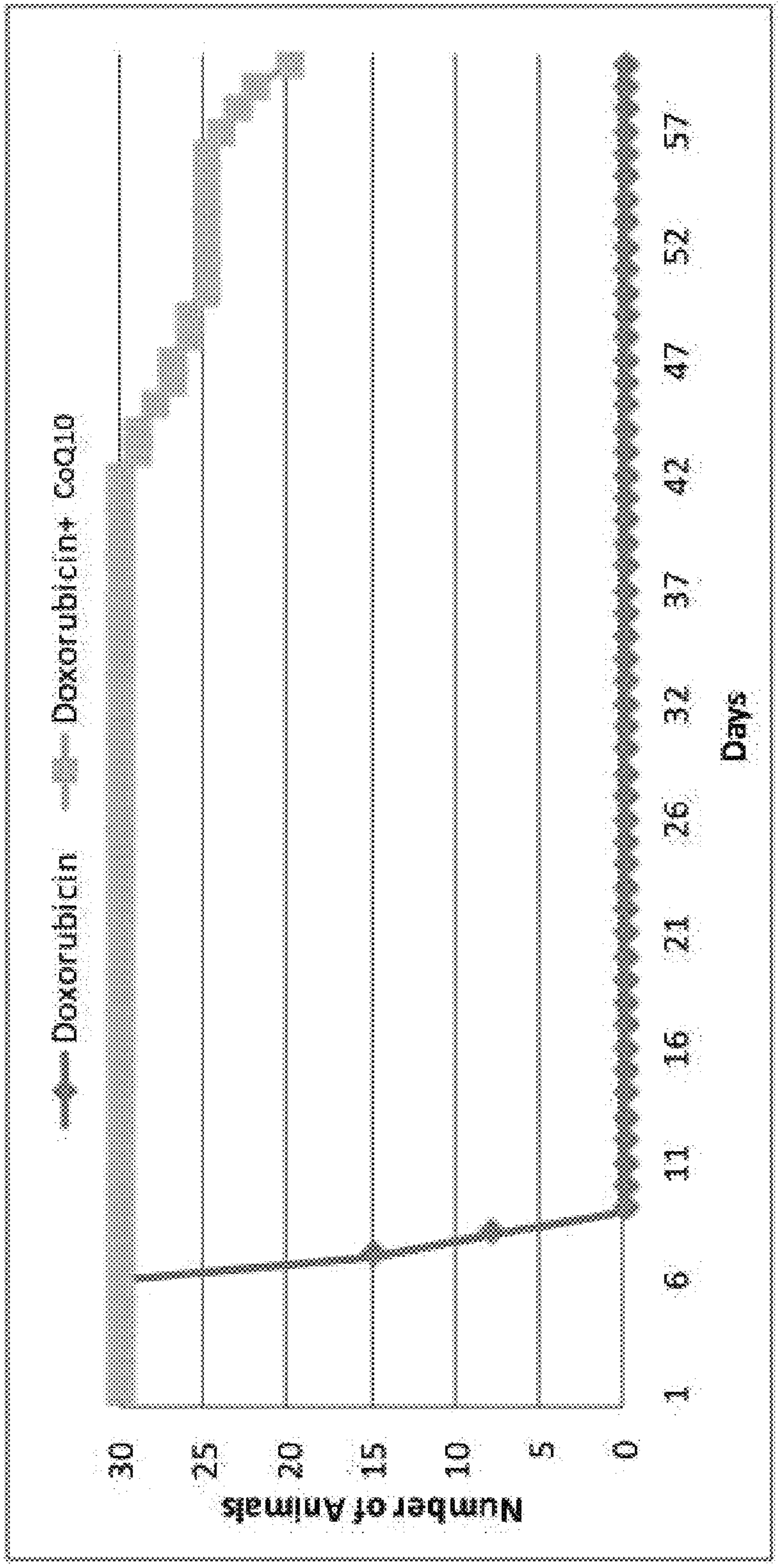
FIG. 7 is a graph showing the effect of once daily dosing with intravenous CoQ10 with doxorubicin, or doxorubicin alone on survival time in a xenogeneic mouse model of pancreatic cancer using human pancreatic tumor MIAPaCa-2 pancreatic cancer cells.

To confirm the results observed in vitro, the MIAPaca-2 xenogeneic mouse model described above was used to assess the activity of doxorubicin, either alone or in combination with a CoQ10 intravenous formulation to increase survival of the mice. As shown in FIG. 7, the CoQ10 intravenous formulation in combination with doxorubicin extended viability as compared to treatment with doxorubicin alone.

CoQ10 alone or CoQ10 in combination with doxorubicin was found to be more effective than gemcitabine or doxorubicin in effectuating responses associated with favorable therapeutic endpoints in the treatment of pancreatic cancer, most notably an increase in survival. Intravenous CoQ10 also has potential utility in the treatment of breast cancers. CoQ10 formulations, either alone or in combination with gemcitabine, extended viability to 42 days in a xenogeneic mouse model of pancreatic cancer up to 42 days. Administration of CoQ10 in combination with doxorubicin decreased mortality rates observed in of the xenogeneic mouse model of pancreatic cancer as compared to treatment with doxorubicin alone.

Example 5—Regimen 3—Three Times Daily IV CoQ10 and Once Weekly Gemcitabine Combination Equal numbers of MIAPaca2 human pancreatic tumor cells ($1\times10^7$) were suspended in MATRIGEL® and injected into mice. Tumors were allowed to develop for, on average, at least 3 weeks prior to initiation of treatment.

Mice having palpable tumors were randomized into 5 groups of 30 mice each as follows:

i. Group 1—No treatment.
ii. Group 2—Intraperitoneal dose of 4% CoQ10 intravenous formulation, 50 mg/kg/dose, 3 times daily (150 mg/kg/day).
iii. Group 3—Intraperitoneal dose of 4% Coenzyme Q10 intravenous formulation, 75 mg/kg/dose, 3 times daily (225 mg/kg/day).
iv. Group 4—Combination of intraperitoneal dose of 4% Coenzyme Q10 intravenous formulation, 50 mg/kg/dose, 3 times daily (150 mg/kg/day), and intravenous single weekly dose of gemcitabine 150 mg/kg for 3 weeks with one week rest. This cycle was repeated at four week intervals.
v. Group 5—Combination of intraperitoneal dose of 4% Coenzyme Q10 intravenous formulation, 75 mg/kg/dose, 3 times daily (225 mg/kg/day), and intravenous single weekly dose of gemcitabine 150 mg/kg for 3 weeks with one week rest. This cycle was repeated at four week intervals.

The high frequency of administration of Coenzyme Q10 prevented intravenous administration of the Coenzyme Q10 due to vascular damage caused by high frequency intravenous injections. Animals were observed for viability and tumor growth was monitored by palpation.

The survival results collected through day 417 are shown in FIG. 8. All of the mice in the control, untreated group (Group 1) died by day 23 after initiation of administration of therapeutic agents to the mice in Groups 2-5. In contrast, at least 50% of the animals in each of the treatment groups (Groups 2-5) were viable at day 130 after the initiation of treatment. Animals treated with Coenzyme Q10 alone at both treatment doses displayed significantly increased survival as compared to control animals. Further, animals treated with a combination of Coenzyme Q10 and gemcitabine displayed increased survival as compared to mice treated with the same dose of Coenzyme Q10 alone over the course of the treatment.

Example 6—Relative Sensitivities of Oncogenic and Normal Cells to Coenzyme Q10

The effects of Coenzyme Q10 treatment on a variety of oncogenic and normal cell lines were examined and compared. The sensitivity of cells to Coenzyme Q10 was assessed by monitoring induction of apoptosis. CoQ10 treatment of cells was carried out as described in detail below in the Materials and Methods. Induction of apoptosis was assessed in the treated cells by monitoring indicators of early apoptosis (e.g., Bcl-2 expression, caspase activation and by using annexin V assays) as described below. From these studies, the minimal CoQ10 dosage, e.g., concentration of CoQ10 and time of treatment, required to induce apoptosis in the panel of cell lines was determined.

The data demonstrated that efficacy of Coenzyme Q10 treatment was greater in cell types that exhibited increased oncogenicity and/or greater metastatic potential, i.e., cell types that were derived from more aggressive cancers or tumors. The results of these studies are summarized below in the table. The data demonstrates that CoQ10 is more effective in both a time and concentration dependent manner on cells in a more aggressive cancer state. Moreover, a surprising divergent effect was observed on normal cells as compared to oncogenic cells. Specifically, Coenzyme Q10 was unexpectedly found to exhibit a slightly supportive role in a normal tissue environment, wherein increased proliferation and migration was observed in normal cells, including keratinocytes and dermal fibroblasts.

The effect of Coenzyme Q10 on gene regulatory and protein mechanisms in cancer is different in a normal cell. Key cellular machinery and components, such as cytoskeletal architecture, membrance fluidity, transport mechanisms, immunomodulation, angiogenesis, cell cycle control, genomic stability, oxidative control, glycolytic flux, metabolic control and integrity of extracellular matrix proteins, are dysregulated and thus the genetic and molecular fingerprint of the cell is altered. The disease environment favors governance of cellular control processes. The data provided herein suggests that CoQ10 exerts a greater level of efficacy (e.g., in cancer cells vs. normal cells, and in cells of a more aggressive cancer state as compared to cells of a less aggressive or non-aggressive cancer state) by normalizing some of the key aforementioned processes in a manner that allows for restored apoptotic potential.

Minimal CoQ10 concentration and treatment time required for induction of early apoptosis in various cell types.

| Tissue Origin (Cell type) | Indication of Early apoptosis (Bcl-2, annexin V, or caspase activation) | Concentration (μM) | Time (hr) | Level of aggressiveness: 1 = normal tissue 2 = malignant 3 = metastatic |
|---|---|---|---|---|
| SKIN: | | | | |
| Keratinocytes (Heka, Hekn) | None | N/A | N/A | 1 |

-continued

Minimal CoQ10 concentration and treatment time required for induction of early apoptosis in various cell types.

| Tissue Origin (Cell type) | Indication of Early apoptosis (Bcl-2, annexin V, or caspase activation) | Concen-tration (μM) | Time (hr) | Level of aggressiveness: 1 = normal tissue 2 = malignant 3 = metastatic |
|---|---|---|---|---|
| Fibroblasts (nFib) | None | N/A | N/A | 1 |
| Melanocytes (Hema, LP) | None | N/A | N/A | 1 |
| Melanoma (Skmel 28) | Strong | 20 | 24 | 2 |
| Melanoma (Skmel 2) | Very Strong | 25 | 24 | 3 |
| SCC, Squamous cell carcinoma | Very Strong | 25 | 24 | 3 |
| BREAST: | | | | |
| MCF-7 | Strong | 50 | 48 | 2 |
| SkBr-3 | Very Strong | 50 | 24 | 3 |
| BT-20 | Strong | 100 | 48 | 2 |
| ZR-75 | Slight | 200 | 72 | 2 |
| MDA MB 468 | Strong | 100 | 48 | 2 |
| Mammary fiboblasts: 184A1 and 184B5) (Lawrence Berkeley) | None | N/A | | 1 |
| PROSTATE: | | | | |
| PC3 | Very Strong | 25 | 24 | 3 |
| LIVER: | | | | |
| HepG2 | Very Strong | 50 | 24 | 3 |
| Hep3B | Very Strong | 50 | 24 | 3 |
| BONE: | | | | |
| Osteosarcoma (143b) | Very Strong | 50 | 48 | 2 |
| Ewing's sarcoma (NCI) | Extremely strong | 5 | 1 | 3 |
| PANCREAS: | | | | |
| PaCa2 | Very Strong | 25 | 24 | 3 |
| Heart: | | | | |
| Aortic smooth muscle (HASMC) | None | N/A | N/A | 1 |

Materials and Methods

Cell Preparation and Treatment

Cells Prepared in Dishes or Flasks

Cells were cultured in T-75 flasks with relevant medium supplemented with 10% Fetal Bovine Serum (FBS), 1% PSA (penicillin, streptomycin, amphotericin B) (Invitrogen and Cellgro) in a 37° C. incubator with 5% $CO_2$ levels until 70-80% confluence was reached. To harvest cells for treatment, flasks were primed with 1 mL Trypsin, aspirated, trypsinized with an additional 3 mL, and incubated at 37° C. for 3-5 minutes. Cells were then neutralized with an equal volμme of media and the subsequent solution was centrifuged at 10,000 rpm for 8 minutes. The supernatant was aspirated and the cells were resuspended with 8.5 ml of media. A mixture of 500 ul of the resuspension and 9.5 ml of isopropanol was read twice by a coulter counter and the appropriate number of cells to be seeded into each dish was determined. Control and concentration ranging from 0-200 μM groups were examined in triplicate. From a 500 μM CoQ-10 stock solution, serial dilutions were performed to achieve desired experimental concentration in appropriate dishes. Dishes were incubated in a 37° C. incubator with 5% $CO_2$ levels for 0-72 hours depending on cell type and experimental protocol.

Protein Isolation and Quantification

Cells Prepared in Dishes

Following cell treatment incubation period was complete, protein isolation was performed. Dishes of all treatment groups were washed twice with 2 ml, and once with 1 ml of ice cold 1× Phosphate Buffered Saline (PBS). The PBS was aspirated from the dishes after the initial 2 washes only. Cells were gently scraped and collected into microcentrifuge tubes using the final volume from the third wash and centrifuged at 10,000 rpm for 10 minutes. After centrifugation, the supernatant was aspirated and the pellet was lysed with 50 uL of lysis buffer (1 uL of protease and phosphotase inhibitor for every 100 uL of lysis buffer). Samples were then frozen overnight at −20° C.

Cells Prepared in Flasks

After the cell treatment incubation period was complete, protein isolation was performed. Flasks of all treatment groups were washed twice with 5 mL, and once with 3 mL of ice cold 1×PBS. The PBS was aspirated from the flasks after the first 2 washes only. Cells were gently scraped and collected into 15 mL centrifuge tubes using the final volume from the third wash and centrifuged for at 10,000 rpm for 10 minutes. After centrifugation, the supernatant was aspirated and the pellet was lysed with an appropriate amount of lysis buffer (1 uL of protease and phosphotase inhibitor for every 100 uL of lysis buffer). Lysis buffer volμme was dependent on pellet size. Samples were transferred in microcentrifuge tubes and frozen overnight at −20° C.

Protein Quantification

Samples were thawed at −4° C. and sonicated to ensure homogenization the day following protein isolation. Protein quantification was performed using the micro BCA protein assay kit (Pierce). To prepare samples for Immuno-blotting, a 1:19 solution of betamercaptoethanol (Sigma) to sample buffer (Bio-Rad) was prepared. Samples were diluted 1:1 with the betamercaptoethanol-sample buffer solution, boiled at 95° C. for 5 minutes, and frozen overnight at −20° C.

Immuno-Blotting

Bcl-2, Caspase, 9, Cytochrome c

The volume of sample to load per well was determined using the raw mean concentration of protein obtained from the BCA protein assay. Approximately 30-60 μg of protein were loaded for each treatment time point. Proteins were run in triplicate on 12% Tris-HCl ready gels (Bio-Rad®) or hand cast gels in 1× running buffer at 85 and 100 volts. Proteins were then transferred onto nitrocellulose paper for an hour at 100 volts, and blocked for another hour in a 5% milk solution. Membranes were placed in primary antibody (1 uL Ab:1000 uL TBST) (Cell Signaling) overnight at −4° C. The following day, membranes were washed three times for ten minutes each with Tris-Buffered Saline Tween®-20 (TBST), and secondary antibody (anti-rabbit; 1 uL Ab: 1000 uL TBST) was applied for an hour at −4° C. Membranes were washed again three times for ten minutes with TBST and chemoluminescence using Pico or Femto substrate was completed (Pierce®). Membranes were then developed at time intervals that produced the best visual results. After developing, membranes were kept in TBST at −4° C. until Actin levels could be measured.

Actin

Membranes were placed in primary Actin antibody (1 uL Ab:5000 uL TBST) (cell signaling) for 1 hour at −4° C., washed three times for ten minutes each with TBST, and secondary antibody (anti-mouse; 1 uL Ab: 1000 uL TBST)

was applied for an hour at −4° C. Membranes were washed again three times for ten minutes each with TBST and chemoluminescence using Pico substrate was completed (Pierce). Membranes were then developed at time intervals that produced the best visual results.

Annexin V Assay

Cells were washed twice in PBS and resuspended in Binding Buffer (0.1 M HEPES, pH 7.4; 1.4 M NaCl; 25 mM $CaCl_2$). Samples of 100 μl were added to a culture tube with 5 μl of annexin-PE dye or 7-ADD. The cells were mixed and incubated without light at room temperature for 15 minutes. After which, 400 μl of 1× Binding Buffer was added to each sample and they were subjected to analysis by flow cytometry.

Example 7—Treatment with CoQ10 Sensitizes Tumors to Chemotherapeutic Agents In Vivo Using the methods in Example 6, cells are tested to determine if the relative timing of treatment of cells with CoQ10 and chemotherapeutic agents has an effect on cell killing, e.g., by promotion of apoptosis, induction of tumor lysis, inhibition of cell proliferation.

Briefly, cells are cultured as in Example 6. Cells are treated with CoQ10 and chemotherapeutic agents, either alone or in combination, or with appropriate vehicle controls. For the cells treated with both CoQ10 and chemotherapeutic agents, the cells are contacted with the CoQ10 and chemotherapeutic agents in various sequences. Various concentrations of CoQ10 and chemotherapeutic agents are used. Various treatment times are also used. Exemplary conditions are provided in the table below.

| | Treatment #1 | | Treatment #2 | |
|---|---|---|---|---|
| | CoQ10 | Chemotherapy | CoQ10 | Chemotherapy |
| 1 | + | + | + | + |
| 2 | + | -- | + | -- |
| 3 | -- | + | -- | + |
| 4 | + | -- | + | + |
| 5 | + | — | — | + |

Appropriate vehicle controls for each CoQ10 and the chemotherapeutic agent are used.

After treatment with CoQ10 and chemotherapy as indicated, cells are harvested and assayed for viability and apoptosis using the methods provided above. Pretreatment with CoQ10 prior to treatment with chemotherapy is demonstrated to be more effective in cell killing than co-treatment with CoQ10 and chemotherapy or treatment with CoQ10 after chemotherapy. Specifically, pretreatment with CoQ10, followed by concurrent treatment with CoQ10 and chemotherapy, is effective in cell killing. Pretreatment with CoQ10, and discontinuation of CoQ10, followed by treatment with chemotherapy is also effective in cell killing. Without being bound by theory, it is suggested that CoQ10 “reeducates” the glycolysis addicted cancers to utilize mitochondrial respiratory chain as energy source by altering expression of key regulatory enzymes in the pentose phosphate shunt, glycolysis and oxidative phosphorylation. The metabolic switch effectuated by CoQ10 in cancer cells is associated with induction of a novel integrated signaling cross-talk involving TP53, Bcl-2/Bax and VEGF that results in the recapitulation of apoptotic pathways. The data suggest CoQ10 directly influences mitochondrial-centric pathways in sensitizing the cancer cells to the cyotoxic effects of chemotherapy agents while conferring protection to normal cells.

Example 8—Treatment with CoQ10 Sensitizes Tumors to Chemotherapeutic Agents In Vivo In an in vivo tumor xenograft model, mice are implanted with tumors. For example, MIAPaCa-2 pancreatic cancer cells suspended in MATRIGEL are injected into NSG mice. Alternatively, other tumor cell lines, e.g., triple negative breast cancer, hepatic cancer, prostate cancer, melanoma, sarcoma, carcinoma cell lines, are used in the xenograft mouse model. Chemically induced tumors and other animal models of cancer can also be used. In all animals, the presence of tumors is confirmed prior to initiation of treatment.

Various sequential regimens and combinations of CoQ10 and chemotherapeutic agents are tested for the ability to reduce tumor burden and/or reduce tumor metastasis. For example, the exemplary regimens provided in the table in Example 7 are used. Each Treatment #1 and Treatment #2 as shown in the table in Example 7 can be one or more cycles of treatment with the agent. For example, in some animals, 2 or more cycles of CoQ10 are administered in Treatment 1 prior to one or more cycles of the chemotherapeutic agent in Treatment 2. In some animals, one cycle of CoQ10 is administered in Treatment 1 prior to administration of multiple cycles of chemotherapy in Treatment 2.

Tumor volumes are monitored using routine methods, e.g., calipers, imaging analysis. At the end of the study, tumors are excised and analyzed for using routine methods, e.g., for size (e.g., weight and volume), histological characteristics, grade, and vascularization. Treatment with one or more cycles of CoQ10 prior to treatment with a chemotherapeutic agents is demonstrated to be more effective than co-administration of CoQ10 with a chemotherapeutic agent or a chemotherapeutic agent alone.

Example 9—Treatment with CoQ10 Enhances the Efficacy of Chemotherapeutic Agents in the Treatment of Liver Cancer Cells In Vitro Hep3B liver cancer cells were cultured under standard conditions. Cells were treated with the chemotherapeutic agents irinotecan (SN38), cisplatin, 5-fluorouracil, or doxorubicin at the indicated concentrations either alone or in combination with CoQ10 (100 μM) for a predetermined time period.

Growth inhibition/promotion of cell death was assessed by live cell counting. Results are shown in FIGS. 9A-9C and 10. CoQ10 was demonstrated to increase the efficacy of all of the chemotherapeutic agents, increasing cell death and decreasing the number of live cells. These data suggest that the combination of these therapeutic agents is more effective in the treatment of liver cancer than the chemotherapeutic agent alone.

Example 10—Mitochondrial Priming of Apoptotic Machinery in Pancreatic Cancer by C0Q10 to Enhance Efficacy of Chemotherapy Without being bound by mechanism, it is proposed that CoQ10 effectuates a metabolic switch from glycolysis towards enhanced mitochondrial oxidative phosphorylation resulting in the recapitulation of apoptosis in cancer. The effects of CoQ10 were investigated to determine if pretreatment with CoQ10 results in mitochondrial priming, thereby augmenting the cytotoxic effect of standard of care chemotherapeutic agents. MIAPaCa-2 human pancreatic cancer cells were either (a) pretreated with CoQ10 prior to treatment with gemcitabine or (b) co-treated with CoQ10 and gemcitabine. The effects of the treatments on cell viability were monitored and the results are shown in FIGS. 10-14.

CoQ10 treatment resulted in decreased proliferation of the MIAPaca-2 cells as compared to treatment with gemcitabine alone. Treatment of MIAPaca-2 cells with CoQ10 augmented the cytotoxic potential of gemcitabine in both the pre-treatment and the co-treatment regimen.

Example 11—Mitochondrial Priming of Apoptotic Machinery in Pancreatic Cancer by CoQ10 to Enhance Efficacy of Chemotherapy Equal numbers of MIAPaCa-2 human pancreatic tumor cells ($1\times10^7$) were suspended in MATRIGEL® and injected into mice. Tumors were allowed to develop for, on average, at least 3 weeks prior to initiation of treatment.

Mice having palpable tumors were randomized into 5 groups of 30 mice each as follows:

i. Group 1—No treatment.

ii. Group 2—Intraperitoneal dose of 4% Coenzyme Q10 intravenous formulation, 75 mg/kg/dose, 3 times daily (225 mg/kg/day) and intravenous single weekly dose of gemcitabine 150 mg/kg for 3 weeks with one week rest initiated on the same day.

iii. Group 3—Intraperitoneal dose of 4% Coenzyme Q10 intravenous formulation, 75 mg/kg/dose, 3 times daily (225 mg/kg/day) and intravenous single weekly dose of gemcitabine 150 mg/kg for 3 weeks with one week rest initiated one week after the initiation of CoQ10 treatment.

iv. Group 4—Intraperitoneal dose of 4% Coenzyme Q10 intravenous formulation, 75 mg/kg/dose, 3 times daily (225 mg/kg/day) and intravenous single weekly dose of gemcitabine 150 mg/kg for 3 weeks with one week rest initiated two weeks after the initiation of CoQ10 treatment.

v. Group 5—Intraperitoneal dose of 4% Coenzyme Q10 intravenous formulation, 75 mg/kg/dose, 3 times daily (225 mg/kg/day) and intravenous single weekly dose of gemcitabine 150 mg/kg for 3 weeks with one week rest initiated three weeks after the initiation of CoQ10 treatment.

The high frequency of administration of Coenzyme Q10 prevented intravenous administration of the Coenzyme Q10 due to vascular damage caused by high frequency intravenous injections. Animals were observed for survival and tumor growth by palpation.

Figure 15:
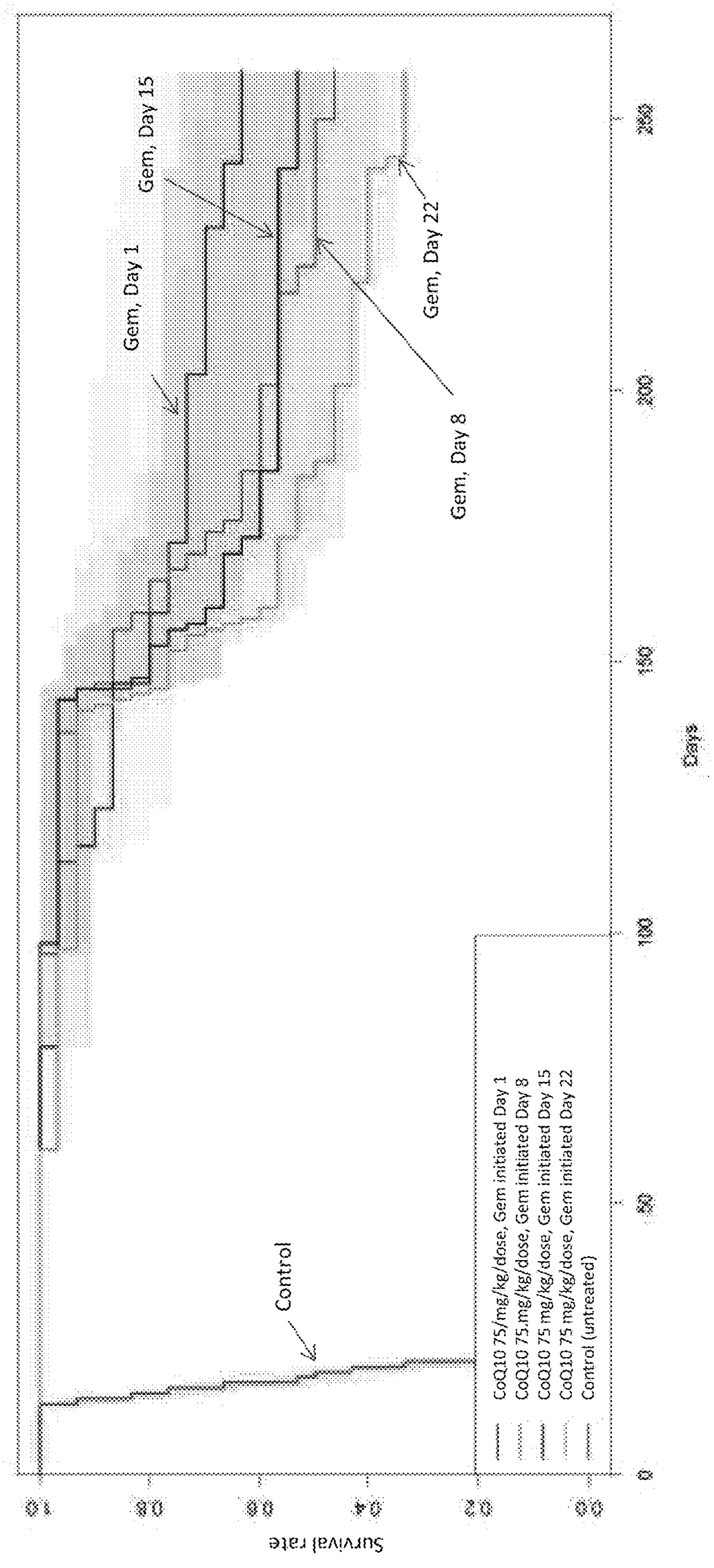
FIG. 15 is a graph showing the effect of three times intraperitoneal daily dosing with an intravenous formulation of CoQ10 (75 mg/kg/dose) in combination with gemcitabine (150 mg/kg/dose, 1× per 3 weeks), on survival time in a xenogeneic mouse model of pancreatic cancer using human pancreatic tumor MIAPaCa-2 pancreatic cancer cells. Administration of CoQ10 was initiated 0, 1, 2, or 3 weeks prior to the initiation of treatment with gemcitabine. In the graph, Day 1 indicates the day that treatment was initiated.

Early time points suggest that pretreatment with intravenous CoQ10 followed by gemcitabine results in improved survival in the pancreatic cancer model compared to the co-treatment regimen (FIG. 15A). Without being bound by mechanism, the data suggest that CoQ10 may be a viable mitochondrial priming agent to sensitize cancer cells to the cytotoxic effects of gemcitabine in pancreatic cancer. The data demonstrates that addition of CoQ10 increases the cytotoxic effect of gemcitabine in pancreatic cancer and increases the survival in a statistically significant manner as compared to untreated control at the latest time point (see below). In addition, treatment with CoQ10 followed by gemcitabine treatment is associated with improved survival (see, e.g., CoQ10 75 mg/kg, co-initiated with chemotherapy vs. CoQ10 75 mg/kg×3 weeks then chemotherapy).

| Condition 1 | Condition 2 | p-value |
|---|---|---|
| Control | CoQ10 75 mg/kg, co-initiated with chemo | <0.00001 |
| Control | CoQ10 75 mg/kg × 1 week then chemo | <0.00001 |
| Control | CoQ10 75 mg/kg × 2 weeks then chemo | <0.00001 |
| Control | CoQ10 75 mg/kg × 3 weeks then chemo | <0.00001 |
| CoQ10 75 mg/kg, co-initiated with chemo | CoQ10 75 mg/kg × 1 week then chemo | 0.26503 |
| CoQ10 75 mg/kg, co-initiated with chemo | CoQ10 75 mg/kg × 2 weeks then chemo | 0.45960 |
| CoQ10 75 mg/kg, co-initiated with chemo | CoQ10 75 mg/kg × 3 weeks then chemo | 0.02724* |
| CoQ10 75 mg/kg × 1 week then chemo | CoQ10 75 mg/kg × 2 weeks then chemo | 0.82980 |
| CoQ10 75 mg/kg × 1 week then chemo | CoQ10 75 mg/kg × 3 weeks then chemo | 0.20885 |
| CoQ10 75 mg/kg × 2 weeks then chemo | CoQ10 75 mg/kg × 3 weeks then chemo | 0.15515 |

Example 12—In Vitro CoQ10 Monotherapy of Various Cancer Cell Types

Figure 16:
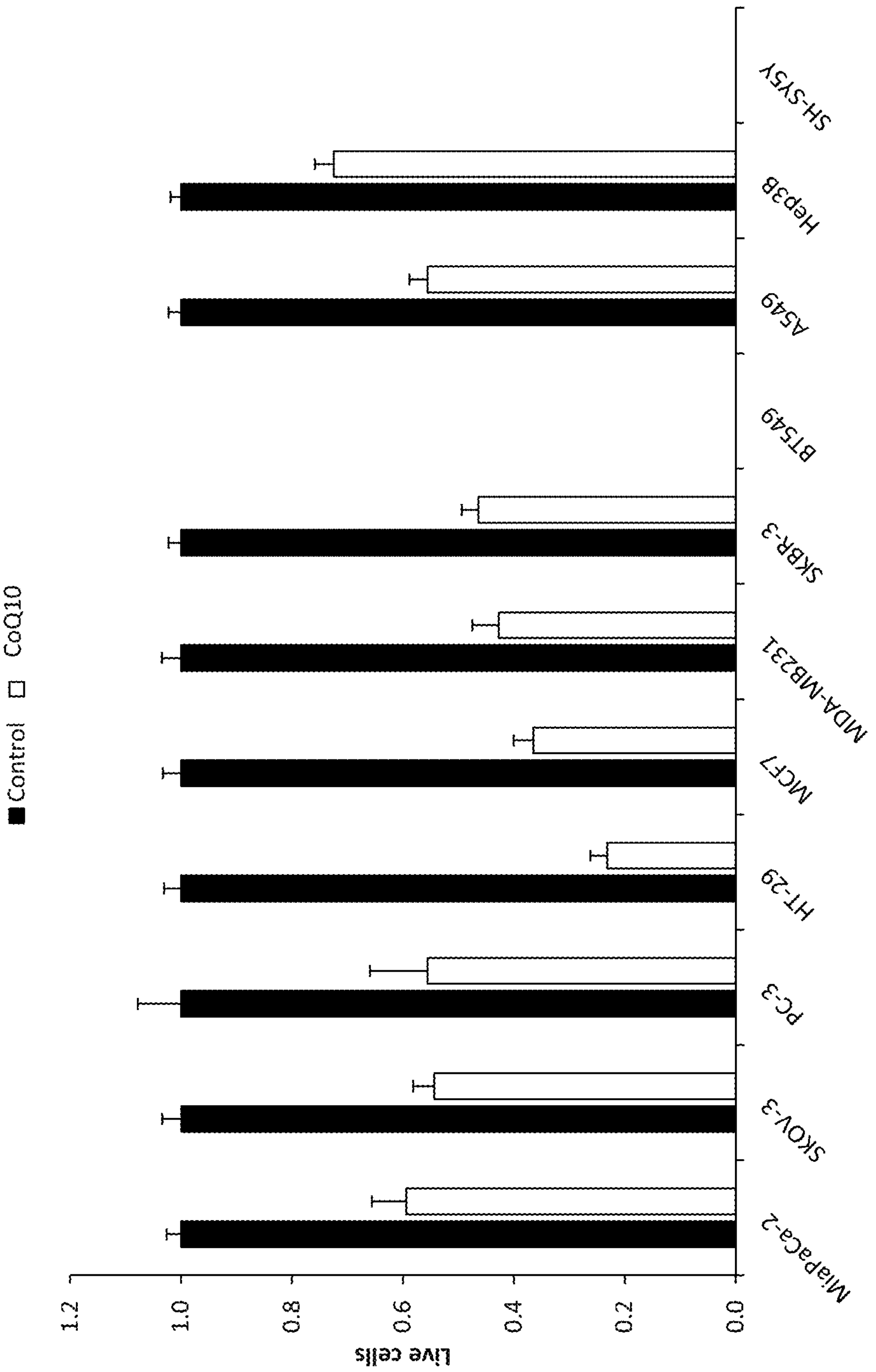
FIG. 16 shows the effect of CoQ10 treatment on the viability of various tumor cell lines in vitro. Cells were treated with 100 μM CoQ10 for 48-72 hours.

To assess the efficacy of CoQ10 in vitro, various cancer cells (MIAPaCa-2 pancreatic carcinoma cells, SKOV-3 ovarian cancer cells, PC-3 prostate cancer cells, HT-29 colon cancer cells, MCF7 breast cancer cells, MDA-MB231 breast cancer cells, SKBR-3 breast cancer cells, A549 lung cancer cells, Hep3B liver cancer cells) were maintained in culture and exposed to 100 μM CoQ10 for 48-72 hours. FIG. 16 shows the effect of CoQ10 treatment on the various cancer cells. The results demonstrate increased cell death in cancer cells following exposure to CoQ10.

Example 13—Effect of CoQ10 on Cell Metabolism and Caspase 3 Activity

Figure 17:
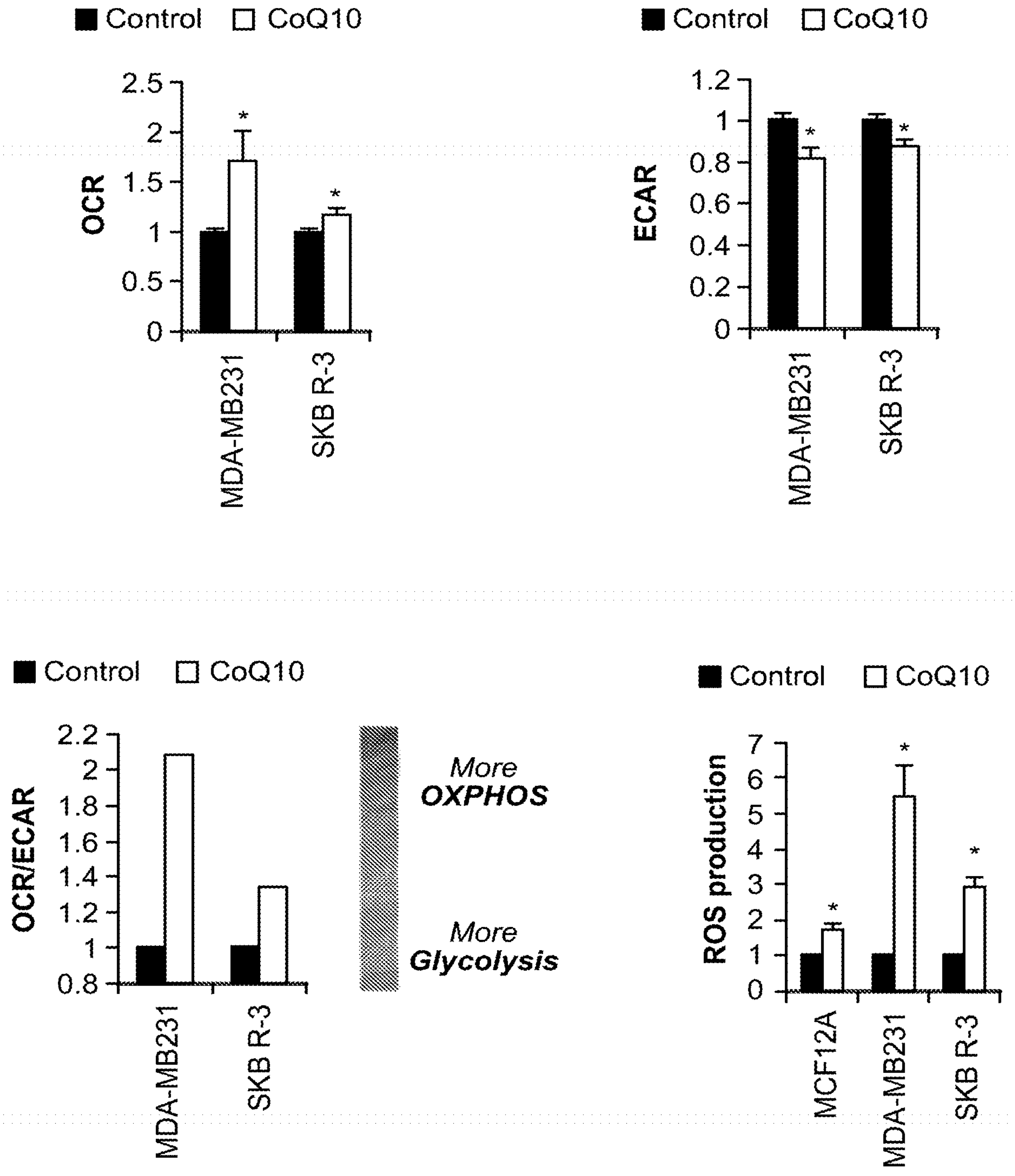
FIG. 17 shows the effect of CoQ10 treatment on basal oxygen consumption rate (OCR), extracellular acidification rate (ECAR) and reactive oxygen species (ROS) in breast cancer cells (MDA-MB231 and SKBR-3) and non-tumorigenic control cells (MCF12A) in vitro. Cells were treated with 100 μM CoQ10 for 24 hours.

Basal oxygen consumption rate (OCR) and extracellular acidification rate (ECAR) were measured in MDA-MB213 and SKBR-3 breast cancer cells treated with 100 μM CoQ10 for 24 hours. FIG. 17 shows the effect of CoQ10 treatment on OCR and ECAR in the breast cancer cells. The higher ratio of OCR to ECAR in breast cancer cells treated with CoQ10 indicates that CoQ10 increases oxidative phosphorylation (OXPHOS) and reduces glycolysis in breast cancer cells. Reactive oxygen species (ROS) production was also measured in MDA-MB213 and SKBR-3 breast cancer cells and non-tumorigenic control cells (MCF12A) treated with 100 μM CoQ10 for 24 hours. Mitochondria represent a significant source of ROS which are known to participate in activation of cell death pathways. FIG. 17 shows that CoQ10 treatment increased ROS production in both breast cancer cells and control cells.

Figure 18:
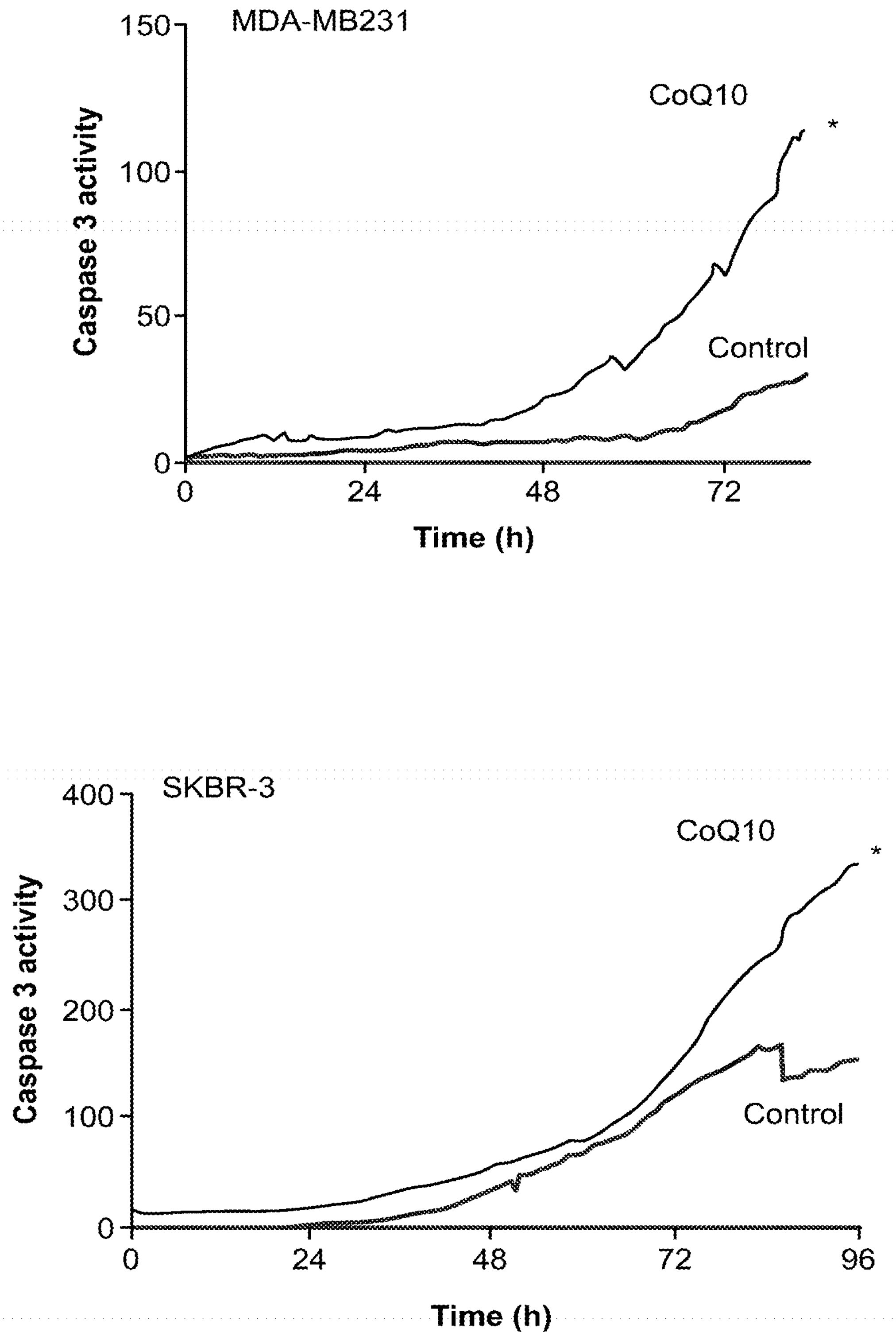
FIG. 18 shows the effect of CoQ10 treatment on caspase 3 activity in breast cancer cells (MDA-MB231 and SKBR-3).

Caspase 3 activity was compared in MDA-MB213 and SKBR-3 breast cancer cells treated with 100 μM CoQ10 for 72-96 hours and control MDA-MB213 and SKBR-3 breast cancer cells that were untreated. Caspase 3 is an executioner caspase required for both intrinsic (mitochondrial) and extrinsic apoptosis pathways. FIG. 18 shows that CoQ10 treatment increased caspase 3 activity in MDA-MB213 and SKBR-3 breast cancer cells.

Figure 19:
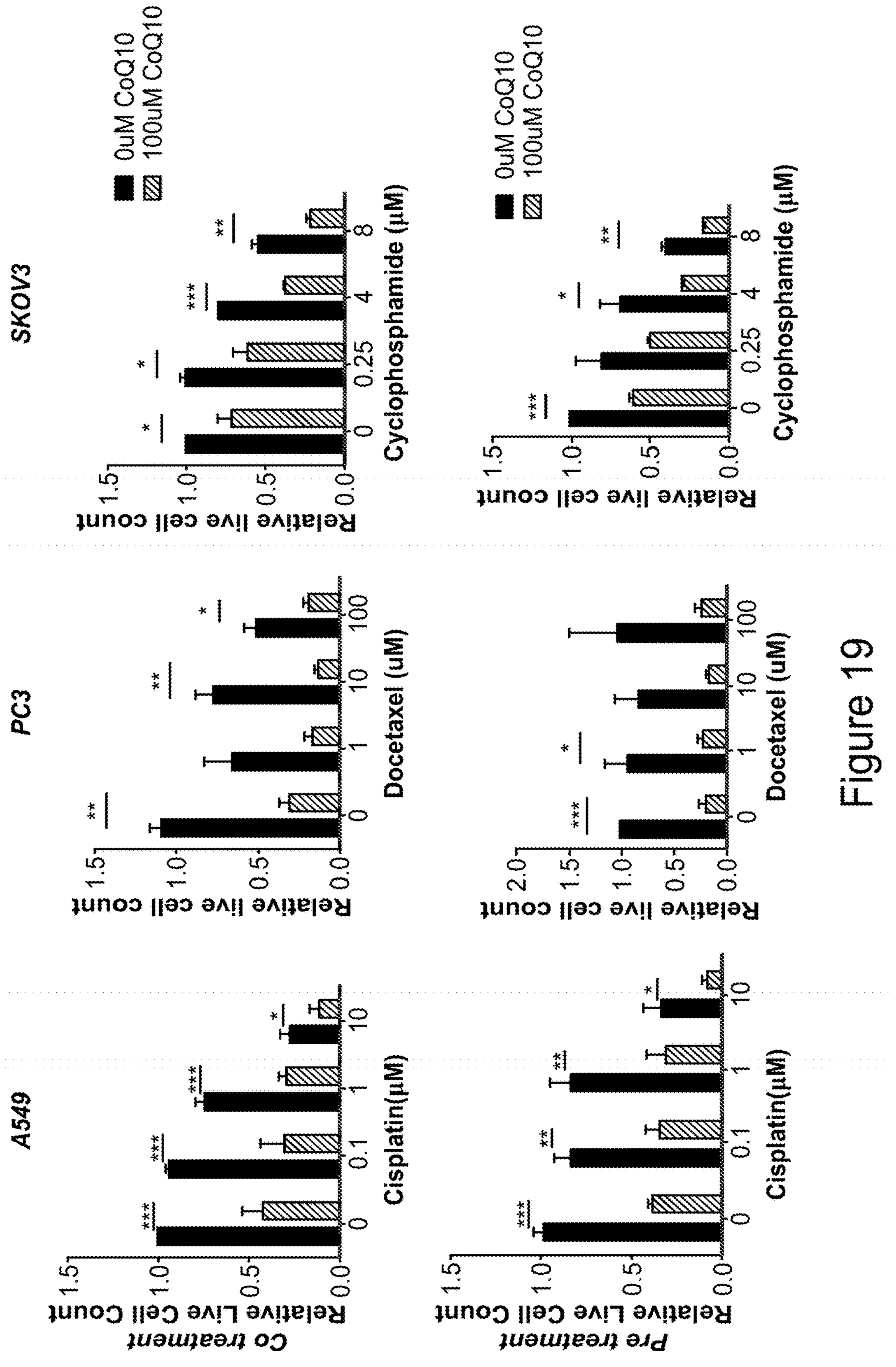
FIG. 19 shows the effect of co-treatment vs. pre-treatment in A549, PC3 and SKOV3 cancer cells with combinations of CoQ10 and various chemotherapeutic agents.

Example 14—In Vitro Assay of CoQ10 Pre-Treatment and Co-Treatment in Various Cancer Cells A549 lung cancer cells, PC3 prostate cancer cells, and SKOV3 ovarian cancer cells were pre-treated or co-treated with CoQ10 and the chemotherapeutic agents cisplatin, docetaxel, and cyclophosphamide, respectively. For pre-treatment, cells were treated for 6 hours with CoQ10 and then the designated chemotherapeutic agent was added to the medium. Thus CoQ10 treatment continued during treatment with the chemotherapeutic agent for the pre-treatment groups. The length of time of treatment with the chemotherapeutic agent varied by cell type. A549 cells were treated with cisplatin for 48 hours, PC3 cells were treated with docetaxel for 48 hours, and SKOV3 cells were treated with cyclophosphamide for 72 hours. Co-treated and pre-treated cells were treated with the chemotherapeutic agent for the same length of time. FIG. 19 shows the effect of cotreatment or pretreatment with CoQ10 and the chemotherapeutic agent.

Figure 21:
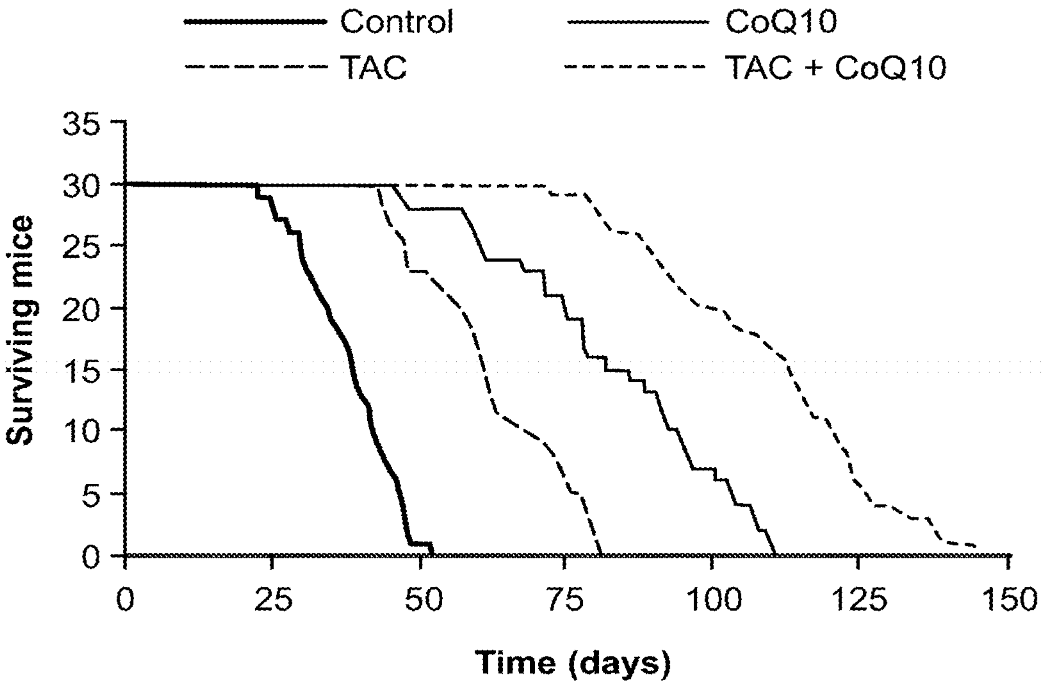
FIG. 21 shows a survival curve for mice bearing triple-negative breast cancer (TNBC) xenografts and treated with the TAC regimen (5 mg/kg docetaxel, 1 mg/mg doxorubicin, and 35 mg/kg cyclophosphamide) with and without 75 mg/kg body weight CoQ10 (BPM 31510). TAC was given every three weeks for six cycles.

Example 15—Evaluation of a Triple-Negative Breast Cancer (TNBC) Animal Model in Response to CoQ10 Alone or in Combination with Standard-of-Care Chemotherapy Mice bearing triple-negative breast cancer (TNBC) xenografts were treated with the TAC regimen (5 mg/kg docetaxel, 1 mg/mg doxorubicin, and 35 mg/kg cyclophosphamide) with and without CoQ10. TAC was given every three weeks for six cycles. The mice were also treated with CoQ10 alone. CoQ10 alone or in combination with the TAC regimen significantly improved survival. See FIG. 21.

Figure 20A:
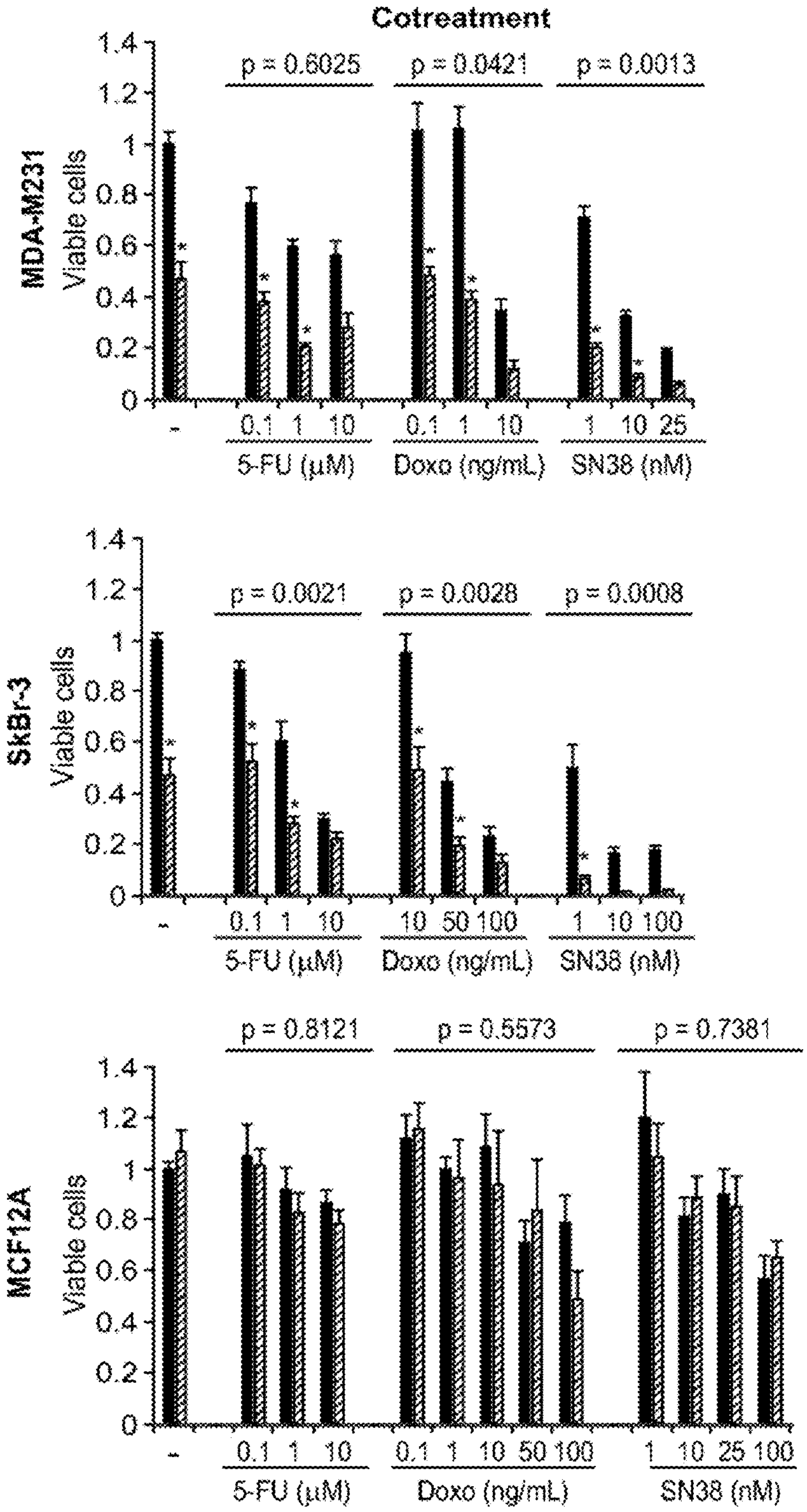
FIGS. 20A and 20B show MDA-MB231 and SkBr-3 breast cancer cells and MCF12A control cells subjected to either cotreatment (FIG. 20A) with CoQ10 (100 μM) and chemotherapeutic agents (5-fluorouracil, 5-FU; doxorubicin, Doxo; SN38, irinotecan active metabolite) or pretreatment (FIG. 20B) with CoQ10 (6 h) followed by co-incubation with chemotherapeutic agents. The number of viable cells was assessed after 48 hours. p values indicate interaction by 2-way ANOVA. *$p<0.05$ compared to chemotherapeutic agent alone.
Figure 20B:
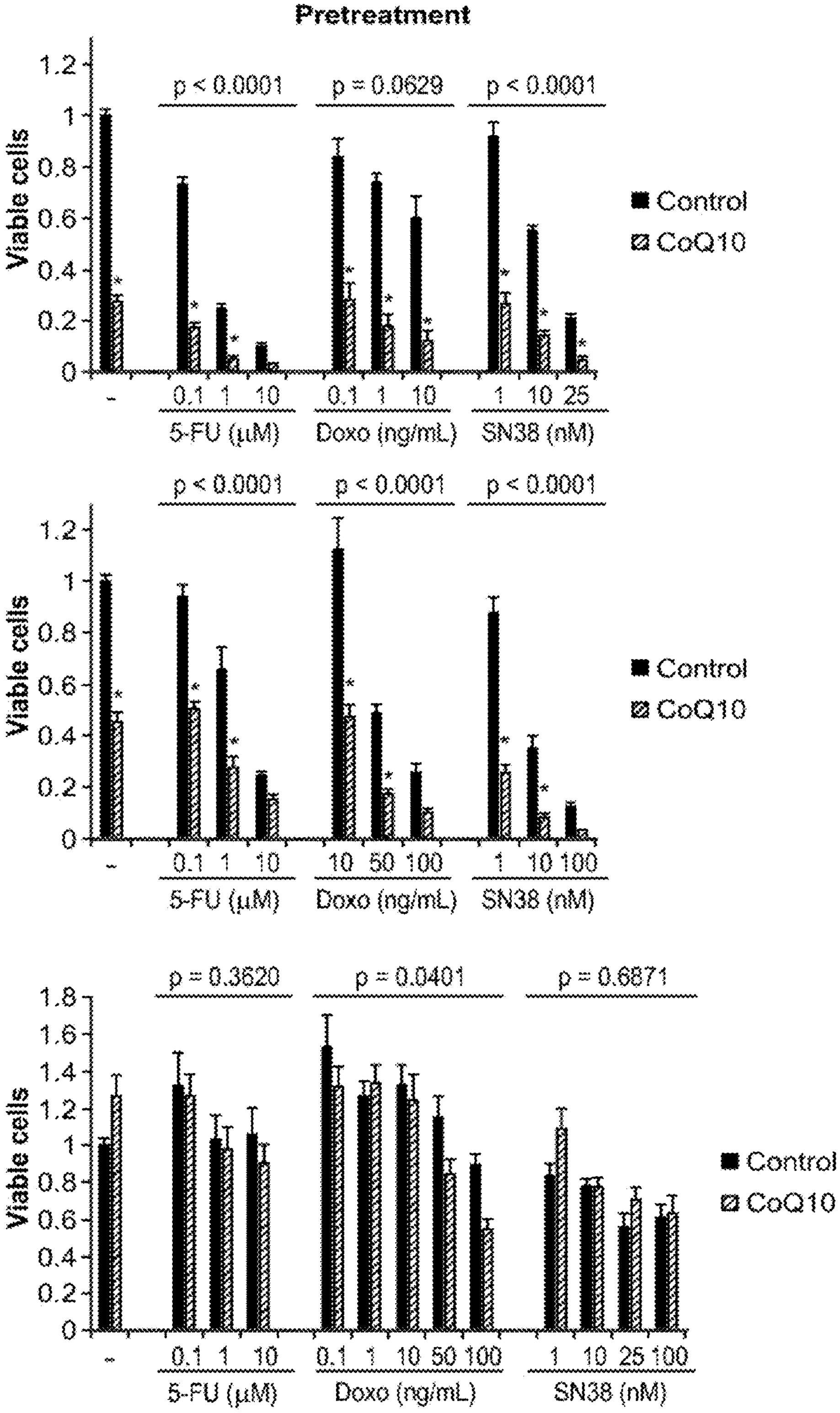
Figure 23:
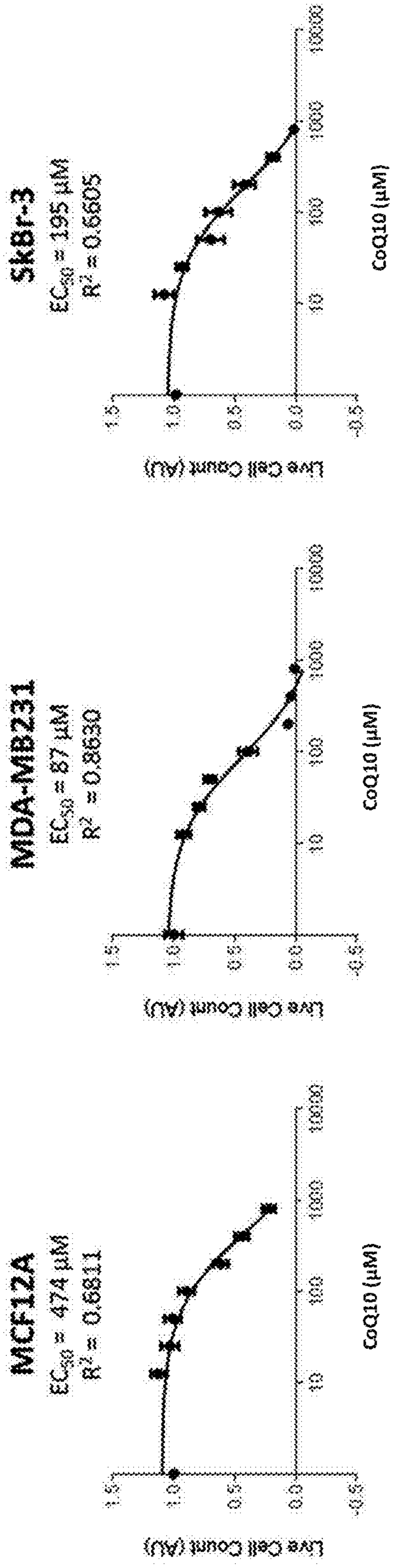
FIG. 23 shows MDA-MB231 and SkBr-3 breast cancer cells and MCF12A non-tumorigenic control cells treated with increasing doses of CoQ10 (BPM 31510). The number of viable cells was assessed after 48 h. $EC_{50}$ values were calculated using non-linear regression analysis.

Example 16—In Vitro Studies of Breast Cancer Cells Treated with CoQ10 and Chemotherapeutic Agents Human breast cancer cells of varying receptor status (SKBR3, MDA-MB231) were subjected to either (a) pretreatment with CoQ10 (6 h) followed by co-incubation with chemotherapeutic agents (5-fluorouracil, 5-FU; doxorubicin, Doxo; SN38, irinotecan active metabolite) for 48 h, or (b) co-treatment with CoQ10 and chemotherapeutic agents. Cancer cell responses were compared to non-tumorigenic mammary cells (MCF12A). The number of viable cells was assessed after 48 hours. Propidium iodide (PI) and CFSE Cell Tracer were used to measure cell death and proliferation, respectively, in the treated cells. Both CoQ10 alone or pretreatment and cotreatment strategies with CoQ10 plus standard of care resulted in significant decreases in viable breast cancer cells when compared to chemotherapeutic agents; however, minimal effects were observed in the non-tumorigenic MCF12A cells. See FIGS. 20, 23 and 24.

Figure 22:
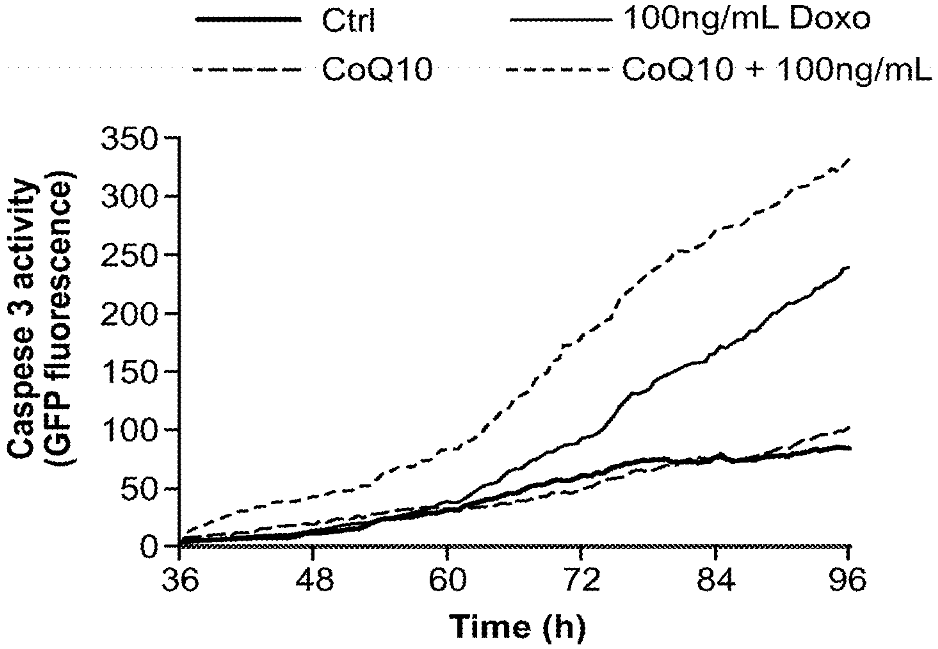
FIG. 22 shows SkBr-3 breast cancer cells cotreated with 100 μM CoQ10 (BPM 31510) and 100 ng/ml doxorubicin. Caspase 3 activity was monitored over time using a cleavable fluorescent substrate.

In addition CoQ10 in combination with chemotherapeutic agents amplified caspase 3 activation and apoptotic cell death, indicating CoQ10 enhances apoptotic signaling. See FIG. 22. Taken together, these data demonstrate that CoQ10 is a novel agent that reengages the cellular metabolic and apoptotic machinery of cancer cells independent of the genetic make-up underlying malignancy. Furthermore, CoQ10 enhances the cytotoxicity of standard-of-care chemotherapeutic agents in breast cancer cells through regulation of mitochondrial metabolism and oxidative stress. These findings confirm that CoQ10 is a novel agent with multiple utilities (as a single agent or in combination) in breast cancer including TNBCs that otherwise have poor prognosis and limited therapeutic options.

Figure 25:
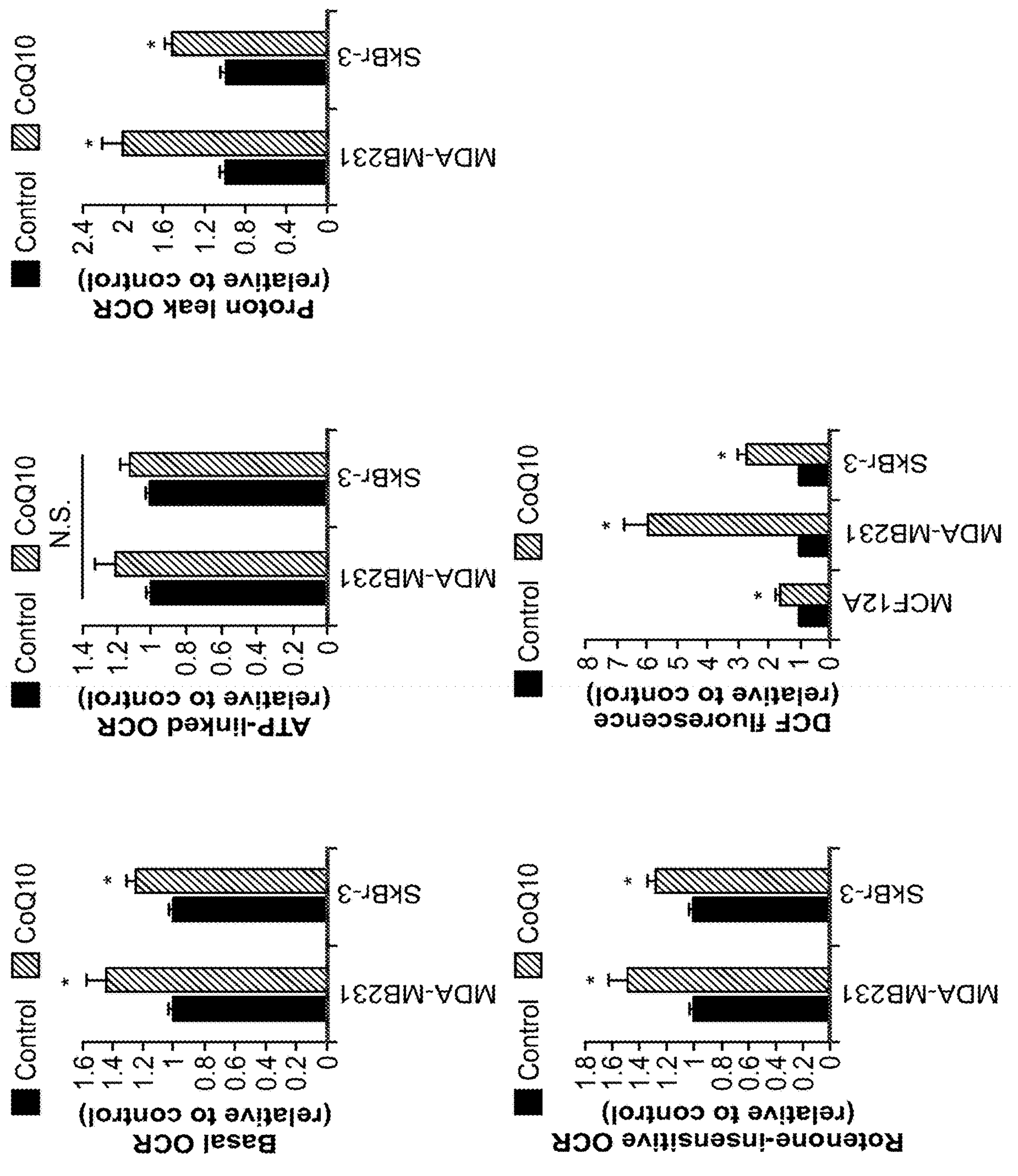
FIG. 25 shows MDA-MB231 and SkBr-3 breast cancer cells and MCF12A non-tumorigenic control cells treated with 100 μM CoQ10 (BPM 31510) for 24 hours. Mitochondrial function was assessed using sequential injection of mitochondrial toxins (oligomycin, CCCP, and rotenone) in a Seahorse XF96 analyzer. DCF fluorescence was also measured as an indicator of reactive oxygen species production in cells treated in the same manner. *$p<0.05$ compared to control, N.S. denotes no statistical significance.

To determine the effect of mitochondrial bioenergetics and reactive oxygen species production, MDA-MB231 and SkBr-3 breast cancer cells and MCF12A control cells were treated with 100 μM CoQ10 (BPM 31510) for 24 hours. Mitochondrial function was assessed using sequential injection of mitochondrial toxins (oligomycin, CCCP, and rotenone) in a Seahorse XF96 analyzer. DCF fluorescence was also measured as an indicator of reactive oxygen species production in cells treated in the same manner. Cellular bioenergetics profiling revealed that CoQ10 shifted cellular metabolism from glycolysis to mitochondrial metabolism, and this metabolic shift was associated with significant increases in reactive oxygen species (ROS). See FIG. 25.

Figure 27:
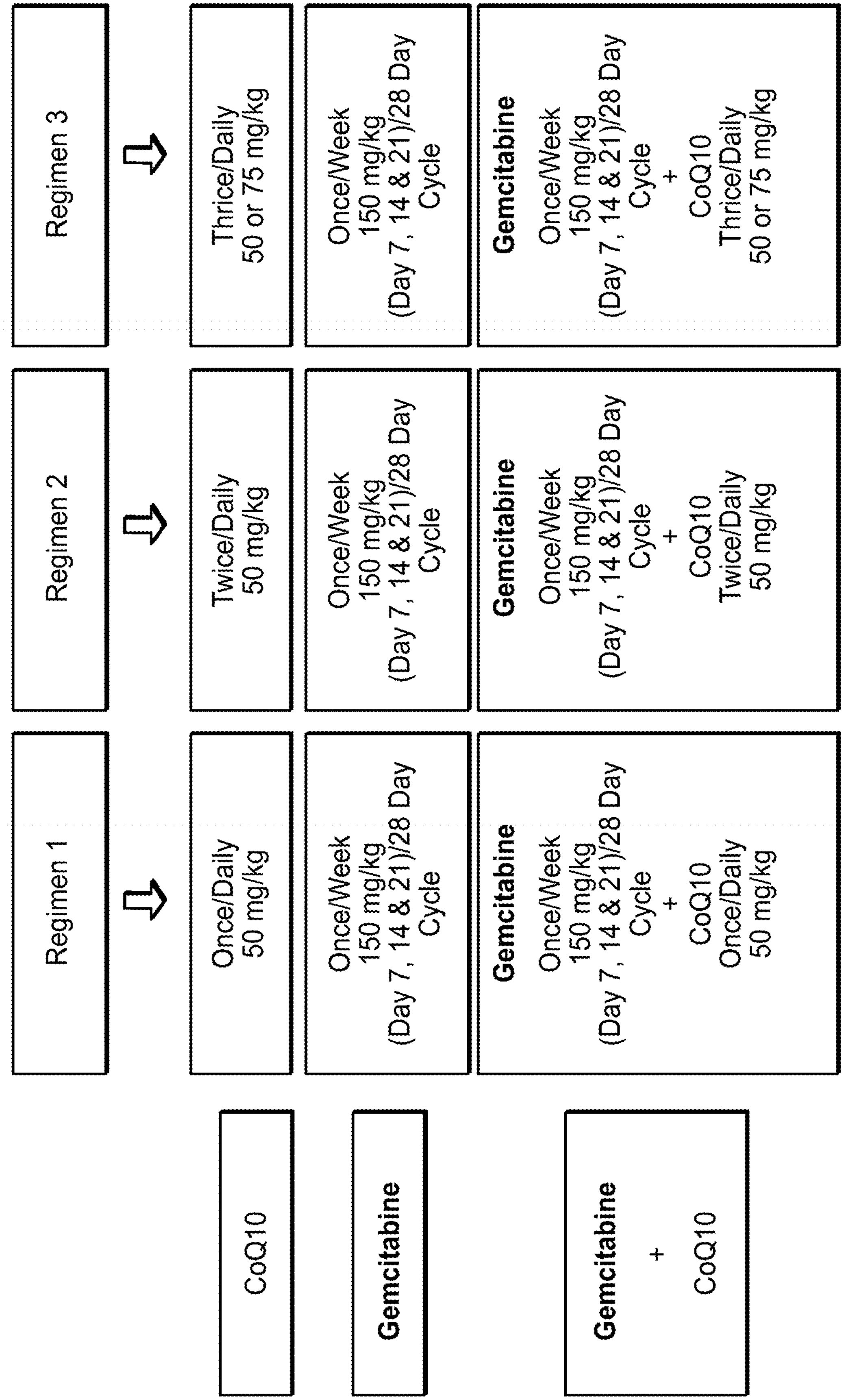
FIG. 27 shows three treatment regimens for evaluating the effect of CoQ10 (BPM 31510) alone or in combination with gemcitabine on animal survival in a xenograft mouse model of human pancreatic cancer.
Figure 28:
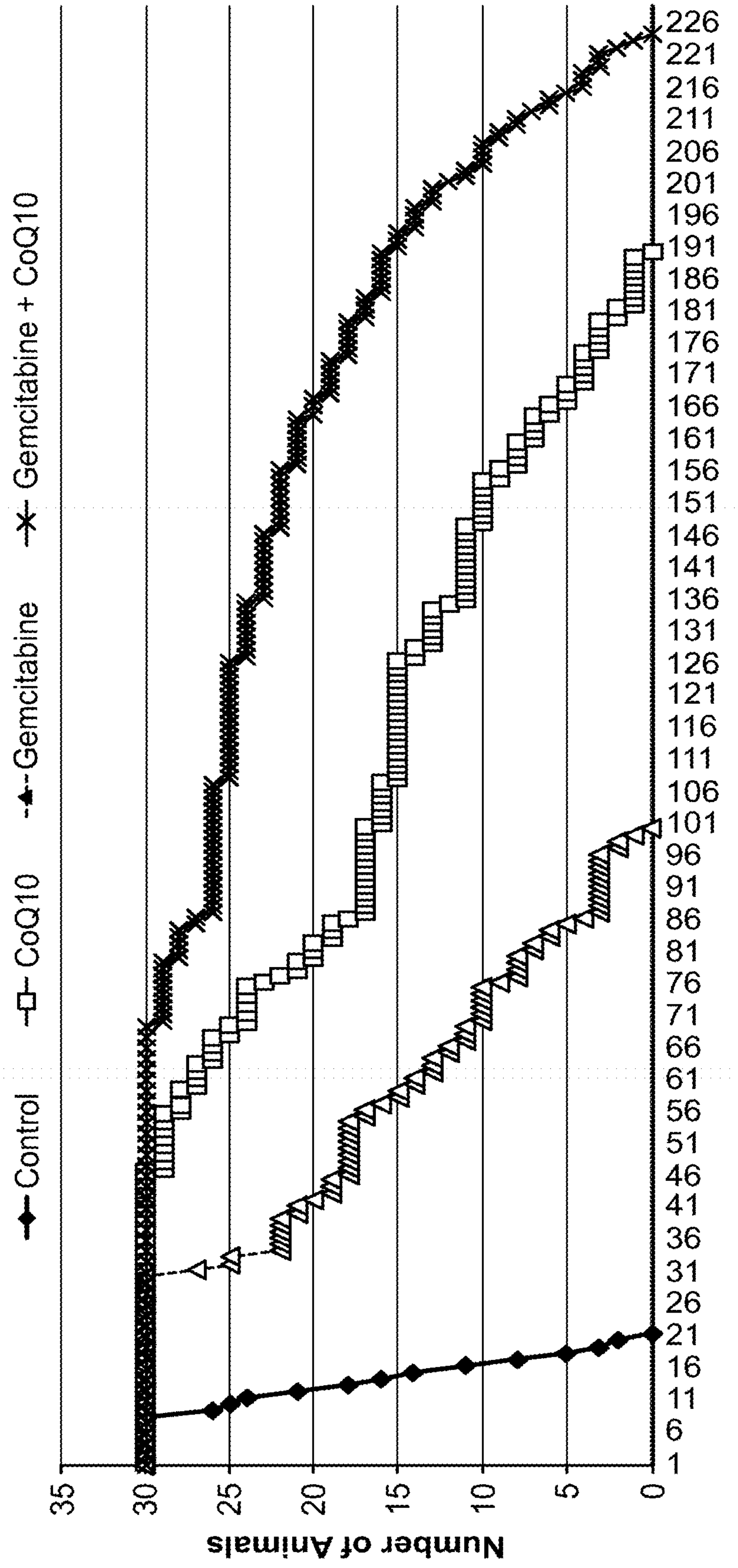
FIG. 28 shows the effect of regimen 2 (described in FIG. 27) treatment with CoQ10 (API 31510) and gemcitabine on animal survival in a xenograft mouse model of human pancreatic cancer. Gemcitabine alone versus gemcitabine+ CoQ10 (50 mg/kg) p=7.3 E-8
Figure 29:
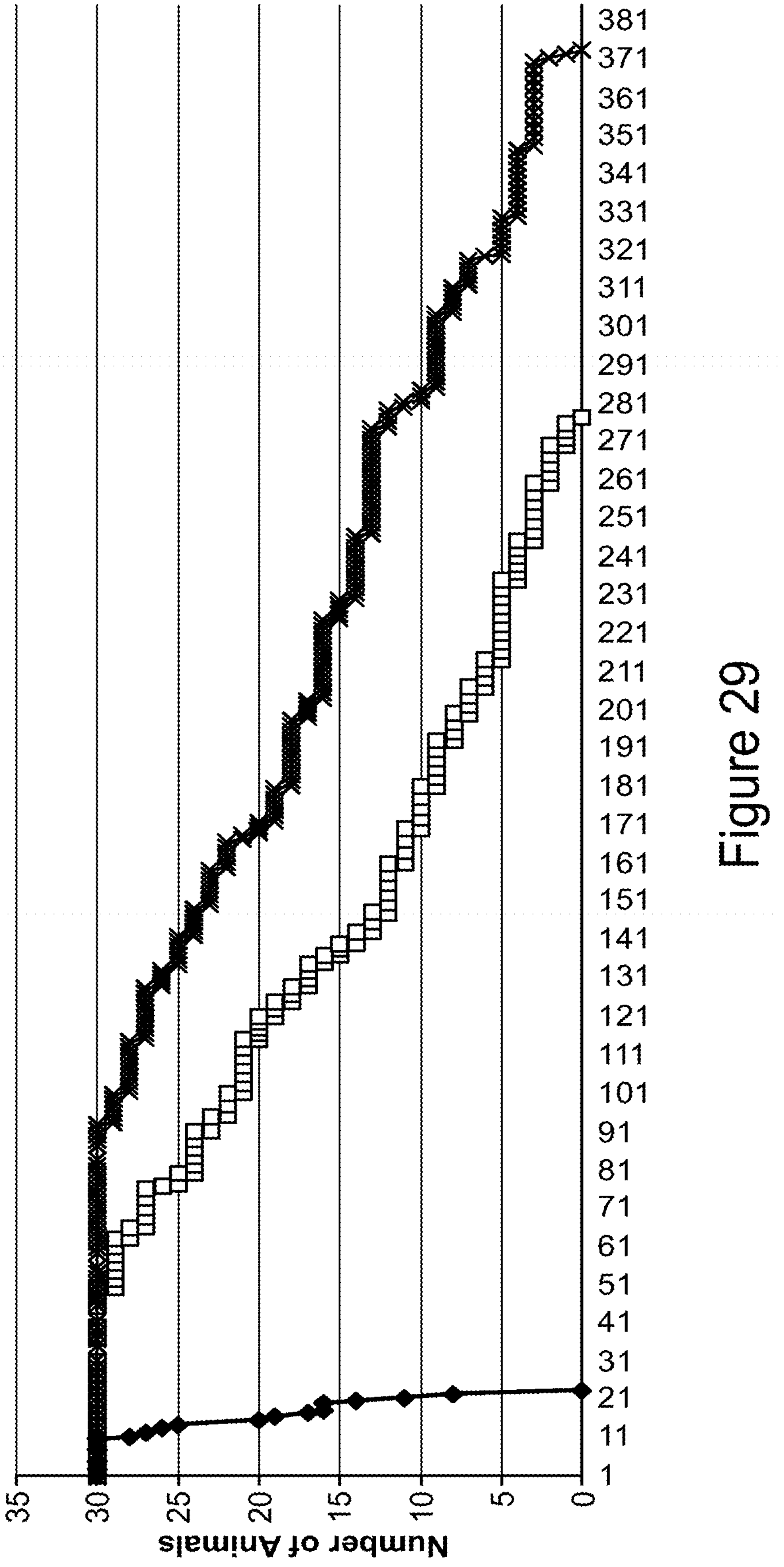
FIG. 29 shows the effect of regimen 3 (described in FIG. 27) treatment with CoQ10 (API 31510) and gemcitabine on animal survival in a xenograft mouse model of human pancreatic cancer. Gemcitabine alone versus gemcitabine+ CoQ10 (50 mg/kg) p=7.3 E-8
Figure 30:
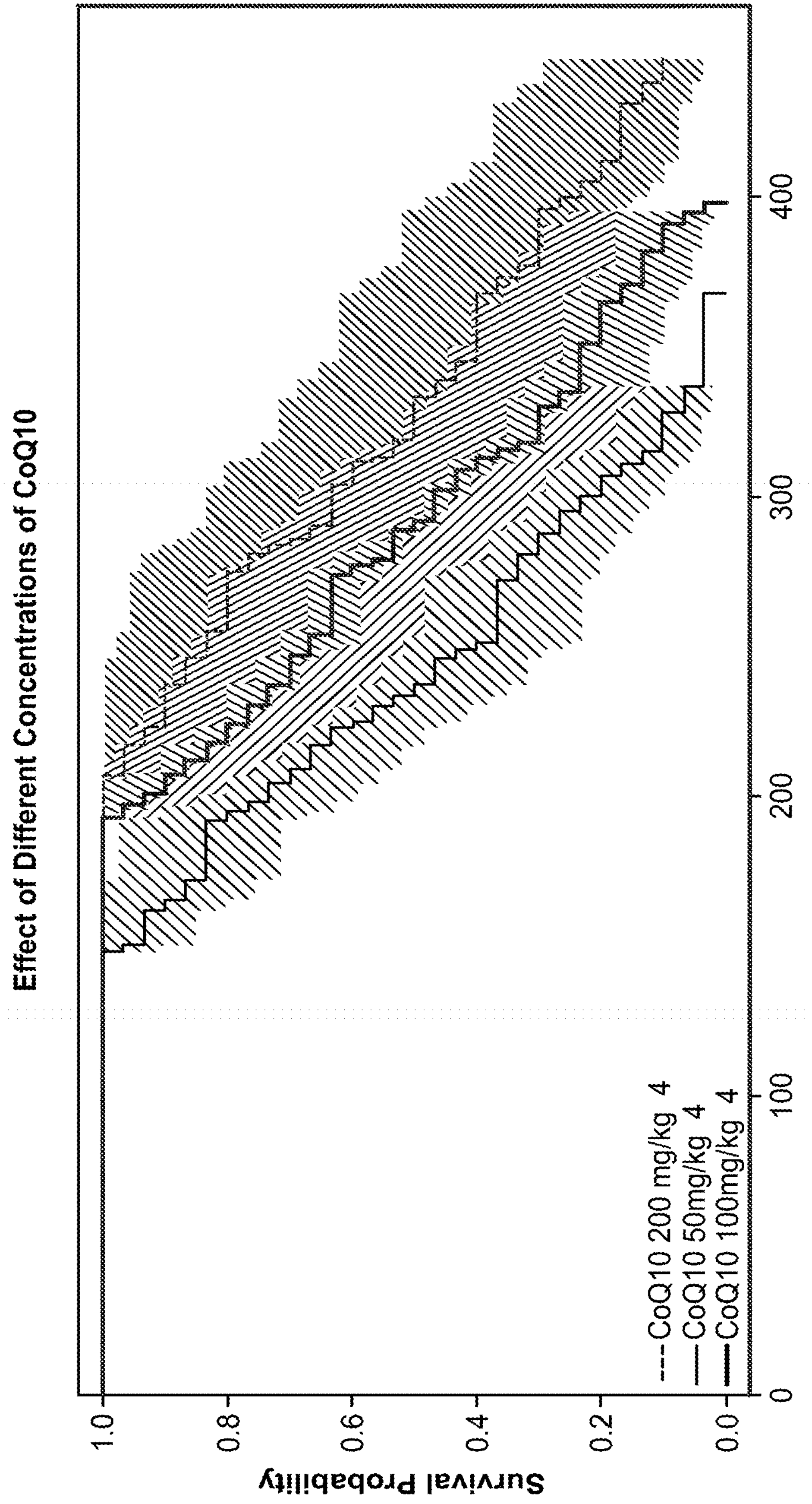
FIG. 30 shows the effect of various concentrations of CoQ10 (BPM 31510) on animal survival in a xenograft mouse model of human pancreatic cancer over time (days). Continuous infusion of CoQ10 at 200 mg/kg significantly improved survival in comparison to 50 mg/kg CoQ10 ($p<0.00001$). For example, mice treated with 200 mg/kg CoQ10 had the highest survival rate (survival probability) at 300 days, mice treated with 50 mg/kg CoQ10 had the lowest survival rate (survival probability) at 300 days, and mice treated with 100 mg/kg CoQ10 had a survival rate (survival probability) at 300 days that was between the other two treatment groups.
Figure 31:
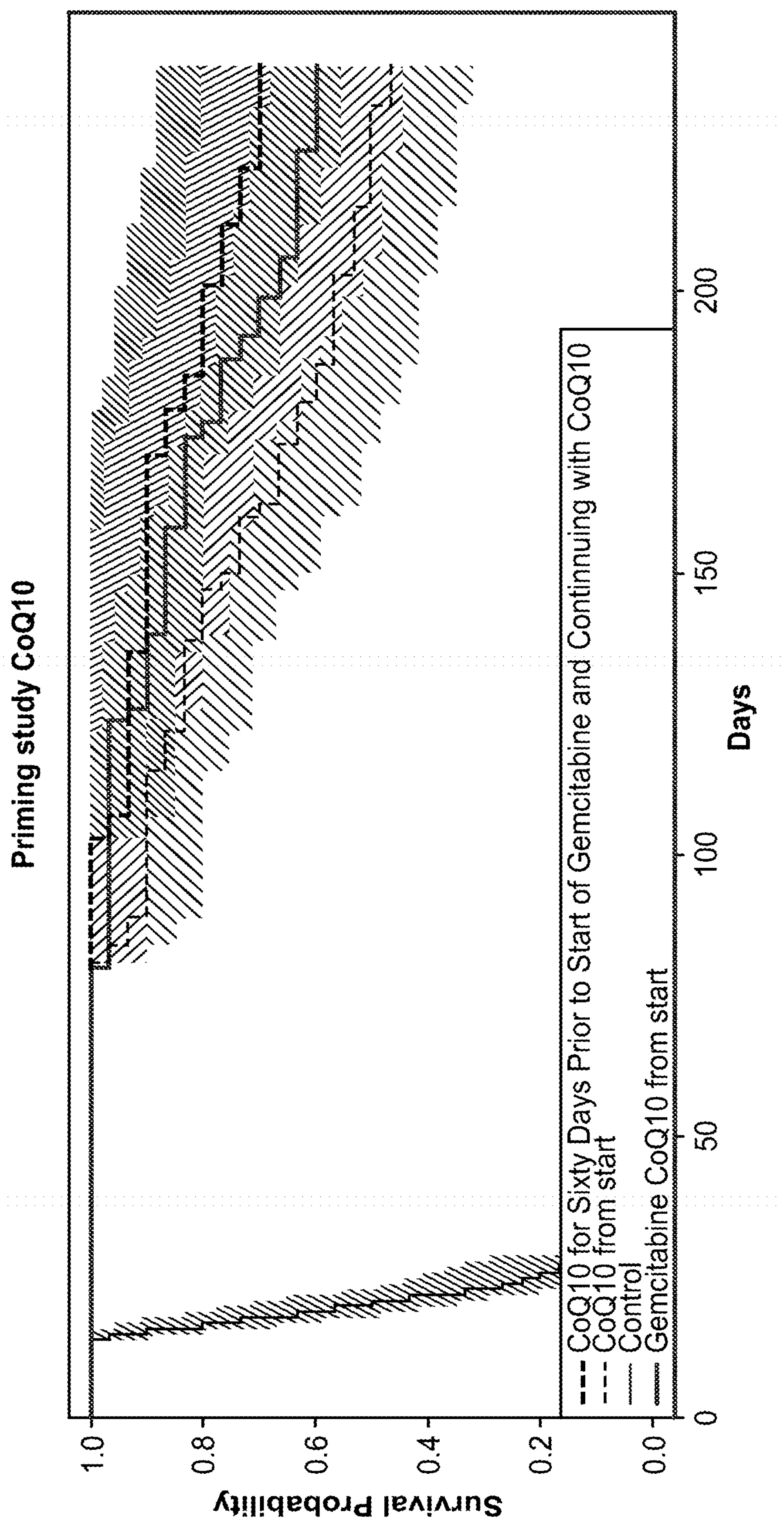
FIG. 31 shows the effect of CoQ10 and gemcitabine on animal survival over time (days) in a mouse xenograft model of human pancreatic cancer. Pretreatment with CoQ10 (200 mg/kg) sixty days prior to start of treatment with gemcitabine+CoQ10 improved survival in comparison to treatment with gemcitabine+CoQ10 from the start of the treatment regimen in a mouse xenograft model of human pancreatic cancer. For example, at 200 days, mice treated with CoQ10 60 days prior to start of gemcitabine and continuing with CoQ10 had the highest survival rate (survival probability), mice treated with gemcitabine and CoQ10 from the start had the next highest survival rate, mice treated with CoQ10 from the start had the next highest survival rate, and control mice had the lowest survival rate.

Example 17—Effect of Pretreatment, Dose and Route of Administration of CoQ10 Alone or in Combination with Gemcitabine in a Xenograft Mouse Model of Human Pancreatic Cancer The three treatment regimens shown in FIG. 27 (Regimen 1, Regimen 2, and Regimen 3) were evaluated in a xenograft mouse model of human pancreatic cancer to determine the effect of CoQ10 alone or in combination with gemcitabine on animal survival. The effect of treatment with Regimen 1 is described in Example 1 above. CoQ10 administered in three different intravenous doses (50 mg/kg or 75 mg/kg body weight daily, Regimen 3) was associated with a dose dependent increase in survival and had an additive effect to gemcitabine. See FIG. 29. Continuous infusion of CoQ10 significantly improved survival rates compared to three doses (50 mg/kg or 75 mg/kg) of CoQ10, with best outcomes at 200 mg/kg. See FIG. 30. Pretreatment for sixty days with CoQ10 alone followed by combination with gemcitabine was also associated with improved survival outcomes with either gemcitabine or CoQ10 alone. See FIG. 31. The data suggest that dose and route of administration of CoQ10 alone or in combination with standard of care chemotherapy agents influences and improves survival in an animal model of pancreatic cancer.

Figure 26:
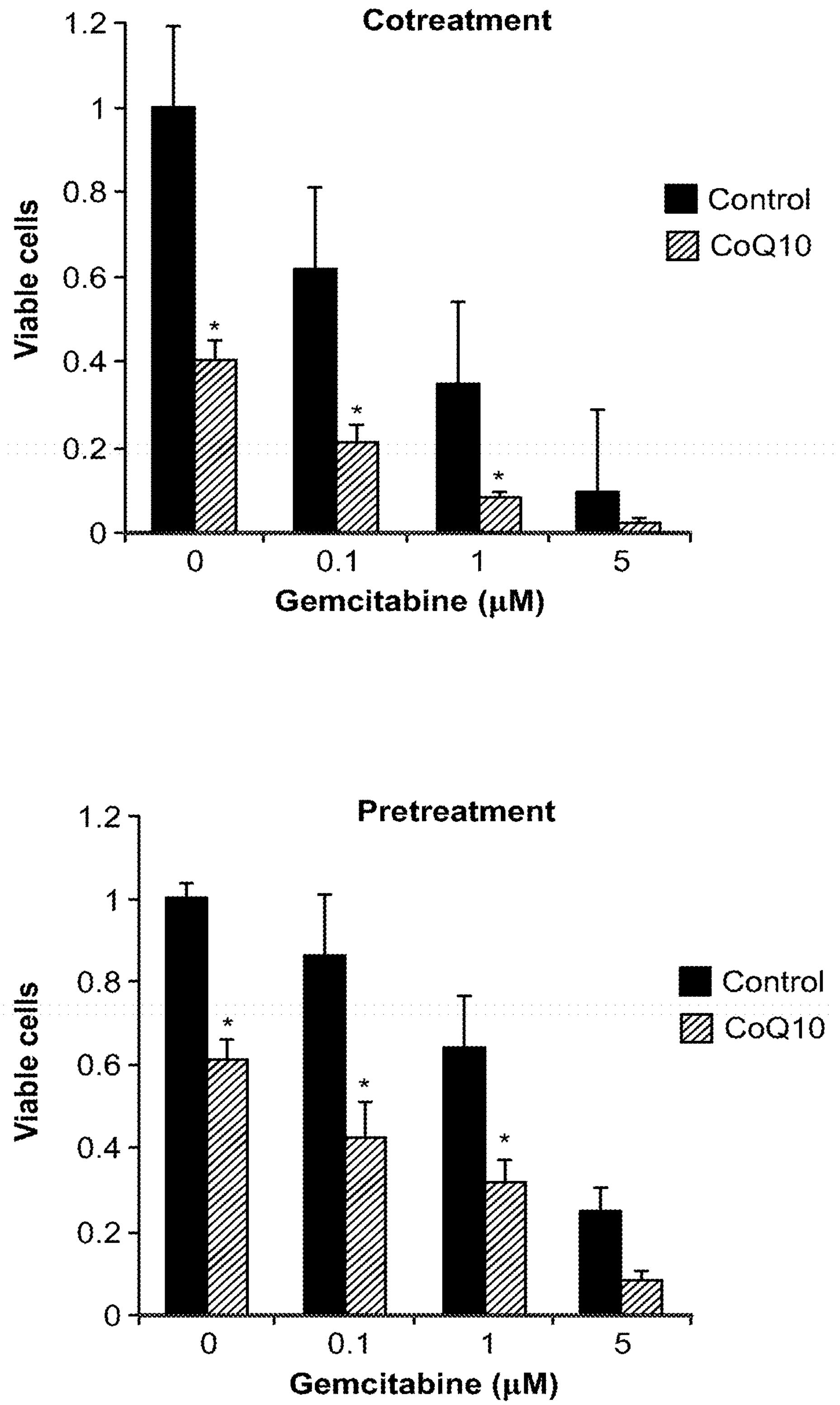
FIG. 26 shows pretreatment of human pancreatic cancer cells (PcCa2) with 100 CoQ10 (BPM31510) followed by treatment with gemcitabine (0.1, 1 and 5 or cotreatment of these cells with CoQ10 and gemcitabine. Both pretreatment and cotreatment significantly decreased the number of viable cells (*$p<0.05$) compared to gemcitabine alone.

Example 18—Effect CoQ10 Pretreatment Followed by Gemcitabine Treatment on Survival of Human Pancreatic Cancer Cells In Vitro Human pancreatic cancer cells (PcCa2) were pretreated with 100 μM CoQ10 followed by treatment with gemcitabine (0.1, 1 and 5 μM), or cotreated with CoQ10 and gemcitabine. Both pretreatment and cotreatment significantly decreased the number of viable cells (*$p<0.05$) compared to gemcitabine alone. See FIG. 26.

Example 19—In Vitro Assays of CoQ10 in Combination with Various Chemotherapies in a Range of Cancer Cells Various cancer cells are treated with a combination of CoQ10 and different cancer therapeutic agents to determine the effect of the combined therapies on cell survival and cell metabolism. The cancer cells and corresponding controls cells are shown in the table below.

| | |
|---|---|
| Breast | SKBR-3 |
| | MDA-231 |
| | BT549 |
| | MCF-7 |
| | MCF12A (control) |
| Pancreatic | PaCa2 |
| | PL-45 |
| | Panc1 |

-continued

| | |
|---|---|
| Lung | A549 |
| Colon | CaCo2 |
| | HT29 |
| Liver | Hep3B |
| | THLE-2 (control) |
| Cervical | Scc25 |
| Prostate | PC-3 |
| | LnCap |
| | PNT2 (control) |
| Ovarian | SKOV-3 |

The following cancer therapeutic agents are tested:

| Drug | Mode of Action | Target |
|---|---|---|
| Herceptin cancers/HER2+ | Antibody that binds HER2 | Most Breast |
| Irinotecan | Inhibits topoisomerase I | All dividing cells |
| Cisplatin | Inter and Crosslinks DNA | All dividing cells |
| 5 fluoracil | Inhibits thymidin formation | All dividing cells |
| Docetaxel | Prevents depolimerization of microtubules | All dividing cells |
| 4-Hydroxy-cyclophosphamide | Alkylating agent | All dividing cells |
| Gemcitabine | Nucleoside with fluorine | All dividing cells |
| Doxorubicine | TopoisoII inhibitor and induces oxidative stress. Inhibits mit complex 1 | All dividing cells |
| Paclitaxel | Microtubule stabilizer | All dividing cells |
| Flutamide containing | Androgen (DHT) receptor blocker | Androgen receptor cells |
| Estramustine | Alkylating agent derivative of estrogen | Estrogen induced cells |
| Etoposide | Topoisomerase II inhibitor | All dividing cells |
| Oxaliplatin | Bidentate platinum plate that crosslinks DNA | All dividing cells |
| Goserelin | GnRH and LHRH agonist | |
| Tamoxifen | Estrogen Receptor antagonist | ER containing cells |

The following assays are used to measure cell survival and metabolism:

| Assay | Method | Instrument |
|---|---|---|
| Cell Counts | Trypan blue | Nexcelon Cellometer |
| Proliferation | Propidium Iodide in Fixed cells | Flow Cytometer |
| Cell death | Propidium iodide | Flow Cytometer |
| Apoptosis (Caspase 3) | Caspase 3 dye | Fluorescent microscopy |
| ROS | CM-DCFDA dye | Flow Cytometer |

-continued

| Assay | Method | Instrument |
|---|---|---|
| Oxygen consumption | Mitochondria stress | Seahorse Xtracellular analyzer |
| Extracellular acidification | Glycolysis pathway | Seahorse Xtracellular analyzer |

Cells are cultured in the following growth media:

| | Medium | Source | Serum | Antibiotics |
|---|---|---|---|---|
| PaCa2 | DMEM no sodium pyruvate | Lonza | 5% FBS; 2.5% HS | 1× Pen/Strep/AmphoB |
| PC-3 | DMEM no sodium pyruvate | Lonza | 5% FBS | 1× Pen/Strep/AmphoB |
| MDA231 | RPMI 1640 | Lonza | 5% FBS | Gentamycin (GA-1000) |
| SKBR-3 | McCoy's 5A | Lonza | 5% FBS | 1× Pen/Strep/AmphoB |
| Hep3B | EMEM | Lonza | 5% FBS | 1× Pen/Strep/AmphoB |
| A549 | KF-12 | Invitrogen | 5% FBS | 1× Pen/Strep/AmphoB |
| HT-29 | McCoy's 5A | Lonza | 5% FBS | 1× Pen/Strep/AmphoB |
| SKOV-3 | McCoy's 5A | Lonza | 5% FBS | 1× Pen/Strep/AmphoB |
| MCF-7 | MEM + NEEA | Invitrogen | 5% FBS | 1× Pen/Strep/AmphoB |
| HUMEC | HUMEC media | Invitrogen | — | 1× Pen/Strep/AmphoB |
| PNT2 | RPMI 1640 | Lonza | 10% FBS | 1× Pen/Strep/AmphoB |
| Panc1 | DMEM | Lonza | 5% FBS | 1× Pen/Strep/AmphoB |
| MCF-12A | HAM/F-12 | Lonza | 5% Horse Serum | 1× Pen/Strep/AmphoB |
| BT-549 | RPMI 1640 | Lonza | 10% FBS | 1× Pen/Strep/AmphoB |

Supplements

| | Supplement | | |
|---|---|---|---|
| Hep3B | 1× Glutamax | | |
| MCF-7 | 1× Glutamax | | |
| MCF-12A | 20 ng/ml hEGF | 10 ug/ml insulin | 500 ng/ml hydrocortisone |
| BT-549 | 0.5 ug/ml insulin | | |

Method for Plating Cells

For cell counts, proliferation, and measurement of reactive oxygen species (ROS), the amount of cells and method for plating and treating are the same. Cells are seeded at the same time that the treatment is added. Cells are seeded in a 24-well plate as follows:

| Sample | Cell/well | Sample | Cell/well | Sample | Cell/well |
|---|---|---|---|---|---|
| SKBR-3 | 60k | PC3 | 60k | HT-29 | 100k |
| MDA231 | 60k | PaCa2 | 50K | BT549 | 30K |
| MCF-7 | 50K | Panc-1 | 50K | Hep3B | 60K |
| MCF12A | 60k | A-549 | 100k | SKOV-3 | 60k |

For caspase 3 assays to measure apoptosis, cells are plated in glass 12-well plates in which cells are in the ratio of 110 k/well and allowed to attached from 5 h to 18 h, then treatment is added. To measure oxygen consumption and extracellular acidification the cells are plated in the Seahorse XF-96 plate. Examples of cell numbers for various cell lines are shown in the table below:

| Sample | Cell/well |
|---|---|
| SKBR-3 | 10k |
| MDA231 | 10k |
| MCF12A | 30k |

Sources, solvents and stock concentrations for the chemotherapeutic agents are shown in the table below:

| Stock preparation | Cat # | Solvent | vial | Stock [ ] |
|---|---|---|---|---|
| SN38 | Sigma H0165-10mg | 255 ul DMSO | 10 mg | 100 mM |
| Cisplatin*** | Enzo ALX-400-040-M050 | 33 ml of 0.9% Saline | 50 mg | 5 mM |
| Doxo | Sigma D-1515 | 1 ml DMSO | 10 mg | 10 mg/ml |
| 5FU | Amresco 0597-5G | 1 ml DMSO | weigh 13 mg | 100 mM |
| Herceptin | Thermo Fisher | 20 ml provided H2O | 400 mg | 20 mg/ml |
| Cyclophosphamide | Santa Cruz sc-219703 | 500 ul H2O + thiosulfate | 25 mg | 4.4 mM |
| Gemcitabine | Sigma G6423-10mg | 3.3 ml H2O | 10 mg | 10 mM |
| Paclitaxel | Sigma T7402-1mg | 118 ul DMSO | 1 mg | 10 mM |
| Docetaxel | Sigma 01885-5mg-F | 618 ul DMSO | 5 mg | 10 mM |
| Tamoxifen | Sigma H7904 | 1290 ul EtOH | 5 mg | 10 mM |
| Avastin | Myoderm Medical supply | | | |
| Estramustine | Sigma#SLBD7083V | 1 ml DMSO | 5.6 mg | 100 mM |
| Etoposide | Sigma lot# BCBH0586V | 425 ul DMSO | 25 mg | 100 mM |
| Oxaliplatin | Sigma lot# SLBD0630V | 1.25 ml DMSO | 5 mg | 100 mM |

For each chemotherapy, concentration ranges for testing may be derived from concentration ranges known in the art. Dose response curves are generated for each chemotherapeutic agent as shown in the table below:

| Drugs | Dose response curve concentrations | | | | |
|---|---|---|---|---|---|
| SN38 | 0.1 nM | 1 nM | 10 nM | 100 nM | 1000 nM |
| Cisplatin | 1 uM | 6 uM | 12 uM | 25 uM | 50 uM |
| Doxo | 1 ng/ml | 10 ng/ml | 100 ng/ml | 1 ug/ml | 10 ug/ml |
| 5FU | 0.1 uM | 1 uM | 10 uM | 100 uM | 1000 uM |
| | 1 uM | 5 uM | 10 uM | 25 uM | 50 uM |
| Herceptin | 10 ug/ml | 25 ug/ml | 50 ug/ml | 100 ug/ml | 250 ug/ml |
| | 1 ug/ml | 5 ug/ml | 10 ug/ml | 25 ug/ml | 50 ug/ml |
| Cyclophosphamide | 0.05 uM | 0.25 uM | 1 uM | 4 uM | 12.5 uM |
| Gemcitabine | 0.1 uM | 1 uM | 10 uM | 100 uM | 1000 uM |
| Paclitaxel | 5 nM | 10 nM | 25 nM | 50 nM | 100 nM |
| Docetaxel | 0.1 nM | 1 nM | 10 nM | 100 nM | 1000 nM |
| Tamoxifen | 0.3 uM | 0.62 uM | 1.25 uM | 2.5 uM | 5 uM |
| Flutamide | 0.01 uM | 0.1 uM | 1 uM | 10 uM | 100 uM |
| Estramustine | 0.01 uM | 0.1 uM | 1 uM | 10 uM | 100 uM |
| Etoposide | 0.01 uM | 0.1 uM | 1 uM | 10 uM | 100 uM |
| Oxaliplatin | 0.1 uM | 1 uM | 10 uM | 100 uM | 1000 uM |

For the cotreatment experiments, the following doses are chosen for each cell line:

| | Combo Concentrations | | | | | | | | | |
|---|---|---|---|---|---|---|---|---|---|---|
| Drugs | SKBR-3 | Hep3B | MDA231 | Paca2 | A549 | PC-3 | THL E-2 | SKOV-3 | HT-29 | MCF-7 |
| SN38 | 1, 10, 100 nM | 10, 100 nM | 1, 10, 25 nM | | | 25, 100, 250 nM | 1, 10 nM | | 0.5, 1, 10 nM | 1, 5, 10 nM |
| Cisplatin | 1, 5, 10 μM | 1, 5, 10 μM | | | 0.1, 1, 10 μM | | | 0.5, 2.5, 5 μM | | 1.5, 3, 6 μM |
| Doxorubicine | 10, 50, 100 ng/ml | 10, 25, 50 ng/ml | 0.1, 1, 10 ng/ml | 10, 50, 100 μg/ml | | | | | | 2, 4, 8 ng/ml |
| 5-fluorouracil | 0.1, 1, 10 μM | 0.1, 1, 10 μM | 0.1, 1, 10 μM | | | | | | 0.1, 1, 10 nM | |
| Herceptin | 10, 25, 50 μg/ml | | | | | | | | | |
| Cyclophosphamide | 0.5, 1, 2 μM | | 1, 2, 4 μM, 0.5, 1, 2 μM | | | | | 0.25, 4, 8 μM | | 0.5, 1, 2 μM |
| Gemcitabine | | | | 0.1, 1, 5 μM | 0.01, 0.1, 1 μM | 25, 100, 200 nM | | | | |

-continued

| | Combo Concentrations | | | | | | | | | |
|---|---|---|---|---|---|---|---|---|---|---|
| Drugs | SKBR-3 | Hep3B | MDA231 | Paca2 | A549 | PC-3 | THL E-2 | SKOV-3 | HT-29 | MCF-7 |
| Paclitaxel | | | 10, 50, 100 nM, 10, 25, 50 nM | | 5, 10, 25 nM | 25, 100, 200 nM | | | | |
| Docetaxel | 0.01, 0.1, 1 nM | | | | 0.1, 1, 10 nM | 1, 10, 100 μM | | | | |
| Tamoxifen | | | | | | | | | | 2, 4, 6 μM |
| Flutamide | | | | | | 0.01, 0.1, 1 μM | | | | |
| Estramustine | | | | | | 1, 10 100 μM | | | | |
| Etoposide | | | | | | 0.01, 0.1, 1 μM | | | | |
| Oxaliplatin | | | | 1, 10, 50 μM | | | | 10, 50, 100 μM | | |

Treatment time is optimized according to the endpoint assay, e.g: for metabolic assays shorter incubation times are used; for cell counts, longer incubation times are used. The incubations that involve proliferation and cell counts are chosen based on the cell doubling time, i.e. how fast the cells grow. The table below provides incubation times for various cell types and assays.

| | Cell Counts, ROS, Cell Proliferation (Propidium Iodide) | OCR, ECAR | Caspase 3 |
|---|---|---|---|
| SKBR-3 | 48 h | 24 h | 96 h |
| MDA-231 | 48 h | 24 h | 96 h |
| BT549 | 48 h | 24 h | 96 h |
| MCF-7 | 72 h | 24 h | 96 h |
| MCF12A | 48 h | 24 h | 96 h |
| PaCa2 | 72 h | 24 h | 96 h |
| PL-45 | 48 h | 24 h | 96 h |
| Panc1 | 48 h | 24 h | 96 h |
| A549 | 48 h | 24 h | 96 h |
| CaCo2 | 48 h | 24 h | 96 h |
| HT29 | 48 h | 24 h | 96 h |
| Hep3B | 48 h | 24 h | 96 h |
| THLE-2 | 48 h | 24 h | 96 h |
| Scc25 | 48 h | 24 h | 96 h |
| PC-3 | 48 h | 24 h | 96 h |
| LnCap | 48 h | 24 h | 96 h |
| PNT2 | 48 h | 24 h | 96 h |
| SKOV-3 | 72 h | 24 h | 96 h |

Example 20—Effect of Pretreatment with CoQ10 Followed by Treatment with Chemotherapeutic Agents on Various Tumors In Vivo A concentrated aqueous nanodispersion of CoQ10 in a 4:3:1.5 ratio of CoQ10 (4% w/v):DMPC (3% w/v):Poloxamer 188 (1.5% w/v) in water is used; the nanodispersion concentrate contains 40 mg/mL of CoQ10 at 30-50 nm particle size. A single vehicle control group receives a sterile solution of 3% w/v DMPC and 1.5% w/v Poloxamer 188 dosed at the highest tolerated dose (1000 mg API equivalent) A single negative control group receives buffered sterile physiological saline. The CoQ10 nanodispersion is prepared within 2 weeks of the start of the study and stored at 4-25 C throughout the study. Test samples are assayed for CoQ10 activity and for particle size distribution at the beginning and end of the study.

The excipients used in the nanodispersion, DMPC and Poloxamer 188, are used for the formulation of an aqueous nanodispersion of CoQ10. The concentrated nanodispersion is diluted at point of use with sterile buffered physiologic saline (PBS). The vehicle contains PBS as the diluents and PBS is used undiluted as the saline control. Immunocompromised mice from Jackson Laboratories and Harlan Laboratories are used. Immunocompromised mice lack the innate and adaptive immune systems. This provides a biological environment suitable for the growth of human tumors in vivo. These animals are particularly suitable for the grafting of different human cancers.

4-week old mice arrive at the facilities and 48 hours later experiments are performed. Mice are housed in litters of 5 per cage under a single identifier number. Animals are weighed on arrival and throughout the entire experiment to have another parameter in response to the different formulae. The diet employed is the formulation Lab Diet® 5001 Rodent Diet, manufactured by PMI Nutrition International, LLC. This manufacturer is an ISO 9001:2000-certified facility. The diet is purchased every 6 months, and lot numbers can be traced to each room and will be recorded by the technician. The food administered to the NSG mice must be autoclaved before being placed in animal cages. Water is fed ad libitum to all mice. Water is obtained from the Florida Water Department and is dispensed in clean bottles to each cage by the animal technicians. Water is checked daily for the presence of debris and replaced with clean water. Water administered to the NSG mice must be sterile prior to administration to animals. Animals are sacrificed by $CO_2$ inhalation by 20 days of age. To ensure death, cervical dislocation is performed for each animal and diaphragms are punctured.

Sterile CoQ10 formula and the suitable sterile control is administered intravenously. CoQ10 doses are administered based on ongoing results. Prior experiments exhibited no signs of toxicity when CoQ10 was administered three times per week at up to 50 mg/kg and the MTD in rats has been established at 250 mg/kg given three times per week for 4 weeks. The effect of CoQ10 is compared with other chemotherapy regimens specific for each cancer line. Another arm of the study evaluates synergistic effects between CoQ10 and other chemotherapeutic agents.

The following cancer cells are evaluated:

| | | Cell Designation |
|---|---|---|
| Breast | Triple negative | MDA-MB-231 |
| Lung | Small cell | H522 |
| | Non-small cell | A549 |
| Ovarian | | SK-OV-3 |
| Liver | | HepG2 |
| Prostate | | LnCap |
| Acute Leukemia | | Kg1, K562 |
| Colon | | HT29, CaCo |
| Glioblastoma | | LN229 |

All cells are cultured in a 5% $CO_2$ incubator with 100% humidity at 37° C. The base medium varies according to each cell, To make the complete growth medium, the following components are added to the base medium: fetal bovine serum to a final concentration of 10%. Prior to the injection of cells into the animals, they are grown to 50% confluency, and thereafter attached or centrifuged as per cell protocol. The following organs are harvested: kidney, pancreas, lungs, heart and liver. Organs are weighed and recorded. A pathological report of routine stain Wright's or Hematoxylin/Eosin stains is performed. CoQ10 formulations and chemotherapeutic agents are administered intraperitoneally or intravenously.

The presence of lack of lactation, lethargy and decrease in body weight are observed. Such signs of morbidity are the basis of early scarification and an autopsy is performed in the animal (i.e., organ weights, pathology slides).
Under sterile conditions, animals are injected as outlined above. Litters are randomized according to the cage card number identifier and the weight of each animal is recorded. Mice are then returned to their cages. Thereafter, mice are injected intraperitoneally daily until they are sacrificed due to tumor burden or their survival.

The following chemotherapy regimens are tested on various cancer cells as indicated:

| Breast Cancer (non-metastatic) |
|---|
| Combination Chemotherapy |
| Doxorubicin/Cyclophosphamide |
| Cyclophosphamide/Doxorubicin/5-fluororacil |

-continued

| Lung Cancer (small cell) |
|---|
| Combination Chemotherapy |
| Cyclophosphamide/Doxorubicin/Vincristine |
| Cyclophosphamide/Doxorubicin/Etoposide |
| Lung Cancer (non-small cell) |
| Combination Chemotherapy |
| Cisplatin/Paclitaxel |
| Docetaxel/Cisplatin |
| Gemcitabine/Cisplatin |
| Ovarian Cancer |
| Combination Chemotherapy |
| Cisplatin/Cyclophosphamide |
| Cisplatin/Paclitaxel |
| Hepatocellular Cancer |
| Single agents |
| Doxorubicin |
| Cisplatin |
| Capecitabine |
| Prostate Cancer |
| Combination Chemotherapy |
| Paclitaxel/Estramustine |
| Docetaxel/Estramusine |
| Acute Leukemia |
| Combination Chemotherapy |
| Cytarabine/Daunorubicin |
| Cytarabine/Idarubicin |
| Cytarabine/Doxorubicin |
| Colon Cancer |
| Single agent |
| Capecitabine |
| Glioblastoma |
| Single agent |
| Bevacitumab |
| Valganciclovir |

Example 21—In Vitro Assays of Various Cancer Cell Lines Treated with CoQ10 and Chemotherapeutic Agents Various cancer cell lines were cotreated or pretreated with CoQ10 and various chemotherapeutic agents as described in Example 14 above. Cell/chemotherapeutic agent combinations that significantly reduced viable cell numbers are shown in Table 2 below.

TABLE 2

Summary of in vitro studies with various cancer cell lines treated with CoQ10 and various chemotherapeutic agents.

| | PC3 Prostate | SkBr-3 Breast | MB231 TNBC | MCF-7 Breast | MiaPaCa2 Pancreatic | BT549 Breast | Hep3B Liver | A549 Lung | SKOV3 Ovarian |
|---|---|---|---|---|---|---|---|---|---|
| SN38 | | Co | | | | | Co and Pre | | |
| Doxo | | Pre | | Pre | Pre | Pre | Co | | |
| 5-FU | | Co | Co | | | | Co | | |
| Cisplatin | | | | | | | | Pre | |
| 4-HCP | | Co | Co | Co | | | | | Co |
| Paclitaxel | | | | | | | | Co | |
| Tamoxifen | | | | Pre | | | | | |
| Gemcitabine | | | | | | | | Pre | |
| Flutamide | Pre | | | | | | | | |
| Goserelin | Pre | | | | | | | | |

Co: cotreatment; Pre: pretreatment.

TABLE 3

| Standard dosages of chemotherapeutic agents. Standard dosages were obtained from the manufacturer's product insert for the chemotherapeutic agent. | |
|---|---|
| Chemotherapeutic Agent | Recommended Dosages |
| Doxorubicin | Administer DOXIL at an initial rate of 1 mg/min to minimize the risk of infusion reactions. If no infusion related reactions occur, increase rate of infusion to complete administration over 1 hour.<br>Do not administer as bolus injection or undiluted solution.<br>Ovarian cancer: 50 $mg/m^2$ IV every 4 weeks for 4 courses minimum<br>AIDS-related Kaposi's Sarcoma: 20 $mg/m^2$ IV every 3 weeks<br>Multiple Myeloma: 30 $mg/m^2$ IV on day 4 following bortezomib which is administered at 1.3 $mg/m^2$ bolus on days 1, 4, 8 and 11, every 3 weeks |
| Cyclophosphamide | Treatment of Malignant Diseases - Adults and Children:<br>When used as the only oncolytic drug therapy, the initial course of CYTOXAN for patients with no hematologic deficiency usually consists of 40 to 50 mg/kg given intravenously in divided doses over a period of 2 to 5 days. Other intravenous regimens include 10 to 15 mg/kg given every 7 to 10 days or 3 to 5 mg/kg twice weekly.<br>Oral CYTOXAN dosing is usually in the range of 1 to 5 mg/kg/day for both initial and maintenance dosing.<br>When CYTOXAN is included in combined cytotoxic regimens, it may be necessary to reduce the dose of CYTOXAN as well as that of the other drugs.<br>Treatment of Nonmalignant Diseases - Biopsy Proven "Minimal Change" Nephrotic Syndrome In Children:<br>An oral dose of 2.5 to 3 mg/kg daily for a period of 60 to 90 days is recommended. In males, the incidence of oligospermia and azoospermia increases if the duration of CYTOXAN treatment exceeds 60 days. Treatment beyond 90 days increases the probability of sterility.<br>Adrenocorticosteroid therapy may be tapered and discontinued during the course of CYTOXAN therapy. |
| 5-fluorouracil | Fluorouracil Injection should be administered only intravenously.<br>Dosage: 12 mg/kg are given intravenously once daily for 4 successive days. The daily dose should not exceed 800 mg. If no toxicity is observed, 6 mg/kg are given on the 6th, 8th, 10th and 12th days unless toxicity occurs. No therapy is given on the 5th, 7th, 9th or 11th days. Therapy is to be discontinued at the end of the 12th day, even if no toxicity has become apparent.<br>Poor risk patients or those who are not in an adequate nutritional state should receive 6 mg/kg/day for 3 days. If no toxicity is observed, 3 mg/kg may be given on the 5th, 7th and 9th days unless toxicity occurs. No therapy is given on the 4th, 6th or 8th days. The daily dose should not exceed 400 mg.<br>Maintenance Therapy: In instances where toxicity has not been a problem, it is recommended that therapy be continued using either of the following schedules:<br>1. Repeat dosage of first course every 30 days after the last day of the previous course of treatment.<br>2. When toxic signs resulting from the initial course of therapy have subsided, administer a maintenance dosage of 10 to 15 mg/kg/week as a single dose. Do not exceed 1 gm per week. |
| Vincristine | The drug is administered intravenously at weekly intervals.<br>The usual dose of vincristine sulfate for pediatric patients is 2 $mg/m^2$. For pediatric patients weighing 10 kg or less, the starting dose should be 0.05 mg/kg, administered once a week.<br>The usual dose of vincristine sulfate for adults is 1.4 $mg/m^2$. A 50% reduction in the dose of vincristine sulfate is recommended for patients having a direct serum bilirubin value above 3 mg/100 mL. |
| Etoposide | In testicular cancer, the usual dose of Etoposide Injection in combination with other approved chemotherapeutic agents ranges from 50 to 100 $mg/m^2$/day, on days 1 through 5 to 100 $mg/m^2$/day, on days 1, 3, and 5.<br>In small cell lung cancer, the Etoposide Injection dose in combination with other approved chemotherapeutic drugs ranges from 35 $mg/m^2$/day for 4 days to 50 $mg/m^2$/day for 5 days.<br>Chemotherapy courses are repeated at 3 to 4 week intervals after adequate recovery from any toxicity. |
| Cisplatin | Cisplatin is administered by slow intravenous infusion.<br>Metastatic Testicular Tumors: The usual cisplatin (cisplatin injection) dose for the treatment of testicular cancer in combination with other approved chemotherapeutic agents is 20 $mg/m^2$ IV daily for 5 days per cycle.<br>Metastatic Ovarian Tumors: The usual cisplatin (cisplatin injection) dose for the treatment of metastatic ovarian tumors in combination with cyclophosphamide is 75 to 100 $mg/m^2$ IV per cycle once every 4 weeks (DAY 1).<br>The dose of cyclophosphamide when used in combination with cisplatin (cisplatin injection)is 600 $mg/m^2$ IV once every 4 weeks (DAY 1). In combination therapy, cisplatin (cisplatin injection) and cyclophosphamide are administered sequentially.<br>As a single agent, cisplatin (cisplatin injection) should be administered at a |

TABLE 3-continued

Standard dosages of chemotherapeutic agents. Standard dosages were obtained from the manufacturer's product insert for the chemotherapeutic agent.

| Chemotherapeutic Agent | Recommended Dosages |
|---|---|
| | dose of 100 $mg/m^2$ IV per cycle once every 4 weeks.<br>Advanced Bladder Cancer: cisplatin (cisplatin injection) should be administered as a single agent at a dose of 50 to 70 $mg/m^2$ IV per cycle once every 3 to 4 weeks depending on the extent of prior exposure to radiation therapy and/or prior chemotherapy. For heavily pretreated patients an initial dose of 50 $mg/m^2$ per cycle repeated every 4 weeks is recommended. |
| Paclitaxel | All patients should be premedicated prior to Paclitaxel administration in order to prevent severe hypersensitivity reactions. Such premedication may consist of dexamethasone 20 mg PO administered approximately 12 and 6 hours before Paclitaxel, diphenhydramine (or its equivalent) 50 mg IV 30 to 60 minutes prior to Paclitaxel, and cimetidine (300 mg) or ranitidine (50 mg) IV 30 to 60 minutes before Paclitaxel.<br>Ovarian Carcinoma:<br>1) For previously untreated patients with carcinoma of the ovary, one of the following recommended regimens may be given every 3 weeks.<br>Paclitaxel administered intravenously over 3 hours at a dose of 175 $mg/m^2$ followed by cisplatin at a dose of 75 $mg/m^2$; or<br>Paclitaxel administered intravenously over 24 hours at a dose of 135 $mg/m^2$ followed by cisplatin at a dose of 75 $mg/m^2$.<br>2) In patients previously treated with chemotherapy for carcinoma of the ovary, Paclitaxel has been used at several doses and schedules; however, the optimal regimen is not yet clear. The recommended regimen is Paclitaxel 135 $mg/m^2$ or 175 $mg/m^2$ administered intravenously over 3 hours every 3 weeks.<br>Breast Carcinoma:<br>1) For the adjuvant treatment of node-positive breast cancer, the recommended regimen is Paclitaxel, at a dose of 175 $mg/m^2$ intravenously over 3 hours every 3 weeks for 4 courses administered sequentially to doxorubicin-containing combination chemotherapy.<br>2) After failure of initial chemotherapy for metastatic disease or relapse within 6 months of adjuvant chemotherapy, Paclitaxel at a dose of 175 $mg/m^2$ administered intravenously over 3 hours every 3 weeks has been shown to be effective.<br>Non-small cell lung carcinoma:<br>The recommended regimen, given every 3 weeks, is Paclitaxel administered intravenously over 24 hours at a dose of 135 $mg/m^2$ followed by cisplatin, 75 $mg/m^2$.<br>AIDS-related Kaposi's sarcoma:<br>Paclitaxeladministered at a dose of 135 $mg/m^2$ given intravenously over 3 hours every 3 weeks or at a dose of 100 $mg/m^2$ given intravenously over 3 hours every 2 weeks is recommended (dose intensity 45-50 $mg/m^2$/week).<br>Advanced HIV disease:<br>1) Reduce the dose of dexamethasone as 1 of the 3 premedication drugs to 10 mg PO (instead of 20 mg PO);<br>2) Initiate or repeat treatment with Paclitaxel only if the neutrophil count is at least 1000 cells/$mm^3$;<br>3) Reduce the dose of subsequent courses of Paclitaxel by 20% for patients who experience severe neutropenia (neutrophil <500 cells/$mm^3$ for a week or longer); and<br>4) Initiate concomitant hematopoietic growth factor (G-CSF) as clinically indicated.<br>Hepatic Impairment:<br>Recommendations for dosage adjustment for the first course of therapy are shown in the table below for both 3- and 24-hour infusions. Further dose reduction in subsequent courses should be based on individual tolerance. |

RECOMMENDATIONS FOR DOSING IN PATIENTS WITH HEPATIC IMPAIRMENT BASED ON CLINICAL TRIAL DATA[a]

| Degree of Hepatic Impairment: Transaminase Levels | | Bilirubin Levels[b] | Recommended TAXOL Dose[c] |
|---|---|---|---|
| 24-hour infusion | | | |
| <2 × ULN | and | ≤1.5 mg/dL | 135 $mg/m^2$ |
| 2 to <10 × ULN | and | ≤1.5 mg/dL | 100 $mg/m^2$ |
| <10 × ULN | and | 1.6-7.5 mg/dL | 50 $mg/m^2$ |
| ≥10 xxULN | or | >7.5 mg/dL | Not recommended |

TABLE 3-continued

Standard dosages of chemotherapeutic agents. Standard dosages were obtained from the manufacturer's product insert for the chemotherapeutic agent.

| Chemotherapeutic Agent | Recommended Dosages | | | |
|---|---|---|---|---|
| | 3-hour infusion | | | |
| | <10 × ULN | and | ≤1.25 × ULN | 175 mg/m$^2$ |
| | <10 × ULN | and | 1.26-2.0 × ULN | 135 mg/m$^2$ |
| | <10 × ULN | and | 2.01-5.0 × ULN | 90 mg/m$^2$ |
| | ≥10 × ULN | or | >5.0 × ULN | Not recommended |
| | [a]These recommendations are based on dosages for patients without hepatic impairment of 135 mg/m$^2$ over 24 hours or 175 mg/m$^2$ over 3 hours; data are not available to make dose adjustment recommendations for other regimens (eg, for AIDS-related Kaposi's sarcoma).<br>[b]Differences in criteria for bilirubin levels between 3- and 24-hour infusion are due to differences in clinical trial design.<br>[c]Dosage recommendations are for the first course of therapy; further dose reduction in subsequent courses should be based on individual tolerance. | | | |
| Docetaxel | Administer in a facility equipped to manage possible complications (e.g., anaphylaxis). Administer intravenously (IV) over 1 hr every 3 weeks. PVC equipment is not recommended. Use only a 21 gauge needle to withdraw TAXOTERE from the vial.<br>BC locally advanced or metastatic: 60 mg/m$^2$ to 100 mg/m$^2$ single agent<br>BC adjuvant: 75 mg/m$^2$ administered 1 hour after doxorubicin 50 mg/m$^2$ and cyclophosphamide 500 mg/m$^2$ every 3 weeks for 6 cycles<br>NSCLC: after platinum therapy failure: 75 mg/m$^2$ single agent<br>NSCLC: chemotherapy-naive: 75 mg/m$^2$ followed by cisplatin 75 mg/m$^2$<br>HRPC: 75 mg/m$^2$ with 5 mg prednisone twice a day continuously<br>GC: 75 mg/m$^2$ followed by cisplatin 75 mg/m$^2$ (both on day 1 only) followed by fluorouracil 750 mg/m$^2$ per day as a 24-hr IV (days 1-5), starting at end of cisplatin infusion<br>SCCHN: 75 mg/m$^2$ followed by cisplatin 75 mg/m$^2$ IV (day 1), followed by fluorouracil 750 mg/m$^2$ per day as a 24-hr IV (days 1-5), starting at end of cisplatin infusion; for 4 cycles<br>SCCHN: 75 mg/m$^2$ followed by cisplatin 100 mg/m$^2$ IV (day 1), followed by fluorouracil 1000 mg/m$^2$ per day as a 24-hr IV (days 1-4); for 3 cycles<br>For all patients: premedicate with oral corticosteroids, and adjust dose as needed | | | |
| Gemcitabine | Gemzar is for intravenous use only.<br>Ovarian Cancer: 1000 mg/m$^2$ over 30 minutes on Days 1 and 8 of each 21-day cycle.<br>Breast Cancer: 1250 mg/m$^2$ over 30 minutes on Days 1 and 8 of each 21-day cycle.<br>Non-Small Cell Lung Cancer: 1000 mg/m$^2$ over 30 minutes on Days 1, 8, and 15 of each 28-day cycle or 1250 mg/m$^2$ over 30 minutes on Days 1 and 8 of each 21-day cycle.<br>Pancreatic Cancer: 1000 mg/m$^2$ over 30 minutes once weekly for the first 7 weeks, then one week rest, then once weekly for 3 weeks of each 28-day cycle. | | | |
| Capecitabine | Take XELODA with water within 30 min after a meal.<br>Monotherapy: 1250 mg/m$^2$ administered orally twice daily (morning and evening; equivalent to 2500 mg/m$^2$ total daily dose) for 2 weeks followed by a 1-week rest period given as 3-week cycles.<br>Adjuvant treatment is recommended for a total of 6 months (8 cycles)<br>In combination with docetaxel, the recommended dose of XELODA is 1250 mg/m$^2$ twice daily for 2 weeks followed by a 1-week rest period, combined with docetaxel at 75 mg/m$^2$ as a 1-hour IV infusion every 3 weeks.<br>XELODA dosage may need to be individualized to optimize patient management.<br>Reduce the dose of XELODA by 25% in patients with moderate renal impairment. □ | | | |
| Estramustine | The recommended daily dose is 14 mg per kg of body weight (ie, one 140 mg capsule for each 10 kg or 22 lb of body weight), given in 3 or 4 divided doses. Most patients in studies in the United States have been treated at a dosage range of 10 to 16 mg per kg per day.<br>Patients should be instructed to take EMCYT Capsules at least 1 hour before or 2 hours after meals. EMCYT should be swallowed with water. Milk, milk products, and calcium-rich foods or drugs (such as calcium-containing antacids) must not be taken simultaneously with EMCYT.<br>Patients should be treated for 30 to 90 days before the physician determines the possible benefits of continued therapy. Therapy should be continued as long as the favorable response lasts. Some patients have been maintained on therapy for more than 3 years at doses ranging from 10 to 16 mg per kg of body weight per day. | | | |
| Cytarabine | Cytarabine is not active orally. The schedule and method of administration varies with the program of therapy to be used. Cytarabine may be given by | | | |

TABLE 3-continued

| Chemotherapeutic Agent | Recommended Dosages |
|---|---|
| Standard dosages of chemotherapeutic agents. Standard dosages were obtained from the manufacturer's product insert for the chemotherapeutic agent. | |
| | intravenous infusion or injection, subcutaneously, or intrathecally.<br>In the induction therapy of acute non-lymphocytic leukemia, the usual cytarabine dose in combination with other anticancer drugs is 100 $mg/m^2$/day by continuous IV infusion (days 1 to 7) or 100 $mg/m^2$ IV every 12 hours (days 1 to 7).<br>Intrathecal Use In Meningeal Leukemia: Cytarabine has been used intrathecally in acute leukemia in doses ranging from 5 to 75 mg/m2 of body surface area. The frequency of administration varied from once a day for 4 days to once every 4 days. |
| Daunorubicin | Adult Acute Nonlymphocytic Leukemia:<br>In Combination:<br>For patients under age 60, daunorubicin hydrochloride 45 $mg/m^2$/day IV on days 1, 2, and 3 of the first course and on days 1, 2 of subsequent courses AND cytosine arabinoside 100 $mg/m^2$/day IV infusion daily for 7 days for the first course and for 5 days for subsequent courses.<br>For patients 60 years of age and above, daunorubicin hydrochloride 30 $mg/m^2$/day IV on days 1, 2, and 3 of the first course and on days 1, 2 of subsequent courses AND cytosine arabinoside 100 $mg/m^2$/day IV infusion daily for 7 days for the first course and for 5 days for subsequent courses.<br>Pediatric Acute Lymphocytic Leukemia:<br>In Combination:<br>Daunorubicin hydrochloride 25 $mg/m^2$ IV on day 1 every week, vincristine 1.5 $mg/m^2$ IV on day 1 every week, prednisone 40 $mg/m^2$ PO daily.<br>In children less than 2 years of age or below 0.5 $m^2$ body surface area, it has been recommended that the daunorubicin hydrochloride dosage calculation should be based on weight (1 mg/kg) instead of body surface area.<br>Adult Acute Lymphocytic Leukemia:<br>In Combination:<br>Daunorubicin hydrochloride 45 $mg/m^2$/day IV on days 1, 2, and 3 AND vincristine 2 mg IV on days 1, 8, and 15; prednisone 40 $mg/m^2$/day PO on days 1 through 22, then tapered between days 22 to 29; L-asparaginase 500 IU/kg/day x 10 days IV on days 22 through 32. |
| Idarubicin | For induction therapy in adult patients with AML the following dose schedule is recommended:<br>Idarubicin hydrochloride injection 12 $mg/m^2$ daily for 3 days by slow (10 to 15 min) intravenous injection in combination with cytarabine. The cytarabine may be given as 100 $mg/m^2$ daily by continuous infusion for 7 days or as cytarabine 25 $mg/m^2$ intravenous bolus followed by cytarabine 200 $mg/m^2$ daily for 5 days continuous infusion.<br>In patients with unequivocal evidence of leukemia after the first induction course, a second course may be administered. Administration of the second course should be delayed in patients who experience severe mucositis, until recovery from this toxicity has occurred, and a dose reduction of 25% is recommended.<br>In patients with hepatic and/or renal impairment, a dose reduction of idarubicin hydrochloride injection should be considered. Idarubicin hydrochloride injection should not be administered if the bilirubin level exceeds 5 mg %. |
| Bevacitumab | Do not administer as an IV push or bolus.<br>Do not initiate Avastin for 28 days following major surgery and until surgical wound is fully healed.<br>Metastatic colorectal cancer<br>5 mg/kg IV every 2 weeks with bolus-IFL<br>10 mg/kg IV every 2 weeks with FOLFOX4<br>5 mg/kg IV every 2 weeks or 7.5 mg/kg IV every 3 weeks with fluoropyrimidine-irinotecan or fluoropyrimidine-oxaliplatin based chemotherapy after progression on a first-line Avastin containing regimen<br>Non-squamous non-small cell lung cancer<br>15 mg/kg IV every 3 weeks with carboplatin/paclitaxel<br>Glioblastoma<br>10 mg/kg IV every 2 weeks<br>Metastatic renal cell carcinoma (mRCC)<br>10 mg/kg IV every 2 weeks with interferon alfa □ |
| Valganciclovir | Adult Patients With Normal Renal Function<br>Treatment of CMV Retinitis<br>Induction: The recommended dose is 900 mg (two 450 mg tablets) twice a day for 21 days.<br>Maintenance: Following induction treatment, or in adult patients with inactive CMV retinitis, the recommended dose is 900 mg (two 450 mg tablets) once a day.<br>Prevention of CMV Disease<br>For adult patients who have received a heart or kidney-pancreas transplant, the recommended dose is 900 mg (two 450 mg tablets) once a day starting within 10 days of transplantation until 100 days posttransplantation. |

TABLE 3-continued

| Chemotherapeutic Agent | Recommended Dosages |
| --- | --- |
| Standard dosages of chemotherapeutic agents. Standard dosages were obtained from the manufacturer's product insert for the chemotherapeutic agent. | |
| | For adult patients who have received a kidney transplant, the recommended dose is 900 mg (two 450 mg tablets) once a day starting within 10 days of transplantation until 200 days post-transplantation.<br>Pediatric Patients<br>Prevention of CMV Disease<br>For pediatric patients 4 months to 16 years of age who have received a kidney or heart transplant, the recommended once daily dose of Valcyte starting within 10 days of transplantation until 100 days post-transplantation is based on body surface area (BSA) and creatinine clearance (CrCl) derived from a modified Schwartz formula, and is calculated using the equation below:<br>Pediatric Dose (mg) = 7 × BSA × CrCl (calculated using a modified Schwartz formula). If the calculated Schwartz creatinine clearance exceeds 150 mL/min/1.73 $m^2$, then a maximum value of 150 mL/min/1.73 $m^2$ should be used in the equation.<br>Mosteller BSA ($m^2$) = √Height (cm) × Weight (kg)/3600<br>Schwartz Creatinine Clearance mL/min/1.73 $m^2$) = k × Height (cm)/Serum Creatinine (mg/dL)<br>where k = 0.45 for patients aged 4 months to <1 year, 0.45 for patients aged 1 to <2 years (note k value is 0.45 instead of the typical value of 0.55), 0.55 for boys aged 2 to <13 years and girls aged 2 to 16 years, and 0.7 for boys aged 13 to 16 years.<br>All calculated doses should be rounded to the nearest 25 mg increment for the actual deliverable dose. If the calculated dose exceeds 900 mg, a maximum dose of 900 mg should be administered. Valcyte for oral solution is the preferred formulation since it provides the ability to administer a dose calculated according to the formula above; however, Valcyte tablets may be used if the calculated doses are within 10% of available tablet strength (450 mg). For example, if the calculated dose is between 405 mg and 495 mg, one 450 mg tablet may be taken |
| Methotrexate | Neoplastic Diseases: Oral administration in tablet form is often preferred when low doses are being administered since absorption is rapid and effective serum levels are obtained. Methotrexate injection may be given by the intramuscular, intravenous or intra-arterial route.<br>Choriocarcinoma and similar trophoblastic diseases: Methotrexate is administered orally or intramuscularly in doses of 15 to 30 mg daily for a five-day course. Such courses are usually repeated for 3 to 5 times as required, with rest periods of one or more weeks interposed between courses, until any manifesting toxic symptoms subside. The effectiveness of therapy is ordinarily evaluated by 24 hour quantitative analysis of urinary chorionic gonadotropin (hCG), which should return to normal or less than 50 IU/24 hr usually after the third or fourth course and usually be followed by a complete resolution of measurable lesions in 4 to 6 weeks. One to two courses of methotrexate after normalization of hCG is usually recommended. Before each course of the drug careful clinical assessment is essential. Cyclic combination therapy of methotrexate with other antitumor drugs has been reported as being useful.<br>Leukemia: Methotrexate alone or in combination with steroids was used initially for induction of remission in acute lymphoblastic leukemias. More recently corticosteroid therapy, in combination with other anti-leukemic drugs or in cyclic combinations with methotrexate included, has appeared to produce rapid and effective remissions. When used for induction, methotrexate in doses of 33 mg/m2 in combination with 60 mg/$m^2$ of prednisone, given daily, produced remissions in 50% of patients treated, usually within a period of 4 to 6 weeks. Methotrexate in combination with other agents appears to be the drug of choice for securing maintenance of drug-induced remissions. When remission is achieved and supportive care has produced general clinical improvement, maintenance therapy is initiated, as follows: Methotrexate is administered 2 times weekly either by mouth or intramuscularly in total weekly doses of 30 mg/$m^2$. It has also been given in doses of 2.5 mg/kg intravenously every 14 days. If and when relapse does occur, reinduction of remission can again usually be obtained by repeating the initial induction regimen.<br>Lymphomas: In Burkitt's tumor, Stages I-II, methotrexate has produced prolonged remissions in some cases. Recommended dosage is 10 to 25 mg/day orally for 4 to 8 days. In Stage III, methotrexate is commonly given concomitantly with other antitumor agents. Treatment in all stages usually consists of several courses of the drug interposed with 7 to 10 day rest periods. Lymphosarcomas in Stage III may respond to combined drug therapy with methotrexate given in doses of 0.625 to 2.5 mg/kg daily.<br>Mycosis fungoides (cutaneous T Cell lymphoma): Therapy with methotrexate as a single agent appears to produce clinical responses in up to 50% of patients treated. Dosage in early stages is usually 5 to 50 mg once weekly. Dose reduction or cessation is guided by patient response and |

TABLE 3-continued

Standard dosages of chemotherapeutic agents. Standard dosages were obtained from the manufacturer's product insert for the chemotherapeutic agent.

| Chemotherapeutic Agent | Recommended Dosages |
|---|---|
| | hematologic monitoring. Methotrexate has also been administered twice weekly in doses ranging from 15 to 37.5 mg in patients who have responded poorly to weekly therapy. Combination chemotherapy regimens that include intravenous methotrexate administered at higher doses with leucovorin rescue have been utilized in advanced stages of the disease.<br>Osteosarcoma: An effective adjuvant chemotherapy regimen requires the administration of several cytotoxic chemotherapeutic agents. In addition to high-dose methotrexate with leucovorin rescue, these agents may include doxorubicin, cisplatin, and the combination of bleomycin, cyclophosphamide and dactinomycin (BCD) in the doses and schedule shown in the table below: The starting dose for high-dose methotrexate treatment is 12 grams/$m^2$. If this dose is not sufficient to produce a peak serum methotrexate concentration of 1,000 micromolar at the end of the methotrexate infusion, the dose may be escalated to 15 grams/$m^2$ in subsequent treatments. If the patient is vomiting or is unable to tolerate oral medication, leucovorin is given IV or IM at the same dose and schedule.<br>Adult Rheumatoid Arthritis: Recommended Starting Dosage Schedules<br>1. Single oral doses of 7.5 mg once weekly.<br>2. Divided oral dosages of 2.5 mg at 12 hour intervals for 3 doses given as a course once weekly.<br>Polyarticular Course Juvenile Rheumatoid Arthritis: The recommended starting dose is 10 mg/$m^2$ given once weekly.<br>Psoriasis: Recommended Starting Dose Schedule:<br>1. Weekly single oral, IM or IV dosage schedule: 10 to 25 mg per week until adequate response is achieved<br>2. Divided oral dose schedule 2.5 mg at 12 hour intervals for three doses |
| Epirubicin | Administer intravenously in repeated 3-to 4-week cycles, either total dose on Day 1 of each cycle or divided equally and given on Days 1 and 8 of each cycle<br>The recommended starting dose of epirubicin hydrochloride injection is 100 to 120 mg/$m^2$.<br>The following regimens are recommended:<br>CEF-120: Cyclophosphamide 75 mg/$m^2$ PO D 1 to 14, Epirubicin hydrochloride injection 60 mg/$m^2$ IV D 1 and 8,5-Fluorouracil 500 mg/$m^2$ IV D 1 and 8, Repeated every 28 days for 6 cycles<br>FEC-100: 5-Fluorouracil 500 mg/$m^2$, Epirubicin hydrochloride injection 100 mg/$m^2$, Cyclophosphamide 500 mg/$m^2$<br>All drugs administered intravenously on Day 1 and repeated every 21 days for 6 cycles.<br>Dosage reductions are possible when given in certain combinations.<br>Dosage adjustments after the first treatment cycle should be made based on hematologic and nonhematologic toxicities.<br>Reduce dose in patients with hepatic impairment.<br>Consider lower doses in patients with severe renal impairment. |
| Mitoxantrone | Multiple Sclerosis: the recommended dosage of NOVANTRONE is 12 mg/$m^2$ given as a short (approximately 5 to 15 minutes) intravenous infusion every 3 months.<br>Hormone-Refractory Prostate Cancer: the recommended dosage of NOVANTRONE is 12 to 14 mg/$m^2$ given as a short intravenous infusion every 21 days<br>Combination Initial Therapy for ANLL in Adults: for induction, the recommended dosage is 12 mg/$m^2$ of NOVANTRONE daily on Days 1-3 given as an intravenous infusion, and 100 mg/$m^2$ of cytarabine for 7 days given as a continuous 24-hour infusion on Days 1-7. |
| Teniposide | In one study, childhood ALL patients failing induction therapy with a cytarabine-containing regimen were treated with the combination of VUMON 165 mg/$m^2$ and cytarabine 300 mg/$m^2$ intravenously, twice weekly for 8 to 9 doses.<br>In another study, patients with childhood ALL refractory to vincristine/prednisone-containing regimens were treated with the combination of VUMON 250 mg/$m^2$ and vincristine 1.5 mg/$m^2$ intravenously, weekly for 4 to 8 weeks and prednisone 40 mg/$m^2$ orally for 28 days. |
| Irontecan | Colorectal cancer combination regimen 1: CAMPTOSAR 125 mg/$m^2$ intravenous infusion over 90 minutes on days 1, 8, 15, 22 with LV 20 mg/$m^2$ intravenous bolus infusion on days 1, 8, 15, 22 followed by 5-FU intravenous bolus infusion on days 1, 8, 15, 22 every 6 weeks.<br>Colorectal cancer combination regimen 2: CAMPTOSAR 180 mg/$m^2$ intravenous infusion over 90 minutes on days 1, 15, 29 with LV 200 mg/$m^2$ intravenous infusion over 2 hours on days 1, 2, 15, 16, 29, 20 followed by 5-FU 400 mg/$m^2$ intravenous bolus infusion on days 1, 2, 15, 16, 29, 30 and 5-FU 600 mg/$m^2$ intravenous infusion over 22 hours on days 1, 2, 15, 16, 29, 30.<br>Colorectal cancer single agent regimen 1: CAMPTOSAR 125 mg/$m^2$ |

TABLE 3-continued

Standard dosages of chemotherapeutic agents. Standard dosages were obtained from the manufacturer's product insert for the chemotherapeutic agent.

| Chemotherapeutic Agent | Recommended Dosages |
|---|---|
| | intravenous infusion over 90 minutes on days 1, 8, 15, 22 then 2-week rest.<br>Colorectal cancer single agent regimen 2: CAMPTOSAR 350 mg/m$^2$ intravenous infusion over 90 minutes on day 1 every 3 weeks. |
| Topotecan | The recommended dose of HYCAMTIN capsules is 2.3 mg/m$^2$/day once daily for 5 consecutive days repeated every 21 days.<br>The recommended dose of HYCAMTIN is 1.5 mg/m$^2$ by intravenous infusion over 30 minutes daily for 5 consecutive days, starting on day 1 of a 21-day course. In the absence of tumor progression, a minimum of 4 courses is recommended because tumor response may be delayed.<br>Renal Functional Impairment: dosage adjustment to 0.75 mg/m$^2$ is recommended for patients with moderate renal impairment (20 to 39 mL/min). |
| Busulfan | Busulfan is administered orally. The usual adult dose range for remission induction is 4 to 8 mg, total dose, daily. Dosing on a weight basis is the same for both pediatric patients and adults, approximately 60 mcg/kg of body weight or 1.8 mg/m$^2$ of body surface, daily.<br>BUSULFEX ® (busulfan) Injection is administered as a component of the BuCy conditioning regimen prior to bone marrow or peripheral blood progenitor cell replacement, the recommended doses are as follows:<br>The usual adult dose is 0.8 mg/kg of ideal body weight or actual body weight, whichever is lower, administered every six hours for four days (a total of 16 doses). For obese, or severely obese patients, BUSULFEX should be administered based on adjusted ideal body weight. Ideal body weight (IBW) should be calculated as follows (height in cm, and weight in kg): IBW (kg; men) = 50 + 0.91 × (height in cm − 152); IBW (kg; women) = 45 + 0.91 × (height in cm − 152). Adjusted ideal body weight (AIBW) should be calculated as follows: AIBW = IBW + 0.25 × (actual weight − IBW).<br>Cyclophosphamide is given on each of two days as a one-hour infusion at a dose of 60 mg/kg beginning on BMT day −3, no sooner than six hours following the 16th dose of BUSULFEX. |
| Melphalan | Melphalan for injection:<br>The usual IV dose is 16 mg/m$^2$. The drug is administered as a single infusion over 15 to 20 minutes. ALKERAN is administered at 2-week intervals for four doses, then, after adequate recovery from toxicity, at 4-week intervals. The dose is adjusted, as required, on the basis of blood counts done at approximately weekly intervals. After 2 to 3 weeks of treatment, the drug should be discontinued for up to 4 weeks, during which time the blood count should be followed carefully.<br>Melphalan tablet:<br>Multiple Myeloma: The usual oral dose is 6 mg (3 tablets) daily.<br>Epithelial Ovarian Cancer: One commonly employed regimen for the treatment of ovarian carcinoma has been to administer ALKERAN at a dose of 0.2 mg/kg daily for 5 days as a single course. Courses are repeated every 4 to 5 weeks depending upon hematologic tolerance. |
| Cladribine | Hairy Cell Leukemia:<br>the recommended dose and schedule of LEUSTATIN Injection is as a single course given by continuous infusion for 7 consecutive days at a dose of 0.09 mg/kg/day.<br>Chronic Lymphocytic Leukemia: the recommended treatment consists of a continuous infusion of LEUSTATIN injection for 2 hours on days 1 to 5 of a 28 day cycle at a dose of 0.12 mg/kg/day (4.8 mg/m$^2$/day). It is recommended that LEUSTATIN injection be administered in responding patients up to a maximum of 6 monthly cycles and that non-responding patients receive no more than 2 cycles of treatment. |
| Vinblastine | This preparation is for intravenous use only.<br>Adult patients:<br>A simplified and conservative incremental approach to dosage at weekly intervals for adults may be outlined as follows:<br>First dose—3.7 mg/m$^2$ bsa<br>Second dose—5.5 mg/m$^2$ bsa<br>Third dose—7.4 mg/m$^2$ bsa<br>Fourth dose—9.25 mg/m$^2$ bsa<br>Fifth dose—11.1 mg/m$^2$ bsa<br>The above-mentioned increases may be used until a maximum dose not exceeding 18.5 mg/m$^2$ bsa for adults is reached.<br>Pediatric Patients<br>As a single agent for Letterer-Siwe disease (histiocytosis X), the initial dose of vinblastine sulfate was reported as 6.5 mg/m$^2$.<br>When vinblastine sulfate was used in combination with other chemotherapeutic agents for the treatment of Hodgkin's disease, the initial dose was reported as 6 mg/m$^2$. For testicular germ cell carcinomas, the initial dose of vinblastine sulfate was reported as 3 mg/m$^2$ in a combination regimen.<br>Patients with Renal or Hepatic Impairment |

TABLE 3-continued

Standard dosages of chemotherapeutic agents. Standard dosages were obtained from the manufacturer's product insert for the chemotherapeutic agent.

| Chemotherapeutic Agent | Recommended Dosages |
|---|---|
| | A reduction of 50% in the dose of vinblastine sulfate is recommended for patients having a direct serum bilirubin value above 3 mg/100 mL. Since metabolism and excretion are primarily hepatic, no modification is recommended for patients with impaired renal function. |
| Chorambucil | The usual oral dosage is 0.1 to 0.2 mg/kg body weight daily for 3 to 6 weeks as required. This usually amounts to 4 to 10 mg per day for the average patient. The entire daily dose may be given at one time.<br>Patients with Hodgkin's disease usually require 0.2 mg/kg daily, whereas patients with other lymphomas or chronic lymphocytic leukemia usually require only 0.1 mg/kg daily. When lymphocytic infiltration of the bone marrow is present, or when the bone marrow is hypoplastic, the daily dose should not exceed 0.1 mg/kg (about 6 mg for the average patient).<br>Alternate schedules for the treatment of chronic lymphocytic leukemia employing intermittent, biweekly, or once-monthly pulse doses of chlorambucil have been reported. Intermittent schedules of chlorambucil begin with an initial single dose of 0.4 mg/kg. Doses are generally increased by 0.1 mg/kg until control of lymphocytosis or toxicity is observed. Subsequent doses are modified to produce mild hematologic toxicity.<br>If maintenance dosage is used, it should not exceed 0.1 mg/kg daily and may well be as low as 0.03 mg/kg daily. A typical maintenance dose is 2 mg to 4 mg daily, or less, depending on the status of the blood counts. |
| Tamoxifen | For patients with breast cancer, the recommended daily dose is 20-40 mg. Dosages greater than 20 mg per day should be given in divided doses (morning and evening).<br>Ductal Carcinoma in Situ (DCIS): The recommended dose is 20 mg daily for 5 years.<br>Reduction in Breast Cancer Incidence in High Risk Women: The recommended dose is 20 mg daily for 5 years. |
| Actinomycin-D | Not for oral administration<br>The dose intensity per 2-week cycle for adults or children should not exceed 15 mcg/kg/day or 400-600 mcg/$m^2$/day intravenously for five days.<br>Wilms' Tumor, Childhood Rhabdomyosarcoma and Ewing's Sarcoma: Regimens of 15 mcg/kg intravenously daily for five days administered in various combinations and schedules with other chemotherapeutic agents have been utilized in the treatment of Wilms' tumor, rhabdomyosarcoma and Ewing's sarcoma.<br>Metastatic Nonseminomatous Testicular Cancer: 1000 mcg/$m^2$ intravenously on Day 1 as part of a combination regimen with cyclophosphamide, bleomycin, vinblastine, and cisplatin.<br>Gestational Trophoblastic Neoplasia: 12 mcg/kg intravenously daily for five days as a single agent. 500 mcg intravenously on Days 1 and 2 as part of a combination regimen with etoposide, methotrexate, folinic acid, vincristine, cyclophosphamide and isplatin.<br>Regional Perfusion in Locally Recurrent and Locoregional Solid Malignancies: In general, the following doses are suggested:<br>50 mcg (0.05 mg) per kilogram of body weight for lower extremity or pelvis.<br>35 mcg (0.035 mg) per kilogram of body weight for upper extremity.<br>It may be advisable to use lower doses in obese patients, or when previous chemotherapy or radiation therapy has been employed |
| Mitomycin C | Mitomycin should be given intravenously only.<br>The following dosage schedule may be used at 6 to 8 week intervals: 20 mg/$m^2$ intravenously as a single dose via a functioning intravenous catheter. When mitomycin is used in combination with other myelosuppressive agents, the doses should be adjusted accordingly. If the disease continues to progress after two courses of mitomycin, the drug should be stopped since chances of response are minimal. |
| Verapamil | Verapamil hydrochloride extended-release tablets:<br>Initiate therapy with 180 mg of verapamil hydrochloride extended-release tablets given in the morning. Lower initial doses of 120 mg a day may be warranted in patients who may have an increased response to verapamil (e.g., the elderly or small people).<br>If adequate response is not obtained with 180 mg of verapamil hydrochloride extended-release tablets, the dose may be titrated upward in the following manner:<br>1.240 mg each morning,<br>2.180 mg each morning plus 180 mg each evening; or 240 mg each morning plus 120 mg each evening,<br>3.240 mg every 12 hours.<br>Verapamil hydrochloride - injection:<br>The recommended intravenous doses of verapamil are as follows:<br>ADULT:<br>Initial dose: 5 to 10 mg (0.075 to 0.15 mg/kg body weight) given as an intravenous bolus over at least 2 minutes.<br>Repeat dose: 10 mg (0.15 mg/kg body weight) 30 minutes after the first dose |

TABLE 3-continued

Standard dosages of chemotherapeutic agents. Standard dosages were obtained from the manufacturer's product insert for the chemotherapeutic agent.

| Chemotherapeutic Agent | Recommended Dosages |
|---|---|
| | if the initial response is not adequate. An optimal interval for subsequent I.V. doses has not been determined, and should be individualized for each patient.<br>Older Patients: The dose should be administered over at least 3 minutes to minimize the risk of untoward drug effects.<br>PEDIATRIC:<br>Initial dose:<br>0-1 yr: 0.1 to 0.2 mg/kg body weight (usual single dose range 0.75 to 2 mg) should be administered as an intravenous bolus over at least 2 minutes under continuous ECG monitoring.<br>1-15 yrs: 0.1 to 0.3 mg/kg body weight (usual single dose range 2 to 5 mg) should be administered as an intravenous bolus over at least 2 minutes. Do not exceed 5 mg.<br>Repeat dose:<br>0-1 yr: 0.1 to 0.2 mg/kg body weight (usual single dose range 0.75 to 2 mg) 30 minutes after the first dose if the initial response is not adequate (under continuous ECG monitoring).<br>1-15 yrs: 0.1 to 0.3 mg/kg body weight (usual single dose range 2 to 5 mg) 30 minutes after the first dose if the initial response is not adequate. Do not exceed 10 mg as a single dose. |
| Podophyllotoxin | Apply twice daily morning and evening (every 12 hours), for 3 consecutive days, then withhold use for 4 consecutive days. This one week cycle of treatment may be repeated up to four times until there is no visible wart tissue. |

The invention claimed is:

1. A method of treating an oncological disorder in a subject comprising:

(a) administering coenzyme Q10 (CoQ10) to the subject by continuous intravenous infusion for at least 24 hours;

(b) discontinuing administration of CoQ10; and (c) administering at least one chemotherapeutic agent to the subject after administration with CoQ10 has been discontinued, such that the oncological disorder is treated, wherein the oncological disorder is a solid tumor.

2. A method of treating an oncological disorder in a subject comprising:

(a) administering coenzyme Q10 (CoQ10) to the subject by continuous intravenous infusion for at least 24 hours;

(b) administering at least one chemotherapeutic agent to the subject after administration of the CoQ10 is initiated; and (c) continuing treatment with CoQ10 after administration of the at least one chemotherapeutic agent is initiated, such that the oncological disorder is treated, wherein the oncological disorder is a solid tumor.

3. The method of claim 2, wherein administration of the at least one chemotherapeutic agent is initiated at least 24 hours after administration of CoQ10 is initiated, one or more weeks after administration of CoQ10 is initiated, two or more weeks after administration of CoQ10 is initiated, three or more weeks after administration of CoQ10 is initiated, four or more weeks after administration of CoQ10 is initiated, five or more weeks after administration of CoQ10 is initiated, six or more weeks after administration of CoQ10 is initiated, seven or more weeks after administration of CoQ10 is initiated, or eight or more weeks after administration of CoQ10 is initiated.

4. The method of claim 2, wherein a response of the oncological disorder to treatment is improved relative to a treatment with the at least one chemotherapeutic agent alone.

5. The method of claim 4, wherein the response is improved by at least 5%, at least 10%, at least 15%, at least 20%, at least 30%, at least 40% or at least 50% relative to treatment with the at least one chemotherapeutic agent alone.

6. The method of claim 4, wherein the response comprises any one or more of reduction in tumor burden, reduction in tumor size, inhibition of tumor growth, achieving stable oncological disorder in a subject with a progressive oncological disorder prior to treatment, increased time to progression of the oncological disorder, and increased time of survival.

7. The method of claim 2, wherein the CoQ10 is administered at a dose of about 5 mg/kg, about 10 mg/kg, about 12.5 mg/kg, about 20 mg/kg, about 25 mg/kg, t about 30 mg/kg, about 35 mg/kg, about 40 mg/kg, about 45 mg/kg, about 50 mg/kg, about 55 mg/kg, about 58 mg/kg, about 58.6 mg/kg, about 60 mg/kg, about 75 mg/kg, about 78 mg/kg, about 100 mg/kg, about 104 mg/kg, about 125 mg/kg, about 150 mg/kg, about 175 mg/kg, about 200 mg/kg, about 300 mg/kg, or about 400 mg/kg.

8. A method of improving a chemotherapeutic treatment regimen for an oncological disorder in a subject, comprising pre-treating a subject having an oncological disorder with Coenzyme Q10 (CoQ10) for a sufficient time prior to initiation of a chemotherapeutic treatment regimen, wherein the chemotherapeutic treatment regimen comprises administration of one or more chemotherapeutic agents, such that a response of the oncological disorder is improved relative to treatment with the chemotherapeutic treatment regimen alone, wherein the Coenzyme Q10 is administered by continuous intravenous infusion for at least 24 hours, and wherein the oncological disorder is a solid tumor.

9. The method of claim 2, wherein the at least one chemotherapeutic agent comprises a chemotherapeutic agent selected from the group consisting of a topoisomerase I inhibitor, a topoisomerase II inhibitor, a mitotic inhibitor, an alkylating agent, a platinum compound, and an antimetabolite.

10. The method of claim 2, wherein the at least one chemotherapeutic agent comprises a chemotherapeutic agent selected from the group consisting of amifostine (ethyol), cisplatin, dacarbazine (DTIC), dactinomycin, mechlorethamine (nitrogen mustard), streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, S-I capecitabine, ftorafur, 5'deoxyflurouridine, UFT, eniluracil, deoxycytidine, 5-azacytosine, 5-azadeoxycytosine, allopurinol, 2-chloro adenosine, trimetrexate, aminopterin, methylene-10-deazaaminopterin (MDAM), oxaplatin, picoplatin, tetraplatin, satraplatin, platinum-DACH, ormaplatin, CI-973, JM-216, and analogs thereof, epirubicin, etoposide phosphate, 9-aminocamptothecin, 10, 11-methylenedioxycamptothecin, karenitecin, 9-nitrocamptothecin, TAS 103, vindesine, L-phenylalanine mustard, ifosphamidemefosphamide, perfosfamide, trophosphamide carmustine, semustine, epothilones A-E, tomudex, 6-mercaptopurine, 6-thioguanine, amsacrine, etoposide phosphate, karenitecin, acyclovir, valacyclovir, ganciclovir, amantadine, rimantadine, lamivudine, zidovudine, bevacizumab, trastuzumab, rituximab, 5-Fluorouracil, Capecitabine, Pentostatin, Trimetrexate, Cladribine, floxuridine, fludarabine, hydroxyurea, ifosfamide, idarubicin, mesna, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil, cisplatin, doxorubicin, paclitaxel (taxol), bleomycin, mTor, epidermal growth factor receptor (EGFR), and fibroblast growth factors (FGF) and combinations thereof.

11. The method of claim 2, wherein the at least one chemotherapeutic agent comprises at least one of gemcitabine, 5-fluorouracil, cisplatin, capecitabine, methotrexate, edatrexate, docetaxel, cyclophosphamide, doxorubicin, and irinotecan.

12. The method of claim 2, wherein the oncological disorder is selected from the group consisting of a carcinoma, sarcoma, lymphoma, and melanoma.

13. The method of claim 2, wherein the oncological disorder is selected from the group consisting of pancreatic cancer, breast cancer, liver cancer, skin cancer, lung cancer, colon cancer, prostate cancer, thyroid cancer, bladder cancer, rectal cancer, endometrial cancer, kidney cancer, bone cancer, brain cancer, cervical cancer, stomach cancer, mouth and oral cancers, neuroblastoma, testicular cancer, uterine cancer, and vulvar cancer.

14. The method of claim 2, wherein the subject is human.

15. The method of claim 2, wherein the method comprises administering 5 mg/kg docetaxel, 1 mg/kg doxorubicin, and 35 mg/kg cyclophosphamide to the subject every three weeks for six cycles.

16. The method of claim 2, wherein the oncological disorder is glioblastoma.

17. The method of claim 16, wherein the at least one chemotherapeutic agent comprises an alkylating agent.

18. The method of claim 1, wherein the oncological disorder is selected from the group consisting of a carcinoma, sarcoma, lymphoma, and melanoma.

19. The method of claim 1, wherein the oncological disorder is selected from the group consisting of pancreatic cancer, breast cancer, liver cancer, skin cancer, lung cancer, colon cancer, prostate cancer, thyroid cancer, bladder cancer, rectal cancer, endometrial cancer, kidney cancer, bone cancer, brain cancer, cervical cancer, stomach cancer, mouth and oral cancers, neuroblastoma, testicular cancer, uterine cancer, and vulvar cancer.

20. The method of claim 1, wherein the subject is human.

21. The method of claim 1, wherein the oncological disorder is glioblastoma.

22. The method of claim 21, wherein the at least one chemotherapeutic agent comprises an alkylating agent.

* * * * *